US010093978B2

(12) United States Patent
Yaspan et al.

(10) Patent No.: US 10,093,978 B2
(45) Date of Patent: Oct. 9, 2018

(54) COMPOSITIONS FOR DETECTING COMPLEMENT FACTOR H (CFH) AND COMPLEMENT FACTOR I (CFI) POLYMORPHISMS

(71) Applicant: Genentech, Inc., South San Francisco, CA (US)

(72) Inventors: Brian Yaspan, Pacifica, CA (US); Robert Royal Graham, San Francisco, CA (US); Amy Dressen, San Francisco, CA (US); Zhengrong Li, San Francisco, CA (US); Erich Strauss, San Francisco, CA (US); Teodorica Bugawan, San Leandro, CA (US)

(73) Assignee: GENENTECH, INC., South San Francisco, CA (US)

( * ) Notice: Subject to any disclaimer, the term of this patent is extended or adjusted under 35 U.S.C. 154(b) by 56 days.

(21) Appl. No.: 14/456,268

(22) Filed: Aug. 11, 2014

(65) Prior Publication Data
US 2015/0044205 A1 Feb. 12, 2015

Related U.S. Application Data

(60) Provisional application No. 61/864,941, filed on Aug. 12, 2013, provisional application No. 61/866,651, filed on Aug. 16, 2013, provisional application No. 61/872,098, filed on Aug. 30, 2013, provisional application No. 61/988,012, filed on May 2, 2014, provisional application No. 62/021,487, filed on Jul. 7, 2014.

(51) Int. Cl.
*C12Q 1/6883* (2018.01)
*C07K 16/40* (2006.01)
*A61K 39/00* (2006.01)

(52) U.S. Cl.
CPC ............ *C12Q 1/6883* (2013.01); *C07K 16/40* (2013.01); *A61K 2039/505* (2013.01); *C12Q 2600/106* (2013.01); *C12Q 2600/118* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 3,773,919 A | 11/1973 | Boswell et al. | |
| 4,179,337 A | 12/1979 | Davis et al. | |
| 4,741,900 A | 5/1988 | Alvarez et al. | |
| 4,816,567 A | 3/1989 | Cabilly et al. | |
| 4,935,465 A | 6/1990 | Garman | |
| 4,946,778 A | 8/1990 | Ladner et al. | |
| 5,166,322 A | 11/1992 | Shaw et al. | |
| 5,206,344 A | 4/1993 | Katre et al. | |
| 5,225,539 A | 7/1993 | Winter | |
| 5,244,800 A | 9/1993 | DeLucas et al. | |
| 5,456,909 A | 10/1995 | Marsh, Jr. et al. | |
| 5,530,101 A | 6/1996 | Queen et al. | |
| 5,534,615 A | 7/1996 | Baker et al. | |
| 5,571,894 A | 11/1996 | Wels et al. | |
| 5,587,458 A | 12/1996 | King et al. | |
| 5,624,837 A | 4/1997 | Fodor et al. | |
| 5,627,264 A | 5/1997 | Fodor et al. | |
| 5,679,345 A | 10/1997 | Sanfilippo et al. | |
| 5,679,354 A | 10/1997 | Morein et al. | |
| 5,679,546 A | 10/1997 | Ko et al. | |
| 5,679,564 A | 10/1997 | Pace et al. | |
| 5,849,535 A | 12/1998 | Cunningham et al. | |
| 5,851,528 A | 12/1998 | Ko et al. | |
| 5,853,722 A | 12/1998 | Rollins et al. | |
| 5,856,297 A | 1/1999 | Fearon et al. | |
| 5,856,300 A | 1/1999 | Rittershaus et al. | |
| 5,858,969 A | 1/1999 | Marsh, Jr. et al. | |
| 5,861,156 A | 1/1999 | George et al. | |
| 5,869,046 A | 2/1999 | Presta et al. | |
| 5,919,623 A * | 7/1999 | Taylor .................. | C12N 15/102 204/456 |
| 6,267,958 B1 | 7/2001 | Andya et al. | |
| 6,333,034 B1 | 12/2001 | Gupta-Bansal et al. | |
| 6,376,653 B1 | 4/2002 | Holmes et al. | |
| 6,407,213 B1 | 6/2002 | Carter et al. | |
| 6,410,708 B1 | 6/2002 | Ashkenazi et al. | |
| 6,472,520 B2 | 10/2002 | Fisher | |
| 6,534,058 B2 | 3/2003 | Fung et al. | |
| 6,569,992 B1 | 5/2003 | LaFleur et al. | |
| 6,642,353 B1 | 11/2003 | McConnell et al. | |

(Continued)

FOREIGN PATENT DOCUMENTS

| | | |
|---|---|---|
| EP | 0245993 A2 | 11/1987 |
| EP | 0239400 B1 | 8/1994 |

(Continued)

OTHER PUBLICATIONS

Hirschhorn et al. Genetics in Medicine. 2002. 4(2): 45-61.*
Hattersley et al. The Lancet. 2005. 366: 1315-1323.*
Lucentini et al The Scientist (2004) vol. 18, p. 20.*
Todeschi-Blok et al. Opthalmology. Jan. 2007. 114:99-103.*
Cui et al (IOVS. Feb. 2010. 51: 1116-1120.*
Gagneux et al. Molecular Phylogenetics and Evolution. 2001. 18: 2-13.*
Halushka et al. Nature. Jul. 1999. 22: 239-247.*
NCBI dbSNP Database (rs4698775, ss70817155. Apr. 20, 2007. National Center for Biotechnology Information, National Library of Medicine (Bethesda, MD, USA.*
Wang et al(IOVS. Mar. 2012. 153:1322.*
Fritsche et al Nature Genetics. Available online Mar. 3, 2013. 45(4): 433 and Supplementary Material pp. 1-46.*

(Continued)

*Primary Examiner* — Carla J Myers
(74) *Attorney, Agent, or Firm* — Jones Day

(57) ABSTRACT

The invention provides methods and compositions for treating various degenerative diseases (e.g., AMD) with a factor D inhibitor (e.g., anti-factor D antibody or antigen-binding fragment thereof). Also provided are methods of selecting or identifying patients for treatment with a factor D inhibitor. Methods include the use of prognostic and/or predictive biomarkers.

7 Claims, 14 Drawing Sheets
Specification includes a Sequence Listing.

(56) References Cited

U.S. PATENT DOCUMENTS

| | | |
|---|---|---|
| 6,828,401 B2 | 12/2004 | Nho et al. |
| 6,838,554 B2 | 1/2005 | Ashkenazi et al. |
| 6,867,189 B2 | 3/2005 | Lucas et al. |
| 6,884,879 B1 | 4/2005 | Baca et al. |
| 6,956,107 B2 | 10/2005 | Fung et al. |
| 7,005,504 B2 | 2/2006 | Hsei et al. |
| 7,112,327 B2 | 9/2006 | Fung et al. |
| 7,122,636 B1 | 10/2006 | Hsei et al. |
| 7,192,589 B2 | 3/2007 | Ashkenazi et al. |
| 7,211,400 B2 | 5/2007 | Ashkenazi et al. |
| 7,282,565 B2 | 10/2007 | Goddard et al. |
| 7,351,524 B2 | 4/2008 | Hageman et al. |
| 7,419,663 B2 | 9/2008 | Ashkenazi et al. |
| 7,432,356 B2 | 10/2008 | Fung et al. |
| 7,439,331 B2 | 10/2008 | Fung et al. |
| 7,807,164 B2 | 10/2010 | Furfine et al. |
| 7,816,497 B2 | 10/2010 | Ambati |
| 7,943,135 B2 | 5/2011 | Fung et al. |
| 8,007,791 B2 | 8/2011 | Hass et al. |
| 8,007,798 B2 | 8/2011 | Ashkenazi et al. |
| 8,067,002 B2 | 11/2011 | An et al. |
| 8,124,090 B2 | 2/2012 | Fung et al. |
| 8,142,776 B2 | 3/2012 | Liu et al. |
| 8,187,604 B2 | 5/2012 | An et al. |
| 8,193,329 B2 | 6/2012 | An et al. |
| 8,236,317 B2 | 8/2012 | Fung et al. |
| 8,268,310 B2 | 9/2012 | Hass et al. |
| 8,273,352 B2 | 9/2012 | Huang et al. |
| 8,277,830 B2 | 10/2012 | de Juan, Jr. et al. |
| 8,372,403 B2 | 2/2013 | An et al. |
| 8,383,802 B2 | 2/2013 | Fung et al. |
| 8,399,006 B2 | 3/2013 | de Juan, Jr. et al. |
| 8,481,046 B2 | 7/2013 | Furfine et al. |
| 8,614,306 B2 | 12/2013 | Huang et al. |
| 8,753,826 B2 | 6/2014 | An et al. |
| 8,765,131 B2 | 7/2014 | Fung et al. |
| 8,795,712 B2 | 8/2014 | de Juan, Jr. et al. |
| 8,808,727 B2 | 8/2014 | de Juan, Jr. et al. |
| 2002/0081293 A1 | 6/2002 | Fung et al. |
| 2002/0136719 A1 | 9/2002 | Shenoy et al. |
| 2003/0021790 A1 | 1/2003 | Hsei et al. |
| 2003/0129187 A1 | 7/2003 | Fung et al. |
| 2003/0207309 A1 | 11/2003 | Hageman et al. |
| 2004/0152105 A1 | 8/2004 | Vogt et al. |
| 2004/0177387 A1 | 9/2004 | Jayakrishna |
| 2005/0036991 A1 | 2/2005 | Fodor |
| 2005/0191298 A1 | 9/2005 | Bell et al. |
| 2005/0196394 A1 | 9/2005 | Fung |
| 2005/0197285 A1 | 9/2005 | Rosen et al. |
| 2005/0222027 A1 | 10/2005 | Chiang et al. |
| 2005/0232920 A1 | 10/2005 | Fung et al. |
| 2006/0067935 A1 | 3/2006 | Ambati |
| 2006/0233803 A1 | 10/2006 | Ashkenazi et al. |
| 2006/0240020 A1 | 10/2006 | Fung et al. |
| 2006/0281120 A1 | 12/2006 | Gorin et al. |
| 2007/0020647 A1* | 1/2007 | Hageman .............. C12Q 1/6883 435/6.11 |
| 2007/0077233 A1 | 4/2007 | Giordano |
| 2007/0092940 A1 | 4/2007 | Eigenbrot et al. |
| 2007/0098692 A1 | 5/2007 | Kovesdi et al. |
| 2007/0190054 A1 | 8/2007 | Ashkenazi et al. |
| 2008/0118506 A1 | 5/2008 | An et al. |
| 2008/0146501 A1 | 6/2008 | Hageman et al. |
| 2008/0193442 A1 | 8/2008 | Fung et al. |
| 2008/0280825 A1 | 11/2008 | Hageman et al. |
| 2009/0111708 A1 | 4/2009 | Seddon et al. |
| 2009/0124542 A1 | 5/2009 | Hageman et al. |
| 2009/0181017 A1 | 7/2009 | Hass et al. |
| 2009/0214538 A1 | 8/2009 | Fung et al. |
| 2009/0233277 A1 | 9/2009 | Murakami |
| 2009/0253689 A1 | 10/2009 | Baeschlin et al. |
| 2009/0269338 A1 | 10/2009 | Huang et al. |
| 2009/0304694 A1 | 12/2009 | Oliner et al. |
| 2010/0104568 A1 | 4/2010 | Beirnaert et al. |
| 2010/0129379 A1 | 5/2010 | Carpenter et al. |
| 2010/0174272 A1 | 7/2010 | Weiner |
| 2011/0014716 A1* | 1/2011 | Swaroop .............. C12Q 1/6883 436/94 |
| 2011/0123528 A1 | 5/2011 | An et al. |
| 2011/0165622 A1 | 7/2011 | An et al. |
| 2011/0195069 A1 | 8/2011 | Fung et al. |
| 2011/0212433 A1 | 9/2011 | Barker et al. |
| 2011/0268728 A1 | 11/2011 | Borras et al. |
| 2011/0282034 A1 | 11/2011 | Hass et al. |
| 2011/0286956 A1 | 11/2011 | Zhao et al. |
| 2012/0107315 A1 | 5/2012 | Behrens et al. |
| 2012/0141480 A1 | 6/2012 | Fung et al. |
| 2012/0190578 A1 | 7/2012 | Seddon et al. |
| 2012/0230985 A1 | 9/2012 | An et al. |
| 2012/0230990 A1 | 9/2012 | Beckmann et al. |
| 2012/0322975 A1 | 12/2012 | Fung et al. |
| 2012/0328613 A1 | 12/2012 | Huang et al. |
| 2013/0171070 A1 | 7/2013 | An et al. |
| 2013/0171155 A1 | 7/2013 | Fung et al. |
| 2013/0302333 A1 | 11/2013 | Hass et al. |
| 2014/0065137 A1 | 3/2014 | Huang et al. |
| 2014/0135486 A1 | 5/2014 | Zhao et al. |
| 2015/0073155 A1 | 3/2015 | Yoshioka et al. |
| 2016/0017052 A1 | 1/2016 | Kelley et al. |

FOREIGN PATENT DOCUMENTS

| | | |
|---|---|---|
| EP | 1287364 B1 | 10/2008 |
| RU | 2232991 C1 | 7/2004 |
| WO | 1993/000109 A1 | 1/1993 |
| WO | 1993/016185 A2 | 8/1993 |
| WO | 1994/004188 A1 | 3/1994 |
| WO | 1994/012219 A2 | 6/1994 |
| WO | 1994/022466 A1 | 10/1994 |
| WO | 1995/029697 A1 | 11/1995 |
| WO | 1998/045331 A2 | 10/1998 |
| WO | 1999/001556 A2 | 1/1999 |
| WO | 1999/003887 A1 | 1/1999 |
| WO | 1999/027098 A2 | 6/1999 |
| WO | 1999/040100 A1 | 8/1999 |
| WO | 1999/042133 A1 | 8/1999 |
| WO | 1999/046281 A2 | 9/1999 |
| WO | 2000/012703 A2 | 3/2000 |
| WO | 2000/036103 A2 | 6/2000 |
| WO | 2000/037638 A2 | 6/2000 |
| WO | 2000/042072 A2 | 7/2000 |
| WO | 2000/053749 A2 | 9/2000 |
| WO | 2000/053758 A2 | 9/2000 |
| WO | 2001/004311 A1 | 1/2001 |
| WO | 2001/036432 A2 | 5/2001 |
| WO | 2001/040466 A2 | 6/2001 |
| WO | 2001/084149 A2 | 11/2001 |
| WO | 2002/000690 A2 | 1/2002 |
| WO | 2002/008284 A2 | 1/2002 |
| WO | 2002/030985 A2 | 4/2002 |
| WO | 2002/030986 A2 | 4/2002 |
| WO | 2003/029420 A2 | 4/2003 |
| WO | 2004/001009 A2 | 12/2003 |
| WO | 2004/014953 A2 | 2/2004 |
| WO | 2004/022594 A2 | 3/2004 |
| WO | 2004/032828 A2 | 4/2004 |
| WO | 2004/075837 A2 | 9/2004 |
| WO | 2005/012359 A2 | 2/2005 |
| WO | 2005/025509 A2 | 3/2005 |
| WO | 2005/044853 A2 | 5/2005 |
| WO | 2005/086770 A2 | 9/2005 |
| WO | 2005/102387 A2 | 11/2005 |
| WO | 2006/042329 A2 | 4/2006 |
| WO | 2006/062716 A2 | 6/2006 |
| WO | 2006/071856 A2 | 7/2006 |
| WO | 2006/088950 A2 | 8/2006 |
| WO | 2006/133295 A2 | 12/2006 |
| WO | 2007/044668 A2 | 4/2007 |
| WO | 2007/053447 A2 | 5/2007 |
| WO | 2007/056227 A2 | 5/2007 |
| WO | 2007/087384 A2 | 8/2007 |
| WO | 2008/055206 A2 | 5/2008 |
| WO | 2008/147883 A1 | 12/2008 |
| WO | 2009/029587 A2 | 3/2009 |

(56) References Cited

FOREIGN PATENT DOCUMENTS

| WO | 2009/042686 A1 | 4/2009 |
|---|---|---|
| WO | 2009/134709 A2 | 11/2009 |
| WO | 2009/134711 A1 | 11/2009 |
| WO | 2009/146204 A1 | 12/2009 |
| WO | 2010/054110 A2 | 5/2010 |
| WO | 2010/075519 A2 | 7/2010 |
| WO | 2010/085542 A2 | 7/2010 |
| WO | 2010/132459 A2 | 11/2010 |
| WO | 2267028 A2 | 12/2010 |
| WO | WO 2011006161 A2 | 1/2011 |
| WO | 2011/017229 A2 | 2/2011 |
| WO | 2011/057014 A1 | 5/2011 |
| WO | 2011/069104 A2 | 6/2011 |
| WO | 2012/061421 A1 | 5/2012 |
| WO | 2013/055998 A1 | 4/2013 |
| WO | 2015/023596 A1 | 2/2015 |
| WO | 2015/032776 A1 | 3/2015 |
| WO | 2015/168468 A1 | 11/2015 |

OTHER PUBLICATIONS

Baird et al (Clinical and Experimental Ophthalmology. Published online Sep. 30, 2013. 42: 53-64 (Year: 2013).*
1000 Genomes Project Consortium, "A Map of Human Genome Variation from Population-Scale Sequencing" Nature 467(7319):1061-1073 (Oct. 28, 2010).
Accession NM_001928, 'Homo sapiens Complement Factor D (Adipsin) (CFD), mRNA'.
Aderem et al., "Mechanisms of Phagocytosis in Macrophages" Annu Rev. Immunol. 17:593-623 (1999).
Age-Related Eye Disease Study (AREDS) Research Group, "Potential Public Health Impact of Age-Related Eye Disease Study Results" Arch. Ophthalmol. 121:1621-24 (2003).
Ahamed et al., "Phase Behavior of an Intact Monoclonal Antibody" Biophysical Journal 93:610-619 (Jul. 2007).
Altshuler et al., "Genetic Mapping in Human Disease" Science 322:881-888 (Nov. 7, 2008).
Ambati et al., "An Animal Model of Age-Related Macular Degeneration in Senescent Ccl-2- or Ccr-2-Deficient Mice" Nature Medicine 9(11):1390-1397 (Nov. 2003).
Amin et al., "Genetic Scoring Analysis: A Way Forward in Genome Wide Association Studies?" Eur. J. Epidemiol. 24:585-587 (2009).
Amit et al., "Three-Dimensional Structure of an Antigen-Antibody Complex at 2.8 A Resolution" Science 233:747-753 (Aug. 15, 1986).
Amsterdam et al., "Limitation of Reperfusion Injury by a Monoclonal Antibody to C5a During Myocardial Infarction in Pigs" Am. J. Physiol. 268(1):H448-H457 (Jan. 1995).
Anderson et al., "A Role for Local Inflammation in the Formation of Drusen in the Aging Eye" American Journal of Ophthalmology 134(3):411-431 (Sep. 2002).
Arrate et al., "Cloning of Human Junctional Adhesion Molecule 3 (JAM3) and Its Identification as the JAM2 Counter-Receptor" Journal of Biological Chemistry 276(49):45826-45832 (Dec. 7, 2001).
Attwood, Teresa K., "The Babel of Bioinformatics" Science 290(5491):471-473 (Oct. 2000).
Barnum et al., "Quantitation of Complement Factor D in Human Serum by a Solid-Phase Radioimmunoassay" Journal of Immunological Methods 67(2):303-309 (Mar. 16, 1984).
Benvenuti et al., "Crystallization of Soluble Proteins in Vapor Diffusion for X-Ray Crystallography" Nature Protocols 2(7):1633-1651 (2007).
Bertozzi et al., "An ELISA for Selectins Based on Binding to a Physiological Ligand" Journal of Immunological Methods 203(2):157-165 (Apr. 25, 1997).
Biomarkers Definitions Working Group, "Biomarkers and Surrogate Endpoints: Preferred Definitions and Conceptual Framework" Clinical Pharmacology & Therapeutics 69(3):89-95 (Mar. 2001).

Bok, "Evidence for an Inflammatory Process in Age-Related Macular Degeneration Gains New Support" PNAS 102(20):7053-7054 (May 17, 2005).
Bora et al., "Complement Activation Via Alternative Pathway is Critical in the Development of Laser-Induced Choroidal Neovascularization: Role of Factor B and Factor H" Journal of Immunology 177(3):1872-1878 (2006).
Bora et al., "Role of Complement and Complement Membrane Attack Complex in Laser-Induced Choroidal Neovascularization" Journal of Immunology 174(1):491-497 (2005).
Bora et al., "The Role of Complement in Ocular Pathology" Semin. Immunopathol. 30(2):85-95 (2008).
Brown et al., "Mechanisms of Disease: The Complement System in Renal Injury—New Ways of Looking at an Old Foe" Nature Clinical Practice Nephrology 3(5):277-286 (May 2007).
Brown, "Complement Receptors, Adhesion, and Phagocytosis" Infectious Agents and Disease 1(2):63-70 (1992).
Cancer Genome Atlas Research Network, "Comprehensive Genomic Characterization Defines Human Glioblastoma Genes and Core Pathways" Nature 455(7216):1061-1068 (Oct. 23, 2008).
Carroll, "The Complement System in Regulation of Adaptive Immunity" Nature Immunology 5(10):981-986 (Oct. 2004).
Carter et al., "Humanization of an Anti-P185HER2 Antibody for Human Cancer Therapy" PNAS 89(10):4285-4289 (May 1992).
Casset et al., "A Peptide Mimetic of an Anti-CD4 Monoclonal Antibody by Rational Design" Biochemical and Biophysical Research Communications 307(1):198-205 (Jul. 18, 2003).
Champe et al., "Monoclonal Antibodies that Block the Activity of Leukocyte Function-Associated Antigen 1 Recognize Three Discrete Epitopes in the Inserted Domain of CD11a" Journal of Biological Chemistry 270(3):1388-1394 (Jan. 20, 1995).
Chen et al., "Association between Variant Y402H in Age-Related Macular Degeneration (AMD) Susceptibility Gene CFH and Treatment Response of AMD: A Meta-Analysis" PLoS One 7(8):1-7 (Aug. 2012).
Chen et al., "Enhancement and Destruction of Antibody Function by Somatic Mutation: Unequal Occurrence is Controlled by V Gene Combinatorial Associations" EMBO Journal 14(12):2784-2794 (Jun. 1995).
Chen et al., "Genetic Variants Near TIMP3 and High-Density Lipoprotein-Associated Loci Influence Susceptibility to Age-Related Macular Degeneration" PNAS 107(16):7401-7406 (Apr. 20, 2010).
Chen et al., "Selectin and Analysis of an Optimized Anti-VEGF Antibody: Crystal Structure of an Affinity-Matured Fab in Complex with Antigen" Journal of Molecular Biology 293:865-881 (1999).
Chothia et al., "Canonical Structures for the Hypervariable Regions of Immunoglobulins" Journal of Molecular Biology 196:901-917 (1987).
Collins et al., "Mapping the Cancer Genome: Pinpointing the Genes Involved in Cancer Will Help Chart a New Course Across the Complex Landscape of Human Malignancies" Scientific American 296(3):50-57 (Mar. 2007).
Colman, "Effects of Amino Acid Sequence Changes on Antibody-Antigen Interactions" Res. Immunol. 145:33-36 (1994).
Cudney, "Protein Crystallization and Dumb Luck" The Rigaku Journal 16(1):1-7 (1999).
Database Accession No. NLM20510150, 'Genetic Factors Associated with Age-Related Macular Degeneration', Abstract, May 2010.
de Jong, "Age-Related Macular Degeneration" New England Journal of Medicine 355(14):1474-1485 (Oct. 5, 2006).
Demirkan et al., "Genetic Risk Profiles for Depression and Anxiety in Adult and Elderly Cohorts" Molecular Physhiatry 16:773-783 (2011).
Diamond et al., "Somatic Mutation of the T15 Heavy Chain Gives Rise to an Antibody with Autoantibody Specificity" PNAS 81(18):5841-5844 (Sep. 1984).
Do et al., "A Phase IA Dose-Escalation Study of the Anti-Factor D Monoclonal Antibody Fragment FCFD4514S in Patients with Geographic Atrophy" Retina 34(2):313-320 (2014).
Drenth. Principles of Protein X-Ray Crystallography; "Chapter 1: Crystallizing a Protein" 2nd edition, New York: Springer:1-20.

(56) References Cited

OTHER PUBLICATIONS

EBI. Accession No. UNIPORT: P00746 'Complement Factor D' (Jul. 21, 1986).
Edwards et al., "Complement Factor H Polymorphism and Age-Related Macular Degeneration" Science 308(5720):421-424 (Apr. 15, 2005).
Esparza-Gordillo et al., "Genetic and Environmental Factors Influencing the Human Factor H Plasma Levels" Immunogenetics 56(2):77-82 (2004).
Evans et al., "Rapid Expression of an Anti-Human C5 Chimeric Fab Utilizing a Vector that Replicates in COS and 293 Cells" Journal of Immunological Methods 184(1):123-138 (1995).
Extended European Search Report of European Application No. 06836941.2, dated Mar. 2, 2011.
Extended European Search Report of European Application No. 12172001.5, dated Oct. 24, 2012.
Eye Disease Prevalence Research Group, "Prevalence of Age-Related Macular Degeneration in the United States" Arch. Ophthalmol. 122(4):564-572 (Apr. 2004).
Faelber et al., "The 1.85 A Resolution Crystal Structures of Tissue Factor in Complex with Humanized Fab D3h44 and of Free Humanized Fab D3h44: Revisting the Solvation of Antigen Combining Sites" Journal of Molecular Biology 313:83-97 (2001).
Fagerness et al., "Variation Near Complement Factor I is Associated with Risk of Advanced AMD" European Journal of Human Genetics 17(1):100-104 (2009).
Farries et al., "The Mechanism of Activation of the Alternative Pathway of Complement by Cell-Bound C4b" Molecular Immunology 27(11):1155-1161 (1990).
Ferris et al., "A Simplified Severity Scale for Age-Related Macular Degeneration" Arch. Ophthalmol. 123:1570-1574 (Nov. 2005).
Foote et al., "Antibody Framework Residues Affecting the Conformation of the Hypervariable Loops" Journal of Molecular Biology 224:487-499 (1992).
Francis et al., "Polymorphisms in C2, CFB and C3 are Associated with Progression to Advanced Age Related Macular Degeneration Associated with Visual Loss" J. Med. Genet. 46(5):300-307 (2008).
Fritsche et al., "Seven New Loci Associated with Age-Related Macular Degeneration" Nature Genetics 45(4):435-441 (Apr. 2013).
Fung et al., "Inhibition of Complement Neutrophil and Platelet Activation by an Anti-Factor D Antibody During Extracorporeal Circulation" (Abstract) Presented at the 18th Annual Houston Conference on Biomedical Engineering Research, Houston, Texas, (Feb. 10-11, 2000).
Fung et al., "Inhibition of Complement, Neutrophil, and Platelet Activation by an Anti-Factor D Monoclonal Antibody in Simulated Cardiopulmonary Bypass Circuits" Journal of Thoracic and Cardiovascular Surgery 122(1):113-122 (Jul. 2001).
Gao et al., "An Enzyme-Linked Immunosorbent Assay to Identify Inhibitors of Activation of Platelet Integrin Alpha IIb Beta 3" Journal of Immunological Methods 181(1):55-64 (Apr. 12, 1995).
Gold et al., "Variation in Factor B (BF) and Complement Component 2 (C2) Genes is Associated with Age-Related Macular Degeneration" Nature Genetics 38(4):458-462 (Apr. 2006).
Gorin, "Genetic Insights into Age-Related Macular Degeneration: Controversies Addressing Risk, Causality, and Therapeutics" Mol. Aspects Med. 33(4):467-486 (Aug. 2012).
Hageman et al., "A Common Haplotype in the Complement Regulatory Gene Factor H (HF1/CFH) Predisposes Individuals to Age-Related Macular Degeneration" PNAS 102(20):7227-7232 (May 17, 2005).
Hageman et al., "An Integrated Hypothesis that Considers Drusen as Biomarkers of Immune-Mediated Processes at the RPE-Bruch's Membrane Interface in Aging and Age-Related Macular Degeneration" Progress in Retinal and Eye Research 20(6):705-732 (2001).
Haines et al., "Complement Factor H Variant Increases the Risk of Age-Related Macular Degeneration" Science 308:419-421 (Apr. 15, 2005).
Hakimi et al., "Reduced Immunogenicity and Improved Pharmacokinetics of Humanized Anti-Tac in Cynomolgus Monkeys" Journal of Immunology 147(4):1352-1359 (Aug. 15, 1991).
Harboe et al., "The Quantitative Role of Alternative Pathway Amplification in Classical Pathway Induced Terminal Complement Activation" Clin. Exp. Immunol. 138(3):439-446 (2004).
Harlow et al., Antibodies, A Laboratory Manual "Chapter 14: Immunoassays" Cold Spring Harbor Laboratory:553-612 (1988).
Haubenwallner et al., "A Novel Missense Mutation in the Gene for Lipoprotein Lipase Resulting in a Highly Conservative Amino Acid Substitution (Asp180→Glu) Causes Familial Chylomicronemia (Type I Hyperlipoproteinemia)" Genomics 18(2):392-396 (1993).
Heurich et al., "Common Polymorphisms in C3, Factor B, and Factor H Collaborate to Determine Systemic Complement Activity and Disease Risk" PNAS 108(21):8761-8766 (May 24, 2011).
Hirschhorn et al., "A Comprehensive Review of Genetic Association Studies" Genetics in Medicine 4(2):45-61 (Mar./Apr. 2002).
Hoffman et al., "Rare Complement Factor H Variant Associated with Age-Related Macular Degeneration in the Amish" Investigative Ophthalmology & Visual Science 55(7):4455-4460 (Jul. 2014).
Holers Clinical Immunology: Principles and Practice "Chapter 24: Complement" ed. R.R. Rich, Mosby Press:363-391 (1996).
Holers et al., "The Evolution of Mouse and Human Complement C3-Binding Proteins: Divergence of Form but Conservation of Function" Immunology Today 13(6):231-236 (1992).
Holers, "The Spectrum of Complement Alternative Pathway-Mediated Diseases" Immunological Reviews 223:300-316 (2008).
Holland et al., "Detection of Specific Polymerase Chain Reaction Product by Utilizing the 5'→3' Exonuclease Activity of Thermus Aquaticus DNA Polymerase" PNAS 88(16): 7276-7280 (Aug. 15, 1991).
Holm et al., "Functional Mapping and Single Chain Construction of the Anti-Cytokeratin 8 Monoclonal Antibody TS1" Molecular Immunology 44:1075-1084 (2007).
Holz et al., "Geographic Atrophy: Clinical Features and Potential Therapeutic Approaches" Ophthalmology 121(5):1079-1091 (May 2014).
Holz et al., "Recent Developments in the Treatment of Age-Related Macular Degeneration" Journal of Clinical Investigation 124(4):1430-1438 (Apr. 2014).
Homeister et al., "Soluble Complement Receptor Type 1 Prevents Human Complement-Mediated Damage of the Rabbit Isolated Heart" Journal of Immunology 150(3):1055-1064 (Feb. 1, 1993).
Houghten et al., "The Use of Synthetic Peptide Combinatorial Libraries for the Identification of Bioactive Peptides" BioTechniques 13(3):412-21 (Sep. 1992).
Howie et al., "A Flexible and Accurate Genotype Imputation Method for the Next Generation of Genome-Wide Association Studies" PLoS Genetics 5(6):1-15 (Jun. 2009).
Huber-Lang et al., "Role of C5a in Multiorgan Failure During Sepsis" Journal of Immunology 166(2):1193-1199 (2001).
Inagi et al., "Decreased Activity of Complement-Mediated Immune Complex Clearance in Hemodialysis Patients" Clinical Immunology and Immunopathology 68(3):333-339 (Sep. 1993).
International Preliminary Report on Patentability for PCT/US2006/043103, dated May 6, 2008.
International Preliminary Report on Patentability for PCT/US2007/083172, dated Nov. 2, 2006.
International Preliminary Report on Patentability for PCT/US2008/064526, dated Nov. 24, 2009.
International Preliminary Report on Patentability for PCT/US2011/058829, dated May 7, 2013.
International Preliminary Report on Patentability for PCT/US2009/041785, dated Nov. 2, 2010.
International Search Report for PCT/US1999/003566, dated Jun. 2, 1999.
International Search Report for PCT/US2006/043103, dated Aug. 10, 2007.
International Search Report for PCT/US2007/083172, dated Jun. 26, 2008.
International Search Report for PCT/US2008/064526, dated Aug. 14, 2008.

(56) References Cited

OTHER PUBLICATIONS

International Search Report for PCT/US2009/041785, dated Sep. 15, 2009.
International Search Report for PCT/US2011/058829, dated Jan. 4, 2012.
International Search Report for PCT/US2014/050579, dated Nov. 28, 2014.
International SNP Working Group, "A Map of Human Genome Sequence Variation Containing 1.42 Million Single Nucleotide Polymorphisms" Nature 409:928-933 (Feb. 15, 2001).
Ioannidis et al., "Replication Validity of Genetic Association Studies" Nature Genetics 29(3):306-309 (Nov. 2001).
Jaffers et al., "Monoclonal Antibody Therapy: Anti-Idiotypic and Non-Anti-Idiotypic Antibodies to OKT3 Arising Despite Intense Immunosuppression" Transplantation 41(5):572-578 (May 1986).
Jager et al., "Age-Related Macular Degeneration" New England Journal of Medicine 359(16):1735-1736 (Oct. 16, 2008).
Janeway et al., Immunobiology: The Immune System in Health and Disease "13:5-13:7" 3rd edition, London, England :Current Biology Limited (1997).
Janssen et al., "Structural Insights into the Central Complement Component C3" Molecular Immunology 44:3-10 (2007).
Jing et al., "Structural Basis of Profactor D Activation: from a Highly Flexible Zymogen to a Novel Self-Inhibited Serine Protease, Complement Factor D" EMBO Journal 18(4):804-814 (1999).
Jing et al., "Structures of Native and Complexed Complement Factor D: Implications of the Atypical His57 Conformation and Self-Inhibitory Loop in the Regulation of Specific Serine Protease Activity" Journal of Molecular Biology 282:1061-1081 (1998).
Johnson et al., "Complement Activation and Inflammatory Processes in Drusen Formation and Age Related Macular Degeneration" Exp. Eye Res. 73(6):887-896 (2001).
Jones et al., "Replacing the Complementarity-Determining Regions in a Human Antibody with those from a Mouse" Nature 321:522-525 (May 29, 1986).
Junghans et al., "Anti-Tac-H, a Humanized Antibody to the Interleukin 2 Receptor with New Features for Immunotherapy in Malignant and Immune Disorders" Cancer Research 50(5):1495-1502 (Mar. 1, 1990).
Kathiresan et al., "Polymorphisms Associated with Cholesterol and Risk of Cardiovascular Events" (Abstract), Journal of Vascular Surgery:1372 (Jun. 2008).
Katschke et al., "A Novel Inhibitor of the Alternative Pathway of Complement Reverses Inflammation and Bone Destruction in Experimental Arthritis" Journal of Experimental Medicine 204(6):1319-1325 (Jun. 11, 2007).
Katschke et al., "Inhibiting Alternative Pathway Complement Activation by Targeting the Factor D Exosite" Journal of Biological Chemistry 287(16):12886-12892 (Apr. 13, 2012).
Khazaeli et al., "Phase I Trial of Multiple Large Doses of Murine Monoclonal Antibody C017-1A. II. Pharmacokinetics and Immune Response" Journal of the National Cancer Institute 80(12):937-942 (Aug. 17, 1988).
Kim et al., "Characterization of Monoclonal Antibody Specific to the Z39Ig Protein, a Member of Immunoglobulin Superfamily" Immunology Letters 99(2):153-161 (2005).
Kim et al., "Crystal Structure of a Complement Factor D Mutant Expressing Enhanced Catalytic Activity" Journal of Biological Chemistry 270(41):24399-24405 (Oct. 13, 1995).
Klein et al., "Complement Factor H Polymorphism in Age-Related Macular Degeneration" Science 308(5720):385-389 (Apr. 15, 2005).
Kloeckener-Gruissem et al., "Genetic Association with Response to Intravitreal Ranibizumab in Patients with Neovascular AMD" Investigative Ophthalmology & Visual Science 52(7):4694-4702 (Jun. 2011).
Klohs et al., "Inhibitors of Tyrosine Kinase" Current Opinion in Oncology 9(6):562-568 (Nov. 1997).
Kostavasili et al., "Mechanism of Complement Inactivation by Glycoprotein C of Herpes Simplex Virus" Journal of Immunology 158(4):1763-1771 (Feb. 15, 1997).

Kozlov et al., "Isotyping of Human C4 Complement Using Difference in the Functional Activity of Isotypes C4A and C4B" Russian Journal of Bioorganic Chemistry 26(7):482-489 (2000).
Kroshus et al., "Complement Inhibition with an Anti-C5 Monoclonal Antibody Prevents Acute Cardiac Tissue Injury in an Ex Vivo Model of Pig-to-Human Xenotransplantation" Transplantation 60(11):1194-1202 (Dec. 15, 1995).
Krzystolik et al., "Prevention of Experimental Choroidal Neovascularization with Intravitreal Anti-Vascular Endothelial Growth Factor Antibody Fragment" Arch. Ophthalmol. 120(3):338-46 (Mar. 2002).
Kumagai et al., "Generation of Novel Functional Antibody Molecules by in Vitro Selection System" Tanpakushitsu Kakusan Koso (Protein Nucleic Acid and Enzyme Review) (Japanese with English translation of Abstract), 43(2):159-67 (1998).
Kundrot, "Which Strategy for a Protein Crystallization Project?" Cellular and Molecular Life Sciences 61:525-536 (2004).
Kussie et al., "A Single Engineered Amino Acid Substitution Changes Antibody Fine Specificity" Journal of Immunology 152(1):146-152 (Jan. 1994).
Lam et al., "Application of Combinatorial Library Methods in Cancer Research and Drug Discovery" Anti-Cancer Drug Design 12(3):145-167 (Apr. 1997).
Langnaese et al., "Cloning of Z39Ig, a Novel Gene with Immunoglobulin-Like Domains Located on Human Chromosome X1" Biochimica et Biophysica Acta 1492:522-525 (2000).
Lee et al., "Z39Ig is Expressed on Macrophages and May Mediate Inflammatory Reactions in Arthritis and Atherosclerosis" Journal of Leukocyte Biology 80(4):922-928 (Oct. 2006).
Lesavre et al., "Mechanism of Action of Factor D of the Alternative Complement Pathway" Journal of Experimental Medicine 148(6):1498-1509 (Dec. 1978).
Lettre et al., "Autoimmune Diseases: Insights from Genome-Wide Association Studies" Human Molecular Genetics 17(2):R116-R121 (2008).
Lim et al., "Age-Related Macular Degeneration" Lancet 379(9827):1728-1738 (May 5, 2012).
Loubser et al., "Inhibition of Complement, Neutrophil and Platelet Activation by an Anti-Factor D Antibody During Extracorporeal Circulation", Presented at the Annual Meeting of American Society of Anesthesiologists, San Francisco, California, Oct. 14-18, 2000 (Abstract A-657).
Loyet et al., "Activation of the Alternative Complement Pathways in Vitreous is Controlled by Genetics in Age-Related Macular Degeneration" Investigative Ophthalmology & Visual Science 53(10):6628-6637 (Sep. 2012).
Loyet et al., "Anti-Factor D Fab Specifically Inhibits the Alternative Complement Pathway: In Vitro Characterization and In Vivo Effects Following Administration to Cynomolgus Monkeys" (Abstract) Investigative Ophthalmology & Visual Science 51(13) (Apr. 2010).
MacCallum et al., "Antibody-Antigen Interactions: Contact Analysis and Binding Site Topography" Journal of Molecular Biology 262(5):732-745 (Oct. 11, 1996).
Makrides, "Therapeutic Inhibition of the Complement System" Pharmacological Reviews 50(1):59-87 (1998).
Matson et al., "Evolving Concepts of Therapy for Sepsis and Septic Shock and the Use of Hyperpermeable Membranes" Current Opinion in Critical Care 6:431-436 (2000).
McPherson, "Current Approaches to Macromolecular Crystallization" Eur. J. Biochem. 189:1-23 (1990).
Meredith et al., Intraocular Drug Delivery, ed. G. J. Jaffe, Taylor & Francis:86-95, 111-128, 193-225, 249-263 (2006).
Miller et al., "Monoclonal Antibody Therapeutic Trials in Seven Patients with T-Cell Lymphoma" Blood 62(5):988-995 (Nov. 1983).
Mohlke et al., "Metabolic and Cardiovascular Traits: An Abundance of Recently Identified Common Genetic Variants" Human Molecular Genetics 17(2):R102-R108 (2008).
Moon et al., "A Synergistic Approach to Protein Crystallization: Combination of a Fixed-Arm Carrier with Surface Entropy Reduction" Protein Science 19:901-913 (2010).
Morgan, "Clinical Complementology: Recent Progress and Future Trends" European Journal of Clinical Investigation 24:219-228 (1994).

(56) References Cited

OTHER PUBLICATIONS

Mulligan et al., "Protective Effects of Soluble CR1 in Complement- and Neutrophil-Mediated Tissue Injury" Journal of Immunology 148(5):1479-1485 (Mar. 1, 1992).
Mullins et al., "Drusen Associated with Aging and Age-Related Macular Degeneration Contain Proteins Common to Extracellular Deposits Associated with Atherosclerosis, Elastosis, Amyloidosis, and Dense Deposit Disease" FASEB Journal 14(7):835-846 (May 2000).
Narayana et al., "Structure of Human Factor D: A Complement System Protein at 2.0 A Resolution" Journal of Molecular Biology 235(2):695-708 (1994).
Neale et al., "Genome-Wide Association Study of Advanced Age-Related Macular Degeneration Identifies a Role of the Hepatic Lipase Gene (LIPC)" PNAS 107(16):7395-7400 (Apr 20, 2010).
New American Webster Handy College Dictionary, 4th Edition, pp. 556-567 and 694, 2006.
Niemann et al., "The Use of Monoclonal Antibodies as Probes of the Three-Dimensional Structure of Human Complement Factor D" Journal of Immunology 132(2):809-815 (Feb. 1984).
Ohno et al., "Antigen Binding Specificities of Antibodies are Primarily Determined by Seven Residues of $V_H$" PNAS 82(9):2945-2949 (May 1985).
Oliphant et al., "BeadArray™ Technology: Enabling an Accurate, Cost-Effective Approach to High-Throughput Genotyping" BioTechniques 32 (Suppl S56-S61):56-61 (Jun. 2002).
Omer et al., "CA1A2X-Competitive Inhibitors of Farnesyltransferase as Anti-Cancer Agents" TiPS 18(11):437-444 (Nov. 1997).
Padlan et al., "Structure of an Antibody-Antigen Complex: Crystal Structure of the HyHEL-10 Fab-Lysozyme Complex" PNAS 86:5938-5942 (Aug. 1989).
Pascual et al., "A Monoclonal Antibody which Blocks the Function of Factor D of Human Complement" Journal of Immunological Methods 127(2):263-269 (Mar. 9, 1990).
Pascual et al., "Inhibition of Complement Alternative Pathway in Mice, with Fab Antibody to Recombinant Adipsin/Factor D" Eur. J. Immunol. 23(6):1389-1392 (Jun. 1993).
Pascual et al., "Metabolism of Complement Factor D in Renal Failure" Kidney International 34(4):529-536 (Oct. 1988).
Paul et al., Fundamental Immunology, 3rd edition, Raven Press: 292-295 (1993).
PCT Written Opinion of the International Searching Authority for PCT/US2006/043103.
PCT Written Opinion of the International Searching Authority for PCT/US2009/041785.
PCT Written Opinion of the International Searching Authority for PCT/US2014/050579.
PCT Written Opinion of the International Searching Authority for PCT/US2007/083172.
PCT Written Opinion of the International Searching Authority for PCT/US2011/058829.
PCT Written Opinion of the International Searching Authority for PCT/US2008/064526.
Petrukhin, "New Therapeutic Targets in Atrophic Age-Related Macular Degeneration" Expert Opin. Ther. Targets 11(5):625-639 (2007).
Plackett, "Studies in the History of Probability and Statistics. XXIX: The Discovery of the Method of Least Squares" Biometricka 59(2):239-251 (1972).
Powell et al., "A Compendium and Hydropathy/Flexibility Analysis of Common Reactive Sites in Proteins: Reactivity at Asn, Asp, Gln, and Met Motifs in Neutral pH Solution" Pharm. Biotechnol. 9:1-140 (1996).
Prosser et al., "Structural Basis for Complement Factor H-Linked Age-Related Macular Degeneration" Journal of Experimental Medicine 204(10):2277-2283 (Oct. 1, 2007).
Purcell et al., "Common Polygenic Variation Contributes to Risk of Schizophrenia and Bipolar Disorder" Nature 460:748-752 (Aug. 6, 2009).
Pyz et al., "C-Type Lectin-Like Receptors on Myeloid Cells" Annals of Medicine 38(4):242-251 (2006).
Rabinovici et al., "Role of Complement in Endotoxin/Platelet-Activating Factor-Induced Lung Injury" Journal of Immunology 149(5):1744-1750 (Sep. 1, 1992).
Ray et al., "Thrombin Receptor: A Novel Target for Antiplatelet Drug Development" Thrombosis Research 87(1):37-50 (1997).
Reynolds et al., "Plasma Complement Components and Activation Fragments: Associations with Age-Related Macular Degeneration Genotypes and Phenotypes" Invest Ophthalmol. Vis Sci. 50(12):5818-5827 (Dec. 2009).
Ricklin et al., "Complement: A Key System for Immune Surveillance and Homeostasis" Nat. Immunol. 11(9):785-797 (Sep. 2010).
Ricklin et al., "Complement-Targeted Therapeutics" Nature Biotechnology 25(11):1265-1275 (Nov. 2007).
Riechmann et al., "Reshaping Human Antibodies for Therapy" Nature 332:323-327 (Mar. 24, 1988).
Rinder et al., "Blockade of C5a and C5b-9 Generation Inhibits Leukocyte and Platelet Activation during Extracorporeal Circulation" J. Clin. Invest. 96(3):1564-1572 (Sep. 1995).
Rodriguez de Cordoba et al., "The Human Complement Factor H: Functional Roles, Genetic Variations and Disease Associations" Molecular Immunology 41:355-367 (2004).
Rohrer et al., "A Targeted Inhibitor of the Alternative Complement Pathway Reduces Angiogenesis in a Mouse Model of Age-Related Macular Degeneration" Investigative Ophthalmology & Visual Science 50(7):3056-64 2009.
Rohrer et al., "Eliminating Complement Factor D Reduces Photoreceptor Susceptibility to Light-Induced Damage" Investigative Ophthalmology & Visual Science 48(11):5282-5289 (Nov. 2007).
Roitt et al., Immunology (Translated from Russian by the McElroy Translation Company), 5th edition, London: Mosby:110-113 (1998).
Ross et al., "Membrane Complement Receptors Specific for Bound Fragments of C3" Advances in Immunology 37:217-267 (1985).
Roversi et al., "Structural Basis for Complement Factor I Control and Its Disease-Associated Sequence Polymorphisms" PNAS 108(31):12839-12844 (Aug. 2, 2011).
Rudikoff et al., "Single Amino Acid Substitution Altering Antigen-Binding Specificity" PNAS 79:1979-1983 (Mar. 1982).
Sahu et al., "Identification of Multiple Sites of Interaction Between Heparin and the Complement System" Molecular Immunology 30(7):679-684 (May 1993).
Sallo et al., "The International Classification System and the Progression of Age-Related Macular Degeneration" Current Eye Research 34(3):238-240 (Mar. 2009).
Sambrook et al., Molecular Cloning "Chapter 5" Cold Spring Harbor Laboratory Press, 3rd edition (2001).
Sambrook et al., Molecular Cloning "Chapter 9" Cold Spring Harbor Laboratory Press, 3rd edition (2001).
Sato et al., "A New Method for Studying the Binding of Human IgE to CD23 and the Inhibition of This Binding" Journal of Immunological Methods 209(1):59-66 (Nov. 10, 1997).
Scheffe, The Analysis of Variance "1.2, Mathematical Models" New York: John Wiley & Sons:4-7 (1999).
Schifferli et al., Complements Facts Book "Factor D" Morley, vol. 17:69-72 (2000).
Scholl et al., "Systemic Complement Activation in Age-Related Macular Degeneration" PLoS One 3(7):1-7 (Jul. 2008).
Schweitzer et al., "Combining Nucleic Acid Amplification and Detection" Current Opinion in Biotechnology 12(1):21-27 (2001).
Sears et al., "Effects of Monoclonal Antibody Immunotherapy on Patients with Gastrointestinal Adenocarcinoma" Journal of Biological Response Modifiers 3(2):138-150 (1984).
Seddon et al., "Association of CFH Y402H and LOC387715 A698 with Progression of Age-Related Macular Degeneration" JAMA 297(16): 1793-1800, 2585 (Apr. 25, 2007).
Seddon et al., "Prediction Model for Prevalence and Incidence of Advanced Age-Related Macular Degeneration Based on Genetic, Demographic, and Environmental Variables" Investigative Ophthalmology & Visual Science 50(5):2044-2053 (May 2009).
Seddon et al., "Rare Variants in CFI, C3 and C9 are Associated with High Risk of Advanced Age-Related Macular Degeneration" Nature Genetics 45(11):1366-1370 (Nov. 2013).

(56) References Cited

OTHER PUBLICATIONS

Seddon et al., "Risk Models for Progression to Advanced Age-Related Macular Degeneration Using Demographic, Environmental, Genetic, and Ocular Factors" Ophthalmology 118(11):2203-2211 (Nov. 2011).
Shawler et al., "Human Immune Response to Multiple Injections of Murine Monoclonal IgG[1]" Journal of Immunology 135(2):1530-1535 (Aug. 1985).
Sim et al., "Serine Proteases of the Complement System" Biochemical Society Transactions 28(5):545-550 (2000).
Sims et al., "A Humanized CD18 Antibody Can Block Function Without Cell Destruction" Journal of Immunology 151(4):2296-2308 (Aug. 15, 1993).
Skolnick et al., "From Genes to Protein Structure and Function: Novel Applications of Computational Approaches in the Genomic Era" TibTech 18:34-39 (Jan. 2000).
Stadel et al., "Orphan G Protein-Coupled Receptors: A Neglected Opportunity for Pioneer Drug Discovery" TiPS 18(11):430-437 (Nov. 1997).
Stanton et al., "Complement Factor D in Age-Related Macular Degeneration" Investigative Ophthalmology & Visual Science 52(12):8828-8834 (Nov. 2011).
Strausberg et al., "Generation and Initial Analysis of More than 15,000 Full-Length Human and Mouse cDNA Sequences" PNAS 99(26):16899-16903 (Dec. 24, 2002).
Strawn et al., "Flk-1 as a Target for Tumor Growth Inhibition" Cancer Research 56(15):3540-3545 (Aug. 1, 1996).
Streiner Encyclopedia of Research Design "Last Observation Carried Forward" Salkind, Thousand Oaks:Sage Publications, Inc., vol. 2:687-689 (2010).
Stuart et al., "Phagocytosis: Elegant Complexity" Immunity 22(5):539-550 (2005).
Sunness et al., "Designing Clinical Trials for Age-Related Geographic Atrophy of the Macula" Retina 27(2):204-210 (2007).
Sunness et al., "Visual Function Abnormalities and Prognosis in Eyes with Age-Related Geographic Atrophy of the Macula and Good Visual Acuity" Ophthalmology 104(10):1677-1691 (Oct. 1997).
Tamura et al., "Structural Correlates of an Anticarcinoma Antibody: Identification of Specificity-Determining Residues (SDRs) and Development of a Minimally Immunogenic Antibody Variant by Retention of SDRs Only" Journal of Immunology 164:1432-1441 (2000).
Tanhehco et al., "The Anti-Factor D Antibody, MAb 166-32, Inhibits the Alternative Pathway of the Human Complement System" Transplantation Proceedings 31(5):2168-2171 (Aug. 1999).
Taylor et al., "Macrophage Receptors and Immune Recognition" Annu. Rev. Immunol. 23:901-944 (2005).
Taylor et al., "Pattern Recognition Receptors and Differentiation Antigens Define Murine Myeloid Cell Heterogeneity Ex Vivo" Eur. J. Immunol. 33(8):2090-2097 (2003).
Thurman et al., "The Central Role of the Alternative Complement Pathways in Human Disease" Journal of Immunology 176(3):1305-10 (2006).
Tsuchihashi et al., "Complement Factor H and High-Temperature Requirement A-1 Genotypes and Treatment Response of Age-Related Macular Degeneration" Ophthalmology 118(1):93-100 (Jan. 2011).
Tsukita et al., "Multifunctional Strands in Tight Junctions" Nature Reviews: Molecular Cell Biology 2(4):285-293 (Apr. 2001).
Undar et al., "Novel Anti-Factor D Monoclonal Antibody Inhibits Complement, Neutrophil, and Platelet Activation in a Simulated Pediatric Cardiopulmonary Bypass Circuit" (Abstract) 2000 Abstracts & Information, presented at the 46th Annual Conference of the American Society for Artificial Internal Organs, New York City, USA, (Jun. 28, 2000-Jul. 1, 2000).
Undar et al., "Novel Anti-Factor D Monoclonal Antibody Inhibits Complement and Leukocyte Activation in a Baboon Model of Cardiopulmonary Bypass" Ann. Thorac. Surg. 74(2):355-362 (2002).
Underhill et al., "Phagocytosis of Microbes: Complexity in Action" Annual Review of Immunology 20:825-852 (2002).
Vajdos et al., "Comprehensive Functional Maps of the Antigen-Binding Site of an Anti-ErbB2 Antibody Obtained with Shotgun Scanning Mutagenesis" Journal of Molecular Biology 320:415-428 (2002).
van de Ven et al., "A Functional Variant in the CFI Gene Confers a High Risk of Age-Related Macular Degeneration" Nature Genetics 45(7):813-819 (Jul. 2013).
van Lookeren Campagne et al., "Mechanisms of Age-Related Macular Degeneration and Therapeutic Opportunities" Journal of Pathology 232(2):151-164 (2014).
Verhoeyen et al., "Reshaping Human Antibodies: Grafting an Antilysozyme Activity" Science 239:1534-1536 (Mar. 25, 1988).
Volanakis et al., "Complement Factor D, a Novel Serine Protease" Protein Science 5(4):553-564 (1996).
Volanakis et al., "Renal Filtration and Catabolism of Complement Protein D" New England Journal of Medicine 312(7):395-399 (1985).
Volanakis et al., The Human Complement System in Health & Disease "Chapter 4, Complement Enzymes" New York: Marcel Dekker, Inc.:49-81 (1998).
Walker, "Z39Ig is Co-Expressed with Activated Macrophage Genes" Biochimica et Biophysica Acta 1574(3):387-390 (2002).
Walport, "Complement: First of Two Parts" New England Journal of Medicine 344(14):1058-1066 (Apr. 5, 2001).
Wang et al., "Amelioration of Lupus-Like Autoimmune Disease in NZB/WF1 Mice after Treatment with a Blocking Monoclonal Antibody Specific for Complement Component C5" PNAS 93(16):8563-8568 (Aug. 1996).
Wang et al., "Anti-C5 Monoclonal Antibody Therapy Prevents Collagen-Induced Arthritis and Ameliorates Established Disease" PNAS 92(19):8955-8959 (Sep. 1995).
Weber, "Overview of Protein Crystallization Methods" Methods in Enzymology 276:13-22 (1997).
Wei et al., "From Disease Association to Risk Assessment: An Optimistic View from Genome-Wide Association Studies on Type 1 Diabetes" PLoS Genetics 5(10):1-11 (Oct. 2009).
Weisman et al., "Soluble Human Complement Receptor Type 1: In Vivo Inhibitor of Complement Suppressing Post-Ischemic Myocardial Inflammation and Necrosis" Science :249(4965):146-151 (Jul. 13, 1990).
White et al., "Human Adipsin is Identical to Complement Factor D and is Expressed at High Levels in Adipose Tissue" Journal of Biological Chemistry 267(13):9210-9213 (May 5, 1992).
Wiesmann et al., "Structure of C3b in Complex with CRIg Gives Insights into Regulation of Complement Activation" Nature 444:217-220 (Nov. 9, 2006).
Wilson et al., "A Competitive Inhibition ELISA for the Quantification of Human Interferon-gamma" Journal of Immunological Methods 162(2):247-255 (Jun. 18, 1993).
Wong et al., "Global Prevalence of Age-Related Macular Degeneration and Disease Burden Projection for 2020 and 2040: A Systematic Review and Meta-Analysis" Lancet Global Health 2(2):e106-116 (Feb. 2014).
Wu et al., "BioGPS: An Extensible and Customizable Portal for Querying and Organizing Gene Annotation Resources" Genome Biology 10(11):R130.1-R130.8 (2009).
Wu et al., "Fast and SNP-Tolerant Detection of Complex Variants and Splicing in Short Reads" Bioinformatics 26(7):873-81 (2010).
Wu et al., "Humanization of a Murine Monoclonal Antibody by Simultaneous Optimization of Framework and CDR Residues" Journal of Molecular Biology 294(1):151-162 (Nov. 19, 1999).
Yates et al., "Complement C3 Variant and the Risk of Age-Related Macular Degeneration" New England Journal of Medicine 357(6):553-561 (Aug. 9, 2007).
Yu et al., "Prospective Assessment of Genetic Effects on Progression to Different Stages of Age-Related Macular Degeneration Using Multistate Markov Models" Investigative Ophthalmology & Visual Science 53(3):1548-1556 (Mar. 2012).
Zareparsi et al., "Strong Association of the Y402H Variant in Complement Factor H at 1q32 with Susceptibility to Age-Related Macular Degeneration" Am. J. Hum. Genet. 77(1):149-153 (2005).

(56) References Cited

OTHER PUBLICATIONS

Zeng et al., "Lack of Association of CFD Polymorphisms with Advanced Age-Related Macular Degeneration" Molecular Vision 16:2273-2278 (2010).
Carroll, "Exposure of an Executioner" Nature 444:159-160 (Nov. 9, 2006).
Chen et al., "Modulating Antibody Pharmacokinetics Using Hydrophilic Polymers" Expert Opinion on Drug Delivery 8(9):1221-1236 (2011).
Ferris et al., "A Simplified Severity Scale for Age-Related Macular Degeneration: AREDS Report No. 18" Arch Ophthalmol. 123(11):1570-4 (2005).
Gaudreault et al., "Pharmacokinetics and Retinal Distribution of Ranibizumab, a Humanized Antibody Fragment Directed against VEGF-A, Following Intravitreal Administration in Rabbits" Retina 27(9):1260-1266 (2007).
Green, "Studies in the Physical Chemistry of the Proteins" Journal of Biological Chemistry 93:517-542 (1931).
Jevsevar et al., "PEGylation of Therapeutic Proteins" Biotechnol. J. 5:113-128 (2010).
Joubert et al., "Classification and Characterization of Therapeutic Antibody Aggregates" Journal of Biological Chemistry 286(28):25118-25133 (Jul. 15, 2011).
Joubert et al., "Highly Aggregated Antibody Therapeutics Can Enhance the in Vitro Innate and Late-Stage T-Cell Immune Responses" Journal of Biological Chemistry 287(30):25266-25279 (Jul. 20, 2012).
Katschke et al., "Structural and Functional Analysis of a C3b-Specific Antibody that Selectivity Inhibits the Alternative Pathway of Complement" Journal of Biological Chemistry 284(16):10473-10479 (Apr. 17, 2009).
Kontermann, "Strategies to Extend Plasma Half-Lives of Recombinant Antibodies" Biodrugs 23(2):93-109 (2009).
Lowe et al., "Aggregation, Stability, and Formulation of Human Antibody Therapeutics" Advances in Protein Chemistry and Structural Biology 84:41-61 (2011).
Moore et al., "Role of Aggregated Human Growth Hormone (hGH) in Development of Antibodies to hGH" Journal of Clinical Endocrinology and Metabolism 51(4):691-697 (1980).
Pangbum, "Alternative Pathway of Complement" Methods in Enzymology 162:639-653 (1988).
Rosenberg, "Effects of Protein Aggregates: An Immunologic Perspective" The AAPS Journal 8(3):E501-507 (Aug. 4, 2006).
Salas-Solano et al., "Robustness of iCIEF Methodology for the Analysis of Monoclonal Antibodies: An Interlaboratory Study" J Sep. Sci. 35(22):3124-3129 (2012).
Wang et al., "Antibody Structure, Instability, and Formulation" Journal of Pharmaceutical Sciences 96(1):1-26 (2007).
Database dbSNP—NCBI No. rs17792825, retrieved Jan. 10, 2017 (1 page).
Database dbSNP—NCBI No. ss67243395, retrieved Nov. 21, 2015 (2 pages).
Database dbSNP—NCBI No. ss67486158, retrieved Aug. 29, 2016 (2 pages).
Database dbSNP—NCBI No. ss67520449, retrieved Nov. 21, 2015 (2 pages).
International Search Report for PCT/US2015/028641, dated Oct. 8, 2015 (8 pages).
International Search Report for PCT/US2016/059179, dated Jan. 31, 2017 (8 pages).
Written Opinion for PCT/US2015/028641, dated Oct. 8, 2015 (7 pages).
U.S. Appl. No. 09/253,689, filed Feb. 20, 1999, Fung et al.
Almagro et al., "Humanization of Antibodies" Frontiers in Bioscience 13:1619-1633 (Jan. 1, 2008).
Anderson et al., "The Pivotal Role of the Complement System in Aging and Age-Related Macular Degeneration: Hypothesis Re-Visited" Progress in Retinal and Eye Research 29 29:95-112 (2010).
Avery et al., "Systemic Pharmacokinetics Following Intravitreal Injections of Ranibizumab, Bevacizumab or Aflibercept in Patients with Neovascular AMD" Br J Ophthalmol 98:1636-1641 (2014).

Badescu et al., "A New Reagent for Stable Thiol-Specific Conjugation" Bioconjugate Chemistry 25:460-469 (2014).
Bielefeld-Sevigny, "AlphaLISA Immunoassay Platform—The "No-Wash" High-Throughput Alternative to ELISA" Assay Drug Dev Technol 7:90-92 (2009).
BLAST Report, http://expasy.org/cgi-bininiceprot.pl/printable?ac—Q80WA3, dated Mar. 1, 2004.
Beckmann et al., "Functionalization of Poly(ethylene Glycol) and Monomethoxy-Poly(ethylene Glycol)" Makromol. Chem. 182:1379-1384 (1981).
Cacia et al., "Isomerization of an Aspartic Acid Residue in the Complementarity-Determining Regions of a Recombinant Antibody to Human IgE: Identification and Effect on Binding Affinity" Biochemistry 35:1897-1903 (1996).
Clackson et al., "Making antibody fragments using phage display libraries" Nature 352:624-628 (Aug. 15, 1991).
Cunningham et al., "High-Resolution Epitope Mapping of hGH-Receptor Interactions by Alanine-Scanning Mutagenesis" Science 244(4908):1081-1085 (Jun. 2, 1989).
Damico et al., "New Approaches and Potential Treatments for Dry Age-Related Macular Degeneration" Arq Bras Oftalmol 75(1):71-76 (2012).
Database dbSNP Database No. ss6697713 dated Feb. 12, 2003 (2 pages).
Database dbSNP, rs1329428, 6 pgs, 2004 (date retrieved: May 18, 2017).
Database DdSNP ss66926822 (http://www.ncbi.nlm.nih.gov/projects/SNP/snp_ss.cgi?subsnp_id=66926822, Nov. 14, 2006).
Database dsSNP, RS429608, 4 pgs, 2003 (date retrieved: May 18, 2017).
Database Genebank (Apr. 24, 2001), 'Human Pro 1868 Protein' Database Accession No. AAB80272 XP002448361, dated Jun. 15, 2007.
Davis et al., "Soluble, Nonantigenic Polyethylene Gylcol-Bound Enzymes" Biomedical Polymers: Polymeric Materials and Pharmaceuticals for Biomedical Use, Goldberg et al. eds., New York: Academic Press pp. 441-452 (1980).
Duddu et al., "The Relationship Between Protein Aggregration and Molecular Mobility Below the Glass Transition Temperature of Lyophilized Formulations Containing a Monoclonal Antibody" Pharmaceutical Research 14(5):596-600 (1997).
Durairaj et al., "Prediction of Vitreal Half-Life Based on Drug Physicochemical Properties: Quantitative Structure-Pharmacokinetic Relationships (QSPKR)" Pharmaceutical Research, Kluwer Academic Publishers-Plenum Publishers 26(5):1236-1260 (Oct. 8, 2008).
Duvvuri et al., "Drug Delivery to the Retina: Challenges and Opportunities" Expert Opin Biol Ther. 3(1):45-56 (2003).
Ellman et al., "Biosynthetic method for introducing unnatural amino acids site-specifically into proteins" Meth Enzym 202:301-336 (1991).
Evans et al., "Harnessing the Information Contained within Genome-wide Association Studies to Improve Individual Prediction of Complex Disease Risk" Human Molecular Genetics 18(18):3525-3531 (2009).
Fitch et al., "Optimal Sequence Alignments" Proc. Natl. Acad. Sci. USA 80:1382-1386 (Mar. 1983).
Fung et al., "Pre-Neutralization of C5a-Mediated Effects by the Monoclonal Antibody 137-26 Reacting with the C5a Moiety of Native C5 without Preventing C5 Cleavage" Clin Exp Immunol 133:160-169 (2003).
Gaudreault et al., "Preclinical pharmacokinetics of Ranibizumab (rhuFabV2) after a single intravitreal administration" Invest Ophthalmol Vis Sci. 46(2):726-33 (Feb. 2005).
Geiger et al., "Deamidation, Isomerization, and Racemization at Asparaginyl and Aspartyl Residues in Peptides" Journal of Biological Chemistry 262(2):785-794 (Jan. 15, 1987).
Ghate et al., "Ocular Drug Delivery" Expert Opinion on Drug Delivery 3(2):275-287 (2006).
Glickman et al., "A Comparison of ALPHAScreen, TR-FRET, and TRF as Assay Methods for FXR Nuclear Receptors" Journal of Biomolecular Screening 7(1):3-10 (2002).
Gullberg et al., "Cytokine Detection by Antibody-Based Proximity Ligation" PNAS 101(22):8420-8424 (Jun. 1, 2004).

(56) References Cited

OTHER PUBLICATIONS

Harboe et al., "The Alternative Complement Pathway Revisited" J. Cell. Mol. Med. 12(4):1074-1084 (2008).
Holt et al., "Domain antibodies: proteins for therapy" Trends Biotechnol 21(11):484-490 (Nov. 2003).
Humphreys et al., "Alternative Antibody Fab' Fragment PEGylation Strategies: Combination of Strong Reducing Agents, Disruption of the Interchain Disulphide Bond and Disulphide Engineering" Protein Engineering, Design & Selection 20(5):227-234 (2007).
Hutanu et al., "Recent Applications of Polyethylene Glycols (PEGs) and PEG Derivatives" Modern Chemistry & Applications 2(2):1-6 (2014).
Igawa et al., "Engineering the variable region of therapeutic IgG antibodies" mAbs 3(3):243-252 (2011).
International Preliminary Report on Patentability for PCT/US2015/028641 dated Nov. 1, 2016, 8 pages.
Ioannidis, J. P. A. et al., "Replication validity of genetic association studies" Nature Genetics 29:306-309 (2001).
Jevsevar et al., "PEGylation of antibody fragments for half-life extension" Methods in Molecular Biology 901:233-246 (Jan. 1, 2012).
Johnson et al. Methods in Molecular Biology: Antibody Engineering: Methods and Protocols "2: The Kabat Database and a Bioinformatics Example" Lo, Totowa, NJ: Humana Press, vol. 248:1-25 (2004).
Jones, A. J. S., "Analysis of Polypeptides and Proteins." Adv Drug Delivery Rev 10:29-90 (1993).
Junutula et al., "Rapid identification of reactive cysteine residues for site-specific labeling of antibody-Fabs" J Immunol Methods 332:41-52 (2008).
Kabat et al. Sequences of Proteins of Immunological Interest Fifth edition, NIH Publication:91-3242 (1991).
Katre, "The Conjugation of Proteins with Polyethylene Glycol and other Polymers. Altering properties of proteins to enhance their therapeutic potential." Adv Drug Delivery Rev 10(1):91-114 (1993).
Kelley et al. Antibody Methods and Protocols "18" Proetzel et al., Humana Press, vol. 901:277-293 (2012).
Khalili et al., "Fab-PEG-Fab as a Potential Antibody Mimetic" Bioconjugate Chemistry 24(11):1870-1882 (Sep. 27, 2013).
Kindt et al. Kuby Immunology "Antigens and Antibodies Chapter 4" 6th edition, N.Y.:W.H. Freeman and Co: p. 91 (2007).
Kunkel, T., "Rapid and Efficient Site-Specific Mutagenesis Without Phenotypic Selection" PNAS 82(2):488-492 (Jan. 1985).
Le et al., "A Mechanistic Pharmacokinetic/Pharmacodynamic Model of Factor D Inhibition in Cynomolgus Monkeys by Lampalizumab for the Treatment of Geographic Atrophy" Journal of Pharmacology and Experimental Therapeutics 355:288-296 (Nov. 2015).
Lewis et al., "Maleimidocysteineamido-DOTA derivatives: New reagents for radiometal chelate conjugation to antibody sulfhydryl groups undergo pH-dependent cleavage reactions" Bioconj Chem 9:72-86 (1998).
Loyet et al., "Complement Inhibition in Cynomolgus Monkeys by Anti-Factor D Antigen-Binding Fragment for the Treatment of an Advanced Form of Dry Age-Related Macular Degeneration" Journal of Pharmacology and Experimental Therapeutics 351:527-537 (Dec. 2014).
Maynard et al., "Antibody Engineering" Annu. Rev. Biomed. Eng. 02:339-76 (2000).
Michels et al., "Fluorescent Derivatization Method of Proteins for Characterization by Capillary Electrophoresis-Sodium Dodecyl Sulfate with Laser-Induced Fluorescence Detection" Analytical Chemistry 79(15):5963-5971 (Aug. 1, 2007).
Michels et al., "Quantitative Impurity Analysis of Monoclonal Antibody Size Heterogeneity by CE-LIF: Example of Development and Validation Through a Quality-By-Design Framework" Electrophoresis 33:815-826 (2012).
Morrison, "Time-Resolved Detection of Energy Transfer: Theory and Application to Immunoassays" Analytical Biochemistry 174:101-120 (1988).
Needleman et al., "A General Method Applicable to the Search for Similarities in the Amino Acid Sequence of Two Proteins" J Mol Biol 48:443-453 (1970).
Noren et al., "A general method for site-specific incorporation of unnatural amino acids into proteins" Science 244(4901):182-188 (Apr. 14, 1989).
Nozaki et al., "Drusen Complement Components C3a and C5a Promote Choroidal Neovascularization" PNAS 103(7):2328-2333 (Feb. 14, 2006).
Patel et al., "Ocular Drug Delivery Systems: An Overview" World J Pharmacol. 2(2):47-64 (2013).
Patterson et al., "Improving the Serum Stability of Site-Specific Antibody Conjugates with Sulfone Linkers" Bioconjugate Chemistry 25:1402-1407 (2014).
Pearlman, R. et al. Peptide and Protein Drug Delivery "Chapter 6, Analysis of Protein Drugs" Vincent H. L. Lee, Marcel Dekker, Inc.:247-301 (1991).
Pedley et al., "The Potential for Enhanced Tumour Localisation by Poly(ethylene glycol) Modification of Anti-CEA Antibody" Br. J. Cancer 70:1126-1130 (1994).
Pikal et al., "Solid State Chemistry of Proteins: II. The Correlation of Storage Stability of Freeze-Dried Human Growth Hormone (hGH) with Structure and Dynamics in the Glassy Solid" Journal of Pharmaceutical Sciences 97(12):5106-5121 (Dec. 2008).
Pini et al., "Design and Use of a Phage Display Library" The Journal of Biological Chemistry 273:21769-21776 (1998).
Portolano et al., "Lack of promiscuity in autoantigen-specific H and L chain combinations as revealed by human H and L chain 'Roulette'" J Immunol 150(3):880-887 (Feb. 1993).
Presta et al., "Humanization of an antibody directed against IgE" J. Immunol. 151(5):2623-2632 (Sep. 1, 1993).
Rattner et al., "Macular Degeneration: Recent Advances and Therapeutic Opportunities" Nature 7:860-872 (Nov. 2006).
Remington's Pharmaceutical Sciences (Copy of Table of Contents), Osol, 16th edition, Easton, PA: Mack Publishing Company: TOC (1980).
Ryan et al., "Advances in PEGylation of Important Biotech Molecules: Delivery Aspects" Expert Opinion on Drug Delivery 5(4):371-383 (2008).
Selvin, "Fluorescence Resonance Energy Transfer" Methods in Enzymology 246:300-335 (1995).
Sivakumaran et al., "A 32 kb Critical Region Excluding Y402H in CFH Mediates Risk for Age-Related Macular Degeneration" PLoS ONE 6(10 Suppl e25598):1-13 (Oct. 2011).
Stryer, "Fluorescence Energy Transfer as a Spectroscopic Ruler" Ann. Rev. Biochem. 47:819-846 (1978).
Teo et al., "A Genotype Calling Algorithm for the Illumina BeadArray Platform" Bioinformatics 23(20):2741-2746 (2007).
Ullman et al., "Luminescent Oxygen Channeling Assay (LOCI™): Sensitive, Broadly Applicable Homogeneous Immunassay Method" Clinical Chemistry 42(9):1518-1526 (Sep. 1996).
Ullman et al., "Luminescent Oxygen Channeling Immunoassay: Measurement of Particle Binding Kinetics by Chemiluminescence" PNAS 91:5426-5430 (Jun. 1994).
Urtti, "Challenges and Obstacles of Ocular Pharmacokinetics and Drug Delivery" Advanced Drug Delivery Reviews 58:1131-1135 (2006).
Vlasak et al., "Heterogeneity of monoclonal Antibodies Revealed by charge-Sensitive Methods" Current Pharmaceutical Biotechnology 9:468-481 (2008).
Vugmeyster et al., "Pharmacokinetic, biodistribution, and biophysical profiles of TNF nanobodies conjugated to linear or branched poly(ethylene glycol)" Bioconjugate Chemistry 23(7):1454-1462 (Jul. 18, 2012).
Walsh, "Biopharmaceutical Benchmarks" Nature Biotechnology 18:831-833 (Aug. 2000).
Weber et al., "The Role of the Complement System in Age-Related Macular Degeneration" Deutsches Arzteblatt International 111(8):133-138 (2014).
Xie et al., "Secondary Structure and Protein Deamidation" Journal of Pharmaceutical Sciences 88(1):8-13 (Jan. 1999).
Xu et al., "Diversity in the CDR3 region of V(H) is sufficient for most antibody specificities" Immunity 13(1):37-45 (Jul. 2000).

(56) References Cited

OTHER PUBLICATIONS

Yi et al., "Isomerization of Asp-Asp Motif in Model Peptides and a Monoclonal Antibody Fab Fragment" Journal of Pharmaceutical Sciences 102(3):947-959.
Zhang et al., "Identification of Isomerization and Racemization of Aspartate in the Asp-Asp motifs of a Therapeutic Protein" Analytical Biochemisry 410:234-243 (2011).
Tesar et al., "Protein Engineering to Increase the Potential of a Therapeutic Antibody Fab for Long-Acting Delivery to the Eye" mABs 9(8):1297-1305 (Aug. 30, 2017).
Dong et al., "Correlation of complement factor H gene polymorphisms with exudative age-related macular degeneration in a Chinese cohort", Neurosci Lett., 488(3):283-287 (2011).

* cited by examiner

FIGURE 2A

| Characteristic | Sham Monthly (n=20) | Sham Every Other Month (n=20) | FCFD4514S Monthly (n=42) | FCFD4514S Every Other Month (n=41) | All Patients (n=123) |
|---|---|---|---|---|---|
| Demographics | | | | | |
| Age (year), mean (SD) | 78.4 (8.3) | 78.6 (6.3) | 80.4 (7.2) | 77.2 (7.3) | 78.7 (7.3) |
| Sex – Female, n (%) | 11 (55.0%) | 13 (65.0%) | 28 (66.7%) | 18 (43.9%) | 70 (56.9%) |
| Race – White, n (%) | 20 (100.0%) | 20 (100.0%) | 40 (95.2%) | 41 (100.0%) | 121 (98.4%) |
| Study Eye Baseline, *mean (SD)* | | | | | |
| VA (letters) | 45.1 (13.8) | 46.7 (13.2) | 47.6 (12.8) | 49.5 (11.0) | 47.7 (12.4) |
| Total area of GA (mm2) | 8.880 (4.216) | 8.827 (4.244) | 8.555 (3.863) | 8.560 (4.897) | 8.654 (4.298) |

VA = visual acuity; GA = geographic atrophy; DA = disc area (1 DA = 2.54 mm2)

FIGURE 2B

| Baseline Characteristics | CFI Risk Allele Carrier | | No CFI Risk Allele | |
|---|---|---|---|---|
| | Sham pooled (n=15) | afD 1M (n=19) | Sham pooled (n=18) | afD 1M (n=12) |
| Age, mean (SD) | 79 (6) | 81 (6) | 78 (8) | 81 (7) |
| Female, n (%) | 8 (53%) | 13 (68%) | 12 (67%) | 7 (58%) |
| White, n (%) | 15 (100%) | 19 (100%) | 18 (100%) | 11 (92%) |
| VA (letters), mean (SD) | 48.3 (11.3) | 48.3 (13.5) | 44.7 (14.8) | 55.5 (9.3) |
| Snellen equivalent, median (range) | 20/125 (20/50 ~ 20/250) | 20/100 (20/50 ~ 20/400) | 20/100~20/160 (20/50 ~ 20/400) | 20/63 (20/50~20/160) |
| GA (mm2), mean (SD) | 8.9 (4.1) | 9.1 (4.3) | 9.6 (4.8) | 8.6 (4.1) |

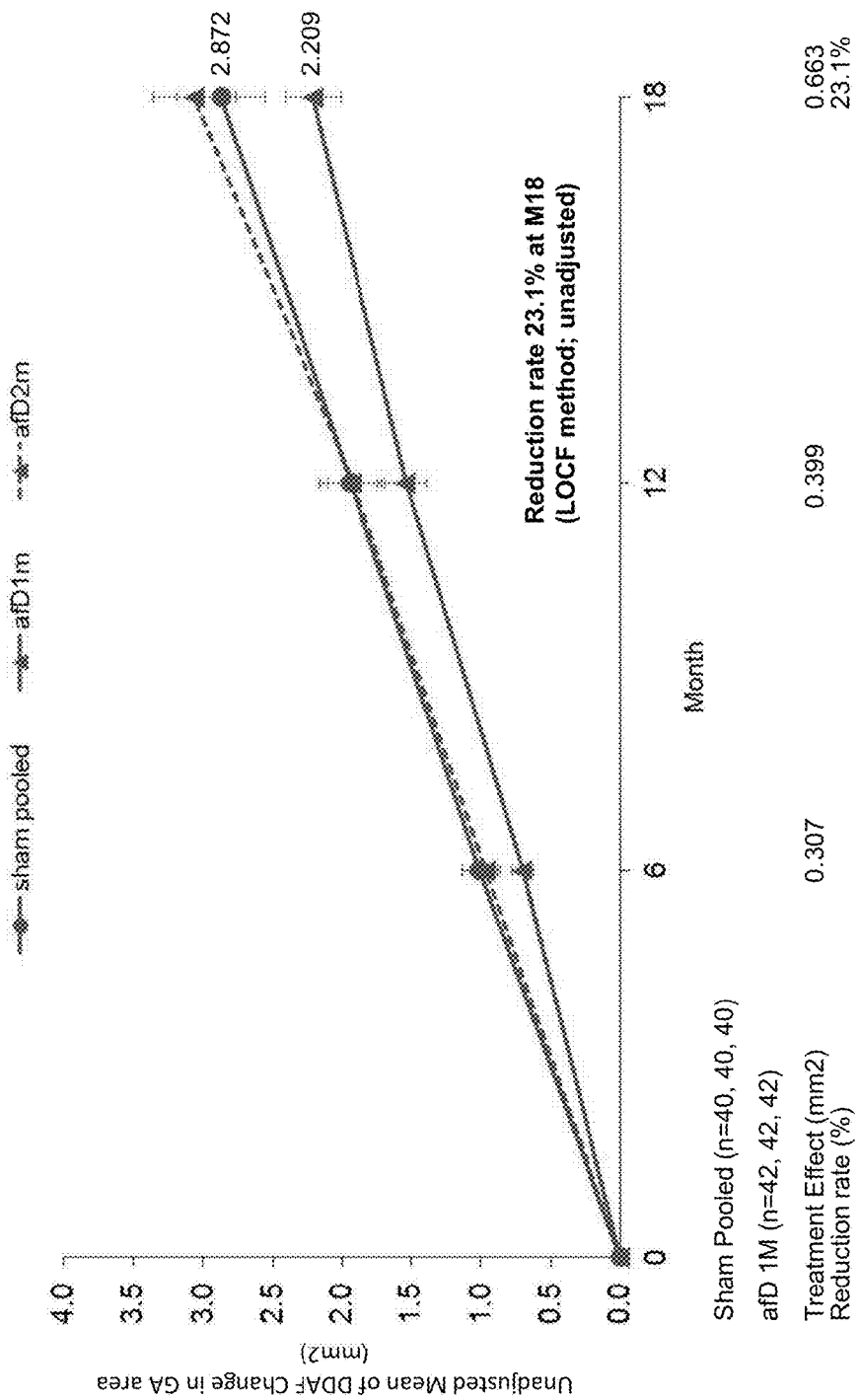

FIGURE 5

| Gene | SNP/Genotype Risk Allele | Sham | | | Monthly | | | Delta (Mean of Sham - Mean of Monthly) | % Reduction in Monthly vs Sham (Mean of Sham - Mean of Monthly/Mean of Sham) |
|---|---|---|---|---|---|---|---|---|---|
| | | N | Mean Change in GA Area (mm²) | STDEV | N | Mean Change in GA Area (mm²) | STDEV | | |
| | All | 29 | 3.36 | 2.07 | 24 | 2.46 | 1.11 | 0.91 | 26.99 |
| C3 | rs2230199 | | | | | | | | |
| | G/G | 2 | 1.76 | 1.15 | 2 | 2.90 | 0.94 | -1.14 | -64.96 |
| | C/G | 13 | 3.44 | 2.23 | 12 | 2.70 | 1.25 | 0.75 | 21.65 |
| | C/C | 14 | 3.52 | 2.02 | 10 | 2.08 | 0.94 | 1.44 | 41.00 |
| CFH | rs1329428 | | | | | | | | |
| | G/G | 21 | 3.47 | 2.18 | 16 | 2.33 | 1.16 | 1.14 | 32.84 |
| | A/G | 6 | 3.13 | 2.01 | 8 | 2.71 | 1.05 | 0.42 | 13.41 |
| | A/A | 2 | 2.97 | 1.82 | 0 | NA | NA | | |
| C2-CFB | rs429608 | | | | | | | | |
| | G/G | 21 | 3.45 | 2.21 | 19 | 2.44 | 1.20 | 1.00 | 29.15 |
| | A/G | 7 | 3.24 | 1.84 | 5 | 2.50 | 0.84 | 0.73 | 22.65 |
| | A/A | 1 | 2.48 | NA | 0 | NA | NA | | |
| CFI | rs17440077 | | | | | | | | |
| | G/G | 1 | 2.77 | NA | 2 | 3.03 | 0.76 | -0.26 | -9.21 |
| | A/G | 11 | 4.35 | 2.44 | 14 | 2.06 | 1.20 | 2.29 | 52.66 |
| | A/A | 17 | 2.76 | 1.64 | 8 | 3.01 | 0.76 | -0.25 | -8.92 |

COMPOSITIONS FOR DETECTING COMPLEMENT FACTOR H (CFH) AND COMPLEMENT FACTOR I (CFI) POLYMORPHISMS

CROSS REFERENCE TO RELATED APPLICATIONS

This application claims the benefit of U.S. Provisional Patent Application Nos. 61/864,941, filed on Aug. 12, 2013, and 61/866,651, filed on Aug. 16, 2013, and 61/872,098, filed on Aug. 30, 2013, and 61/988,012, filed on May 2, 2014, and 62/021,487, filed on Jul. 7, 2014, the contects of the foregoing applications are incorporated herein by reference in their entirety.

SEQUENCE LISTING

The instant application contains a Sequence Listing which has been submitted electronically in ASCII format and is hereby incorporated by reference in its entirety. Said ASCII copy, created on Aug. 11, 2014, is named P5661R1-US_S-L.txt and is 19,281 bytes in size.

FIELD OF THE INVENTION

The invention involves methods and compositions for treating various complement-associated conditions (e.g., age-related macular degeneration) with a factor D inhibitor (e.g., an anti-factor D antibody or antigen-binding fragment thereof). Also provided are methods of selecting or identifying patients for treatment with a factor D inhibitor. Methods include the use of prognostic and/or predictive biomarkers.

BACKGROUND

The complement system plays a central role in the clearance of immune complexes and the immune response to infectious agents, foreign antigens, virus-infected cells and tumor cells. However, complement is also involved in pathological inflammation and in autoimmune diseases. Therefore, inhibition of excessive or uncontrolled activation of the complement cascade could provide clinical benefit to patients with such diseases and conditions.

The complement system encompasses two distinct activation pathways, designated the classical and the alternative pathways (V. M. Holers, In *Clinical Immunology: Principles and Practice*, ed. R. R. Rich, Mosby Press; 1996, 363-391). The classical pathway is a calcium/magnesium-dependent cascade which is normally activated by the formation of antigen-antibody complexes. The alternative pathway is a magnesium-dependent cascade which is activated by deposition and activation of C3 on certain susceptible surfaces (e.g. cell wall polysaccharides of yeast and bacteria, and certain biopolymer materials). Activation of the complement pathway generates biologically active fragments of complement proteins, e.g. C3a, C4a and C5a anaphylatoxins and C5b-9 membrane attack complexes (MAC), which mediate inflammatory activities involving leukocyte chemotaxis, activation of macrophages, neutrophils, platelets, mast cells and endothelial cells, vascular permeability, cytolysis, and tissue injury.

Factor D is a highly specific serine protease essential for activation of the alternative complement pathway. It cleaves factor B bound to C3b, generating the C3b/Bb enzyme which is the active component of the alternative pathway C3/C5 convertases. Factor D may be a suitable target for inhibition, since its plasma concentration in humans is very low (1.8 μg/ml), and it has been shown to be the limiting enzyme for activation of the alternative complement pathway (P. H. Lesavre and H. J. Müller-Eberhard. *J. Exp. Med.*, 1978; 148: 1498-1510; J. E. Volanakis et al., *New Eng. J. Med.*, 1985; 312: 395-401).

The down-regulation of complement activation has been demonstrated to be effective in treating several disease indications in animal models and in ex vivo studies, e.g. systemic lupus erythematosus and glomerulonephritis (Y. Wang et al., *Proc. Natl. Acad. Sci.;* 1996, 93: 8563-8568), rheumatoid arthritis (Y. Wang et al., *Proc. Natl. Acad. Sci.,* 1995; 92: 8955-8959), cardiopulmonary bypass and hemodialysis (C. S. Rinder, *J. Clin. Invest.*, 1995; 96: 1564-1572), hyperacute rejection in organ transplantation (T. J. Kroshus et al., *Transplantation*, 1995; 60: 1194-1202), myocardial infarction (J. W. Homeister et al., *J. Immunol.*, 1993; 150: 1055-1064; H. F. Weisman et al., Science, 1990; 249: 146-151), reperfusion injury (E. A. Amsterdam et al., *Am. J. Physiol.*, 1995; 268: H448-H457), and adult respiratory distress syndrome (R. Rabinovici et al., *J. Immunol.*, 1992; 149: 1744-1750). In addition, other inflammatory conditions and autoimmune/immune complex diseases are also closely associated with complement activation (V. M. Holers, ibid., B. P. Morgan. *Eur. J. Clin. Invest.*, 1994:24:219-228), including thermal injury, severe asthma, anaphylactic shock, bowel inflammation, urticaria, angioedema, vasculitis, multiple sclerosis, myasthenia gravis, membranoproliferative glomerulonephritis, and Sjögren's syndrome.

Age-related macular degeneration (AMD), when left untreated, is the leading cause of irreversible blindness in people 50 years of age or older in the developed world (Friedman et al., *Arch Opthalmol*, 122:564-72 (2004)). Approximately 8 million Americans have an intermediate stage of AMD (characterized by the presence of large-sized drusen in the macula (center of the retina)), placing them at risk for developing advanced disease and vision loss. Advanced AMD is classified into two clinical forms: geographic atrophy (GA) and an exudative or wet form characterized by choroidal neovascularization (CNV) (Age-Related Eye Disease Study [AREDS] Research Group, *Arch Ophthalmol*, 121:1621-24 (2003)). GA refers to confluent areas of retinal pigment epithelial (RPE) cell death accompanied by overlying photoreceptor atrophy. GA has a substantial impact on visual function: approximately 40% of a subset of patients has been shown to lose at least 3 Snellen equivalent lines of vision over 2 years (Sunness et al., *Retina*, 7:204-10 (2007)). Although the etiology of AMD is largely unknown, age, smoking ethnicity, diet and genetics have been suggested to be risk factors in AMD (Amabti et al., *Surv Opthalmol*, 48(3): 257-93 (2003); Gorin et al., *Mol Aspects Med*, 33:467-486 (2012)) and the alternative complement pathway (ACP) have been implicated in AMD (de Jong, *N. Engl J. Med.*, 355: 1474-1485 (2006)). Increased activation of ACP has been found in drusen, lipoproteinous depositions in the space between the RPE and Bruch's membrane, which are a hallmark of AMD. Moreover, a role for ACP activation in AMD has been supported by human genetics (Yates et al., *New Engl J Med*, 357: 553-61 (2007)). Complement factor D is a rate-limiting enzyme that plays a pivotal role in the activation of the alternative complement pathway (ACP). Evidence for factor D in the pathogenesis of AMD includes protection against oxidative stress-mediated photoreceptor degeneration in a murine model with genetic deficiency of factor D (Rohrer et al., *Invest Ophthalmol Vis Sci*, 48:5282-89 (2007)) and detection of increased systemic activation of complement, including factor D, in the serum of AMD patients versus controls, suggesting that AMD may be a systemic disease with local manifestations in the aging macula (Scholl et al., *PLos ONE,* 3(7):e2593 (2008)). Moreover, multiple papers on the genetics of AMD have independently confirmed a single nucleotide polymorphism in complement factor H(CFH). Y402H that was strongly linked to increased risk of developing both early and late AMD (Edwards et al., *Science,* 308(5720): 421-4 (2005); Hageman et al., *PNAS,* 102(20): 7227-32 (2005); Haines et al., *Science,* 208(5720): 419-21 (2005); Klein et al., *Science,* 308(5720): 385-9 (2005); Prosser et al., *J. Exp. Med.,* 204(10: 2277-83 (2007); Zareparsi et al., *Am J. Hum Genet,* 77:149-153 (2005)). Other risk alleles include polymorphisms in a complement factor H(CFH) risk locus (rs10737680), in a complement factor I (CFI) risk locus (rs4698775), in a complement component 2/complement factor B (C2/CFB) risk locus (rs429608), and in a complement component (C3) risk locus (rs2230199) (Fritsche et al., *Nat Genet,* 45:433-439 (2013)). CFI, CFH, C2, CFB and C3 are additional members of the complement pathway. Additional SNPs associated with genes in the complement pathway and their correlation with AMD have been implicated in, e.g., PCT publications WO2011/017229, WO2009/146204 and WO2009/134709. None of these references, however, disclosed or suggested correlation of the identified SNPs with how the patient's disease progresses over time or how well the patient responds to AMD therapy. In a prospective study of genetic effects on AMD progression, genetic variants such as SNPs in the complement pathway were associated with progression from intermediate drusen to large drusen and from large drusen to GA or NV. Yu et al., *Invest. Ophthalm. & Visual Sci.,* 53:1548-56 (2012). The results suggest that genes associated with AMD may be involved in transitions between distinctly different AMD stages during progression. It was not known, however, whether the identified genes are associated with rate of disease progression, e.g., within an advanced stage such as GA.

Currently, anti-VEGF (vascular endothelial growth factor) is the standard of care for treatment of most cases of the wet from of advanced AMD. There is currently no effective treatment that halts or slows the progression of GA. There is no approved treatment to prevent progression of GA, creating a significant unmet need for patients with GA. Thus, there is a need to identify efficacious therapies for GA and improved methods for understanding how to treat GA patients. Specifically, diagnostic methods useful for identifying patients at risk for increased GA progression rate and likely to benefit from anti-factor D antibody treatment would greatly benefit clinical management of these patients. This invention meets these and other needs.

All references cited herein, including patent applications and publications, are incorporated by reference in their entirety for any purpose.

SUMMARY OF THE INVENTION

The present invention is based in part on the novel and surprising findings collected from a clinical trial that certain polymorphisms related to genes in the complement pathway are reliable predictors for AMD patients' progression rate as well as their response to an anti-Factor D therapy. Methods of treatment, diagnosis/prognosis and predicting response to treatment as provided herein can be applied to patients suffering from age-related macular degeneration.

One embodiment of the invention provides methods of identifying an individual who has an increased risk for progression of AMD (e.g. intermediate or advanced AMD such as wet (neovascular/exudative) AMD or geographic atrophy), the method comprising determining the genotype of an individual, wherein an individual who is determined to carry a risk allele (e.g. a degenerative disease-associated polymorphisms such as an AMD-associated polymorphism) is identified as an individual with an increased risk of progression of AMD (e.g. intermediate or advanced AMD such as wet (neovascular/exudative) AMD or geographic atrophy). In some embodiments, increased risk of progression of AMD includes progression from early to intermediate AMD and/or intermediate to advanced AMD. In some embodiments, the risk allele is the minor allele of a selected SNP. In some embodiments, the risk allele is the major allele of a selected SNP. In some embodiments, increased risk of progression of AMD includes progression from early to more advanced disease in each of the AMD stages (includes early AMD, intermediate AMD and advanced AMD) wherein early AMD is characterized by multiple small (<63 µm), or ≥1 intermediate drusen (≥63 µm and <125 µm); intermediate AMD is characterized by many intermediate or ≥1 large drusen (≥125 µm) often accompanied by hyper- or hypopigmentation of the retinal pigment epithelium; and advanced AMD is characterized by geographic atrophy (GA) or neovascular (wet) AMD). In some embodiments, the risk allele may be a complement factor I (CFI) risk allele, a complement factor H(CFH) risk allele, a complement component 2 (C2) risk allele, a complement factor B (CFB) risk allele and/or a complement component 3 (C3) risk allele. In some embodiments, the CFI risk allele is the rs4698775:G allele, or equivalent allele thereof, or comprises a G at the selected SNP rs4698775, or an alternate SNP in linkage disequilibrium to rs4698775. In some embodiments, the CFI risk allele is the rs17440077 G: allele, or equivalent allele thereof, or comprises a G at the selected SNP rs17440077, or an alternate SNP in linkage disequilibrium to rs17440077. In some embodiments, the CFH risk allele is the rs10737680:A allele, or equivalent allele thereof, or comprises an A at the SNP rs10737680, or an alternate SNP in linkage disequilibrium to rs10737680. In some embodiments, the CFH risk allele is the rs1329428:G allele, or equivalent allele thereof, or comprises a G at the SNP rs1329428, or an alternate SNP in linkage disequilibrium to rs1329428. In some embodiments, the C2 risk allele is the rs429608:G allele, or equivalent allele thereof, or comprises a G at the SNP rs429608 or an alternate SNP in linkage disequilibrium to rs429608. In some embodiments, the CFB risk allele is the rs429608:G allele, or equivalent allele thereof, or comprises a G at SNP rs429608 or an alternate SNP in linkage disequilibrium to rs429608. In some embodiments, the C3 risk allele is the rs2230199:G allele, or equivalent allele thereof, or comprises a G at the SNP rs2230199 or an alternate SNP in linkage disequilibrium to rs2230199. In some embodiments, the linkage disequilibrium is a D' measure or an $r^2$ measure. In some embodiments, the D' measure between the selected SNP and the alternate SNP is ≥0.60. In some embodiments, the D' measure between the selected SNP and the alternate SNP is ≥0.70, 0.80 or 0.90. In some embodiments, the D' measure between the selected SNP and the alternate SNP is 1.0. In some embodiments, the $r^2$ measure between the selected SNP and the alternate SNP is ≥0.60. In some embodiments, the $r^2$ measure between the selected SNP and the alternate SNP is ≥0.70, 0.80 or 0.90. In some embodiments, the $r^2$ measure between the selected SNP and the alternate SNP is 1.0. In some embodiments, the alternate SNP is a SNP designated in Tables 4-7. In some embodiments, the SNP rs4698775 is located at position 110590479 on human chromosome 4 (Genome Reference Consortium GRCh37; UCSC Genome HG19 Assembly; February 2009). The G allele changes the nucleotide sequence from T to G. In some embodiments, the SNP rs17440077 is located at position 110537567 on human chromosome 4 (Genome Reference Consortium GRCh37; UCSC Genome HG19 Assembly; February 2009). The G allele changes the nucleotide sequence from A to G. In some embodiments, the SNP rs10737680 is located at position 196679455 on human chromosome 1 (Genome Reference Consortium GRCh37; UCSC Genome HG19 Assembly; February 2009). The A allele changes the nucleotide sequence form C to A. In some embodiments, the SNP rs1329428 is located at position 196702810 on human chromosome 1 (Genome Reference Consortium GRCh37; UCSC Genome HG19 Assembly; February 2009). The G allele changes the nucleotide sequence from A to G. In some embodiments, the SNP rs429608 is located at position 31930462 on human chromosome 6 (Genome Reference Consortium GRCh37; UCSC Genome HG19 Assembly; February 2009). The G allele changes the nucleotide sequence from A to G. In some embodiments, the SNP rs2230199 is located at position 6718387 on human chromosome 19 (Genome Reference Consortium GRCh37; UCSC Genome HG19 Assembly; February 2009). The G allele changes the nucleotide sequence from C to G and the encoded amino acid from an arginine to glycine. In some embodiments, the alternate SNP is located on human chromosome 4 between SEC24B gene and EGF gene (for rs4698775) (Genome Reference Consortium GRCh37; UCSC Genome HG19 Assembly; February 2009), human chromosome 4 between SEC24B gene and EGF gene (Genome Reference Consortium GRCh37; UCSC Genome HG19 Assembly; February 2009) (for rs17440077), human chromosome 1 between KCNT2 gene and LHX9 gene (Genome Reference Consortium GRCh37; UCSC Genome HG19 Assembly; February 2009) (for rs10737680), human chromosome 1 between KCNT2 gene and LHX9 gene (Genome Reference Consortium GRCh37; UCSC Genome HG19 Assembly; February 2009) (for rs1329428), human chromosome 6 between SLC44A4 gene and TNXB gene (Genome Reference Consortium GRCh37; UCSC Genome HG19 Assembly; February 2009) (for rs429608), human chromosome 19 between TNFSF14 gene and VAV1 gene (Genome Reference Consortium GRCh37; UCSC Genome HG19 Assembly; February 2009) (for rs2230199). In some embodiments, the alternate SNP is located within 500,000 base pairs upstream or downstream of the selected SNP In some embodiments, the patient is determined to carry a CFI risk allele and/or a CFH risk allele and/or a C2 risk allele and/or a CFB risk allele and/or a C3 risk allele. In some embodiments, the individual is determined to carry 1, 2, 3, 4, 5, 6, 7, 8, 9, 10, etc. AMD risk alleles. In some embodiments, presence of a risk allele in an individual comprises determining the identity of the nucleotide at the polymorphism from nucleic acid provided from a sample from an individual. In some embodiments, the nucleic acid sample comprises DNA. In some embodiments, the nucleic acid sample comprises RNA. In some embodiments, the nucleic acid sample is amplified. In some embodiments, the nucleic acid sample is amplified by a polymerase chain reaction. In some embodiments, the polymorphism is detected by polymerase chain reaction or sequencing. In some embodiments, the polymorphism is detected by amplification of a target region containing at least one polymorphism, and hybridization with at least one sequence-specific oligonucleotide that hybridizes under stringent conditions to at least one polymorphism and detecting the hybridization. In some embodiments, the polymorphism is detected by a technique selected from the group consisting of scanning probe and nanopore DNA sequencing, pyrosequencing, Denaturing Gradient Gel Electrophoresis (DGGE), Temporal Temperature Gradient Electrophoresis (TTGE), Zn(II)-cyclen polyacrylamide gel electrophoresis, homogeneous fluorescent PCR-based single nucleotide polymorphism analysis, phosphate-affinity polyacrylamide gel electrophoresis, high-throughput SNP genotyping platforms, molecular beacons, 5' nuclease reaction, Taqman assay, MassArray (single base primer extension coupled with matrix-assisted laser desorption/ionization time-of-flight mass spectrometry), trityl mass tags, genotyping platforms (such as the Invader Assay®), single base primer extension (SBE) assays, PCR amplification (e.g. PCR amplification on magnetic nanoparticles (MNPs), restriction enzyme analysis of PCR products (RFLP methods), allele-specific PCR, multiple primer extension (MPEX), and isothermal smart amplification. In some embodiments, the sample is any biological sample from which genomic DNA may be isolated, for example, but not to be limited to a tissue sample, a sample of saliva, a cheek swab sample, blood, or other biological fluids that contain genomic DNA. In some embodiments, the sample comprises DNA. In some embodiments, the sample comprises RNA. In some embodiments, the identity of the nucleotide at the polymorphism in a patient is determined via genotyping. In some embodiments the genotyping is performed by PCR analysis, sequence analysis or LCR analysis. In some embodiments, the patient is identified as a patient with increased risk of progression of AMD (e.g. intermediate or advanced AMD such as wet (neovascular/exudative) AMD or geographic atrophy) when at least one allele comprising a nucleotide selected from the group consisting of a G nucleotide at the SNP rs4698775 is present, a G nucleotide at the SNP rs17440077 is present, an A nucleotide at the SNP rs10737680 is present, a G nucleotide at the SNP rs1329428 is present, a G nucleotide at the SNP rs429608 is present or the G nucleotide at the SNP rs2230199 is present. The patient is identified as being at increased risk of AMD progression if the patient has one or two copies of the G allele at rs4698775 or rs17440077 associated with CFI, or equivalent alleles thereof, at rs1329428 associated with CFH, or equivalent allele thereof, or at rs429608 associated with C2/CFB, or equivalent allele thereof, or at rs2230199 associated with C3, or equivalent allele thereof or one or two copies of the A allele at rs10737680 associated with CFH, or equivalent allele thereof. The patient is identified as being at decreased risk of AMD progression if the patient does not have one or two copies of the G allele at rs4698775 or rs17440077 associated with CFI, or equivalent alleles thereof, at rs1329428 associated with CFH, or equivalent allele thereof, at rs429608 associated with C2/CFB, or equivalent allele thereof, or at rs2230199 associated with C3, or equivalent allele thereof or one or two copies of the A allele at rs10737680 associated with CFH, or equivalent allele thereof.

One embodiment of the invention provides methods of predicting progression of AMD (e.g. intermediate or advanced AMD such as wet (neovascular/exudative) AMD or geographic atrophy), the method comprising determining the genotype of a patient, wherein a patient who is determined to carry a risk allele (e.g. AMD-associated polymorphism) is identified as a patient with an increased risk of progression of AMD (e.g. intermediate or advanced AMD such as wet (neovascular/exudative) AMD or geographic atrophy). In some embodiments, increased risk of progression of AMD includes progression from early AMD to intermediate AMD and intermediate to advanced AMD. In some embodiments, the risk allele is the minor allele of a selected SNP. In some embodiments, the risk allele is the major allele of a selected SNP. In some embodiments, increased risk of progression of AMD includes progression from early to more advanced disease in each of the AMD stages (includes early AMD, intermediate AMD and advanced AMD) wherein early AMD is characterized by multiple small (<63 μm), or ≥1 intermediate drusen (≥63 μm and <125 μm); intermediate AMD is characterized by many intermediate or ≥1 large drusen (≥125 μm) often accompanied by hyper- or hypopigmentation of the retinal pigment epithelium; and advanced AMD is characterized by geographic atrophy (GA) or neovascular (wet) AMD). In some embodiments, the risk allele may be a complement factor I (CFI) risk allele, a complement factor H(CFH) risk allele, a complement component 2 (C2) risk allele, a complement factor B (CFB) risk allele and/or a complement component 3 (C3) risk allele. In some embodiments, the CFI risk allele is the rs4698775:G allele, or equivalent allele thereof, or comprises a G at the selected SNP rs4698775, or comprises an alternate SNP in linkage disequilibrium to rs4698775. In some embodiments, the alternate SNP comprises a minor allele or the allele which resides on the same haplotype of the risk allele of the selected SNP rs4698775. In some embodiments, the CFI risk allele is the rs17440077 G: allele, or equivalent allele thereof, or comprises a G at the selected SNP rs17440077, or comprises an alternate SNP in linkage disequilibrium to rs17440077. In some embodiments, the alternate SNP comprises a minor allele or the allele which resides on the same haplotype of the risk allele of the selected SNP rs17440077. In some embodiments, the CFH risk allele is the rs10737680:A allele, or equivalent allele thereof, or comprises an A at the SNP rs10737680, or comprises an alternate SNP in linkage disequilibrium to rs10737680. In some embodiments, the alternate SNP comprises a minor allele or the allele which resides on the same haplotype of the risk allele of the selected SNP rs10737680. In some embodiments, the CFH risk allele is the rs1329428:G allele, or equivalent allele thereof, or comprises a G at the SNP rs1329428, or comprises an alternate SNP in linkage disequilibrium to rs1329428. In some embodiments, the alternate SNP comprises a minor allele or the allele which resides on the same haplotype of the risk allele of the selected SNP rs1329428. In some embodiments, the C2 risk allele is the rs429608:G allele, or equivalent allele thereof, or comprises a G at the SNP rs429608 or comprises an alternate SNP in linkage disequilibrium to rs429608. In some embodiments, the alternate SNP comprises a minor allele or the allele which resides on the same haplotype of the risk allele of the selected SNP rs429608. In some embodiments, the CFB risk allele is the rs429608:G allele, or equivalent allele thereof, or comprises a G at SNP rs429608 or comprises an alternate SNP in linkage disequilibrium to rs429608. In some embodiments, the alternate SNP comprises a minor allele or the allele which resides on the same haplotype of the risk allele of the selected SNP rs429608. In some embodiments, the C3 risk allele is the rs2230199:G allele, or equivalent allele thereof, or comprises a G at the SNP rs2230199 or comprises an alternate SNP in linkage disequilibrium to rs2230199. In some embodiments, the alternate SNP comprises a minor allele or the allele which resides on the same haplotype of the risk allele of the selected SNP rs2230199. In some embodiments, the linkage disequilibrium is a D' measure or an $r^2$ measure. In some embodiments, the D' measure between the selected SNP and the alternate SNP is ≥0.60. In some embodiments, the D' measure between the selected SNP and the alternate SNP is ≥0.70, 0.80 or 0.90. In some embodiments, the D' measure between the selected SNP and the alternate SNP is 1.0. In some embodiments, the $r^2$ measure between the selected SNP and the alternate SNP is ≥0.60. In some embodiments the $r^2$ measure between the selected SNP and the alternate SNP is ≥0.70, 0.80 or 0.90. In some embodiments, the $r^2$ measure between the selected SNP and the alternate SNP is 1.0. In some embodiments, the alternate SNP is a SNP designated in Tables 4-7. In some embodiments, the SNP rs4698775 is located at position 110590479 on human chromosome 4 (Genome Reference Consortium GRCh37; UCSC Genome HG19 Assembly; February 2009) and the G allele changes the nucleotide sequence from T to G. In some embodiments, the SNP rs17440077 is located at position 110537567 on human chromosome 4 (Genome Reference Consortium GRCh37; UCSC Genome HG19 Assembly; February 2009) and the G allele changes the nucleotide sequence from A to G. In some embodiments, the SNP rs10737680 is located at position 196679455 on human chromosome 1 (Genome Reference Consortium GRCh37; UCSC Genome HG19 Assembly; February 2009) and the A allele changes the nucleotide sequence form C to A. In some embodiments, the SNP rs1329428 is located at position 196702810 on human chromosome 1 (Genome Reference Consortium GRCh37; UCSC Genome HG19 Assembly; February 2009) and the G allele changes the nucleotide sequence from A to G. In some embodiments, the SNP rs429608 is located at position 31930462 on human chromosome 6 (Genome Reference Consortium GRCh37; UCSC Genome HG19 Assembly; February 2009) and the G allele changes the nucleotide sequence from A to G. In some embodiments, the SNP rs2230199 is located at position 6718387 on human chromosome 19 (Genome Reference Consortium GRCh37; UCSC Genome HG19 Assembly; February 2009) and the G allele changes the nucleotide sequence from C to G and the encoded amino acid from an arginine to glycine. In some embodiments, the alternate SNP is located on human chromosome 4 between SEC24B gene and EGF gene (for rs4698775) (Genome Reference Consortium GRCh37; UCSC Genome HG19 Assembly; February 2009), human chromosome 4 between SEC24B gene and EGF gene (Genome Reference Consortium GRCh37; UCSC Genome HG19 Assembly; February 2009) (for rs17440077), human chromosome 1 between KCNT2 gene and LHX9 gene (Genome Reference Consortium GRCh37; UCSC Genome HG19 Assembly; February 2009) (for rs10737680), human chromosome 1 between KCNT2 gene and LHX9 gene (Genome Reference Consortium GRCh37; UCSC Genome HG19 Assembly; February 2009) (for rs1329428), human chromosome 6 between SLC44A4 gene and TNXB gene (Genome Reference Consortium GRCh37; UCSC Genome HG19 Assembly; February 2009) (for rs429608), human chromosome 19 between TNFSF14 gene and VAV1 gene (Genome Reference Consortium GRCh37; UCSC Genome HG19 Assembly; February 2009) (for rs2230199). In some embodiments, the alternate SNP is located within 500,000 base pairs upstream and downstream of the selected SNP. In some embodiments, the alternate SNP is located within 500,000 base pairs upstream or downstream of the selected SNP. In some embodiments, the patient is determined to carry a CFI risk allele and/or a CFH risk allele and/or a C2 risk allele and/or a CFB risk allele and/or a C3 risk allele. In some embodiments, the patient is determined to carry 1, 2, 3, 4, 5, 6, 7, 8, 9, 10, etc. AMD risk alleles. In some embodiments, presence of a risk allele in a patient comprises determining the identity of the nucleotide at the polymorphism from nucleic acid provided from a sample from a patient. In some embodiments, the nucleic acid sample comprises DNA. In some embodiments, the nucleic acid sample comprises RNA. In some embodiments, the nucleic acid sample is amplified. In some embodiments, the nucleic acid sample is amplified by a polymerase chain reaction. In some embodiments, the polymorphism is detected by polymerase chain reaction or sequencing. In some embodiments, the polymorphism is detected by amplification of a target region containing at least one polymorphism, and hybridization with at least one sequence-specific oligonucleotide that hybridizes under stringent conditions to at least one polymorphism and detecting the hybridization. In some embodiments, the polymorphism is detected by a technique selected from the group consisting of scanning probe and nanopore DNA sequencing, pyrosequencing, Denaturing Gradient Gel Electrophoresis (DGGE), Temporal Temperature Gradient Electrophoresis (TTGE), Zn(II)-cyclen polyacrylamide gel electrophoresis, homogeneous fluorescent PCR-based single nucleotide polymorphism analysis, phosphate-affinity polyacrylamide gel electrophoresis, high-throughput SNP genotyping platforms, molecular beacons, 5' nuclease reaction, Taqman assay, MassArray (single base primer extension coupled with matrix-assisted laser desorption/ionization time-of-flight mass spectrometry), trityl mass tags, genotyping platforms (such as the Invader Assay®), single base primer extension (SBE) assays, PCR amplification (e.g. PCR amplification on magnetic nanoparticles (MNPs), restriction enzyme analysis of PCR products (RFLP methods), allele-specific PCR, multiple primer extension (MPEX), and isothermal smart amplification. In some embodiments, the sample is any biological sample from which genomic DNA may be isolated, for example, but not to be limited to a tissue sample, a sample of saliva, a cheek swab sample, blood, or other biological fluids that contain genomic DNA. In some embodiments, the identity of the nucleotide at the polymorphism in a patient is determined via genotyping. In some embodiments the genotyping is performed by PCR analysis, sequence analysis or LCR analysis. In some embodiments, the patient is identified as a patient with increased risk of progression of AMD (e.g. intermediate or advanced AMD such as wet (neovascular/exudative) AMD or geographic atrophy) when at least one allele comprising a nucleotide selected from the group consisting of a G nucleotide at the SNP rs4698775 is present, a G nucleotide at the SNP rs17440077 is present, an A nucleotide at the SNP rs10737680 is present, a G nucleotide at the SNP rs1329428 is present, a G nucleotide at the SNP rs429608 is present or the G nucleotide at the SNP rs2230199 is present. The patient is identified as being at increased risk of progressing to more advanced AMD if the patient has one or two copies of the G allele at rs4698775 or rs17440077 associated with CFI, or equivalent allele thereof, at rs1329428 associated with CFH, or equivalent allele thereof, at rs429608 associated with C2/CFB, or equivalent allele thereof, or at rs2230199 associated with C3, or equivalent allele thereof or one or two copies of the A allele at rs1329428 associated with CFH, or equivalent allele thereof. The patient is identified as being at decreased risk of progressing to more advanced AMD if the patient does not have one or two copies of the G allele at rs4698775 associated with CFI, or equivalent allele thereof, at rs1329428 associated with CFH, or equivalent allele thereof, at rs429608 associated with C2/CFB, or equivalent allele thereof, or at rs2230199 associated with C3, or equivalent allele thereof or one or two copies of the A allele at rs10737680 associated with CFH, or equivalent allele thereof.

The present invention involves, at least in part, a method of treating a degenerative disease (e.g. AMD) in a patient with an anti-factor D antibody, or antigen-binding fragment thereof. In one aspect, the invention involves methods and compositions for treating various degenerative disorders (e.g., age-related macular degeneration) with a complement inhibitor. In one embodiment, the degenerative disease is an ocular degenerative disease. In one embodiment, the ocular degenerative disease is age-related macular degeneration. In any of the embodiments disclosed herein, a complement inhibitor is an anti-factor D antibody, or antigen-binding fragment thereof. In some embodiments, the antibody is lampalizumab. Accordingly, one embodiment of the invention provides methods of treating age-related macular degeneration in a patient, the method comprising administering an effective amount of an anti-factor D antibody, or antigen-binding fragment thereof, to a patient diagnosed with age-related macular degeneration, wherein the patient carries one or more risk alleles for age-related macular degeneration (e.g. AMD-associated polymorphism). In some embodiments, the risk allele is the minor allele of a selected SNP. In some embodiments, the risk allele is the major allele of a selected SNP. In some embodiments, the risk allele may be a CFI risk allele, a CFH risk allele, a C2 risk allele, a CFB risk allele and/or a C3 risk allele. In some embodiments, the risk allele is a CFI risk allele. In some embodiments, the CFI risk allele is the rs4698775:G allele, or equivalent allele thereof, or comprises a G at the selected SNP rs4698775, or comprises an alternate SNP in linkage disequilibrium to rs4698775. In some embodiments, the alternate SNP comprises a minor allele or the allele which resides on the same haplotype of the risk allele of the selected SNP rs4698775. In some embodiments, the CFI risk allele is the rs17440077 G: allele, or equivalent allele thereof, or comprises a G at the selected SNP rs17440077, or comprises an alternate SNP in linkage disequilibrium to rs17440077. In some embodiments, the alternate SNP comprises a minor allele or the allele which resides on the same haplotype of the risk allele of the selected SNP rs17440077. In some embodiments, the CFH risk allele is the rs10737680:A allele, or equivalent allele thereof, or comprises an A at the selected SNP rs10737680, or comprises an alternate SNP in linkage disequilibrium to rs10737680. In some embodiments, the alternate SNP comprises a minor allele or the allele which resides on the same haplotype of the risk allele of the selected SNP rs10737680. In some embodiments, the CFH risk allele is the rs1329428:G allele, or equivalent allele thereof, or comprises a G at the SNP rs1329428, or comprises an alternate SNP in linkage disequilibrium to rs1329428. In some embodiments, the alternate SNP comprises a minor allele or the allele which resides on the same haplotype of the risk allele of the selected SNP rs1329428. In some embodiments, the C2 risk allele is the rs429608:G allele, or equivalent allele thereof, or comprises a G at the selected SNP rs429608, or comprises an alternate SNP in linkage disequilibrium to rs429608. In some embodiments, the alternate SNP comprises a minor allele or the allele which resides on the same haplotype of the risk allele of the selected SNP rs429608. In some embodiments, the CFB risk allele is the rs429608:G allele, or equivalent allele thereof, or comprises a G at the selected SNP rs429608, or comprises an alternate SNP in linkage disequilibrium to rs429608. In some embodiments, the alternate SNP comprises a minor allele or the allele which resides on the same haplotype of the risk allele of the selected SNP rs429608. In some embodiments, the C3 risk allele is the rs2230199:G allele, or equivalent allele thereof, or comprises a G at the selected SNP rs2230199 or comprises an alternate SNP in linkage disequilibrium to rs2230199. In some embodiments, the alternate SNP comprises a minor allele or the allele which resides on the same haplotype of the risk allele of the selected SNP rs2230199. In some embodiments, the linkage disequilibrium is a D' measure or an $r^2$ measure. In some embodiments, the D' measure between the selected SNP and the alternate SNP is ≥0.60. In some embodiments, the D' measure between the selected SNP and the alternate SNP is ≥0.70, 0.80 or 0.90. In some embodiments, the D' measure between the selected SNP and the alternate SNP is 1.0. In some embodiments, the $r^2$ measure between the selected SNP and the alternate SNP is ≥0.60. In some embodiments the $r^2$ measure between the selected SNP and the alternate SNP is ≥0.70, 0.80 or 0.90. In some embodiments, the $r^2$ measure between the selected SNP and the alternate SNP is 1.0. In some embodiments, the alternate SNP is a SNP designated in Tables 4-7. In some embodiments, the SNP rs4698775 is located at position 110590479 on human chromosome 4 (Genome Reference Consortium GRCh37; UCSC Genome HG19 Assembly; February 2009). The G allele changes the nucleotide sequence from T to G. In some embodiments, the SNP rs17440077 is located at position 110537567 on human chromosome 4 (Genome Reference Consortium GRCh37; UCSC Genome HG19 Assembly; February 2009). The G allele changes the nucleotide sequence from A to G. In some embodiments, the SNP rs10737680 is located at position 196679455 on human chromosome 1 (Genome Reference Consortium GRCh37; UCSC Genome HG19 Assembly; February 2009). The A allele changes the nucleotide sequence form C to A. In some embodiments, the SNP rs1329428 is located at position 196702810 on human chromosome 1 (Genome Reference Consortium GRCh37; UCSC Genome HG19 Assembly; February 2009). The G allele changes the nucleotide sequence from A to G. In some embodiments, the SNP rs429608 is located at position 31930462 on human chromosome 6 (Genome Reference Consortium GRCh37; UCSC Genome HG19 Assembly; February 2009). The G allele changes the nucleotide sequence from A to G. In some embodiments, the SNP rs2230199 is located at position 6718387 on human chromosome 19 (Genome Reference Consortium GRCh37; UCSC Genome HG19 Assembly; February 2009). The G allele changes the nucleotide sequence from C to G and the encoded amino acid from arginine to glycine In some embodiments, the alternate SNP is located on human chromosome 4 between SEC24B gene and EGF gene (for rs4698775) (Genome Reference Consortium GRCh37; UCSC Genome HG19 Assembly; February 2009), human chromosome 4 between SEC24B gene and EGF gene (Genome Reference Consortium GRCh37; UCSC Genome HG19 Assembly; February 2009) (for rs17440077), human chromosome 1 between KCNT2 gene and LHX9 gene (Genome Reference Consortium GRCh37; UCSC Genome HG19 Assembly; February 2009) (for rs10737680), human chromosome 1 between KCNT2 gene and LHX9 gene (Genome Reference Consortium GRCh37; UCSC Genome HG19 Assembly; February 2009) (for rs1329428), human chromosome 6 between SLC44A4 gene and TNXB gene (Genome Reference Consortium GRCh37; UCSC Genome HG19 Assembly; February 2009) (for rs429608), human chromosome 19 between TNFSF14 gene and VAV1 gene (Genome Reference Consortium GRCh37; UCSC Genome HG19 Assembly; February 2009) (for rs2230199). In some embodiments, the alternate SNP is located within 500,000 base pairs upstream and downstream of the selected SNP. In some embodiments, the alternate SNP is located within 500,000 base pairs upstream or downstream of the selected SNP In some embodiments, the patient is determined to carry a CFI risk allele and/or a CFH risk allele and/or a C2 risk allele and/or a CFB risk allele and/or a C3 risk allele. In some embodiments, the patient is determined to carry 1, 2, 3, 4, 5, 6, 7, 8, 9, 10, etc. AMD risk alleles. In some embodiments, presence of a risk allele in a patient comprises determining the identity of the nucleotide at the polymorphism from nucleic acid provided from a sample from a patient. In some embodiments, the nucleic acid sample comprises DNA. In some embodiments, the nucleic acid sample comprises RNA. In some embodiments, the nucleic acid sample is amplified. In some embodiments, the nucleic acid sample is amplified by a polymerase chain reaction. In some embodiments, the polymorphism is detected by polymerase chain reaction or sequencing. In some embodiments, the polymorphism is detected by amplification of a target region containing at least one polymorphism, and hybridization with at least one sequence-specific oligonucleotide that hybridizes under stringent conditions to at least one polymorphism and detecting the hybridization. In some embodiments, the polymorphism is detected by a technique selected from the group consisting of scanning probe and nanopore DNA sequencing, pyrosequencing, Denaturing Gradient Gel Electrophoresis (DGGE), Temporal Temperature Gradient Electrophoresis (TTGE), Zn(II)-cyclen polyacrylamide gel electrophoresis, homogeneous fluorescent PCR-based single nucleotide polymorphism analysis, phosphate-affinity polyacrylamide gel electrophoresis, high-throughput SNP genotyping platforms, molecular beacons, 5' nuclease reaction, Taqman assay, MassArray (single base primer extension coupled with matrix-assisted laser desorption/ionization time-of-flight mass spectrometry), trityl mass tags, genotyping platforms (such as the Invader Assay®), single base primer extension (SBE) assays, PCR amplification (e.g. PCR amplification on magnetic nanoparticles (MNPs), restriction enzyme analysis of PCR products (RFLP methods), allele-specific PCR, multiple primer extension (MPEX), and isothermal smart amplification. In some embodiments, the sample is any biological sample from which genomic DNA may be isolated, for example, but not to be limited to a tissue sample, a sample of saliva, a cheek swab sample, blood, or other biological fluids that contain genomic DNA. In some embodiments, the identity of the nucleotide at the polymorphism in a patient is determined via genotyping. In some embodiments the genotyping is performed by PCR analysis, sequence analysis or LCR analysis. In some embodiments, the patient is identified as having an increased at risk for AMD progression and more likely to respond to a therapy comprising an anti-factor D antibody, or antigen-binding fragment thereof, when at least one allele comprising a nucleotide selected from the group consisting of a G nucleotide at the SNP rs4698775 is present, a G nucleotide at the SNP rs17440077 is present, an A nucleotide at the SNP rs10737680 is present, a G nucleotide at the SNP rs1329428 is present, a G nucleotide at the SNP rs429608 is present or the G nucleotide at the SNP rs2230199 is present. The patient is identified as having an increased risk for AMD progression and more likely to respond to a treatment comprising an anti-factor D antibody, or antigen-binding fragment thereof, if the patient has one or two copies of the G allele at rs4698775 or rs17440077 associated with CFI, or equivalent allele thereof, at rs1329428 associated with CFH, or equivalent allele thereof, at rs429608 associated with C2/CFB, or equivalent allele thereof, or at rs2230199 associated with C3, or equivalent allele thereof or one or two copies of the A allele at rs10737680 associated with CFH, or equivalent allele thereof. The patient is identified as having a decreased risk of progressing to more advanced AMD and less likely to respond to a treatment comprising an anti-factor D antibody, or antigen-binding fragment thereof, if the patient does not have one or two copies of the G allele at rs4698775 associated with CFI, or equivalent allele thereof, at rs1329428 associated with CFH, or equivalent allele thereof, at rs429608 associated with C2/CFB, or equivalent allele thereof, or at rs2230199 associated with C3, or equivalent allele thereof or one or two copies of the A allele at rs10737680 associated with CFH, or equivalent allele thereof. In one embodiment, the study eye in the patient has a BCVA between 20/2.5 and 20/400. In one embodiment, the study eye in the patient has a BCVA between 20/25 and 20/100. In one embodiment, the study eye in the patient has a BCVA between 20/50 and 20/400. In one embodiment, the study eye in the patient has a BCVA between 20/50 and 20/100. In one embodiment, the study eye in the patient has a BCVA better than 20/25 or worse than 20/400. In one embodiment, the BCVA was determined using ETDRS charts. In some embodiments, the antibody or antigen-binding fragment thereof is administered intravitreally. In some embodiments, the age-related macular degeneration is dry AMD. In some embodiments, the dry AMD is advanced dry AMD. In some embodiments, the advanced dry AMD is geographic atrophy. In some embodiments, the patient has a reduced mean change in geographic atrophy (GA) area following administration of the antibody as compared to control patients that do not receive the antibody treatment. In some embodiments, the mean change in GA area is determined by measurements of GA area via standard imaging methods (e.g. fundus autofluorescence (FAF) or color fundus photography (CFP). In some embodiments, the age-related macular degeneration is early AMD or intermediate AMD. In some embodiments, the patient with early AMD or intermediate AMD has a reduction or delay in appearance of clinical signs (e.g. may include measuring the number and size of drusen (for early and intermediate AMD) and monitoring hypo- and hyperpigmentation associated with drusen (for intermediate AMD)). In some embodiments, the methods further comprise administering a second medicament to the subject. In some embodiments, the second medicament is VEGF inhibitor.

A further embodiment of the invention provides methods of identifying a degenerative disease patient (e.g. AMD patient) who may benefit from and/or respond to treatment with an anti-factor D antibody, the method comprising determining the genotype of a patient, wherein a patient who is determined to carry a risk allele is identified as a patient who may benefit from treatment with an anti-factor D antibody or antigen-binding fragment thereof. In some embodiments, the method further comprises selecting the therapy comprising an anti-factor D antibody, or antigen-binding fragment thereof. In some embodiments, the antibody is lampalizumab. In one embodiment, the degenerative disease is an ocular degenerative disease. In one embodiment, the ocular degenerative disease is age-related macular degeneration. In some embodiments, the risk allele is the minor allele of a selected SNP. In some embodiments, the risk allele is the major allele of a selected SNP. In some embodiments, the risk allele (e.g. AMD-associated polymorphism) may be a CFI risk allele, a CFH risk allele, a C2 risk allele, a CFB risk allele and/or a C3 risk allele. In some embodiments, the risk allele is a CFI risk allele. In some embodiments, the CFI allele is the rs4698775:G allele, or equivalent allele thereof or comprises a G at the selected SNP rs4698775, or comprises an alternate SNP in linkage disequilibrium to rs4698775. In some embodiments, the alternate SNP comprises a minor allele or the allele which resides on the same haplotype of the risk allele of the selected SNP rs4698775. In some embodiments, the CFI allele is the rs17440077:G allele, or equivalent allele thereof or comprises a G at the selected SNP rs17440077, or comprises an alternate SNP in linkage disequilibrium to rs17440077. In some embodiments, the alternate SNP comprises a minor allele or the allele which resides on the same haplotype of the risk allele of the selected SNP rs17440077. In some embodiments, the CFH risk allele is the rs10737680:A allele, or equivalent allele thereof, or comprises an A at the selected SNP rs10737680, or comprises an alternate SNP in linkage disequilibrium to rs10737680. In some embodiments, the alternate SNP comprises a minor allele or the allele which resides on the same haplotype of the risk allele of the selected SNP rs10737680. In some embodiments, the CFH risk allele is the rs1329428:G allele, or equivalent allele thereof, or comprises a G at the selected SNP rs1329428, or comprises an alternate SNP in linkage disequilibrium to rs1329428. In some embodiments, the alternate SNP comprises a minor allele or the allele which resides on the same haplotype of the risk allele of the selected SNP rs1329428. In some embodiments, the C2 risk allele is the rs429608:G allele, or equivalent allele thereof, or comprises a G at the selected SNP rs429608, or comprises an alternate SNP in linkage disequilibrium to rs429608. In some embodiments, the alternate SNP comprises a minor allele or the allele which resides on the same haplotype of the risk allele of the selected SNP rs429608. In some embodiments, the CFB risk allele is the rs429608:G allele, or equivalent allele thereof, or comprises a G at the selected SNP rs429608, or comprises an alternate SNP in linkage disequilibrium to rs429608. In some embodiments, the alternate SNP comprises a minor allele or the allele which resides on the same haplotype of the risk allele of the selected SNP rs429608. In some embodiments, the C3 risk allele is the rs2230199:G allele, or equivalent allele thereof, or comprises a G at the selected SNP rs2230199 or comprises an alternate SNP in linkage disequilibrium to rs2230199. In some embodiments, the alternate SNP comprises a minor allele or the allele which resides on the same haplotype of the risk allele of the selected SNP rs2230199. In some embodiments, the linkage disequilibrium is a D' measure or an $r^2$ measure. In some embodiments, the D' measure between the selected SNP and the alternate SNP is ≥0.60. In some embodiments, the D' measure between the selected SNP and the alternate SNP is ≥0.70, 0.80 or 0.90. In some embodiments, the D' measure between the selected SNP and the alternate SNP is 1.0. In some embodiments, the $r^2$ measure between the selected SNP and the alternate SNP is ≥0.60. In some embodiments the $r^2$ measure between the selected SNP and the alternate SNP is ≥0.70, 0.80 or 0.90. In some embodiments, the $r^2$ measure between the selected SNP and the alternate SNP is 1.0. In some embodiments, the alternate SNP is a SNP designated in Tables 4-7. In some embodiments, the SNP rs4698775 is located at position 110590479 on human chromosome 4 (Genome Reference Consortium GRCh37; UCSC Genome HG19 Assembly; February 2009) and he G allele changes the nucleotide sequence from T to G. In some embodiments, the SNP rs17440077 is located at position 110537567 on human chromosome 4 (Genome Reference Consortium GRCh37; UCSC Genome HG19 Assembly; February 2009) and the G allele changes the nucleotide sequence from A to G. In some embodiments, the SNP rs10737680 is located at position 196679455 on human chromosome 1 (Genome Reference Consortium GRCh37; UCSC Genome HG19 Assembly; February 2009) and the A allele changes the nucleotide sequence form C to A. In some embodiments, the SNP rs1329428 is located at position 196702810 on human chromosome 1 (Genome Reference Consortium GRCh37; UCSC Genome HG19 Assembly; February 2009) and the G allele changes the nucleotide sequence from A to G. In some embodiments, the SNP rs429608 is located at position 31930462 on human chromosome 6 (Genome Reference Consortium GRCh37; UCSC Genome HG19 Assembly; February 2009) and the G allele changes the nucleotide sequence from A to G. In some embodiments, the SNP rs2230199 is located at position 6718387 on human chromosome 19 (Genome Reference Consortium GRCh37; UCSC Genome HG19 Assembly; February 2009) and the G allele changes the nucleotide sequence from C to G and the encoded amino acid from arginine to glycine. In some embodiments, the alternate SNP is located on human chromosome 4 between SEC24B gene and EGF gene (for rs4698775) (Genome Reference Consortium GRCh37; UCSC Genome HG19 Assembly; February 2009), human chromosome 4 between SEC24B gene and EGF gene (Genome Reference Consortium GRCh37; UCSC Genome HG19 Assembly; February 2009) (for rs17440077), human chromosome 1 between KCNT2 gene and LHX9 gene (Genome Reference Consortium GRCh37; UCSC Genome HG19 Assembly; February 2009) (for rs10737680), human chromosome 1 between KCNT2 gene and LHX9 gene (Genome Reference Consortium GRCh37; UCSC Genome HG19 Assembly; February 2009) (for rs1329428), human chromosome 6 between SLC44A4 gene and TNXB gene (Genome Reference Consortium GRCh37; UCSC Genome HG19 Assembly; February 2009) (for rs429608), human chromosome 19 between TNFSF14 gene and VAV1 gene (Genome Reference Consortium GRCh37; UCSC Genome HG19 Assembly; February 2009) (for rs2230199). In some embodiments, the alternate SNP is located within 500,000 base pairs upstream or downstream of the selected SNP. In some embodiments, the patient is determined to carry a CFI risk allele and/or a CFH risk allele and/or a C2 risk allele and/or a CFB risk allele and/or a C3 risk allele. In some embodiments, the patient is determined to carry 1, 2, 3, 4, 5, 6, 7, 8, 9, 10, etc. AMD risk alleles. In some embodiments, presence of a risk allele in a patient comprises determining the identity of the nucleotide at the polymorphism from nucleic acid provided from a sample from a patient. In some embodiments, the nucleic acid sample comprises DNA. In some embodiments, the nucleic acid sample comprises RNA. In some embodiments, the nucleic acid sample is amplified. In some embodiments, the nucleic acid sample is amplified by a polymerase chain reaction. In some embodiments, the polymorphism is detected by polymerase chain reaction or sequencing. In some embodiments, the polymorphism is detected by amplification of a target region containing at least one polymorphism, and hybridization with at least one sequence-specific oligonucleotide that hybridizes under stringent conditions to at least one polymorphism and detecting the hybridization. In some embodiments, the polymorphism is detected by a technique selected from the group consisting of scanning probe and nanopore DNA sequencing, pyrosequencing, Denaturing Gradient Gel Electrophoresis (DGGE), Temporal Temperature Gradient Electrophoresis (TTGE), Zn(II)-cyclen polyacrylamide gel electrophoresis, homogeneous fluorescent PCR-based single nucleotide polymorphism analysis, phosphate-affinity polyacrylamide gel electrophoresis, high-throughput SNP genotyping platforms, molecular beacons, 5' nuclease reaction, Taqman assay, MassArray (single base primer extension coupled with matrix-assisted laser desorption/ionization time-of-flight mass spectrometry), trityl mass tags, genotyping platforms (such as the Invader Assay®), single base primer extension (SBE) assays, PCR amplification (e.g. PCR amplification on magnetic nanoparticles (MNPs), restriction enzyme analysis of PCR products (RFLP methods), allele-specific PCR, multiple primer extension (MPEX), and isothermal smart amplification. In some embodiments, the sample is any biological sample from which genomic DNA may be isolated, for example, but not to be limited to a tissue sample, a sample of saliva, a cheek swab sample, blood, or other biological fluids that contain genomic DNA. In some embodiments, the sample comprises DNA. In some embodiments, the sample comprises RNA. In some embodiments, the identity of the nucleotide at the polymorphism in a patient is determined via genotyping. In some embodiments the genotyping is performed by PCR analysis, sequence analysis or LCR analysis. In some embodiments, the patient is identified as having an increased risk for AMD progression and is more likely to benefit from and/or respond to treatment comprising an anti-factor D antibody, or antigen-binding fragment thereof when at least one allele comprising a nucleotide selected from the group consisting of a G nucleotide at the SNP rs4698775 is present, a G nucleotide at the SNP rs17440077 is present, an A nucleotide at the SNP rs10737680 is present, a G nucleotide at the SNP rs1329428 is present, a G nucleotide at the SNP rs429608 is present or the G nucleotide at the SNP rs2230199 is present. The patient is identified as being at increased risk of AMD progression if the patient has one or two copies of the G allele at rs4698775 associated with CFI, or equivalent allele thereof, at rs1329428 associated with CFH, or equivalent allele thereof, at rs429608 associated with C2/CFB, or equivalent allele thereof, or at rs2230199 associated with C3, or equivalent allele thereof or has one or two copies of the A allele at rs10737680 associated with CFH, or equivalent allele thereof. The patient is identified as having a decreased risk of progressing to more advanced AMD if the patient does not have one or two copies of the G allele at rs4698775 associated with CFI, or equivalent allele thereof, at rs1329428 associated with CFH, or equivalent allele thereof, at rs429608 associated with C2/CFB, or equivalent allele thereof, or at rs2230199 associated with C3, or equivalent allele thereof or one or two copies of the A allele at rs10737680 associated with CFH, or equivalent allele thereof. In one embodiment, the study eye in the patient has a BCVA between 20/25 and 20/400. In one embodiment, the study eye in the patient has a BCVA between 20/25 and 20/100. In one embodiment, the study eye in the patient has a BCVA between 20/50 and 20/400. In one embodiment, the study eye in the patient has a BC VA between 20/50 and 20/100. In one embodiment, the study eye in the patient has a BC VA better than 20/25 or worse than 20/400. In one embodiment, the BCVA was determined using ETDRS charts. In some embodiments, the antibody or antigen-binding fragment thereof is administered intravitreally. In some embodiments, the age-related macular degeneration is dry AMD. In some embodiments, the dry AMD is advanced dry AMD. In some embodiments, the advanced dry AMD is geographic atrophy. In some embodiments, the age-related macular degeneration is early AMD or intermediate AMD. In some embodiments, the patient with early AMD or intermediate AMD has a reduction or delay in appearance of clinical signs (e.g. may include measuring the number and size of drusen (for early and intermediate AMD) and monitoring hypo- and hyperpigmentation associated with drusen (for intermediate AMD)).

Another embodiment of the invention provides methods of optimizing therapeutic efficacy for treatment of a degenerative disease (e.g. AMD), the method comprising determining the genotype of a patient, wherein a patient who is determined to carry a risk allele (e.g. AMD-associated polymorphism) is more likely to respond to treatment with the anti-factor D antibody, or antigen-binding fragment thereof or antigen-binding fragment thereof. In one embodiment, the degenerative disease is an ocular degenerative disease. In one embodiment, the ocular degenerative disease is age-related macular degeneration. In some embodiments, the antibody is lampalizumab. In some embodiments, the risk allele is the minor allele of a selected SNP. In some embodiments, the risk allele is the major allele of a selected SNP. In some embodiments, the risk allele may be a CFI risk allele, a CFH risk allele, a C2 risk allele, a CFB allele and/or a C3 risk allele. In some embodiments, the risk allele is a CFI risk allele. In some embodiments, the CFI risk allele is the rs4698775:G allele, or equivalent allele thereof or comprises a G at the selected SNP rs4698775, or comprises an alternate SNP in linkage disequilibrium to rs4698775. In some embodiments, the alternate SNP comprises a minor allele or the allele which resides on the same haplotype of the risk allele of the selected SNP rs4698775. In some embodiments, the CFI risk allele is the rs17440077:G allele, or equivalent allele thereof or comprises a G at the selected SNP rs17440077, or comprises an alternate SNP in linkage disequilibrium to rs17440077. In some embodiments, the alternate SNP comprises a minor allele or the allele which resides on the same haplotype of the risk allele of the selected SNP rs17440077. In some embodiments, the CFH risk allele is the rs10737680:A allele, or equivalent allele thereof, or comprises an A at the selected SNP rs10737680, or comprises an alternate SNP in linkage disequilibrium to rs10737680. In some embodiments, the alternate SNP comprises a minor allele or the allele which resides on the same haplotype of the risk allele of the selected SNP rs10737680. In some embodiments, the CFH risk allele is the rs1329428:G allele, or equivalent allele thereof, or comprises an G at the selected SNP rs1329428, or comprises an alternate SNP in linkage disequilibrium to rs1329428 In some embodiments, the alternate SNP comprises a minor allele or the allele which resides on the same haplotype of the risk allele of the selected SNP rs1329428. In some embodiments, the C2 risk allele is the rs429608:G allele, or equivalent allele thereof, or comprises a G at the selected SNP rs429608, or comprises an alternate SNP in linkage disequilibrium to rs429608. In some embodiments, the alternate SNP comprises a minor allele or the allele which resides on the same haplotype of the risk allele of the selected SNP rs429608. In some embodiments, the CFB risk allele is the rs429608:G allele, or equivalent allele thereof, or comprises a G at the selected SNP rs429608, or comprises an alternate SNP in linkage disequilibrium to rs429608. In some embodiments, the alternate SNP comprises a minor allele or the allele which resides on the same haplotype of the risk allele of the selected SNP rs429608. In some embodiments, the C3 risk allele is the rs2230199:G allele, or equivalent allele thereof, or comprises a G at the selected SNP rs2230199 or comprises an alternate SNP in linkage disequilibrium to rs2230199. In some embodiments, the alternate SNP comprises a minor allele or the allele which resides on the same haplotype of the risk allele of the selected SNP rs2230199. In some embodiments, the linkage disequilibrium is a D' measure or an $r^2$ measure. In some embodiments, the D' measure between the selected SNP and the alternate SNP is ≥0.60. In some embodiments, the D' measure between the selected SNP and the alternate SNP is ≥0.70, 0.80 or 0.90. In some embodiments, the D' measure between the selected SNP and the alternate SNP is 1.0. In some embodiments, the $r^2$ measure between the selected SNP and the alternate SNP is ≥0.60. In some embodiments the $r^2$ measure between the selected SNP and the alternate SNP is ≥0.70, 0.80 or 0.90. In some embodiments, the $r^2$ measure between the selected SNP and the alternate SNP is 1.0. In some embodiments, the alternate SNP is a SNP designated in Tables 4-7. In some embodiments, the SNP rs4698775 is located at position 110590479 on human chromosome 4 (Genome Reference Consortium GRCh37; UCSC Genome HG19 Assembly; February 2009) and the G allele changes the nucleotide sequence from T to G. In some embodiments, the SNP rs17440077 is located at position 110537567 on human chromosome 4 (Genome Reference Consortium GRCh37; UCSC Genome HG19 Assembly; February 2009) and the G allele changes the nucleotide sequence from A to G. In some embodiments, the SNP rs10737680 is located at position 196679455 on human chromosome 1 (Genome Reference Consortium GRCh37; UCSC Genome HG19 Assembly; February 2009) and the A allele changes the nucleotide sequence form C to A. In some embodiments, the SNP rs1329428 is located at position 196702810 on human chromosome 1 (Genome Reference Consortium GRCh37; UCSC Genome HG19 Assembly; February 2009) and the G allele changes the nucleotide sequence from A to G. In some embodiments, the SNP rs429608 is located at position 31930462 on human chromosome 6 (Genome Reference Consortium GRCh37; UCSC Genome HG19 Assembly; February 2009) and the G allele changes the nucleotide sequence from A to G. In some embodiments, the SNP rs2230199 is located at position 6718387 on human chromosome 19 (Genome Reference Consortium GRCh37; UCSC Genome HG19 Assembly; February 2009) and the G allele changes the nucleotide sequence from C to G and changes the encoded amino acid from arginine to glycine. In some embodiments, the alternate SNP is located on human chromosome 4 between SEC24B gene and EGF gene (for rs4698775) (Genome Reference Consortium GRCh37; UCSC Genome HG19 Assembly; February 2009), human chromosome 4 between SEC24B gene and EGF gene (Genome Reference Consortium GRCh37; UCSC Genome HG19 Assembly; February 2009) (for rs17440077), human chromosome 1 between KCNT2 gene and LHX9 gene (Genome Reference Consortium GRCh37; UCSC Genome HG19 Assembly; February 2009) (for rs10737680), human chromosome 1 between KCNT2 gene and LHX9 gene (Genome Reference Consortium GRCh37; UCSC Genome HG19 Assembly; February 2009) (for rs1329428), human chromosome 6 between SLC44A4 gene and TNXB gene (Genome Reference Consortium GRCh37; UCSC Genome HG19 Assembly; February 2009) (for rs429608), human chromosome 19 between TNFSF14 gene and VAV1 gene (Genome Reference Consortium GRCh37; UCSC Genome HG19 Assembly; February 2009) (for rs2230199). In some embodiments, the alternate SNP is located within 500,000 base pairs upstream or downstream of the selected SNP. In some embodiments, the alternate SNP is located within 500 base pairs upstream and downstream of the selected SNP In some embodiments, the patient is determined to carry a CFI risk allele and/or a CFH risk allele and/or a C2 risk allele and/or a CFB risk allele and/or a C3 risk allele. In some embodiments, the patient is determined to carry 1, 2, 3, 4, 5, 6, 7, 8, 9, 10, etc. AMD risk alleles. In some embodiments, presence of a risk allele in a patient comprises determining the identity of the nucleotide at the polymorphism nucleic acid provided from a sample from a patient. In some embodiments, the nucleic acid sample comprises DNA. In some embodiments, the nucleic acid sample comprises RNA. In some embodiments, the nucleic acid sample is amplified. In some embodiments, the nucleic acid sample is amplified by a polymerase chain reaction. In some embodiments, the polymorphism is detected by polymerase chain reaction or sequencing. In some embodiments, the polymorphism is detected by amplification of a target region containing at least one polymorphism, and hybridization with at least one sequence-specific oligonucleotide that hybridizes under stringent conditions to at least one polymorphism and detecting the hybridization. In some embodiments, the polymorphism is detected by a technique selected from the group consisting of scanning probe and nanopore DNA sequencing, pyrosequencing, Denaturing Gradient Gel Electrophoresis (DGGE), Temporal Temperature Gradient Electrophoresis (TTGE), Zn(II)-cyclen polyacrylamide gel electrophoresis, homogeneous fluorescent PCR-based single nucleotide polymorphism analysis, phosphate-affinity polyacrylamide gel electrophoresis, high-throughput SNP genotyping platforms, molecular beacons, 5' nuclease reaction, Taqman assay, MassArray (single base primer extension coupled with matrix-assisted laser desorption/ionization time-of-flight mass spectrometry), trityl mass tags, genotyping platforms (such as the Invader Assay®), single base primer extension (SBE) assays, PCR amplification (e.g. PCR amplification on magnetic nanoparticles (MNPs), restriction enzyme analysis of PCR products (RFLP methods), allele-specific PCR, multiple primer extension (MPEX), and isothermal smart amplification. In some embodiments, the sample is any biological sample from which genomic DNA may be isolated, for example, but not to be limited to a tissue sample, a sample of saliva, a cheek swab sample, blood, or other biological fluids that contain genomic DNA. In some embodiments, the sample comprises DNA. In some embodiments, the sample comprises RNA. In some embodiments, the identity of the nucleotide at the polymorphism in a patient is determined via genotyping. In some embodiments the genotyping is performed by PCR analysis, sequence analysis or LCR analysis. In some embodiments, the patient is identified as having an increased risk for AMD progression and is more likely to benefit from treatment comprising an anti-factor D antibody, or antigen-binding fragment thereof when at least one allele comprising a nucleotide selected from the group consisting of a G nucleotide at the SNP rs4698775 is present, a G nucleotide at the SNP rs17440077 is present, an A nucleotide at the SNP rs10737680 is present, a G nucleotide at the SNP rs1329428 is present, a G nucleotide at the SNP rs429608 is present or the G nucleotide at the SNP rs2230199 is present. The patient is identified as being at increased risk of AMD progression if the patient has one or two copies of the G allele at rs4698775 or rs17440077 associated with CFI, or equivalent allele thereof, at rs1329428 associated with CFH, or equivalent allele thereof, at rs429608 associated with C2/CFB, or equivalent allele thereof, or at rs2230199 associated with C3, or equivalent allele thereof or one or two copies of the A allele at rs10737680 associated with CFH, or equivalent allele thereof. In one embodiment, the study eye in the patient has a BCVA between 20/25 and 20/400. It one embodiment, the study eye in the patient has a BCVA between 20/25 and 20/100. In one embodiment, the study eye in the patient has a BCVA between 20/50 and 20/400. In one embodiment, the study eye in the patient has a BCVA between 20/50 and 20/100. In one embodiment, the study eye in the patient has a BCVA better than 20/25 or worse than 20/400. In one embodiment, the BCVA was determined using ETDRS charts. In some embodiments, the antibody or antigen-binding fragment thereof is administered intravitreally. In some embodiments, the age-related macular degeneration is dry AMD. In some embodiments, the dry AMD is advanced dry AMD. In some embodiments, the advanced dry AMD is geographic atrophy. In some embodiments, the patient has a reduced mean change in geographic atrophy (GA) area following administration of the antibody as compared to control patients that did not receive the antibody treatment. In some embodiments, the mean change in GA area is determined by measuring GA area via standard imaging methods (e.g. fundus autofluorescence (FAF) or color fundus photography (CFP). In some embodiments, the age-related macular degeneration is early AMD or intermediate AMD. In some embodiments, the patient with early AMD or intermediate AMD has a reduction or delay in appearance of clinical signs (e.g. may include measuring the number and size of drusen (for early and intermediate AMD) and monitoring hypo- and hyperpigmentation associated with drusen (for intermediate AMD)). In some embodiments, the methods further comprise administering a second medicament to the subject. In some embodiments, the second medicament is VEGF inhibitor.

Even another embodiment of the invention provides methods of predicting responsiveness of a degenerative disease (e.g. AMD) patient to treatment with an anti-factor D antibody or antigen-binding fragment thereof, the method comprising determining the genotype of the patient, wherein a patient who is determined to carry a risk allele is identified as a patient who has an increased risk for AMD progression (e.g. GA progression) and is more likely to respond to treatment with the anti-factor D antibody or antigen-binding fragment thereof. In one embodiment, the degenerative disease is an ocular degenerative disease. In one embodiment, the ocular degenerative disease is age-related macular degeneration. In some embodiments, the antibody is lampalizumab. In some embodiments, the risk allele is the minor allele of a selected SNP. In some embodiments, the risk allele is the major allele of a selected SNP. In some embodiments, the risk allele (e.g. AMD-associated polymorphism) may be a CFI risk allele, a CFH risk allele, a C2 risk allele, a CFB risk allele and/or a C3 risk allele. In some embodiments, the risk allele is a CFI risk allele. In some embodiments, the CFI risk allele is the rs4698775:G allele, or equivalent allele thereof or comprises a G at the selected SNP rs4698775, or comprises an alternate SNP in linkage disequilibrium to rs4698775. In some embodiments, the alternate SNP comprises a minor allele or the allele which resides on the same haplotype of the risk allele of the selected SNP rs4698775. In some embodiments, the CFI risk allele is the rs17440077:G allele, or equivalent allele thereof or comprises a G at the selected SNP rs17440077, or comprises an alternate SNP in linkage disequilibrium to rs17440077. In some embodiments, the alternate SNP comprises a minor allele or the allele which resides on the same haplotype of the risk allele of the selected SNP rs17440077. In some embodiments, the CFH risk allele is the rs10737680:A allele, or equivalent allele thereof, or comprises an A at the selected SNP rs10737680, or comprises an alternate SNP in linkage disequilibrium to rs10737680. In some embodiments, the alternate SNP comprises a minor allele or the allele which resides on the same haplotype of the risk allele of the selected SNP rs10737680. In some embodiments, the CFH risk allele is the rs1329428:G allele, or equivalent allele thereof, or comprises a G at the selected SNP rs1329428, or comprises an alternate SNP in linkage disequilibrium to rs1329428. In some embodiments, the alternate SNP comprises a minor allele or the allele which resides on the same haplotype of the risk allele of the selected SNP rs1329428. In some embodiments, the C2 risk allele is the rs429608:G allele, or equivalent allele thereof, or comprises a G at the selected SNP rs429608, or comprises an alternate SNP in linkage disequilibrium to rs429608. In some embodiments, the alternate SNP comprises a minor allele or the allele which resides on the same haplotype of the risk allele of the selected SNP rs429608. In some embodiments, the CFB risk allele is the rs429608:G allele, or equivalent allele thereof, or comprises a G at the selected SNP rs429608, or comprises an alternate SNP in linkage disequilibrium to rs429608. In some embodiments, the alternate SNP comprises a minor allele or the allele which resides on the same haplotype of the risk allele of the selected SNP rs429608. In some embodiments, the C3 risk allele is the rs2230199:G allele, or equivalent allele thereof, or comprises a G at the selected SNP rs2230199 or comprises an alternate SNP in linkage disequilibrium to rs2230199. In some embodiments, the alternate SNP comprises a minor allele or the allele which resides on the same haplotype of the risk allele of the selected SNP rs2230199. In some embodiments, the linkage disequilibrium is a D' measure or an $r^2$ measure. In some embodiments, the D' measure is between the selected SNP and the alternate SNP is ≥0.60. In some embodiments, the D' measure between the selected SNP and the alternate SNP is ≥0.70, 0.80, or 0.90. In some embodiments, the D' measure between the selected SNP and the alternate SNP is 1.0. In some embodiments, the $r^2$ measure is between the selected SNP and the alternate SNP is ≥0.60. In some embodiments, the $r^2$ measure between the selected SNP and the alternate SNP is ≥0.70, 0.80, or 0.90. In some embodiments, the $r^2$ measure between the selected SNP and the alternate SNP is 1.0. In some embodiments, the alternate SNP is a SNP designated in Tables 4-7. In some embodiments, the SNP rs4698775 is located at position 110590479 on human chromosome 4 (Genome Reference Consortium GRCh37; UCSC Genome HG19 Assembly; February 2009) and the G allele changes the nucleotide sequence from T to G. In some embodiments, the SNP rs17440077 is located at position 110537567 on human chromosome 4 (Genome Reference Consortium GRCh37; UCSC Genome HG19 Assembly; February 2009) and the G allele changes the nucleotide sequence from A to G. In some embodiments, the SNP rs10737680 is located at position 196679455 on human chromosome 1 (Genome Reference Consortium GRCh37; UCSC Genome HG19 Assembly; February 2009) and the A allele changes the nucleotide sequence form C to A. In some embodiments, the SNP rs1329428 is located at position 196702810 on human chromosome 1 (Genome Reference Consortium GRCh37; UCSC Genome HG19 Assembly; February 2009) and the G allele changes the nucleotide sequence from A to G. In some embodiments, the SNP rs429608 is located at position 31930462 on human chromosome 6 (Genome Reference Consortium GRCh37; UCSC Genome HG19 Assembly; February 2009) and the G allele changes the nucleotide sequence from A to G. In some embodiments, the SNP rs2230199 is located at position 6718387 on human chromosome 19 (Genome Reference Consortium GRCh37; UCSC Genome HG19 Assembly; February 2009) and the G allele changes the nucleotide sequence from C to G and changes the encoded amino acid from arginine to glycine. In some embodiments, the alternate SNP is located on human chromosome 4 between SEC24B gene and EGF gene (for rs4698775) (Genome Reference Consortium GRCh37; UCSC Genome HG19 Assembly; February 2009), human chromosome 4 between SEC24B gene and EGF gene (Genome Reference Consortium GRCh37; UCSC Genome HG19 Assembly; February 2009) (for rs17440077), human chromosome 1 between KCNT2 gene and LHX9 gene (Genome Reference Consortium GRCh37; UCSC Genome HG19 Assembly; February 2009) (for rs10737680), human chromosome 1 between KCNT2 gene and LHX9 gene (Genome Reference Consortium GRCh37; UCSC Genome HG19 Assembly; February 2009) (for rs1329428), human chromosome 6 between SLC44A4 gene and TNXB gene (Genome Reference Consortium GRCh37; UCSC Genome HG19 Assembly; February 2009) (for rs429608), human chromosome 19 between TNFSF14 gene and VAV1 gene (Genome Reference Consortium GRCh37; UCSC Genome HG19 Assembly; February 2009) (for rs2230199). In some embodiments, the alternate SNP is located within 500,000 base pairs upstream and downstream of the selected SNP. In some embodiments, the patient is determined to carry a CFI risk allele and/or a CFH risk allele and/or a C2 risk allele and/or a CFB risk allele and/or a C3 risk allele. In some embodiments, the patient is determined to carry 1, 2, 3, 4, 5, 6, 7, 8, 9, 10, etc. AMD risk alleles. In some embodiments, presence of a risk allele in a patient comprises determining the identity of the nucleotide at the polymorphism from nucleic acid provided from a sample from a patient. In some embodiments, the nucleic acid sample comprises DNA. In some embodiments, the nucleic acid sample comprises RNA. In some embodiments, the nucleic acid sample is amplified. In some embodiments, the nucleic acid sample is amplified by a polymerase chain reaction. In some embodiments, the polymorphism is detected by polymerase chain reaction or sequencing. In some embodiments, the polymorphism is detected by amplification of a target region containing at least one polymorphism, and hybridization with at least one sequence-specific oligonucleotide that hybridizes under stringent conditions to at least one polymorphism and detecting the hybridization. In some embodiments, the polymorphism is detected by a technique selected from the group consisting of scanning probe and nanopore DNA sequencing, pyrosequencing, Denaturing Gradient Gel Electrophoresis (DGGE), Temporal Temperature Gradient Electrophoresis (TTGE), Zn(II)-cyclen polyacrylamide gel electrophoresis, homogeneous fluorescent PCR-based single nucleotide polymorphism analysis, phosphate-affinity polyacrylamide gel electrophoresis, high-throughput SNP genotyping platforms, molecular beacons, 5' nuclease reaction, Taqman assay, MassArray (single base primer extension coupled with matrix-assisted laser desorption/ionization time-of-flight mass spectrometry), trityl mass tags, genotyping platforms (such as the Invader Assay®), single base primer extension (SBE) assays, PCR amplification (e.g. PCR amplification on magnetic nanoparticles (MNPs), restriction enzyme analysis of PCR products (RFLP methods), allele-specific PCR, multiple primer extension (MPEX), and isothermal smart amplification. In some embodiments, the sample is any biological sample from which genomic DNA may be isolated, for example, but not to be limited to a tissue sample, a sample of saliva, a cheek swab sample, blood, or other biological fluids that contain genomic DNA. In some embodiments, the blood sample includes whole-blood, blood-derived cells, plasma, serum and combinations thereof. In some embodiments, the identity of the nucleotide at the polymorphism in a patient is determined via genotyping. In some embodiments the genotyping is performed by PCR analysis, sequence analysis or LCR analysis. In some embodiments, the patient is identified as having an increased risk for AMD progression and is more likely to benefit from treatment comprising an anti-factor D antibody, or antigen-binding fragment thereof when at least one allele comprising a nucleotide selected from the group consisting of a G nucleotide at the SNP rs4698775 is present, a G nucleotide at the SNP rs17440077 is present, an A nucleotide at the SNP rs10737680 is present, a G nucleotide at the SNP rs1329428 is present, a G nucleotide at the SNP rs429608 is present or the G nucleotide at the SNP rs2230199 is present. The patient is identified as being at increased risk of AMD progression if the patient has one or two copies of the G allele at rs4698775 or rs17440077 associated with CFI, or equivalent allele thereof, at rs1329428 associated with CFH, or equivalent allele thereof, at rs429608 associated with C2/CFB, or equivalent allele thereof, or at rs2230199 associated with C3, or equivalent allele thereof or one or two copies of the A allele at rs10737680 associated with CFH, or equivalent allele thereof. In one embodiment, the study eye in the patient has a BCVA between 20/25 and 20/400. In one embodiment, the study eye in the patient has a BCVA between 20/25 and 20/100. In one embodiment, the study eye in the patient has a BCVA between 20/50 and 20/400. In one embodiment; the study eye in the patient has a BCVA between 20/50 and 20/100. In one embodiment, the study eye in the patient has a BCVA better than 20/25 or worse than 20/400. In one embodiment, the BCVA was determined using ETDRS charts, In some embodiments, the antibody or antigen-binding fragment thereof is administered intravitreally. In some embodiments, the age-related macular degeneration is dry AMD. In some embodiments, the dry AMD is advanced dry AMD. In some embodiments, the advanced dry AMD is geographic atrophy. In some embodiments, the age-related macular degeneration is early AMD or intermediate AMD. In some embodiments, the patient with early AMD or intermediate AMD has a reduction or delay in appearance of clinical signs (e.g. may include measuring the number and size of drusen (for early and intermediate AMD) and monitoring hypo- and hyperpigmentation associated with drusen (for intermediate AMD)). In some embodiments, the methods further comprise administering a second medicament to the subject. In some embodiments, the second medicament is VEGF inhibitor.

Yet another embodiment of the invention provides methods for determining the likelihood that a AMD patient will benefit from treatment with an anti-factor D antibody, or antigen-binding fragment thereof, the method comprising determining genotype of the patient, wherein a patient who carries a risk allele, is identified as a patient who has an increased risk of AMD progression and is more likely to respond to treatment with an anti-factor D antibody, or antigen-binding fragment thereof. In some embodiments, the antibody is lampalizumab. In some embodiments, the risk allele is the minor allele of a selected SNP. In some embodiments, the risk allele is the major allele of a selected SNP. In some embodiments, the risk allele (e.g. AMD-associated polymorphism) may be a CFI risk allele, a CFH risk allele, a C2 risk allele, a CFB risk allele and/or a C3 risk allele. In some embodiments, the risk allele is a CFI risk allele. In some embodiments, the CFI risk allele is the rs4698775:G allele, or equivalent allele thereof or comprises a G at the selected SNP rs4698775, or comprises an alternate SNP in linkage disequilibrium to rs4698775. In some embodiments, the alternate SNP comprises a minor allele or the allele which resides on the same haplotype of the risk allele of the selected SNP rs4698775. In some embodiments, the CFI risk allele is the rs17440077:G allele, or equivalent allele thereof or comprises a G at the selected SNP rs17440077, or comprises an alternate SNP in linkage disequilibrium to rs17440077. In some embodiments, the alternate SNP comprises a minor allele or the allele which resides on the same haplotype of the risk allele of the selected SNP rs17440077. In some embodiments, the CFH risk allele is the rs10737680:A allele, or equivalent allele thereof, or comprises an A at the selected SNP rs10737680, or comprises an alternate SNP in linkage disequilibrium to rs10737680. In some embodiments, the alternate SNP comprises a minor allele or the allele which resides on the same haplotype of the risk allele of the selected SNP rs10737680. In some embodiments, the CFH risk allele is the rs1329428:G allele, or equivalent allele thereof, or comprises an G at the selected SNP rs1329428, or comprises an alternate SNP in linkage disequilibrium to rs1329428. In some embodiments, the alternate SNP comprises a minor allele or the allele which resides on the same haplotype of the risk allele of the selected SNP rs1329428. In some embodiments, the C2 risk allele is the rs429608:G allele, or equivalent allele thereof, or comprises a G at the selected SNP rs429608, or comprises an alternate SNP in linkage disequilibrium to rs429608. In some embodiments, the alternate SNP comprises a minor allele or the allele which resides on the same haplotype of the risk allele of the selected SNP rs429608. In some embodiments, the CFB allele is the rs429608:G allele, or equivalent allele thereof, or comprises a G at the selected SNP rs429608, or comprises an alternate SNP in linkage disequilibrium to rs429608. In some embodiments, the alternate SNP comprises a minor allele or the allele which resides on the same haplotype of the risk allele of the selected SNP rs429608. In some embodiments, the C3 risk allele is the rs2230199:G allele, or equivalent allele thereof, or comprises a G at the selected SNP rs2230199 or comprises an alternate SNP in linkage disequilibrium to rs2230199. In some embodiments, the alternate SNP comprises a minor allele or the allele which resides on the same haplotype of the risk allele of the selected SNP rs2230199. In some embodiments, the linkage disequilibrium is a D' measure or an $r^2$ measure. In some embodiments, the D' measure between the selected SNP and the alternate SNP is ≥0.60. In some embodiments, the D' measure between the selected SNP and the alternate SNP is ≥0.70, 0.80 or 0.90. In some embodiments, the D' measure between the selected SNP and the alternate SNP is 1.0. In some embodiments, the $r^2$ measure between the selected SNP and the alternate SNP is ≥0.60. In some embodiments the $r^2$ measure between the selected SNP and the alternate SNP is ≥0.70, 0.80 or 0.90. In some embodiments, the $r^2$ measure between the selected SNP and the alternate SNP is 1.0. In some embodiments, the alternate SNP is a SNP designated in Tables 4-7. In some embodiments, the SNP rs4698775 is located at position 110590479 on human chromosome 4 (Genome Reference Consortium GRCh37; UCSC Genome HG19 Assembly; February 2009) and the G allele changes the nucleotide sequence from T to G. In some embodiments, the SNP rs17440077 is located at position 110537567 on human chromosome 4 (Genome Reference Consortium GRCh37; UCSC Genome HG19 Assembly; February 2009) and the G allele changes the nucleotide sequence from A to G. In some embodiments, the SNP rs10737680 is located at position 196679455 on human chromosome 1 (Genome Reference Consortium GRCh37; UCSC Genome HG19 Assembly; February 2009) and the A allele changes the nucleotide sequence form C to A. In some embodiments, the SNP rs1329428 is located at position 196702810 on human chromosome 1 (Genome Reference Consortium GRCh37; UCSC Genome HG19 Assembly; February 2009) and the G allele changes the nucleotide sequence from A to G. In some embodiments, the SNP rs429608 is located at position 31930462 on human chromosome 6 (Genome Reference Consortium GRCh37; UCSC Genome HG19 Assembly; February 2009) and the G allele changes the nucleotide sequence from A to G. In some embodiments, the SNP rs2230199 is located at position 6718387 on human chromosome 19 (Genome Reference Consortium GRCh37; UCSC Genome HG19 Assembly; February 2009) and the G allele changes the nucleotide sequence from C to G and changes the encoded amino acid from arginine to glycine. In some embodiments, the alternate SNP is located on human chromosome 4 between SEC24B gene and EGF gene (for rs4698775) (Genome Reference Consortium GRCh37; UCSC Genome HG19 Assembly; February 2009), human chromosome 4 between SEC24B gene and EGF gene (Genome Reference Consortium GRCh37; UCSC Genome HG19 Assembly; February 2009) (for rs17440077), human chromosome 1 between KCNT2 gene and LHX9 gene (Genome Reference Consortium GRCh37; UCSC Genome HG19 Assembly; February 2009) (for rs10737680), human chromosome 1 between KCNT2 gene and LHX9 gene (Genome Reference Consortium GRCh37; UCSC Genome HG19 Assembly; February 2009) (for rs1329428), human chromosome 6 between SLC44A4 gene and TNXB gene (Genome Reference Consortium GRCh37; UCSC Genome HG19 Assembly; February 2009) (for rs429608), human chromosome 19 between TNFSF14 gene and VAV1 gene (Genome Reference Consortium GRCh37; UCSC Genome HG19 Assembly; February 2009) (for rs2230199). In some embodiments, the alternate SNP is located within 500,000 base pairs upstream and downstream of the selected SNP In some embodiments, the patient is determined to carry a CFI risk allele and/or a CFH risk allele and/or a C2 risk allele and/or a CFB risk allele and/or a C3 risk allele. In some embodiments, the patient is determined to carry 1, 2, 3, 4, 5, 6, 7, 8, 9, 10, etc. AMD risk alleles. In some embodiments, presence of a risk allele in a patient comprises determining the identity of the nucleotide at the polymorphism from nucleic acid provided from a sample from a patient. In some embodiments, the nucleic acid sample comprises DNA. In some embodiments, the nucleic acid sample comprises RNA. In some embodiments, the nucleic acid sample is amplified. In some embodiments, the nucleic acid sample is amplified by a polymerase chain reaction. In some embodiments, the polymorphism is detected by polymerase chain reaction or sequencing. In some embodiments, the polymorphism is detected by amplification of a target region containing at least one polymorphism, and hybridization with at least one sequence-specific oligonucleotide that hybridizes under stringent conditions to at least one polymorphism and detecting the hybridization. In some embodiments, the polymorphism is detected by a technique selected from the group consisting of scanning probe and nanopore DNA sequencing, pyrosequencing, Denaturing Gradient Gel Electrophoresis (DGGE), Temporal Temperature Gradient Electrophoresis (TTGE), Zn(II)-cyclen polyacrylamide gel electrophoresis, homogeneous fluorescent PCR-based single nucleotide polymorphism analysis, phosphate-affinity polyacrylamide gel electrophoresis, high-throughput SNP genotyping platforms, molecular beacons, 5' nuclease reaction, Taqman assay, MassArray (single base primer extension coupled with matrix-assisted laser desorption/ionization time-of-flight mass spectrometry), trityl mass tags, genotyping platforms (such as the Invader Assay®), single base primer extension (SBE) assays, PCR amplification (e.g. PCR amplification on magnetic nanoparticles (MNPs), restriction enzyme analysis of PCR products (RFLP methods), allele-specific PCR, multiple primer extension (MPEX), and isothermal smart amplification. In some embodiments, the sample is any biological sample from which genomic DNA may be isolated, for example, but not to be limited to a tissue sample, a sample of saliva, a cheek swab sample, blood, or other biological fluids that contain genomic DNA. In some embodiments, the identity of the nucleotide at the polymorphism in a patient is determined via genotyping. In some embodiments the genotyping is performed by PCR analysis, sequence analysis or LCR analysis. In some embodiments, the patient is identified as having an increased risk for AMD progression and is more likely to benefit from treatment comprising an anti-factor D antibody, or antigen-binding fragment thereof when at least one allele comprising a nucleotide selected from the group consisting of a G nucleotide at the SNP rs4698775 is present, a G nucleotide at the SNP rs17440077 is present, a G nucleotide at the SNP rs10737680 is present, a G nucleotide at the SNP rs1329428 is present, a G nucleotide at the SNP rs429608 is present or the G nucleotide at the SNP rs2230199 is present. The patient is identified as being at increased risk of AMD progression if the patient has one or two copies of the G allele at rs4698775 or rs17440077 associated with CFI, or equivalent allele thereof, at rs1329428 associated with CFH, or equivalent allele thereof, at rs429608 associated with C2/CFB, or equivalent allele thereof, or at rs2230199 associated with C3, or equivalent allele thereof or one or two copies of the A allele at rs10737680 associated with CFH, or equivalent allele thereof. In one embodiment, the study eye in the patient has a BCVA between 20/25 and 20/400. In one embodiment, the study eye in the patient has a BCVA between 20/25 and 20/100. In one embodiment, the study eye in the patient has a BCVA between 20/50 and 20/400. In one embodiment, the study eye in the patient has a BCVA between 20/50 and 20/100. In one embodiment, the study eye in the patient has a BCVA better than 20/25 or worse than 20/400. In one embodiment, the BCVA was determined using ETDRS charts. In some embodiments, the antibody or antigen-binding fragment thereof is administered intravitreally. In some embodiments, the age-related macular degeneration is dry AMD. In some embodiments, the dry AMD is advanced dry AMD. In some embodiments, the advanced dry AMD is geographic atrophy. In some embodiments, the age-related macular degeneration is early AMD or intermediate AMD. In some embodiments, the patient with early AMD or intermediate AMD has a reduction or delay in appearance of clinical signs (e.g. may include measuring the number and size of drusen (for early and intermediate AMD) and monitoring hypo- and hyperpigmentation associated with drusen (for intermediate AMD)). In some embodiments, the methods further comprise administering a second medicament to the subject. In some embodiments, the second medicament is VEGF inhibitor.

Even another embodiment of the invention provides methods of treating degenerative disease (e.g. AMD) in a patient, the method comprising administering an effective amount of an anti-factor D antibody or antigen-binding fragment thereof to a patient diagnosed with a degenerative disease, wherein the patient has decreased progression of AMD following treatment compared to a control. In some embodiments, the antibody is lampalizumab. In one embodiment, the degenerative disease is an ocular degenerative disease. In one embodiment, the ocular degenerative disease is age-related macular degeneration. In one embodiment, the study eye in the patient has a BCVA between 20/25 and 20/400. In one embodiment, the study eye in the patient has a BCVA between 20/25 and 20/100. In one embodiment, the study eye in the patient has a BCVA between 20/50 and 20/400. In one embodiment, the study eye in the patient has a BCVA between 20/50 and 20/100. In one embodiment, the study eye in the patient has a BCVA better than 20/25 or worse than 20/400. In one embodiment, the BCVA was determined using ETDRS charts. In some embodiments, the antibody or antigen-binding fragment thereof is administered intravitreally. In some embodiments, the age-related macular degeneration is dry AMD. In some embodiments, the dry AMD is advanced dry AMD. In some embodiments, the advanced dry AMD is geographic atrophy. In some embodiments, the patient has a reduced mean change in geographic atrophy (GA) area following administration of the antibody as compared to control patients that did not receive the antibody treatment. In some embodiments, the mean change in GA area is determined by measuring the GA area by standard imaging methods (e.g. fundus autofluorescence (FAF) or color fundus photography (CFP). In some embodiments, the age-related macular degeneration is early AMD or intermediate AMD. In some embodiments, the patient with early AMD or intermediate AMD has a reduction or delay in appearance of clinical signs (e.g. may include measuring the number and size of drusen (for early and intermediate AMD) and monitoring hypo- and hyperpigmentation associated with drusen (for intermediate AMD)). In some embodiments, the methods further comprise administering a second medicament to the subject. In some embodiments, the second medicament is VEGF inhibitor.

Even a further embodiment of the invention provides methods of identifying an degenerative disease patient (e.g., AMD patient) who may benefit from treatment with an anti-factor D antibody, or antigen-binding fragment thereof, the method comprising determining the baseline GA area of the patient, wherein a patient who has a baseline GA area that requires clinical intervention is identified as a patient who may benefit from treatment with an anti-factor D antibody. In one embodiment, the degenerative disease is an ocular degenerative disease. In one embodiment, the ocular degenerative disease is age-related macular degeneration. In some embodiments, the antibody is lampalizumab. In one embodiment, the study eye in the patient has a BCVA between 20/25 and 20/400. In one embodiment, the study eye in the patient has a BC VA between 20/25 and 20/100. In one embodiment, the study eye in the patient has a BC VA between 20/50 and 20/400. In one embodiment, the study eye in the patient has a BCVA between 20/50 and 20/100. In one embodiment, the study eye in the patient has a BCVA better than 20/25 or worse than 20/400. In one embodiment, the BCVA was determined using ETDRS charts. In some embodiments, the antibody or antigen-binding fragment thereof is administered intravitreally. In some embodiments, the age-related macular degeneration is dry AMD. In some embodiments, the dry AMD is advanced dry AMD. In some embodiments, the advanced dry AMD is geographic atrophy. In some embodiments, the patient has a reduced mean change in geographic atrophy (GA) area following administration of the antibody as compared to the control patients that did not receive the antibody treatment. In some embodiments, the mean change in GA area is determined by measuring the GA area by standard imaging methods (e.g. fundus autofluorescence (FAF) or color fundus photography (CFB). In some embodiments, the age-related macular degeneration is early AMD or intermediate AMD. In some embodiments, the patient with early AMD or intermediate AMD has a reduction or delay in appearance of clinical signs (e.g. may include measuring the number and size of drusen (for early and intermediate AMD) and monitoring hypo- and hyperpigmentation associated with drusen (for intermediate AMD)). In some embodiments, the methods further comprise administering a second medicament to the subject. In some embodiments, the second medicament is VEGF inhibitor.

In some embodiments, the complement inhibitor in the methods described herein is an anti-anti-factor D antibody, or antigen-binding fragment thereof. In some embodiments, the antibody specifically binds factor D. In some embodiments, the antibody comprises a light chain comprising HVR-L1 comprising the amino acid sequence ITSTDIDDDMN (SEQ ID NO:1), HVR-L2 comprising the amino acid sequence GGNTLRP (SEQ ID NO:2), and HVR-L3 comprising the amino acid sequence LQSDSLPYT (SEQ ID NO: 3); and/or a heavy chain comprising HVR-H1 comprising the amino acid sequence GYTFTNYGMN (SEQ ID NO: 4), HVR-H2 comprising the amino acid sequence WINTYTGETTYADDFKG (SEQ ID NO:5), and HVR-H3 comprising the amino acid sequence EGGVNN (SEQ ID NO:6). In some embodiments, the antibody comprises a heavy chain variable region sequence of at least 95% sequence identity to the amino acid sequence of SEQ ID NO:7; and/or a light chain variable region sequence of at least 95% sequence identity to the amino acid sequence of SEQ ID NO:8. In some embodiments, the antibody comprises a heavy chain variable region comprising the amino acid sequence of SEQ ID NO:7; and/or a light chain variable region comprising the amino acid sequence of SEQ ID NO:8. In some embodiments, the antibody is lampalizumab having CAS registration number 1278466-20-8. In some embodiments, the anti-factor D antibody may be a monoclonal antibody, antibody fragment, chimeric antibody, humanized antibody, single-chain antibody or antibody that competitively inhibits the binding of an anti-factor D antibody to its respective antigenic epitope. In one embodiment, the anti-factor D antibody competitively inhibits the binding of the anti-factor D antibody comprising a light chain comprising HVR-L1 comprising the amino acid sequence ITSTDIDDDMN (SEQ ID NO:1), HVR-L2 comprising the amino acid sequence GGNTLRP (SEQ ID NO:2), and HVR-L3 comprising the amino acid sequence LQSDSLPYT (SEQ ID NO: 3); and/or a heavy chain comprising HVR-H1 comprising the amino acid sequence GYTFTNYGMN (SEQ ID NO: 4), HVR-H2 comprising the amino acid sequence WINTYTGETTYADDFKG (SEQ ID NO:5), and HVR-H3 comprising the amino acid sequence EGGVNN (SEQ ID NO:6) to its respective antigenic epitope. In one embodiment, the anti-factor D antibody competitively inhibits the binding of the antibody comprising a heavy chain variable region sequence of at least 95% sequence identity to the amino acid sequence of SEQ ID NO:7; and/or a light chain variable region sequence of at least 95% sequence identity to the amino acid sequence of SEQ ID NO:8 to its respective antigenic epitope. In one embodiment, the anti-factor D antibody competitively inhibits the binding of the antibody comprising a heavy chain sequence of at least 95% sequence identity to the amino acid sequence of SEQ ID NO:15;

and/or a light chain sequence of at least 95% sequence identity to the amino acid sequence of SEQ ID NO:16 to its respective antigenic epitope. In one embodiment, the anti-factor D antibody competitively inhibits the binding of the antibody comprising a heavy chain variable region comprising the amino acid sequence of SEQ ID NO:7; and/or a light chain variable region comprising the amino acid sequence of SEQ ID NO:8 to its respective antigenic epitope. In one embodiment, the anti-factor D antibody competitively inhibits the binding of the antibody comprising a heavy chain comprising the amino acid sequence of SEQ ID NO:15; and/or a light chain comprising the amino acid sequence of SEQ ID NO:16 to its respective antigenic epitope. In one embodiment, the anti-factor D antibody competitively inhibits the binding of lampalizumab having CAS registration number 1278466-20-8 to its respective antigenic epitope. In some embodiments, the anti-factor D antibody binds to the same epitope on factor D bound by another factor D antibody. In one embodiment, the anti-factor D antibody binds to the same epitope on factor D bound by the anti-factor D antibody comprising a light chain comprising HVR-L1 comprising the amino acid sequence ITSTDIDDDMN (SEQ ID NO:1), HVR-L2 comprising the amino acid sequence GGNTLRP (SEQ ID NO:2), and HVR-L3 comprising the amino acid sequence LQSDSLPYT (SEQ ID NO: 3); and/or a heavy chain comprising HVR-H1 comprising the amino acid sequence GYTFTNYGMN (SEQ ID NO: 4), HVR-H2 comprising the amino acid sequence WINTYTGETTYADDFKG (SEQ ID NO:5), and HVR-H3 comprising the amino acid sequence EGGVNN (SEQ ID NO:6). In one embodiment, the anti-factor D antibody binds to the same epitope on factor D bound by the antibody comprising a heavy chain variable region sequence of at least 95% sequence identity to the amino acid sequence of SEQ ID NO:7; and/or a light chain variable region sequence of at least 95% sequence identity to the amino acid sequence of SEQ ID NO:8. In one embodiment, the anti-factor D antibody binds to the same epitope on factor D bound by the antibody comprising a heavy chain sequence of at least 95% sequence identity to the amino acid sequence of SEQ ID NO:15; and/or a light chain sequence of at least 95% sequence identity to the amino acid sequence of SEQ ID NO:16. In one embodiment, the anti-factor D antibody binds to the same epitope on factor D bound by the antibody comprising a heavy chain variable region comprising the amino acid sequence of SEQ ID NO:7; and/or a light chain variable region comprising the amino acid sequence of SEQ ID NO:8. In one embodiment, the anti-factor D antibody binds to the same epitope on factor D bound by the antibody comprising a heavy chain comprising the amino acid sequence of SEQ ID NO:15; and/or a light chain comprising the amino acid sequence of SEQ ID NO:16. In one embodiment, the anti-factor D antibody binds to the same epitope on factor D bound by lampalizumab having CAS registration number 1278466-20-8.

In some embodiments, the anti-factor D antibody, or antigen-binding fragment thereof is administered intraocularly or intravitreally. In some embodiments, the antibody is administered at a flat dose of 10 mg. In some embodiments, the antibody is administered at a flat dose of 10 mg monthly or 10 mg every other month. In some embodiments, the antibody is administered intravitreally at a flat dose of 10 mg monthly or 10 mg every other month. In some embodiments, alternative formulations or modes of drug delivery of the anti-factor D antibody or antigen binding fragment may involve lower or higher doses than 10 mg. In some embodiments, the anti-factor D antibody, or antigen-binding fragment thereof, is administered at a dose lower than 10 mg if administered via a long-acting delivery (LAD) device. For example, the anti-factor D antibody, or antigen-binding fragment thereof is administered at a dose of 9, 8, 7, 6, 5, 4, 3, 2, 1 mg. In some embodiments, the anti-factor D antibody, or antigen-binding fragment thereof, is administered at a dose greater than 10 mg if administered intravitreally. For example, the anti-factor D antibody, or antigen-binding fragment thereof, is administered at a dose of 11, 12, 13, 14, 15, 16, 17, 18, 19, 20 mg.

In some embodiments, the administration of the antibody is effective in one or more of the following: (1) reduction in GA area, (2) reduction of vision loss. In some embodiments, the methods described herein further comprise administering a second medicament to the patient. In some embodiments, the second medicament is a VEGF inhibitor. In some embodiments, the second medicament is a standard of care for AMD.

In another aspect, the invention provides a therapeutic regimen for the treatment of a patient carrying a risk allele and in need thereof comprising the administration of a factor D inhibitor. In some embodiments, the complement inhibitor is an anti-factor D antibody, or antigen-binding fragment thereof. In some embodiments, the antibody is administered at a flat dose of 5-30 mg. In some embodiments, the antibody is administered at a flat dose of 5-15 mg monthly or 10-30 mg every other month. In some embodiments, the antibody is administered intraocularly or intravitreally. In some embodiments, the antibody is administered intravitreally at a flat dose of 5 mg or 15 mg monthly. In some embodiments, the antibody comprises a light chain comprising HVR-L1 comprising the amino acid sequence ITSTDIDDDMN (SEQ ID NO:1), HVR-L2 comprising the amino acid sequence GGNTLRP (SEQ ID NO:2), and HVR-L3 comprising the amino acid sequence LQSDSLPYT (SEQ ID NO: 3); and/or a heavy chain comprising HVR-H1 comprising the amino acid sequence GYTFTNYGMN (SEQ ID NO: 4), HVR-H2 comprising the amino acid sequence WINTYTGETTYADDFKG (SEQ ID NO:5), and HVR-H3 comprising the amino acid sequence EGGVNN (SEQ ID NO:6). In some embodiments, the antibody comprises a heavy chain variable region sequence of at least 95% sequence identity to the amino acid sequence of SEQ ID NO:7; and/or a light chain variable region sequence of at least 95% sequence identity to the amino acid sequence of SEQ ID NO:8. In some embodiments, the antibody comprises a heavy chain variable region comprising the amino acid sequence of SEQ ID NO:7

(EVQLVQSGPELKKPGASVKVSCKASGYTFTNYGMNWVRQAPGQGLEWM

GWINTYTGETTYADDFKGRFVFSLDTSVSTAYLQISSLKAEDTAVYYCE

REGGVNNWGQGTLVTVSS; HVRs are underlined and in bold);

and/or a light chain variable region comprising the amino acid sequence of SEQ ID NO:8

(DIQVTQSPSSLSASVGDRVTITCITSTDIDDDMNWYQQKPGKVPKLLI

SGGNTLRPGVPSRFSGSGSGTDFTLTISSLQPEDVATYYCLQSDSLPYT

FGQGTKVEIK; HVRs are underlined and in bold);

In some embodiments, the antibody is lampalizumab having CAS registration number 1278466-20-8. In some embodiments, the anti-factor D antibody may be a monoclonal antibody, antibody fragment, chimeric antibody, humanized antibody, single-chain antibody or antibody that competitively inhibits the binding of an anti-factor D antibody to its respective antigenic epitope. In one embodiment, the anti-factor D antibody competitively inhibits the binding of the anti-factor D antibody comprising a light chain comprising HVR-L1 comprising the amino acid sequence ITSTDID-DDMN (SEQ ID NO:1), HVR-L2 comprising the amino acid sequence GGNTLRP (SEQ ID NO:2), and HVR-L3 comprising the amino acid sequence LQSDSLPYT (SEQ ID NO: 3); and/or a heavy chain comprising HVR-H1 comprising the amino acid sequence GYTFTNYGMN (SEQ ID NO: 4), HVR-H2 comprising the amino acid sequence WINTYTGETTYADDFKG (SEQ ID NO:5), and HVR-H3 comprising the amino acid sequence EGGVNN (SEQ ID NO:6) to its respective antigenic epitope. In one embodiment, the anti-factor D antibody competitively inhibits the binding of the antibody comprising a heavy chain variable region sequence of at least 95% sequence identity to the amino acid sequence of SEQ ID NO:7; and/or a light chain variable region sequence of at least 95% sequence identity to the amino acid sequence of SEQ ID NO:8 to its respective antigenic epitope. In one embodiment, the anti-factor D antibody competitively inhibits the binding of the antibody comprising a heavy chain sequence of at least 95% sequence identity to the amino acid sequence of SEQ ID NO:15; and/or a light chain sequence of at least 95% sequence identity to the amino acid sequence of SEQ ID NO:16 to its respective antigenic epitope. In one embodiment, the anti-factor D antibody competitively inhibits the binding of the antibody comprising a heavy chain variable region comprising the amino acid sequence of SEQ ID NO:7; and/or a light chain variable region comprising the amino acid sequence of SEQ ID NO:8 to its respective antigenic epitope. In one embodiment, the anti-factor D antibody competitively inhibits the binding of the antibody comprising a heavy chain comprising the amino acid sequence of SEQ ID NO:15; and/or a light chain comprising the amino acid sequence of SEQ ID NO:16 to its respective antigenic epitope. In one embodiment, the anti-factor D antibody competitively inhibits the binding of lampalizumab having CAS registration number 1278466-20-8 to its respective antigenic epitope. In some embodiments, the anti-factor D antibody binds to the same epitope on factor D bound by another factor D antibody. In one embodiment, the anti-factor D antibody binds to the same epitope on factor D bound by the anti-factor D antibody comprising a light chain comprising HVR-L1 comprising the amino acid sequence ITSTDIDDDMN (SEQ ID NO:1), HVR-L2 comprising the amino acid sequence GGNTLRP (SEQ ID NO:2), and HVR-L3 comprising the amino acid sequence LQSDSLPYT (SEQ ID NO: 3); and/or a heavy chain comprising HVR-H1 comprising the amino acid sequence GYTFTNYGMN (SEQ ID NO: 4), HVR-H2 comprising the amino acid sequence WINTYTGETTY-ADDFKG (SEQ ID NO:5), and HVR-H3 comprising the amino acid sequence EGGVNN (SEQ ID NO:6). In one embodiment, the anti-factor D antibody binds to the same epitope on factor D bound by the antibody comprising a heavy chain variable region sequence of at least 95% sequence identity to the amino acid sequence of SEQ ID NO:7; and/or a light chain variable region sequence of at least 95% sequence identity to the amino acid sequence of SEQ ID NO:8. In one embodiment, the anti-factor D antibody binds to the same epitope on factor D bound by the antibody comprising a heavy chain sequence of at least 95% sequence identity to the amino acid sequence of SEQ ID NO:15; and/or a light chain sequence of at least 95% sequence identity to the amino acid sequence of SEQ ID NO:16. In one embodiment, the anti-factor D antibody binds to the same epitope on factor D bound by the antibody comprising a heavy chain variable region comprising the amino acid sequence of SEQ ID NO:7; and/or a light chain variable region comprising the amino acid sequence of SEQ ID NO:8. In one embodiment, the anti-factor D antibody binds to the same epitope on factor D bound by the antibody comprising a heavy chain comprising the amino acid sequence of SEQ ID NO:15; and/or a light chain comprising the amino acid sequence of SEQ ID NO:16. In one embodiment, the anti-factor D antibody binds to the same epitope on factor D bound by lampalizumab having CAS registration number 1278466-20-8.

In another aspect, the invention provides a method of identifying an AMD patient who may benefit from an factor D inhibitor treatment, the method comprising determining the genotype from a sample from the patient, wherein a patient who carries the risk allele as measured by genotype assay is identified as a patient who may benefit from the factor D inhibitor treatment. In another aspect, the invention provides a method of predicting responsiveness of an AMD patient to a factor D inhibitor treatment, the method comprising determining the genotype from a sample from the patient, wherein a patient who carries a risk allele is identified as a patient who is likely to respond to the factor D inhibitor treatment. In some embodiments, the genotype assay is performed using a SNP array, Taqman (Hui et al., *Current Protocol in Human Genetics*, Supp 56: 2.10.1-2.10.8 (2008)), fluorescence polarization, Sequenom or other methods for analysis of SNPs as described herein. In some embodiments, the genotype assay utilizes PCR or sequencing.

In another aspect, the invention provides a method of treating a degenerative disease comprising administering an anti-factor D antibody, or antigen-binding fragment thereof, comprising HVRH1, HVRH2, HVRH3, HVRL1, HVRL2, HVRL3, and HVRL3, wherein the respective HVRs have the amino acid sequence of SEQ ID NO: 1, SEQ ID NO: 2, SEQ ID NO: 3, SEQ ID NO: 4, SEQ ID NO: 5 and SEQ ID NO: 6 to a patient suffering from a degenerative disease in a 10 mg dose every month. In one embodiment, the degenerative disease is an ocular degenerative disease. In one embodiment, the ocular degenerative disease is age related macular degeneration. In one embodiment, the age related macular degeneration is early, intermediate or advanced AMD. In one embodiment, the advanced AMD is geographic atrophy. In one embodiment, a second medicament is administered. In one embodiment, the second medicament is a VEGF inhibitor. In one embodiment, the VEGF inhibitor is ranibizumab. In one embodiment, the anti-factor D antibody, or antigen binding fragment thereof, is an antibody or antigen binding fragment thereof comprising a VH comprising SEQ ID NO: 7 and a VL comprising SEQ ID NO: 8. In one embodiment, the treatment results in greater than 5, 6, 7, 8, 9, 10, 11, 12, 13, 14, 15, 16, 17, 18, 19, 20, 21, 22, 23, 24, 25, 2.6, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100% reduction of change in GA area from baseline GA area. In one embodiment, the treatment results in greater than 80% reduction of change in GA area from baseline GA area. In one embodiment, the treatment results in greater than 75% reduction of change in GA area from baseline GA area. In one embodiment, the treatment results in greater than 70% reduction of change in GA area from baseline GA area. In one embodiment, the treatment results in greater than 65% reduction of change in GA area from baseline GA area. In one embodiment, the treatment results in greater than 60% reduction of change in GA area from baseline GA area. In one embodiment, the treatment results in greater than 55% reduction of change in GA area from baseline GA area. In one embodiment, the treatment results in greater than 50% reduction of change in GA area from baseline GA area. In one embodiment, the treatment results in greater than 45% reduction of change in GA area from baseline GA area. In one embodiment, the treatment results in greater than 40% reduction of change in GA area from baseline GA area. In one embodiment, the treatment results in greater than 35% reduction of change in GA area from baseline GA area. In one embodiment, the treatment results in greater than 30% reduction of change in GA area from baseline GA area. In one embodiment, the treatment results in greater than 25% reduction of change in GA area from baseline GA area. In one embodiment, the treatment results in greater than 20% reduction of change in GA area from baseline GA area. In one embodiment, the treatment results in greater than 15% reduction of change in GA area from baseline GA area. In one embodiment, the treatment results in greater than 10% reduction of change in GA area from baseline GA area. In one embodiment, the treatment results in greater than 5% reduction of change in GA area from baseline GA area. In one embodiment, the patient has geographic atrophy secondary to AMD. In one embodiment, the study eye in the patient has a BCVA between 20/25 and 20/400. In one embodiment, the study eye in the patient has a BCVA between 20/25 and 20/100. In one embodiment, the study eye in the patient has a BCVA between 20/50 and 20/400. In one embodiment, the study eye in the patient has a BCVA between 20/50 and 20/100. In one embodiment, the study eye in the patient has a BCVA better than 20/25 or worse than 20/400. In one embodiment, the BCVA was determined using ETDRS charts. In one embodiment, the patient has not received any previous intravitreal treatment, retinal surgery or other retinal therapeutic procedures in the study eye.

In one aspect, the invention provides a kit for genotyping in a biological sample from a degenerative disease patient, wherein the kit comprises oligonucleotides for polymerase chain reaction for detection or sequencing of a risk allele. In another aspect, the invention provides a kit for determining the presence of at least one degenerative disease-associated polymorphism in a biological sample, comprising reagents and instructions for detecting the genotype of the biological sample for the presence of at least one degenerative disease-associated polymorphism, wherein the polymorphism is a risk allele selected from the group consisting of a CFI allele, a CFH allele, a C2 allele, a CFB allele, or a C3 allele. In one embodiment, the biological sample is a blood sample, saliva, cheek swab, tissue sample or a sample of bodily fluids. In one embodiment, the biological sample is a nucleic acid sample. In one embodiment, the nucleic acid sample comprises DNA. In one embodiment, the nucleic acid sample comprises RNA. In one embodiment, the nucleic acid sample is amplified. In one embodiment, the biological sample is obtained from a patient diagnosed with a degenerative disease, such as AMD, including early, intermediate and advanced AMD. In one embodiment, the advanced AMD is GA. In one embodiment, the kit further comprises a package insert for determining whether a degenerative disease patient is likely to respond to an anti-factor D antibody, or antigen binding fragment thereof. In one embodiment, the kit is used to detect the presence of a CFI risk allele, a CFH risk allele, a C2 risk allele, a CFB risk allele or a C3 risk allele. In one embodiment, the kit is used to detect the presence of one or two alleles of the G genotype at the SNP rs4698775, SNP rs17440077, SNP rs1329428, SNP rs429608 or SNP rs2230199 or two alleles of the A genotype at the SNP rs10737680. In one embodiment, the reagents of the kit comprise a set of oligonucleotides specific for detecting a polymorphism in CFI, C2, CFB, C3 or CFH allele. The oligonucleotides according to the invention can be a forward primer and a reverse primer suitable for amplifying a region of the CFI, C2, CFB, C3 or CFH gene comprising a polymorphism in CFI, C2, CFB, C3 or CFH respectively, selected from the group consisting of the G genotype at the SNP rs4698775, SNP rs17440077, SNP rs1329428, SNP rs429608 or SNP rs2230199 or the A genotype at the SNP rs10737680. The kit can further comprises an oligonucleotide probe for detecting the polymorphism. Oligonucleotides useful as primers and probes for the invention included those listed in Table 9 as SEQ ID NOs:17-41. In one aspect, the reagents of the kit comprise (i) a forward primer of SEQ ID NO:17 or 18 combined with a reverse primer of SEQ ID NO:19 or 20 and a labeled probe selected from SEQ ID NOs. 21-24; (ii) a forward primer of SEQ ID NO:25 or 26 combined with a reverse primer of SEQ ID NO:27 or 28 and a labeled probe selected from SEQ ID NOs. 29-33; or (iii) a forward primer of SEQ ID NO:34 or 35 combined with a reverse primer of SEQ ID NO:36 or 37 and a labeled probe selected from SEQ ID NOs. 38-41. In one embodiment, the reagents of the kit combine primers and probes as listed in (i), (ii) and (iii) above.

In another aspect, the invention provides a kit for predicting whether a patient has an increased likelihood of benefiting from treatment with an anti-factor D antibody or antigen binding fragment thereof comprising a first oligonucleotide and a second oligonucleotide specific for a polymorphism in CFI, C2, CFB, C3 or CFH. In one embodiment, said first oligonucleotide and said second oligonucleotide may be used to amplify a region of the CFI, C2, CFB, C3 or CFH gene comprising a polymorphism in CFI, C2, CFB, C3 or CFH respectively, selected from the group consisting of the G genotype at the SNP rs4698775, SNP rs17440077, SNP rs1329428, SNP rs429608 or SNP rs2230199 or the A genotype at the SNP rs10737680. In one embodiment, the anti-factor D antibody, or antigen-binding fragment thereof, comprises HVRH1, HVRH2, HVRH3, HVRL1, HVRL2, HVRL3, and HVRL3, wherein the respective HVRs have the amino acid sequence of SEQ ID NO: 1, SEQ ID NO: 2, SEQ ID NO: 3, SEQ ID NO: 4, SEQ ID NO: 5 and SEQ ID NO: 6.

In one aspect of the invention, the anti-factor D antibody, or antigen-binding fragment thereof, comprises the variable heavy chain of SEQ ID NO: 7 and/or the variable light chain of SEQ ID NO: 8.

In one aspect of the invention, the polymorphism is a CFI polymorphism. In one embodiment, the CFI polymorphism is present in combination with one or more additional polymorphisms selected from the group consisting of a CFH polymorphism, a C2 polymorphism, a C3 polymorphism or a CFB polymorphism.

In one aspect, the invention provides the use of an agent that specifically binds to at least one degenerative disease-associated polymorphism wherein the polymorphism is a minor allele selected from the group consisting of a CFI risk allele, a CFH risk allele, a C2 risk allele, a CFB risk allele or a C3 risk allele for the manufacture of a diagnostic for diagnosing a degenerative disease. In one embodiment, the CFI allele is an equivalent allele thereof, the CFH allele is an equivalent allele thereof, the C2 allele is an equivalent allele thereof, the CFB allele is an equivalent allele thereof, or the C3 allele is an equivalent allele thereof. In one embodiment, the CFI allele comprises a G at the single nucleotide polymorphism (SNP) rs4698775 or rs17440077, the CFH allele comprises an A at the single nucleotide polymorphism (SNP) rs10737680 or a G at the single nucleotide polymorphism (SNP) rs1329428, the C2 allele comprises a G at the single nucleotide polymorphism (SNP) rs429608, the CFB allele comprises a G at the single nucleotide polymorphism (SNP) rs429608, and the C3 allele comprises a G at the single nucleotide polymorphism (SNP) rs2230199. In one embodiment, at least one polymorphism is detected by a technique selected from the group consisting of scanning probe and nanopore DNA sequencing, pyrosequencing, Denaturing Gradient Gel Electrophoresis (DGGE), Temporal Temperature Gradient Electrophoresis (TTGE), Zn(II)-cyclen polyacrylamide gel electrophoresis, homogeneous fluorescent PCR-based single nucleotide polymorphism analysis, phosphate-affinity polyacrylamide gel electrophoresis, high-throughput SNP genotyping platforms, molecular beacons, 5' nuclease reaction, Taqman assay, MassArray (single base primer extension coupled with matrix-assisted laser desorption/ionization time-of-flight mass spectrometry), trityl mass tags, genotyping platforms (such as the Invader Assay®), single base primer extension (SBE) assays, PCR amplification (e.g. PCR amplification on magnetic nanoparticles (MNPs), restriction enzyme analysis of PCR products (RFLP methods), allele-specific PCR, multiple primer extension (MPEX), and isothermal smart amplification. In one embodiment, at least one polymorphism is detected by amplification of a target region containing at least one polymorphism, and hybridization with at least one sequence-specific oligonucleotide that hybridizes under stringent conditions to at least one polymorphism and detecting the hybridization. In one embodiment, the presence of one or two alleles of the G genotype at the SNP rs4698775, SNP rs17440077, SNP rs1329428, SNP rs429608 or SNP rs2230199 or one or two alleles of the A genotype at the SNP rs10737680 in the individual indicates an increased risk for degenerative disease progression. In one embodiment, a polymorphism that is in linkage disequilibrium with at least one single nucleotide polymorphism selected from the group consisting of single nucleotide polymorphism (SNP) rs4698775, rs17440077, rs10737680, rs1329428, rs429608, and rs2230199 is detected. In one embodiment, the degenerative disease is age related macular degeneration. In one embodiment, the age related macular degeneration is early, intermediate or advanced AMD. In one embodiment, the advanced AMD is geographic atrophy.

In one aspect, the invention provides an in vitro use of an agent that binds to at least one degenerative disease-associated polymorphism wherein the polymorphism is a risk allele selected from the group consisting of a CFI risk allele, a CFH risk allele, a C2 risk allele, a CFB risk allele or a C3 risk allele for identifying a patient having a degenerative disease likely to respond to a therapy comprising an anti-factor D antibody, or antigen binding fragment thereof, wherein the presence of said polymorphisms identifies that the patient is more likely to respond to the therapy. In one embodiment, the CFI allele is an equivalent allele thereof, the CFH allele is an equivalent allele thereof, the C2 allele is an equivalent allele thereof, the CFB allele is an equivalent allele thereof, or the C3 allele is an equivalent allele thereof. In one embodiment, the CFI allele comprises a G at the single nucleotide polymorphism (SNP) rs4698775 or rs17440077, the CFH allele comprises an A at the single nucleotide polymorphism (SNP) rs10737680 or a G at the single nucleotide polymorphism (SNP) rs1329428, the C2 allele comprises a G at the single nucleotide polymorphism (SNP) rs429608, the CFB allele comprises a G at the single nucleotide polymorphism (SNP) rs429608, and the C3 allele comprises a G at the single nucleotide polymorphism (SNP) rs2230199. In one embodiment, at least one polymorphism is detected by a technique selected from the group consisting of scanning probe and nanopore DNA sequencing, pyrosequencing, Denaturing Gradient Gel Electrophoresis (DGGE), Temporal Temperature Gradient Electrophoresis (TTGE), Zn(II)-cyclen polyacrylamide gel electrophoresis, homogeneous fluorescent PCR-based single nucleotide polymorphism analysis, phosphate-affinity polyacrylamide gel electrophoresis, high-throughput SNP genotyping platforms, molecular beacons, 5' nuclease reaction, Taqman assay, MassArray (single base primer extension coupled with matrix-assisted laser desorption/ionization time-of-flight mass spectrometry), trityl mass tags, genotyping platforms (such as the Invader Assay®), single base primer extension (SBE) assays, PCR amplification (e.g. PCR amplification on magnetic nanoparticles (MNPs), restriction enzyme analysis of PCR products (RFLP methods), allele-specific PCR, multiple primer extension (MPEX), and isothermal smart amplification. In one embodiment, at least one polymorphism is detected by amplification of a target region containing at least one polymorphism, and hybridization with at least one sequence-specific oligonucleotide that hybridizes under stringent conditions to at least one polymorphism and detecting the hybridization. In one embodiment, the presence of one or two alleles of the G genotype at the SNP rs4698775, SNP rs17440077, SNP rs1329428, SNP rs429608 or SNP rs2230199 or one or two alleles of the A genotype at the SNP rs10737680 in the individual indicates an increased risk for degenerative disease progression. In one embodiment, a polymorphism that is in linkage disequilibrium with at least one single nucleotide polymorphism selected from the group consisting of single nucleotide polymorphism (SNP) rs4698775, rs17440077, rs10737680, rs1329428, rs429608, and rs2230199 is detected. In one embodiment, the degenerative disease is an ocular degenerative disease. In one embodiment, the ocular degenerative disease is age related macular degeneration. In one embodiment, the age related macular degeneration is early, intermediate or advanced AMD. In one embodiment, the advanced AMD is geographic atrophy.

In one aspect, the invention provides an in vitro use of a degenerative disease-associated polymorphism for selecting a patient having a degenerative disease as likely to respond to a therapy comprising an anti-factor D antibody, or an antigen-binding fragment thereof, wherein the patient is identified as more likely to respond to the therapy when the degenerative disease-associated polymorphism is detected in the sample from the patient. In one embodiment, the degenerative-disease associated polymorphism is an AMD-associated polymorphism. In one embodiment, the AMD-associated polymorphism is a risk allele selected from the group consisting of a CFI risk allele, a CFH risk allele, a C2 risk allele, a CFB risk allele or a C3 risk allele for identifying a patient having a degenerative disease likely to respond to a therapy comprising an anti-factor D antibody, or antigen binding fragment thereof, wherein the presence of said polymorphisms identifies that the patient is more likely to respond to the therapy. In one embodiment, the CFI allele is an equivalent allele thereof, the CFH allele is an equivalent allele thereof, the C2 allele is an equivalent allele thereof, the CFB allele is an equivalent allele thereof, or the C3 allele is an equivalent allele thereof. In one embodiment, the CFI allele comprises a G at the single nucleotide polymorphism (SNP) rs4698775 or rs17440077, the CFH allele comprises an A at the single nucleotide polymorphism (SNP) rs10737680 or a G at the single nucleotide polymorphism (SNP) rs1329428, the C2 allele comprises a G at the single nucleotide polymorphism (SNP) rs429608, the CFB allele comprises a G at the single nucleotide polymorphism (SNP) rs429608, and the C3 allele comprises a G at the single nucleotide polymorphism (SNP) rs2230199. In one embodiment, at least one polymorphism is detected by a technique selected from the group consisting of scanning probe and nanopore DNA sequencing, pyrosequencing, Denaturing Gradient Gel Electrophoresis (DGGE), Temporal Temperature Gradient Electrophoresis (TTGE), Zn(II)-cyclen polyacrylamide gel electrophoresis, homogeneous fluorescent PCR-based single nucleotide polymorphism analysis, phosphate-affinity polyacrylamide gel electrophoresis, high-throughput SNP genotyping platforms, molecular beacons, 5' nuclease reaction, Taqman assay, MassArray (single base primer extension coupled with matrix-assisted laser desorption/ionization time-of-flight mass spectrometry), trityl mass tags, genotyping platforms (such as the Invader Assay®), single base primer extension (SBE) assays, PCR amplification (e.g. PCR amplification on magnetic nanoparticles (MNPs), restriction enzyme analysis of PCR products (RFLP methods), allele-specific PCR, multiple primer extension (MPEX), and isothermal smart amplification. In one embodiment, at least one polymorphism is detected by amplification of a target region containing at least one polymorphism, and hybridization with at least one sequence-specific oligonucleotide that hybridizes under stringent conditions to at least one polymorphism and detecting the hybridization. In one embodiment, the presence of one or two alleles of the G genotype at the SNP rs4698775, SNP rs17440077, SNP rs1329428, SNP rs429608 or SNP rs2230199 or one or two alleles of the A genotype at the SNP rs10737680 in the individual indicates an increased risk for degenerative disease progression. In one embodiment, a polymorphism that is in linkage disequilibrium with at least one single nucleotide polymorphism selected from the group consisting of single nucleotide polymorphism (SNP) rs4698775, rs17440077, rs10737680, rs1329428, rs429608, and rs2230199 is detected. In one embodiment, the degenerative disease is an ocular degenerative disease. In one embodiment, the ocular degenerative disease is age related macular degeneration. In one embodiment, the age related macular degeneration is early, intermediate or advanced AMD. In one embodiment, the advanced AMD is geographic atrophy.

In one aspect, the invention provides a use of a degenerative disease-associated polymorphism for the manufacture of a diagnostic for assessing the likelihood of a response of a patient having a degenerative disease to a therapy comprising an anti-factor D antibody, or an antigen-binding fragment thereof. In one embodiment, the degenerative-disease associated polymorphism is an AMD-associated polymorphism. In one embodiment, the AMD-associated polymorphism is a risk allele selected from the group consisting of a CFI risk allele, a CFH risk allele, a C2 risk allele, a CFB risk allele or a C3 risk allele for identifying a patient having a degenerative disease likely to respond to a therapy comprising an anti-factor D antibody, or antigen binding fragment thereof, wherein the presence of said polymorphisms identifies that the patient is more likely to respond to the therapy. In one embodiment, the CFI allele is an equivalent allele thereof, the CFH allele is an equivalent allele thereof, the C2 allele is an equivalent allele thereof, the CFB allele is an equivalent allele thereof, or the C3 allele is an equivalent allele thereof. In one embodiment, the CFI allele comprises a G at the single nucleotide polymorphism (SNP) rs4698775 or rs17440077, the CFH allele comprises an A at the single nucleotide polymorphism (SNP) rs10737680 or a G at the single nucleotide polymorphism (SNP) rs1329428, the C2 allele comprises a G at the single nucleotide polymorphism (SNP) rs429608, the CFB allele comprises a G at the single nucleotide polymorphism (SNP) rs429608, and the C3 allele comprises a G at the single nucleotide polymorphism (SNP) rs2230199. In one embodiment, at least one polymorphism is detected by a technique selected from the group consisting of scanning probe and nanopore DNA sequencing, pyrosequencing, Denaturing Gradient Gel Electrophoresis (DGGE), Temporal Temperature Gradient Electrophoresis (TTGE), Zn(II)-cyclen polyacrylamide gel electrophoresis, homogeneous fluorescent PCR-based single nucleotide polymorphism analysis, phosphate-affinity polyacrylamide gel electrophoresis, high-throughput SNP genotyping platforms, molecular beacons, 5' nuclease reaction, Taqman assay, MassArray (single base primer extension coupled with matrix-assisted laser desorption/ionization time-of-flight mass spectrometry), trityl mass tags, genotyping platforms (such as the Invader Assay®), single base primer extension (SBE) assays, PCR amplification (e.g. PCR amplification on magnetic nanoparticles (MNPs), restriction enzyme analysis of PCR products (RFLP methods), allele-specific PCR, multiple primer extension (MPEX), and isothermal smart amplification. In one embodiment, at least one polymorphism is detected by amplification of a target region containing at least one polymorphism, and hybridization with at least one sequence-specific oligonucleotide that hybridizes under stringent conditions to at least one polymorphism and detecting the hybridization. In one embodiment, the presence of one or two alleles of the G genotype at the SNP rs4698775, SNP rs17440077, SNP rs1329428, SNP rs429608 or SNP rs2230199 or one or two alleles of the A genotype at the SNP rs10737680 in the individual indicates an increased risk for degenerative disease progression. In one embodiment, a polymorphism that is in linkage disequilibrium with at least one single nucleotide polymorphism selected from the group consisting of single nucleotide polymorphism (SNP) rs4698775, rs17440077, rs10737680, rs1329428, rs429608, and rs2230199 is detected. In one embodiment, the degenerative disease is an ocular degenerative disease. In one embodiment, the ocular degenerative disease is age related macular degeneration. In one embodiment, the age related macular degeneration is early, intermediate or advanced AMD. In one embodiment, the advanced AMD is geographic atrophy.

In one aspect, the invention provides an oligonucleotide for detecting polymorphisms at one or more nucleotide positions in complement-associated loci. In one embodiment, the complement-associated loci are selected from CFH, CFI, C3, C2 and CFB risk loci. In one embodiment, the nucleotide position is selected from the group consisting of nucleotide positions associated with rs4698775, rs17440077, rs10737680, rs1329428, rs429608 and rs2230199. In one embodiment the oligonucleotide is at least 90% identical to and having the 3' terminal nucleotide of one or more of the sequences selected from the group consisting of SEQ ID NOs:17-41. The oligonucleotides might comprise 3 or fewer mismatches with one of said sequences, excluding the 3'-terminal nucleotide and/or at least one mismatch among the penultimate 5 nucleotides at the 3'-terminus. The oligonucleotides might further comprise at least one modified nucleotide among the terminal 5 nucleotides at the 3'-terminus. In some embodiments, the oligonucleotide is suitable for detecting one or more of the alleles of rs4698775, rs17440077, rs10737680, rs1329428, rs429608, and rs2230199.

In one aspect, the invention is a diagnostic method of detecting SNPs in the CFH, CFI, C3, C2 or CFB risk loci. In one embodiment, the SNP is selected from rs4698775, rs17440077, rs10737680, rs1329428, rs429608, and rs2230199. In one embodiment, the SNP is detected using oligonucleotides selected from SEQ ID NOs:17-41 or variations at least 90% identical thereto and having the 3'-terminal nucleotide of said oligonucleotide. In one embodiment, the method comprises contacting a biological sample containing nucleic acids with one or more of the oligonucleotides in the presence of the corresponding downstream primer and detection probe. Advantageously, detection of several SNPs can be performed in a single reaction. In some embodiments, several closely positioned polymorphisms can be detected in a single reaction containing two or more allele-specific oligonucleotides, e.g. selected from sequences listed in Table 9 that can be combined in one reaction mixture with a single downstream primer and optionally a single detection probe. In a further embodiment, the method comprises contacting a test sample containing nucleic acids with one or more of the oligonucleotides as SNP-specific probes in the presence of the corresponding forward and reverse primers (i.e. primers capable of hybridizing to the opposite strands of the target DNA nucleic acids so as to enable exponential amplification), nucleoside triphosphates and a nucleic acid polymerase, such that the one or more allele-specific primers is efficiently extended only when a mutation is present in the sample; and detecting the presence or absence of a mutation by directly or indirectly detecting the presence or absence of the primer extension.

In a particular embodiment the presence of the primer extension is detected with a probe. The probe may be labeled with a radioactive, or a chromophore (fluorophore) label, e.g. a label incorporating FAM, JA270, CY5 family dyes, or HEX dyes. As one example of detection using a fluorescently labeled probe, the mutation may be detected by real-time polymerase chain reaction (rt-PCR), where hybridization of the probe results in enzymatic digestion of the probe and detection of the resulting fluorescence (TaqMan™ probe method, Holland et al. (1991) P.N.A.S. USA 88:7276-7280). Alternatively, the presence of the extension product and the amplification product may be detected by gel electrophoresis followed by staining or by blotting and hybridization as described e.g., in Sambrook, J. and Russell, D. W. (2001) *Molecular Cloning*, 3$^{rd}$ ed. CSHL Press, Chapters 5 and 9.

In some embodiments, the factor D inhibitor as described herein and in the uses described herein is an anti-factor D antibody. The antibody specifically binds Factor D. In some embodiments, the antibody comprises a light chain comprising HVR-L1 comprising the amino acid sequence ITSTDIDDDMN (SEQ ID NO:1), HVR-L2 comprising the amino acid sequence GGNTLRP (SEQ ID NO:2), and HVR-L3 comprising the amino acid sequence LQSDSLPYT (SEQ ID NO: 3); and/or a heavy chain comprising HVR-H1 comprising the amino acid sequence GYTFTNYGMN (SEQ ID NO: 4), HVR-H2 comprising the amino acid sequence WINTYTGETTYADDFKG (SEQ ID NO:5), and HVR-H3 comprising the amino acid sequence EGGVNN (SEQ ID NO:6). In some embodiments, the antibody comprises a heavy chain variable region sequence of at least 95% sequence identity to the amino acid sequence of SEQ ID NO:7; and/or a light chain variable region sequence of at least 95% sequence identity to the amino acid sequence of SEQ ID NO:8. In some embodiments, the antibody comprises a heavy chain variable region comprising the amino acid sequence of SEQ ID NO:7; and/or a light chain variable region comprising the amino acid sequence of SEQ ID NO:8. In some embodiments, the antibody is lampalizumab having CAS registration number 1278466-20-8. In some embodiments, the anti-factor D antibody may be a monoclonal antibody, antibody fragment, chimeric antibody, humanized antibody, single-chain antibody or antibody that competitively inhibits the binding of an anti-factor D antibody to its respective antigenic epitope. In one embodiment, the anti-factor D antibody competitively inhibits the binding of the anti-factor D antibody comprising a light chain comprising HVR-L1 comprising the amino acid sequence ITSTDIDDDMN (SEQ ID NO:1), HVR-L2 comprising the amino acid sequence GGNTLRP (SEQ ID NO:2), and HVR-L3 comprising the amino acid sequence LQSDSLPYT (SEQ ID NO: 3); and/or a heavy chain comprising HVR-H1 comprising the amino acid sequence GYTFTNYGMN (SEQ ID NO: 4), HVR-H2 comprising the amino acid sequence WINTYTGETTYADDFKG (SEQ ID NO:5), and HVR-H3 comprising the amino acid sequence EGGVNN (SEQ ID NO:6) to its respective antigenic epitope. In one embodiment, the anti-factor D antibody competitively inhibits the binding of the antibody comprising a heavy chain variable region sequence of at least 95% sequence identity to the amino acid sequence of SEQ ID NO:7; and/or a light chain variable region sequence of at least 95% sequence identity to the amino acid sequence of SEQ ID NO:8 to its respective antigenic epitope. In one embodiment, the anti-factor D antibody competitively inhibits the binding of the antibody comprising a heavy chain sequence of at least 95% sequence identity to the amino acid sequence of SEQ ID NO:15; and/or a light chain sequence of at least 95% sequence identity to the amino acid sequence of SEQ ID NO:16 to its respective antigenic epitope. In one embodiment, the anti-factor D antibody competitively inhibits the binding of the antibody comprising a heavy chain variable region comprising the amino acid sequence of SEQ ID NO:7; and/or a light chain variable region comprising the amino acid sequence of SEQ ID NO:8 to its respective antigenic epitope. In one embodiment, the anti-factor D antibody competitively inhibits the binding of the antibody comprising a heavy chain comprising the amino acid sequence of SEQ ID NO:15; and/or a light chain comprising the amino acid sequence of SEQ ID NO:16 to its respective antigenic epitope. In one embodiment, the anti-factor D antibody competitively inhibits the binding of lampalizumab having CAS registration number 1278466-20-8 to its respective antigenic epitope. In some embodiments, the anti-factor D antibody binds to the same epitope on factor D bound by another factor D antibody. In one embodiment, the anti-factor D antibody binds to the same epitope on factor D bound by the anti-factor D antibody comprising a light chain comprising HVR-L1 comprising the amino acid sequence ITSTDIDDDMN (SEQ ID NO:1), HVR-L2 comprising the amino acid sequence GGNTLRP (SEQ ID NO:2), and HVR-L3 comprising the amino acid sequence LQSDSLPYT (SEQ ID NO: 3); and/or a heavy chain comprising HVR-H1 comprising the amino acid sequence GYTFTNYGMN (SEQ ID NO: 4), HVR-H2 comprising the amino acid sequence WINTYTGETTY- ADDFKG (SEQ ID NO:5), and HVR-H3 comprising the amino acid sequence EGGVNN (SEQ ID NO:6). In one embodiment, the anti-factor D antibody binds to the same epitope on factor D bound by the antibody comprising a heavy chain variable region sequence of at least 95% sequence identity to the amino acid sequence of SEQ ID NO:7; and/or a light chain variable region sequence of at least 95% sequence identity to the amino acid sequence of SEQ ID NO:8. In one embodiment, the anti-factor D antibody binds to the same epitope on factor D bound by the antibody comprising a heavy chain sequence of at least 95% sequence identity to the amino acid sequence of SEQ ID NO:15; and/or a light chain sequence of at least 95% sequence identity to the amino acid sequence of SEQ ID NO:16. In one embodiment, the anti-factor D antibody binds to the same epitope on factor D bound by the antibody comprising a heavy chain variable region comprising the amino acid sequence of SEQ ID NO:7; and/or a light chain variable region comprising the amino acid sequence of SEQ ID NO:8. In one embodiment, the anti-factor D antibody binds to the same epitope on factor D bound by the antibody comprising a heavy chain comprising the amino acid sequence of SEQ ID NO:15; and/or a light chain comprising the amino acid sequence of SEQ ID NO:16. In one embodiment, the anti-factor D antibody binds to the same epitope on factor D bound by lampalizumab having CAS registration number 1278466-20-8.

In another aspect, the invention provides an article of manufacture comprising an IVT administration device, which delivers to a patient a flat dose of an anti-factor D antibody, or antigen-binding fragment thereof, wherein the flat dose is in the microgram to milligram range. In some embodiments, the flat dose is 10 mg monthly or 10 mg every other month. In some embodiments, the concentration of the antibody in the device is about 10 mg. In another aspect, the invention provides an article of manufacture comprising an anti-factor D antibody, or antigen-binding fragment thereof in a concentration of 10 mg. In some embodiments, the antibody comprises a light chain comprising HVR-L1 comprising the amino acid sequence ITSTDIDDDMN (SEQ ID NO:1), HVR-L2 comprising the amino acid sequence GGNTLRP (SEQ ID NO:2), and HVR-L3 comprising the amino acid sequence LQSDSLPYT (SEQ ID NO: 3); and/or a heavy chain comprising HVR-H1 comprising the amino acid sequence GYTFTNYGMN (SEQ ID NO: 4), HVR-H2 comprising the amino acid sequence WINTYTGETTY-ADDFKG (SEQ ID NO:5), and HVR-H3 comprising the amino acid sequence EGGVNN (SEQ ID NO:6). In some embodiments, the antibody comprises a heavy chain variable region sequence of at least 95% sequence identity to the amino acid sequence of SEQ ID NO:7; and/or a light chain variable region sequence of at least 95% sequence identity to the amino acid sequence of SEQ ID NO:8. In some embodiments, the antibody comprises a heavy chain variable region comprising the amino acid sequence of SEQ ID NO:7; and/or a light chain variable region comprising the amino acid sequence of SEQ ID NO:8. In some embodiments, the antibody is lampalizumab having CAS registration number 1278466-20-8.

In another aspect, the invention provides a kit for identifying a degenerative disease patient who may benefit for a factor D inhibitor treatment, comprising a vial for collecting a blood sample from a degenerative disease patient and instructions for determining whether the degenerative disease patient carries a risk allele. In some embodiments, the presence of at least one SNP from the group consisting of complement factor I (CFI), complement factor H(CFH), complement factor B (CFB), complement component 3 (C3) and complement component 2 (C2) is used to determine whether the degenerative disease patient carries the risk allele. In one embodiment, the degenerative disease is an ocular degenerative disease. In some embodiments, the ocular degenerative disease is AMD. In some embodiments, the factor D inhibitor is an anti-factor D antibody, or antigen-binding fragment thereof.

In another aspect, the invention provides a stable lyophilized composition, which, after reconstitution with sterile water for injection, comprises an anti-factor D antibody, or antigen-binding fragment thereof in an amount of about 80 to about 120 mg/mL, sodium chloride in an amount of about 8 to about 40 mM, sucrose in the amount of about 80 mM to about 240 mM, L-histidine in an amount of about 10 to about 60 mM, polysorbate 20 in an amount of about 0.01 to about 0.08% w/v, wherein the composition has a pH from about 5.0 to about 6.0.

It is to be understood that one, some, or all of the properties of the various embodiments described herein may be combined to form other embodiments of the present invention. These and other aspects of the invention will become apparent to one of skill in the art. These and other embodiments of the invention are further described in the detailed description that follows.

BRIEF DESCRIPTION OF THE DRAWINGS

FIG. 2A is a table summarizing baseline characteristics for all efficacy-evaluable patients (n=123) from the phase II component of the study described in Example 1. "Efficacy-evaluable patients" as used herein are defined as all randomized patients who receive at least one injection of treatment and had at least one post-baseline GA area measurement. FIG. 2B is a table summarizing baseline characteristics of assayed patients based on CFI status, with risk allele carriers defined as individuals heterozygous or risk-allele homozygous at the SNP being tested. VA=visual acuity. GA=geographic atrophy. DA=disc area (1 DA=2.54 mm$^2$).

FIGS. 3A and 3B show the preliminary efficacy results after the primary database lock for the MAHALO phase II study with an all-corners population; the study met its primary endpoint of mean change from baseline in GA area at 18 months as measured by fundus autofluorescence (FAF) and met its secondary endpoint of mean change from baseline in GA area at 18 months as assessed by color fundus photography (CFP) in the lampalizumab monthly group. A positive treatment effect in slowing the progression of GA area growth was observed in the monthly group beginning at 6 months and extending through 18 months with primary (FAF) and secondary (CFP) imaging endpoints. FIG. 3A shows that on the basis of the unadjusted means with the LOCF data, the lampalizumab monthly arm had a 23.1% reduction in the progression of GA area growth relative to the pooled sham arm. FIG. 3B shows that on the basis of the least squares means from the stratified analysis of variance (Henry Scheffe. Chapter 1.2 "Mathematical Models" in The Analysis of Variance, New York: John Wiley & Sons, Inc., 1999, p. 4-7), stratified by lesion size categories at baseline, <4 DA vs.>4 DA) with the LOCF data, the lampalizumab monthly arm had a 20.4% reduction in the progression of GA area growth relative to the pooled sham arm. The results demonstrated a clinically meaningful and statistically significant effect of lampalizumab administered monthly on reducing GA area growth over the 18-month study-treatment period. "Sham pooled" refers to the treatment group receiving sham monthly or sham every other month. "afDlm" refers to the treatment group receiving lampalizumab every month. "afD2 m" refers to the treatment group receiving lampalizumab every other month. LOCF method refers to the last-observation-carried-forward method used for the imputation of the missing data (David Streiner. "Last-Observation-Carried-Forward Method" in Encyclopedia of Research Design, Volume 2, Neil Salkind, Ed. Thousand Oaks, Calif.: Sage Publications, Inc., 2010, p. 681-745).

FIG. 5 shows the DDAF change (mean sham minus mean monthly treated) and % reduction in GA area (mean sham minus mean monthly treated divided by the mean ham) in groups at month 18. The total number of patients in the sham and lampalizumab monthly treatment groups are indicated as "All". The numbers of patients in the sham and lampalizumab monthly treatment groups that are heterozygous or homozygous for the CFH risk allele, C2 risk allele, CFB risk allele, C3 risk allele or CFI risk allele are indicated. Patients that are heterozygous for the CFI risk allele (these patients also carry the C2/CFB and CFH risk alleles) showed a mean change in GA area in sham versus monthly treated of −2.29 mm$^2$ and a % reduction in monthly treated versus sham of 52.66%, indicating lesion progression rate in the monthly treatment group was significantly reduced versus the sham control. "DDAF" when used herein refers to GA area. "DDAF change" when used herein refers to change from baseline.

DETAILED DESCRIPTION

Figure 1:
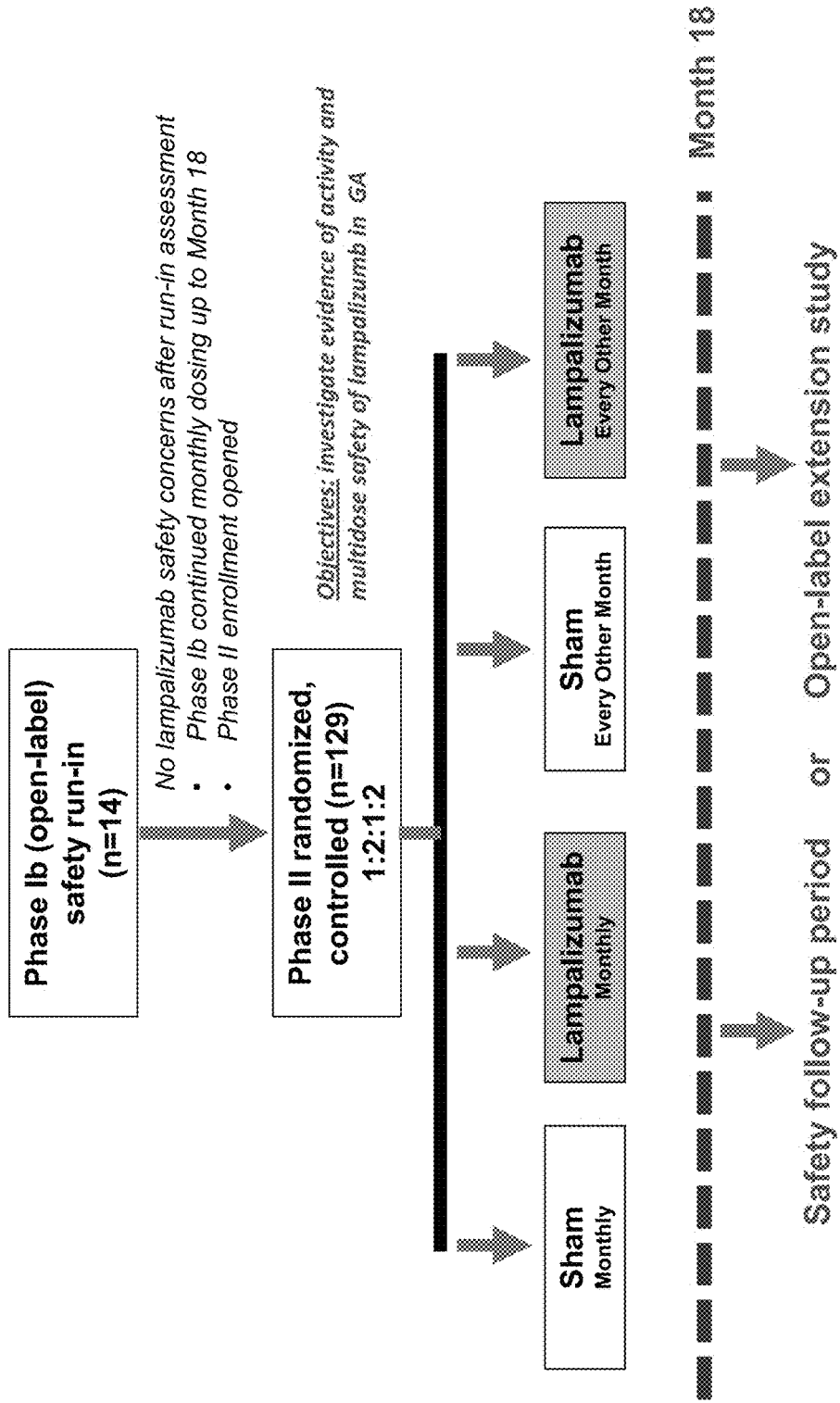
FIG. 1 depicts a diagram of the study design for the MAHALO trial described in Example 1 below.

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application.

I. Introduction

The present invention provides, inter alia, methods of treating AMD (e.g. GA, wet (neovascular/exudative), early AMD or intermediate AMD) patients with an anti-factor D antibody, or antigen-binding fragment thereof, and methods of identifying patients likely to benefit from such treatment (e.g. patient stratification), and methods of diagnosing patients at risk for AMD progression.

II. Definitions

For purposes of interpreting this specification, the following definitions will apply and whenever appropriate, terms used in the singular will also include the plural and vice versa. In the event that any definition set forth below conflicts with any document incorporated herein by reference, the definition set forth below shall control.

As used in this specification and the appended claims, the singular forms "a," "an" and "the" include plural references unless the context clearly dictates otherwise. Thus, for example, reference to "a protein" or an "antibody" includes a plurality of proteins or antibodies, respectively; reference to "a cell" includes mixtures of cells, and the like.

The term "complement-associated disorder" is used in the broadest sense and includes disorders associated with excessive or uncontrolled complement activation. They include complement activation during cardiopulmonary bypass operations; complement activation due to ischemia-reperfusion following acute myocardial infarction, aneurysm, stroke, hemorrhagic shock, crush injury, multiple organ failure, hypobolemic shock, intestinal ischemia or other events causing ischemia. Complement activation has also been shown to be associated with inflammatory conditions such as severe burns, endotoxemia, septic shock, adult respiratory distress syndrome, hemodialysis; anaphylactic shock, severe asthma, angioedema, Crohn's disease, sickle cell anemia, poststreptococcal glomerulonephritis and pancreatitis. The disorder may be the result of an adverse drug reaction, drug allergy, IL-2 induced vascular leakage syndrome or radiographic contrast media allergy. It also includes autoimmune disease such as systemic lupus erythematosus, myasthenia gravis, rheumatoid arthritis, Alzheimer's disease and multiple sclerosis. Complement activation is also associated with transplant rejection. Complement activation is also associated with ocular diseases such as age-related macular degeneration, diabetic retinopathy and other ischemia-related retinopathies, choroidal neovascularization (CNV), geographic atrophy (GA), uveitis, diabetic macular edema, pathological myopia, von Hippel-Lindau disease, histoplasmosis of the eye, Central Retinal Vein Occlusion (CRVO), corneal neovascularization, and retinal neovascularization.

The term "complement-associated eye condition" is used in the broadest sense and includes all eye conditions the pathology of which involves complement, including the classical and the alternative pathways, and in particular the alternative pathway of complement. Complement-associated eye conditions include, without limitation, macular degenerative diseases, such as all stages of age-related macular degeneration (AMD), including dry and wet (non-exudative and exudative) forms, choroidal neovascularization (CNV), geographic atrophy (GA), uveitis, diabetic and other ischemia-related retinopathies, and other intraocular neovascular diseases, such as diabetic macular edema, pathological myopia, von Hippel-Lindau disease, histoplasmosis of the eye, Central Retinal Vein Occlusion (CRVO), corneal neovascularization, and retinal neovascularization. In one example, complement-associated eye conditions includes age-related macular degeneration (AMD), including non-exudative (dry or atrophic) and exudative (wet) AMD, choroidal neovascularization (CNV), diabetic retinopathy (DR), geographic atrophy (GA) and endophthalmitis.

"Age-related Macular Degeneration", also referred to herein as "AMD", as used herein is a disease of the eye caused by degeneration of the cells of the macula which is the part of the retina that is responsible for central vision. AMD can be either (1) wet (exudative) which is characterized by the abnormal growth of blood vessels underneath the retina which leads to leaking of fluid or blood which ultimately damages the photoreceptors or (2) dry (non-exudative) which is characterized by the accumulation of cellular debris called drusen between the retina and the choroid.

"Geographic Atrophy", also referred to herein as "GA", as used herein is a disease involving degeneration of the retinal pigment epithelium (RPE), associated with loss of photoreceptors. GA is the advanced form of dry AMD.

"GA Area", as used herein refers to a discrete area representing loss of retinal anatomy (e.g. photoreceptors and retinal pigment epithelium (RPE). GA area is measured by standard imaging techniques such as fundus autofluorescence (FAF) and digital color fundus photography (CFP), "Early AMD", as used herein is a disease characterized by multiple small (<63 µm) or ≥1 intermediate drusen (≥63 µm and <125 µm).

"Intermediate AMD", as used herein is a disease characterized by many intermediate or ≥1 large drusen (≥125 µm) often accompanied by hyper or hypopigmentation of the retinal pigment epithelium.

"Advanced AMD", as used herein is a disease characterized by geographic atrophy (GA) or neovascular (wet) AMD).

"Prognostic biomarker", as used herein is a marker that indicates the likely course of the disease in an untreated individual.

"Predictive biomarker", as used herein identifies a sub-population of patients who are most likely to respond to a given treatment.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen binding arm). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-target antibody" and "an antibody that binds to target" refer to an antibody that is capable of binding the target (e.g. factor D) with sufficient affinity such that the antibody is useful as a diagonostic and/or therapeutic agent in targeting the target (e.g. factor D). In one embodiment, the extent of binding of an anti-target antibody to an unrelated, non-target protein is less than about 10% of the binding of the antibody to target as measured, e.g., by a radioimmunoassay (RIA) or biacore assay. In certain embodiments, an antibody that binds to a target has a dissociation constant (Kd) of ≤1 µM, ≤100 nM, ≤10 nM, ≤1 nM, ≤0.1 nM, ≤0.01 nM, or ≤0.001 nM (e.g. 10-8 M or less, e.g. from 10-8 M to 10-13 M, e.g., from 10-9 M to 10-13 M). In certain embodiments, an anti-target antibody binds to an epitope of a target that is conserved among different species.

The term "antibody" herein is used in the broadest sense and specifically covers monoclonal antibodies, polyclonal antibodies, multispecific antibodies (e.g. bispecific antibodies) formed from at least two intact antibodies, and antibody fragments so long as they exhibit the desired biological activity.

"Antibody fragments" comprise a portion of an intact antibody, preferably comprising the antigen-binding region thereof. Examples of antibody fragments include Fab, Fab', F(ab')$_2$, and Fv fragments; diabodies; linear antibodies; single-chain antibody molecules; and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. In one aspect, an antibody of the invention is tested for its antigen binding activity, e.g., by known methods such as ELISA, Western Blot, etc. In some embodiments, competition assays may be used to identify an antibody that competes with a reference antibody for binding to factor D. In certain embodiments, such a competing antibody binds to the same epitope (e.g., a linear or a conformational epitope) that is bound by a reference anti-factor D antibody specified herein. Detailed exemplary methods for mapping an epitope to which an antibody binds are provided in Morris (1996A) "Epitope Mapping Protocols," in Methods in Molecular Biology vol. 66 (Humana Press, Totowa, N.J.). In an exemplary competition assay, immobilized factor D is incubated in a solution comprising a first labeled antibody that binds to factor D (e.g. lampalizumab) and a second unlabeled antibody that is being tested for its ability to compete with the first antibody for binding to factor D. The second antibody may be present in a hybridoma supernatant. As a control, immobilized factor D is incubated in a solution comprising the first labeled antibody (e.g. lampalizumab), but not the second unlabeled antibody. After incubation under conditions permissive for binding of the first antibody to factor D, excess unbound antibody is removed, and the amount of label associated with immobilized factor D is measured. If the amount of label associated with immobilized factor D is substantially reduced in the test sample relative to the control sample, then that indicates that the second antibody is competing with the first antibody (e.g. lampalizumab) for binding to factor D. See Harlow and Lane (1988) Antibodies: A Laboratory Manual ch.14 (Cold Spring Harbor Laboratory, Cold Spring Harbor, N.Y.).

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

For the purposes herein, an "intact antibody" is one comprising heavy- and light-variable domains as well as an Fc region.

As used herein, "anti-human factor D antibody" means an antibody which specifically binds to human factor D in such a manner so as to inhibit or substantially reduce complement activation.

As used herein, the term "factor D" is used herein to refer to native sequence and variant factor D polypeptides.

A "native sequence" factor D, is a polypeptide having the same amino acid sequence as a factor D polypeptide derived from nature, regardless of its mode of preparation. Thus, native sequence factor D can be isolated from nature or can be produced by recombinant and/or synthetic means. In addition to a mature factor D protein, such as a mature human factor D protein (NM_001928), the term "native sequence factor D", specifically encompasses naturally-occurring precursor forms of factor D (e.g., an inactive preprotein, which is proteolytically cleaved to produce the active form), naturally-occurring variant forms (e.g., alternatively spliced forms) and naturally-occurring allelic variants of factor D, as well as structural conformational variants of factor D molecules having the same amino acid sequence as a factor D polypeptide derived from nature. Factor D polypeptides of non-human animals, including higher primates and non-human mammals, are specifically included within this definition.

"Factor D variant" means an active factor D polypeptide as defined below having at least about 80% amino acid sequence identity to a native sequence factor D polypeptide, such as the native sequence human factor D polypeptide (NM_001928). Ordinarily, a factor D variant will have at least about 80% amino acid sequence identity, or at least about 85% amino acid sequence identity, or at least about 90% amino acid sequence identity, or at least about 95% amino acid sequence identity, or at least about 98% amino acid sequence identity, or at least about 99% amino acid sequence identity with the mature human amino acid sequence (NM_001928).

The term "factor D inhibitor" as used herein refers to a molecule having the ability to inhibit a biological function of wild-type or mutated factor D. Accordingly, the term "inhibitor" is defined in the context of the biological role of factor D. In one embodiment, a factor D inhibitor referred to herein specifically inhibits the alternative pathway of complement. A factor D inhibitor can be in any form, so long as it is capable of inhibiting factor D activity; inhibitors include antibodies (e.g., monoclonal antibodies as defined herein below and as described in U.S. Pat. Nos. 8,067,002 and 8,273,352), small organic/inorganic molecules, antisense oligonucleotides, aptamers, inhibitory peptides/polypeptides, inhibitory RNAs (e.g., small interfering RNAs), combinations thereof, etc. "Active" or "activity" or "biological activity" in the context of a factor D antagonist or inhibitor of the present invention is the ability to antagonize (partially or fully inhibit) a biological activity of factor D. One example of a biological activity of a factor D antagonist is the ability to achieve a measurable improvement in the state, e.g. pathology, of a factor D-associated disease or condition, such as, for example, a complement-associated eye condition. The activity can be determined in in vitro or in vivo tests, including binding assays, alternative pathway hemolysis assays, using a relevant animal model, or human clinical trials.

The term "biomarker" as used herein refers generally to a molecule, including a single nucleotide polymorphism (SNP), protein, carbohydrate structure, or glycolipid, the expression of which in or on a mammalian tissue or cell can be detected by standard methods (or methods disclosed herein) and is predictive, diagnostic and/or prognostic for a mammalian cell's or tissue's sensitivity to treatment regimens based on inhibition of complement, e.g. alternative pathway of complement. Optionally, a SNP biomarker is determined when a SNP (a binary entity) stratifies a group of individuals into responders and non-responders. For example, given a SNP with two nucleotides, a G and an A in which the A is the risk allele, carriers of the A allele (e.g. AA or GA individuals) respond to treatment whereas individuals without an A allele (e.g. GG individuals) do not respond.

The term "single nucleotide polymorphism" also referred to herein as "SNP" as used herein refers to a single base substitution within a DNA sequence that leads to genetic variability. A nucleotide position in a genome at which more than one sequence is possible in a population is referred to herein as a "polymorphic site" or "polymorphism". A polymorphic site may be a nucleotide sequence of two or more nucleotides, an inserted nucleotide or nucleotide sequence, a deleted nucleotide or nucleotide sequence, or a microsatellite, for example. A polymorphic site that is two or more nucleotides in length may be 3, 4, 5, 6, 7, 8, 9, 10, 11, 12, 13, 14, 15 or more, 20 or more, 30 or more, 50 or more, 75 or more, 100 or more, 500 or more, or about 1000 nucleotides in length, where all or some of the nucleotide sequences differ within the region. A polymorphic site which is a single nucleotide in length is referred to herein as a SNP. When there are two, three or four alternative nucleotide sequences at a polymorphic site, each nucleotide sequence is referred to as a "polymorphic variant" or "nucleic acid variant". Each possible variant in the DNA sequence is referred to as an "allele". Where two polymorphic variants exist, the polymorphic variant represented in a majority of samples from a population is referred to as a "prevalent allele" or "major allele" and the polymorphic variant that is less prevalent in the population is referred to as an "uncommon allele" or "minor allele". An individual who carries two prevalent alleles or two uncommon alleles is "homozygous" with respect to the polymorphism. An individual who carries one prevalent allele and one uncommon allele is "heterozygous" with respect to the polymorphism. With C/G or A/T SNPs, the alleles are ambiguous and dependent on the strand used to extract the data from the genotyping platform. With these C/G or A/T SNPs, the C or G nucleotide or the A or T nucleotide, respectively, may be the risk allele and is determined by correlation of allele frequencies. The allele that correlates with an increased risk for a disease or is associated with an odds ratio or relative risk of >1 is referred to as the "risk allele" or "effect allele". The "risk allele" or "effect allele" may be the minor allele or major allele. For example the risk allele is the minor allele for SNPs rs4698775, rs17440077 and rs2230199 and the risk allele is the major allele for SNPs rs10737680, rs1329428 and rs429608 in a population of individuals with age-related macular degeneration disease (e.g. major and minor allele status of an allele is determined in a population of individuals with the age-related macular degeneration disease). The term "risk locus" is a region of the genome that harbors a risk allele associated with a specific disease (e.g. AMD). In some aspects, risk locus (loci) and risk allele(s) are represented by their association with particular genes (e.g. genes in the complement pathway) that are implicated with a specific disease (e.g. AMD). For example, "CFH risk allele" or "CFH allele" as used interchangeably herein refers to a risk allele associated with the CFH risk locus; "CFI risk allele" or "CFI allele" as used interchangeably herein refers to a risk allele assocaiated with the CFI risk locus, "C3 risk allele" or "C3 allele" as used interchangeably herein refers to a risk allele associated with the C3 risk locus; "C2 risk allele" or "C2 allele" as used interchangeably herein refers to a risk allele associated with the C2 risk locus; "CFB risk allele" or "CFB allele" as used interchangeably herein refers to a risk allele associated with the CFB risk locus; and "C2/CFB risk allele" or "C2/CFB allele" as used interchangeably herein refers to a risk allele associated with the C2/CFB risk locus. "Equivalent allele" or "surrogate allele" as used herein refers to an allele that is expected to behave similarly to a published risk allele and is selected based on allele frequencies and high $r^2$ ($\geq 0.6$) and/or high D' ($\geq 0.6$) with the published risk alleles and/or selected SNP as defined herein. In one embodiment, the high $r^2$ is $\geq 0.6$, 0.7, 0.8, 0.9 or 1.0. In one embodiment, the high D' is $\geq 0.6$, 0.7, 0.8, 0.9 or 1.0. SNPs associated with age related macular degeneration include SNPs in loci for components of the complement cascade, including but not limited to CFH, CFI, C3, C2, CFB risk loci (Fritsche et al. (Nature Genetics, 45(4): 435-441 (2013)). Such SNPs associated with age related macular degeneration are referred to herein as "AMD-associated polymorphism". "Degenerative disease-associated polymorphism" refers to a polymorphism or SNP associated with a degenerative disease and includes age related macular degeneration-associated polymorphisms and/or SNPs. "Linkage disequilibrium or "LD" when used herein refers to alleles at different loci that are not associated at random, i.e. not associated in proportion to their frequencies. If the alleles are in positive linkage disequilibrium, then the alleles occur together more often than expected assuming statistical independence. Conversely, if the alleles are in negative linkage disequilibrium, then the alleles occur together less often than expected assuming statistical independence. "Odds ratio" or "OR" when used herein refers to the ratio of the odds of the disease for individuals with the marker (allele or polymorphism) relative to the odds of the disease in individuals without the marker (allele or polymorphism). "Haplotype" when used herein refers to a group of alleles on a single chromosome that are closely enough linked to be inherited usually as a unit. The SNPs rs4698775 and rs17440077 are located in the CFI risk locus, rs10737680 and rs1329428 are located in the CFH risk locus, rs429608 is located in the C2/CFB risk locus and rs2230199 is located in the C3 risk locus (Genome Reference Consortium GRCh37; UCSC Genome H19 Assembly; February 2009) The SNP rs4698775 is located at position 110590479 on human chromosome 4 (Genome Reference Consortium GRCh37; UCSC Genome HG19 Assembly; February 2009). The G allele changes the nucleotide sequence from T to G. The SNP rs17440077 is located at position 110537567 on human chromosome 4 (Genome Reference Consortium GRCh37; UCSC Genome HG19 Assembly; February 2009). The G allele changes the nucleotide sequence from A to G. The SNP rs10737680 is located at position 196679455 on human chromosome 1 (Genome Reference Consortium GRCh37; UCSC Genome HG19 Assembly; February 2009). The A allele changes the nucleotide sequence form C to A. The SNP rs1329428 is located at position 196702810 on human chromosome 1 (Genome Reference Consortium GRCh37; UCSC Genome HG19 Assembly; February 2009). The G allele changes the nucleotide sequence from A to G. The SNP rs429608 is located at position 31930462 on human chromosome 6 (Genome Reference Consortium GRCh37; UCSC Genome HG19 Assembly; February 2009). The G allele changes the nucleotide sequence from A to G. The SNP rs2230199 is located at position 6718387 on human chromosome 19 (Genome Reference Consortium GRCh37; UCSC Genome HG19 Assembly; February 2009). The G allele changes the nucleotide sequence from C to G and the encoded amino acid from arginine to glycine. A polymorphic variant may be detected on either or both strands of a double-stranded nucleic acid. Also, a polymorphic variant may be located within an intron or exon of a gene or within a portion of a regulatory region such as a promoter, a 5' untranslated region (UTR), a 3'UTR, and in DNA (e.g. genomic DNA (gDNA) and complementary DNA (cDNA)), RNA (e.g. mRNA, tRNA, and RRNA), or a polypeptide. Polymorphic variations may or may not result in detectable differences in gene expression, polypeptide structure or polypeptide function.

The term "selected SNP" when used herein refers to a SNP selected from the group consisting of rs4698775, rs17440077, rs10737680, rs1329428, rs429608, rs2230199.

The term "alternate SNP" when used herein refers to a SNP that is expected to behave similarly to a selected SNP and is selected based on similar allele frequencies and has linkage disequilibrium with a selected SNP as measured by a $r^2 \geq 0.6$ and/or $D' \geq 0.6$. Alternate SNPs include SNPs listed in Tables 4-7 that are in linkage disequilibrium (with a D' or $r^2$ of $\geq 0.6$) with the SNPs described herein including SNP rs1329428, SNP rs2230199, SNP rs17440077 or SNP rs429608. Alternate SNPs include SNPs in linkage disequilibrium (with a D' or $r^2$ of $\geq 0.6$) with the SNPs described herein including SNP rs2230199 or SNP rs4698775. Terms used in Table 4-7 are defined as follows: (i) MAHALO_SNP refers to the SNP used in the present anti-factor D study described in Examples 1-4; (ii) LD_SNP refers to the SNP in LD with the MAHALO_SNP (either rsID designation comes from NCBI dbSNP build 137 (Jun. 6, 2012) or internal nomenclature designation (e.g. X-XXXXX) including chromosome and base pair position (first number=chromosome number and second number after the hyphen=base pair position) from genome build hg18 (UCSC HG18 Genome Assembly; March 2006); (iii) CHR refers to the chromosome location of LD_SNP (genome build hg19; UCSC HG19 Genome Assembly; February 2009); (iv) BP refers to the DNA base pair location of the LD_SNP (genome build hg19; UCSC HG19 Genome Assembly; February 2009). R2 refers to the r-squared value of MAHALO_SNP and LD_SNP; (v) D' refers to the D' value of MAHALO_SNP and LD_SNP; (vi) Ancestry or "ANC" refers to the ancestry of the population used to determine r2 and D' values; (vii) source or "SRC" refers to the database listing common variations in the human genome (internal data or "GID" refers to a non-public database, 1000GP or "GP" refers to the 1000 genomes project public database (1000 Genomes Project Consortium et al., *Nature,* 467 (7319): 1061-73 (2010)) and Hapmap or "HM" refers to the HapMap public database (International HapMap Consortium, *Nature,* 437(7063): 1299-320 (2005)). Populations descriptions include: Caucasian (CAU); African ancestry in Southwest USA (ASW (A)); Utah residents with Northern and Western European ancestry from the CEPH collection (CEU (C)); Han Chinese in Beijing, China (CHB (H)); Chinese in Metropolitan Denver, Colo. (CHD (D)); Gujarati Indians in Houston, Tex. (GIH (G)); Japanese in Tokyo, Japan (JPT (J)); Luhya in Webuye, Kenya (LWK (L)); Mexican ancestry in Los Angeles, Calif. (MEX (M)); Maasai in Kinyawa, Kenya (MKK (K)); Tuscan in Italy (TSI (T)); Yoruban in Ibadan, Nigeria (YR1 (Y)). Table 4 shows LD_SNPs in linkage disequilibrium (LD) with MAHALO_SNP rs17440077. Table 5 shows LD_SNPs in linkage disequilibrium (LD) with MAHALO_SNP rs2230199. Table 6 shows LD_SNPs in linkage disequilibrium (LD) with MAHALO_SNP rs429608. Table 7 shows LD_SNPs in linkage disequilibrium (LD) with MAHALO_SNP rs1329428.

The present invention provides methods of using the SNPs or other genetic based mechanisms as a predictive biomarker to predict response to treatment and as a prognostic biomarker to assess progression of AMD, methods of using the SNPs or other genetic based mechanism to select a treatment strategy, and methods of using the SNPs or other genetic based mechanisms for patient stratification including but not limited to selecting patients for clinical studies or to make clinical treatment decisions. "Patient stratification" when used herein refers to genotyping of individuals to determine the likelihood of response to treatment. The genotyping is performed to identify whether the individual carries a SNP. Many methods exist for the measurement of specific SNP genotypes. Individuals that carry mutations in one or more SNPs may be detected at the DNA level by a variety of techniques including but not limited to SNP array, Taqman, fluorescence polarization, Sequenom (or other methods for analysis of SNPs as described herein). Nucleic acids for diagnosis may be obtained from a patient's cells, such as from blood, urine, saliva, tissue biopsy and autopsy material.

"Increased risk" when used herein refers to when the presence in the genome of an individual of a particular base, at a particular location in the genome correlates with an increased probability of that individual developing more advanced forms of AMD vis-à-vis a population not having that base at that location in the genome, that individual is said to be at "increased risk" of developing more advanced forms of AMD, i.e. to have an increased susceptibility. In the present case, such increased probability exists when the base is present in one or the other or both alleles of the individual. Furthermore, the probability is increased when the base is present in both alleles of the individual rather than one allele of the individual.

"Decreased risk" when used herein refers to when the presence in the genome of an individual of a particular base, at a particular location in the genome correlates with an decreased probability of that individual developing more advanced forms of AMD vis-à-vis a population not having that base at that location in the genome, that individual is said to be at "decreased risk" of developing more advanced forms of AMD, i.e. to have an decreased susceptibility. Such an allele is sometimes referred to in the art as being "protective". As with increased risk, it is also possible for a decreased risk to be characterized as dominant or recessive.

An "altered risk" means an increased or a decreased risk.

The genomic DNA may be used directly for detection or may be amplified by using PCR prior to analysis of the genomic DNA or transcripts. For example, fragmented single-stranded DNA from an individual is hybridized to an array containing hundreds to thousands of immobilized unique nucleotide probe sequences. The nucleotide probe sequences are designed to bind to a target DNA sequence (e.g. for a SNP, an allele-specific probe is used to identify and analyze the presence or absence of the SNP). A detection system is used to record and interpret the hybridization signal between the immobilized probe and the DNA from the individual (either the probe or the DNA is labeled with a fluorophor that is detected and measured). The detection of a specific DNA sequence may be achieved by methods which include, but are not limited to, hybridization, RNAse protection, chemical cleavage, direct DNA sequencing or the use of restriction enzymes, Southern blotting of genomic DNA, in situ analysis, hybridizing a sample and control nucleic acids to high density arrays containing hundreds or thousands of oligonucleotide probes (Cronin et al., Hum Mutat, 7(3): 244-55 (1996) (or other methods for analysis of SNPs as described herein). For example, genetic mutations can be identified using microarrays (Shen et al., Mutat Res, 573(1-2): 70-82 (2005))). These genetic tests are useful for stratifying populations of individuals into subpopulations having different responsiveness to treatment of anti-factor D.

The term "genotyping" as used herein refers to methods of determining differences in the genetic make-up ("genotype") of an individual, including but not limited to the detection of the presence of DNA insertions or deletions, polymorphisms (SNPs or otherwise), alleles (including minor or major or risk alleles in the form of SNPs, by examining the individual's DNA sequence using analytical or biological assays (or other methods for analysis of SNPs as described herein)). For instance, the individual's DNA sequence determined by sequencing or other methodologies (for example other methods for analysis of SNPs as described herein), may be compared to another individual's sequence or a reference sequence. Methods of genotyping are generally known in the art (for example other methods for analysis of SNPs as described herein), including but are not limited to restriction fragment length polymorphism identification (RFLP) of genomic DNA, random amplified polymorphic detection (RAPD) of genomic DNA, amplified fragment length polymorphism detection (AFLPD), polymerase chain reaction (PCR), DNA sequencing, allele specific oligonucleotide (ASO) probes, and hybridization to DNA microarrays or beads. Similarly these techniques may be applied to analysis of transcripts that encode SNPs or other genetic factors. Samples can be conveniently assayed for a SNP using polymerase chain reaction (PCR) analysis, array hybridization or using DNA SNP chip microarrays, which are commercially available, including DNA microarray snapshots. A microarray can be utilized for determining whether a SNP is present or absent in a nucleic acid sample. A microarray may include oligonucleotides, and methods for making and using oligonucleotide microarrays suitable for diagnostic use are disclosed in U.S. Pat. Nos. 5,492,806; 5,525,464; 5,589,330; 5,695,940; 5,849,483; 6,018,041; 6,045,996; 6,136,541; 6,152,681; 6,156,501; 6,197,506; 6,223,127; 6,225,625; 6,229, 911; 6,239,273; WO 00/52625; WO 01/25485; and WO 01/29259.

In some embodiments, the genotyping may be used by clinicians to direct appropriate treatment procedures to individuals who most require them. For example, subjects in a study are genotyped and categorized into (1) a population that responds favorably to a treatment and (2) a population that does not respond significantly to a treatment, and (3) a population that responds adversely to a treatment. Based on the results, a subject is genotyped to predict whether the subject will respond favorably, not respond significantly or respond adversely to a treatment. Potential participants in clinical trials of a treatment may be screened to identify those that are most likely to respond favorably to the treatment and to exclude those likely to experience side effects. Thus, the effectiveness of drug treatment may be measured in individuals who respond positively to the drug. Thus, one embodiment is a method of selecting an individual for inclusion in a clinical trial of a treatment comprising the steps of: (a) obtaining a nucleic acid sample from an individual, (b) determining the presence of a polymorphic variant which is associated with a positive response to the treatment or a polymorphic variant which is associated with a negative response to the treatment. In another embodiment, the invention includes a method of selecting an individual for treatment comprising the steps of: (a) obtaining a nucleic acid sample from an individual, (b) determining the presence of a polymorphic variant which is associated with a positive response to the treatment and (c) treating the individual by administering the treatment.

The term "allele-specific primer" or "AS primer" refers to a primer that hybridizes to more than one variant of the target sequence, but is capable of discriminating between the variants of the target sequence in that only with one of the variants, the primer is efficiently extended by the nucleic acid polymerase under suitable conditions. With other variants of the target sequence, the extension is less efficient or inefficient. Where extension is less efficient or inefficient, the signal is of substantially lesser intensity or preferably, falls below detection limit.

The term "allele-specific probe" or "AS probe" refers to a probe that hybridizes to more than one variant of the target sequence, but is capable of discriminating between the variants of the target sequence in that only with one of the variants, a detectable signal is generated. With other variants of the target sequence, the signal is of substantially lesser intensity or preferably, falls below the detection limit.

The term "primary sequence" refers to the sequence of nucleotides in a polynucleotide or oligonucleotide. Nucleotide modifications such as nitrogenous base modifications, sugar modifications or other backbone modifications are not a part of the primary sequence. Labels, such as chromophores conjugated to the oligonucleotides are also not a part of the primary sequence. Thus two oligonucleotides can share the same primary sequence but differ with respect to the modifications and labels.

The term "primer" refers to an oligonucleotide which hybridizes with a sequence in the target nucleic acid and is capable of acting as a point of initiation of synthesis along a complementary strand of nucleic acid under conditions suitable for such synthesis. As used herein, the term "probe" refers to an oligonucleotide which hybridizes with a sequence in the target nucleic acid and is usually detectably labeled. The probe can have modifications, such as a 3'-terminus modification that makes the probe non-extendable by nucleic acid polymerases, and one or more chromophores. An oligonucleotide with the same sequence may serve as a primer in one assay and a probe in a different assay.

he term "modified nucleotide" refers to a unit in a nucleic acid polymer that contains a modified base, sugar or phosphate group, or that incorporates a non-natural moiety in its structure. Examples of non-natural nucleotides, include nucleotides with a modified nitrogenous base, e.g. alkylated or otherwise substitutes with a group not present among the conventional nitrogenous bases involved in Watson-Crick pairing. By way of illustration and not limitation, modified nucleotides include those with bases substituted with methyl, ethyl, benzyl or butyl-benzyl. In an allele-specific PCR, at least one primer is allele-specific such that primer extension occurs only (or preferentially) when the specific variant of the sequence is present and does not occur (or occurs less efficiently, i.e. with a substantial $\Delta Ct$) when another variant is present. Design of successful allele-specific primers is an unpredictable art. While it is routine to design a primer for a known sequence, no formula exists for designing a primer that can discriminate between very similar sequences. The discrimination is especially challenging when one or more allele-specific primers targeting one or more polymorphic sites are present in the same reaction mixture.

The terms "complementary" or "complementarity" are used in reference to antiparallel strands of polynucleotides related by the Watson-Crick base-pairing rules. The terms "perfectly complementary" or "100% complementary" refer to complementary sequences that have Watson-Crick pairing of all the bases between the antiparallel strands, i.e. there are no mismatches between any two bases in the polynucleotide duplex. However, duplexes are formed between antiparallel strands even in the absence of perfect complementarity. The terms "partially complementary" or "incompletely complementary" refer to any alignment of bases between antiparallel polynucleotide strands that is less than 100% perfect (e.g., there exists at least one mismatch or unmatched base in the polynucleotide duplex). The duplexes between partially complementary strands are generally less stable than the duplexes between perfectly complementary strands.

A "phenotype" is a trait which can be compared between individuals, such as presence or absence of a condition, for example, occurred of intermediate or advanced AMD.

The nucleic acid sample is isolated from a biological sample obtained from a subject. "Biological sample" includes but is not limited to blood, saliva, sputum, urine, cell scrapings and biopsy tissue. The nucleic acid sample may be isolated form a biological sample using standard techniques. The nucleic acid sample may be used in a method for determining the presence of a polymorphic variant. The presence or absence of a polymorphic variant may be determined using one or both chromosomal complements represented in the nucleic acid sample. Determining the presence or absence of the polymorphic variant in both chromosomal complements represented in the nucleic acid sample is useful for determining the zygosity of an individual for the polymorphic variant.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) overnight hybridization in a solution that employs 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with a 10 minute wash at 42° C. in 0.2×SSC (sodium chloride/sodium citrate) followed by a 10 minute high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "sample," or "test sample" as used herein, refers to a composition that is obtained or derived from a subject of interest that contains a cellular and/or other molecular entity that is to be characterized and/or identified, for example based on physical, biochemical, chemical and/or physiological characteristics. In one embodiment, the definition encompasses blood and other liquid samples of biological origin and tissue samples such as a biopsy specimen or tissue cultures or cells derived therefrom. The source of the tissue sample may be solid tissue as from a fresh, frozen and/or preserved organ or tissue sample or biopsy or aspirate; blood or any blood constituents; bodily fluids; and cells from any time in gestation or development of the subject or plasma. The term "sample," "biological sample,' or "test sample" includes biological samples that have been manipulated in any way after their procurement, such as by treatment with reagents, solubilization, or enrichment for certain components, such as proteins or polynucleotides, or embedding in a semi-solid or solid matrix for sectioning purposes. For the purposes herein a "section" of a tissue sample is meant a single part or piece of a tissue sample, e.g. a thin slice of tissue or cells cut from a tissue sample. Samples include, but are not limited to, whole blood, blood-derived cells, serum, plasma, lymph fluid, synovial fluid, cellular extracts, and combinations thereof. In one embodiment, the sample is a clinical sample. In another embodiment, the sample is used in a diagnostic assay.

In one embodiment, a sample is obtained from a subject or patient prior to treatment with a complement inhibitor. In another embodiment, a sample is obtained from a subject or patient following at least one treatment with a complement inhibitor.

A "reference sample," as used herein, refers to any sample, standard, or level that is used for comparison purposes. In one embodiment, a reference sample is obtained from a healthy and/or non-diseased part of the body (e.g., tissue or cells) of the same subject or patient. In another embodiment, a reference sample is obtained from an untreated tissue and/or cell of the body of the same subject or patient. In yet another embodiment, a reference sample is obtained from a healthy and/or non-diseased part of the body (e.g., tissues or cells) of an individual who is not the subject or patient. In even another embodiment, a reference sample is obtained from an untreated tissue and/or cell part of the body of an individual who is not the subject or patient.

In certain embodiments, a reference sample is a single sample or combined multiple samples from the same subject or patient that are obtained at one or more different time points than when the test sample is obtained. For example, a reference sample is obtained at an earlier time point from the same subject or patient than when the test sample is obtained. In certain embodiments, a reference sample includes all types of biological samples as defined above under the term "sample" that is obtained from one or more individuals who is not the subject or patient. In certain embodiments, a reference sample is obtained from one or more individuals with a degenerative disease (e.g., age-related macular degeneration) who is not the subject or patient.

In certain embodiments, a reference sample is a combined multiple samples from one or more healthy individuals who are not the subject or patient. In certain embodiments, a reference sample is a combined multiple samples from one or more individuals with a disease or disorder (e.g., an degenerative disease such as, for example, age-related macular degeneration) who are not the subject or patient. In certain embodiments, a reference sample is pooled RNA samples from normal tissues or pooled plasma or serum samples from one or more individuals who are not the subject or patient.

The terms "Fc receptor" and "FcR" are used to describe a receptor that binds to the Fc region of an antibody. The preferred FcR is a native-sequence human FcR. Moreover, a preferred FcR is one that binds an IgG antibody (a gamma receptor) and includes receptors of the FcγRI, FcγRII, and Fcγ RIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see Daëron Annu. Rev. Immunol. 15:203-234 (1997)). FcRs are reviewed in Ravetch and Kinet Annu. Rev. Immunol 9:457-92 (1991); Capel et al. Immunomethods 4:25-34 (1994); and de Haas et al. J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al, J. Immunol. 117:587 (1976) and Kim et al. J. Immunol. 24:249 (1994)).

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light-chain variable domain is aligned with the variable domain of the heavy chain. Particular amino acid residues are believed to form an interface between the light-chain and heavy-chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light-chain and the heavy-chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al. Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in ADCC.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-binding sites and is still capable of cross-linking antigen.

"Fv" is the minimum antibody fragment that contains a complete antigen-recognition and antigen-binding site. This region consists of a dimer of one heavy-chain and one light-chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy-chain CH1 domain including one or more cysteines from the antibody hinge region. Fab'-SH is the designation herein for Fab' in which the cysteine residue(s) of the constant domains bear at least one free thiol group. F(ab')$_2$ antibody fragments originally were produced as pairs of Fab' fragments that have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, antibodies can be assigned to different classes. There are five major classes of intact antibodies: IgA, IgD, IgE, IgG, and IgM, and several of these may be further divided into subclasses (isotypes), e.g., IgG1, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of immunoglobulins are well known.

"Single-chain Fv" or "scFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains that enables the scFv to form the desired structure for antigen binding. For a review of scFv, see Plückthun in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 1993/11161; and Hollinger et al., Proc. Natl. Acad. Sci. USA, 90:6444-6448 (1993).

The term "monoclonal antibody" as used herein refers to an antibody obtained from a population of substantially homogeneous antibodies, i.e., the individual antibodies comprising the population are identical and/or bind the same epitope, except for possible variants that may arise during production of the monoclonal antibody, such variants generally being present in minor amounts. In contrast to polyclonal antibody preparations that typically include different antibodies directed against different determinants (epitopes), each monoclonal antibody is directed against a single determinant on the antigen. In addition to their specificity, the monoclonal antibodies are advantageous in that they are uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature, 256:495 (1975), or may be made by recombinant DNA methods (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Natl. Acad. Sci. USA, 81:6851-6855 (1984)). Chimeric antibodies of interest herein include "primatized" antibodies comprising variable-domain antigen-binding sequences derived from a non-human primate (e.g. Old World Monkey, such as baboon, rhesus, or cynomolgus monkey) and human constant-region sequences (U.S. Pat. No. 5,693,780).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit, or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence, except for FR substitution(s) as noted above. The humanized antibody optionally also will comprise at least a portion of an immunoglobulin constant region, typically that of a human immunoglobulin. For further details, see Jones et al., Nature 321:522-525 (1986); Riechmann et al., Nature 332: 323-329 (1988); and Presta, Curr. Op. Struct. Biol. 2:593-596 (1992).

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. An HVR as used herein comprise any number of residues located within positions 24-36 (for L1), 46-56 (for L2), 89-97 (for L3), 26-35B (for H1), 47-65 (for H2), and 93-102 (for H3). Therefore, an HVR includes residues in positions described previously:

A) 24-34 (L1), 50-52 (L2), 91-96 (L3), 26-32 (H1), 53-55 (H2), and 96-101 (H3) (Chothia and Lesk, *J. Mol. Biol.* 196:901-917 (1987);

B) 24-34 of L1, 50-56 of L2, 89-97 of L3, 31-35B of H1, 50-65 of H2, and 95-102 of H3 (Kabat et al., *Sequences of Proteins of Immunological Interest*, 5th Ed. Public Health Service, National Institutes of Health, Bethesda, Md. (1991).

C) 30-36 (L1), 46-55 (L2), 89-96 (L3), 30-35 (H1), 47-58 (H2), 93-100a-j (H3) (MacCallum et al. J. Mol. Biol. 262:732-745 (1996).

Unless otherwise indicated, HVR residues and other residues in the variable domain (e.g., FR residues) are numbered herein according to Kabat et al., supra. The Kabat numbering system is generally used when referring to a residue in the variable domain (approximately residues 1-107 of the light chain and residues 1-113 of the heavy chain) (e.g, Kabat et al., Sequences of Immunological Interest. 5th Ed. Public Health Service, National Institutes of Health, Bethesda, Md. (1991), expressly incorporated herein by reference). The "EU numbering system" or "EU index" is generally used when referring to a residue in an immunoglobulin heavy chain constant region (e.g., the EU index reported in Kabat et al., supra; hinge region in constant domain of heavy chain is approximately residues 216-230 (EU numbering) of the heavy chain). The "EU index as in Kabat" refers to the residue numbering of the human IgG1

EU antibody. Unless stated otherwise herein, references to residue numbers in the variable domain of antibodies means residue numbering by the Kabat numbering system. Unless stated otherwise herein, references to residue numbers in the constant domain of antibodies means residue numbering by the EU numbering system (e.g., see U.S. Provisional Application No. 60/640,323, Figures for EU numbering).

A "naked antibody" is an antibody (as herein defined) that is not conjugated to a heterologous molecule, such as a cytotoxic moiety or radiolabel.

An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or non-proteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning-cup sequenator, or (3) to homogeneity by SDS-PAGE under reducing or nonreducing conditions using Coomassie blue or, preferably, silver stain. Isolated antibody includes the antibody in situ within recombinant cells, since at least one component of the antibody's natural environment will not be present. Ordinarily, however, isolated antibody will be prepared by at least one purification step.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "least squares" when used herein refers to the use of least squares method which minimizes the sum of the squares of difference between each observed value and its estimated value (Plackett, R. L. *Biometricka,* 59: 239-251 (1972)). The least squares mean presented herein was an estimate of the mean DDAF change from baseline in GA area based on a linear mixed effect model (Garret Fitzmaurice, Nan Laird, James Ware, *Applied Longitudinal Analysis,* $2^{nd}$ edition, Chapter 8, Publisher (John Wiley & Sons) (August 2011)) which was used to fit the relationship between change in GA area vs. baseline GA lesion size (continuous), baseline GA lesion size category (<4DA vs.≥4DA), time, treatment, and time-by-treatment interaction. See FIGS. 5 and 6.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

A "neutralizing antibody" is an antibody molecule which is able to eliminate or significantly reduce an effector function of a target antigen to which it binds. Accordingly, a "neutralizing" anti-factor D antibody, or antigen-binding fragment thereof is capable of eliminating or significantly reducing an effector function, such as alternative complement activity, of factor D.

An exemplary assay is one that monitors the ability of an anti-factor D antibody, or antigen-binding fragment thereof to neutralize alternative complement activity of factor D. See, for example, the hemolytic inhibition assay as described in PCT/US2007/083172, published on May 8, 2008, whereby neutralization is measured by the ability of a candidate antibody to inhibit rabbit red blood cell hemolysis using C1q-depleted human serum as complement source.

Alternatively, the ability of the anti-factor D antibodies to neutralize the elicitation of a cellular response by factor D may be tested by C3 Fluid Phase Convertase Assay, as described by Wiesmann et al., *Nature,* 444: 217-220 (2006)).

"Significant" reduction means at least about 60%, or at least about 70%, preferably at least about 75%, more preferably at least about 80%, even more preferably at least about 85%, still more preferably at least about 90%, still more preferably at least about 95%, most preferably at least about 99% reduction of an effector function of the target antigen (e.g. factor D), such as alternative complement activity. Preferably, the "neutralizing" antibodies as defined herein will be capable of neutralizing at least about 60%, or at least about 70%, preferably at least about 75%, more preferably at least about 80%, even more preferably at least about 85%, still more preferably at least about 90%, still more preferably at least about 95%, most preferably at least about 99% of the anti-alternative pathway activity of factor D, as determined by the hemolytic assay of PCT/US2007/083172, published on May 8, 2008.

A "subject" or "patient" herein is a human subject or patient. Generally, such subject or patient is eligible for treatment for geographic atrophy. In one embodiment, such eligible subject or patient is one that is experiencing or has experienced one or more signs, symptoms, or other indicators of geographic atrophy or has been diagnosed with geographic atrophy, whether, for example, newly diagnosed, previously diagnosed or is at risk for developing geographic atrophy. In another embodiment, the patient to be treated can be screened using an assay to detect the presence of SNPs associated with AMD. A "stable" formulation is one in which the protein therein essentially retains its physical stability and/or chemical stability and/or biological activity upon storage. Preferably, the formulation essentially retains its physical and chemical stability, as well as its biological activity upon storage. The storage period is generally selected based on the intended shelf-life of the formulation. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993), for example. Stability can be measured at a selected temperature for a selected time period. Preferably, the formulation is stable at about 40° C. for at least about 2-4 weeks, and/or stable at about 5° C. and/or 15° C. for at least 3 months, and/or stable at about −20° C. for at least 3 months or at least 1, 2, 3, or 4 years. Furthermore, the formulation is preferably stable following freezing (to, e.g., −70° C.) and thawing of the formulation, for example following 1, 2 or 3 cycles of freezing and thawing. Stability can be evaluated qualitatively and/or quantitatively in a variety of different ways, including evaluation of aggregate formation (for example using size exclusion chromatography, by measuring turbidity, and/or by visual inspection); by assessing charge heterogeneity using cation exchange chromatography or capillary zone electrophoresis; amino-terminal or carboxy-terminal sequence analysis; mass spectrometric analysis; SDS-PAGE analysis to compare reduced and intact antibody; peptide map (for example tryptic or LYS-C) analysis; evaluating biological activity or antigen binding function of the antibody; etc. Instability may involve any one or more of: aggregation, deamidation (e.g. Asn deamidation), oxidation (e.g. Met oxidation), isomerization (e.g. Asp isomerization), clipping/hydrolysis/fragmentation (e.g. hinge region fragmentation), succinimide formation, unpaired cysteine(s), N-terminal extension, C-terminal processing, glycosylation differences, etc.

A "histidine buffer" is a buffer comprising histidine ions. Examples of histidine buffers include histidine chloride, histidine acetate, histidine phosphate, histidine sulfate. The preferred histidine buffer identified in the examples herein was found to be histidine chloride. In one embodiment, the histidine chloride buffer is prepared by titrating L-histidine (free base, solid) with hydrochloric acid (liquid). In another embodiment, the histidine buffer is prepared by a mixture of histidine and histidine-hydrochloride salt to achieve the desired pH. Preferably, the histidine buffer or histidine chloride buffer is at pH 5.0 to 6.0, preferably pH 5.2 to 5.8.

A "saccharide" herein comprises the general composition $(CH_2O)n$ and derivatives thereof, including monosaccharides, disaccharides, trisaccharides, polysaccharides, sugar alcohols, reducing sugars, nonreducing sugars, etc. Examples of saccharides herein include glucose, sucrose, trehalose, lactose, fructose, maltose, dextran, glycerin, dextran, erythritol, glycerol, arabitol, sylitol, sorbitol, mannitol, mellibiose, melezitose, raffinose, mannotriose, stachyose, maltose, lactulose, maltulose, glucitol, maltitol, lactitol, isomaltulose, etc.

Herein, a "surfactant" refers to a surface-active agent, preferably a nonionic surfactant. Examples of surfactants herein include polysorbate (for example, polysorbate 20 and, polysorbate 80); poloxamer (e.g. poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl oleyl-taurate; and the MONAQUAT™ series (Mona Industries, Inc., Paterson, N.J.); polyethyl glycol, polypropyl glycol, and copolymers of ethylene and propylene glycol (e.g. Pluronics, PF68 etc); etc. The preferred surfactant herein is polysorbate 20.

Diagnosis of GA may be made based on clinical history, clinical examination, and established imaging modalities.

"Treatment" of a subject herein refers to both therapeutic treatment and prophylactic or preventative measures. Those in need of treatment include those already with the GA as well as those in which the GA is to be prevented. Hence, the subject may have been diagnosed as having the GA or may be predisposed or susceptible to the GA.

A "symptom" of GA is any morbid phenomenon or departure from the normal in structure, function, or sensation, experienced by the subject and indicative of disease.

The expression "effective amount" refers to an amount of the antibody that is effective for preventing, ameliorating, or treating the GA.

"Antibody exposure" refers to contact with or exposure to the antibody herein in one or more doses administered over a period of time of about 1 day to about 5 weeks. The doses may be given at one time or at a fixed or irregular time intervals over this period of exposure, such as, for example, one dose weekly for four weeks or two doses separated by a time interval of about 13-17 days. Initial and later antibody exposures are separated in time from each other as described in detail herein.

A "factor D inhibitor" herein is an agent that inhibits, to some extent, a biological function of factor D, generally through binding to factor D and neutralizing its activity. Examples of factor D inhibitors specifically contemplated herein are lampalizumab.

A "package insert" is used to refer to instructions customarily included in commercial packages of therapeutic products, that contain information about the indications, usage, dosage, administration, contraindications, other therapeutic products to be combined with the packaged product, and/or warnings concerning the use of such therapeutic products, etc.

An exposure not being administered or provided until a certain time "from the initial exposure" or from any prior exposure means that the time for the second or later exposure is measured from the time any of the doses from the prior exposure were administered, if more than one dose was administered in that exposure. For example, when two doses are administered in an initial exposure, the second exposure is not given until at least about 16-54 weeks as measured from the time the first or the second dose was administered within that prior exposure. Similarly, when three doses are administered, the second exposure may be measured from the time of the first, second, or third dose within the prior exposure. Preferably, "from the initial exposure" is measured from the time of the first dose.

A "medicament" is an active drug to treat the geographic atrophy or its symptoms or side effects.

The term "administering" as used herein is used in the broadest sense and inter alia encompasses enteral, topical administration and "parenteral administration". "Parenteral administration" and "administered parenterally" as used herein mean modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural, intrasternal injection, infusion, ocular, intraocular, intravitreal, juxtascleral, subtenon and superchoroidal. "IVT or ITV" when used herein refers to intravitreal.

The term "assessing AMD" is used to indicate that the method according to the present invention will aid a medical professional including, e.g., a physician to assess whether an individual is at risk of developing intermediate or advanced AMD or prognosing to intermediate or advanced AMD. The presence of a risk allele for CFI, CFH, C3, C2 or CFB in the sample indicates that the individual is at risk of developing intermediate or advanced AMD or prognosing to advanced AMD.

Results from prognostic tests may be combined with other test results to diagnose progression to more advanced AMD. In some embodiments, the results from predisposition analyses may be combined with other test results, epidemiologic or genetic in nature, indicative of progression to more advanced AMD. In these embodiments, the combination of the prognostic test results with other test results can be probative or progression to more advanced AMD, and the combination can be utilized as an AMD diagnostic.

The term "progression" as used herein refers to the worsening of a disease over time. The "progression rate" or "rate of progression" of a disease refers to how fast or slow a disease develops over time in a patient diagnosed with the disease. The disease is often chronic and the time frame can be weeks, months or years. The progression rate of a disease can be represented by measurable changes over time of particular characteristics of the disease. For example, the progression rate of a patient with GA can be represented by the growth rate of GA lesion area from baseline to month 18 as measured by a standard imaging method such as fundus autofluorescence (FAF) or color fundus photography (CFP). A patient carrying particular genetic trait is said to have, or more likely to have, "increased progression rate" if her disease state progresses faster than those patients without such genetic trait. On the other hand, a patient responding to a therapy is said to have, or more likely to have, "decreased progression rate" if her disease progression slows down after the therapy, when compared to her disease state prior to the treatment or to other patients without the treatment.

"More likely to respond" as used herein refers to patients that are most likely to demonstrate a slowing down or prevention of progression of AMD. With regard to GA, "more likely to respond" refers to patients that are most likely to demonstrate a reduction in loss of GA area by FAF or CFP with treatment. With regard to intermediate AMD, "more likely to respond" refers to patients that are more likely to demonstrate a slowing of progression to advanced AMD. With regard to early AMD, "more likely to respond" refers to patients that are more likely to demonstrate a slowing of progression to intermediate AMD. The phrase "responsive to" in the context of the present invention indicates that a patient suffering from, being suspected to suffer or being prone to suffer from, or diagnosed with a disorder as described herein, shows a response to anti-factor D treatment.

An "individual" or "subject" is a mammal. Mammals include, but are not limited to, domesticated animals (e.g., cows, sheep, cats, dogs and horses, primates (e.g., humans and non-human primates such as monkeys, rabbits, and rodents (e.g. mice and rats). In certain embodiments, the individual or subject is a human.

A "patient" or "subject" herein is any single human subject eligible for treatment who is experiencing or has experienced one or more signs, symptoms, or other indicators of AMD. Intended to be included as a subject are any subjects involved in clinical research trials not showing any clinical sign of disease, or subjects involved in epidemiological studies, or subjects once used as controls. The subject may have been previously treated with an anti-factor D antibody, or antigen-binding fragment thereof or another drug, or not so treated. The subject may be naïve to an additional drug(s) being used when the treatment herein is started, i.e., the subject may not have been previously treated with, for example, a therapy other than anti-factor D at "baseline" (i.e., at a set point in time before the administration of a first dose of anti-factor D in the treatment method herein, such as the day of screening the subject before treatment is commenced). Such "naïve" subjects are generally considered to be candidates for treatment with such additional drug(s).

The phrase "providing an assessment" as used herein refers to using the information or data generated relating to the presence of a risk allele in a sample of a patient to assess AMD in the patient. The information or data may be in any form, written, oral or electronic. In some embodiments, using the information or data generated includes communicating, presenting, reporting, storing, sending, transferring, supplying, transmitting, dispensing, or combinations thereof. In some embodiments, communicating, presenting, reporting, storing, sending, transferring, supplying, transmitting, dispensing, or combinations thereof are performed by a computing device, analyzer unit or combination thereof. In some further embodiments, communicating, presenting, reporting, storing, sending, transferring, supplying, transmitting, dispensing, or combinations thereof are performed by a laboratory or medical professional. In some embodiments, the information or data includes an indication that the risk allele is present or absent in the sample. In some embodiments, the information or data includes an indication that the patient is assessed with intermediate or advanced AMD.

The term "sample" refers to a sample of a body fluid, to a sample of separated cells or to a sample from a tissue or an organ. Samples of body fluids can be obtained by well-known techniques and include, samples of blood, plasma, serum, urine, lymphatic fluid, sputum, ascites, bronchial lavage or any other bodily secretion or derivative thereof. Tissue or organ samples may be obtained from any tissue or organ by, e.g., biopsy. Separated cells may be obtained from the body fluids or the tissues or organs by separating techniques such as centrifugation or cell sorting. E.g., cell-, tissue- or organ samples may be obtained from those cells, tissues or organs which express or produce the biomarker. The sample may be frozen, fresh, fixed (e.g. formalin fixed), centrifuged, and/or embedded (e.g. paraffin embedded), etc. The cell sample can, of course, be subjected to a variety of well-known post-collection preparative and storage techniques (e.g., nucleic acid and/or protein extraction, fixation, storage, freezing, ultrafiltration, concentration, evaporation, centrifugation, etc.) prior to assessing the amount of the marker in the sample. Likewise, biopsies may also be subjected to post-collection preparative and storage techniques, e.g., fixation. The sample could be taken before treatment, during treatment or post-treatment. The sample may be taken from a patient who is suspected of having, or is diagnosed as having AMD, and hence is likely in need of treatment or from a normal individual who is not suspected of having any disorder.

The phrase "selecting a patient" or "identifying a patient" as used herein refers to using the information or data generated relating to the presence of a risk allele in a sample of a patient to identify or select the patient as more likely to benefit to benefit from a treatment comprising anti-factor D antibody. The information or data used or generated may be in any form, written, oral or electronic. In some embodiments, using the information or data generated includes communicating, presenting, reporting, storing, sending, transferring, supplying, transmitting, dispensing, or combinations thereof. In some embodiments, communicating, presenting, reporting, storing, sending, transferring, supplying, transmitting, dispensing, or combinations thereof are performed by a computing device, analyzer unit or combination thereof. In some further embodiments, communicating, presenting, reporting, storing, sending, transferring, supplying, transmitting, dispensing, or combinations thereof are performed by a laboratory or medical professional. In some embodiments, the information or data includes an indication that a risk allele is present or absent in the sample. In some embodiments, the information or data includes an indication that the patient is more likely to respond to a therapy comprising anti-factor D.

The phrase "selecting a therapy as used herein refers to using the information or data generated relating to the presence of a risk allele in a sample of a patient to identify or selecting a therapy for a patient. In some embodiment the therapy may comprise anti-factor D. In some embodiments the phrase "identifying/selecting a therapy" includes the identification of a patient who requires adaptation of an effective amount of anti-factor D being administered. In some embodiments recommending a treatment includes recommending that the amount of anti-factor D being administered is adapted. The phrase "recommending a treatment" as used herein also may refer to using the information or data generated for proposing or selecting a therapy comprising anti-factor D for a patient identified or selected as more likely to respond to the therapy comprising anti-factor D. The information or data used or generated may be in any form, written, oral or electronic. In some embodiments, using the information or data generated includes communicating, presenting, reporting, storing, sending, transferring, supplying, transmitting, dispensing, or combinations thereof. In some embodiments, communicating, presenting, reporting, storing, sending, transferring, supplying, transmitting, dispensing, or combinations thereof are performed by a computing device, analyzer unit or combination thereof. In some further embodiments, communicating, presenting, reporting, storing, sending, transferring, supplying, transmitting, dispensing, or combinations thereof are performed by a laboratory or medical professional. In some embodiments, the information or data includes an indication that a risk allele is present or absent in the sample. In some embodiments, the information or data includes an indication that a therapy comprising anti-factor D is suitable for the patient III. Methods The present invention provides compositions and methods for the treatment, prognosis, diagnosis and/or selection of a population of AMD patients that would be good candidates for treatment with complement inhibitor(s). In one embodiment, the invention provides methods for prognosing progression of a degenerative disease (eg. AMD (including GA and CNV) in a patient, comprising determining the presence of a risk allele in the patient. In one embodiment, the invention provides for methods of treating degenerative diseases (e.g., AMD (including GA and CNV)) in a patient, comprising administering an effective amount of an antibody that binds to factor D, wherein the patient carries a risk allele associated with AMD. In some embodiments, the invention provides methods of treating degenerative diseases (e.g., AMD (including GA and CNV) in a patient, comprising administering a certain antibody that binds to factor D according to a particular dosing regimen. In some embodiments, the invention provides methods of treating degenerative diseases (e.g., AMD (including GA and CNV) in a patient, comprising administering an effective amount of an antibody, or antigen-binding fragment thereof, that binds to factor D, wherein the patient is heterozygous or homozygous for a risk allele associated with a degenerative disease (e.g. AMD (including GA and CNV). In some embodiments, the patient carries a risk allele in one, or all, or a combination of CFH, CFI, C3, C2 and CFB. In one embodiment, the antibody or antigen-binding fragment thereof is lampalizumab. In one embodiment, the invention provides methods for predicting response of a degenerative disease patient to treatment with an anti-factor D antibody, or antigen-binding fragment thereof. In one embodiment, the invention provides methods for optimizing therapeutic efficacy of treatment of a patient with degenerative disease with an anti-factor D antibody, or antigen-binding fragment thereof.

The present invention is based partly on the use of specific genes (e.g., one or more of complement factor I (CFI), complement factor H (CFH), complement component 2 (C2), complement component 3 (C3) and complement factor B (CFB), and combinations thereof) or biomarkers (e.g., SNPs of complement factor I (CFI), complement factor H (CFH), complement component 2 (C2), complement component 3 (C3) and complement factor B (CFB)) that correlate with efficacy of factor D inhibitors (e.g., an anti-factor D antibody or antigen-binding fragment thereof). Thus, the disclosed methods provide convenient, efficient, and potentially cost-effective means to obtain data and information useful in assessing appropriate or effective therapies for treating patients. For example, a sample can be obtained from an AMD patient, and the sample could be examined by various in vitro assays to determine whether the expression level of one or more biomarkers is present as compared to a reference sample. In one embodiment, if the patient carries a risk allele-, then the patient is likely to benefit from treatment with a therapy comprising a factor D inhibitor (e.g., an anti-factor D antibody, or antigen-binding fragment thereof, such as, for example, lampalizumab). Presence of a gene or a biomarker or SNP can be determined based on any suitable criterion known in the art, including but not limited to mRNA, cDNA, proteins, protein fragments and/or gene copy number.

Analysis of SNPs in a sample can be analyzed in blood, tissue or other bodily fluids by a number of methodologies, many of which are known in the art and understood by the skilled artisan, including but not limited to, DNA sequencing, RNA sequencing, polymerase chain reaction analysis of DNA, polymerase chain reaction analysis of RNA, oligonucleotide based hybridization, in situ hybridization, oligonucleotide based primer extension, electrophoresis and HPLC. Additional techniques for detecting SNPs include but are not limited to the following techniques: scanning probe and nanopore DNA sequencing, pyrosequencing, Denaturing Gradient Gel Electrophoresis (DGGE), Temporal Temperature Gradient Electrophoresis (TTGE), Zn(II)-cyclen polyacrylamide gel electrophoresis, homogeneous fluorescent PCR-based single nucleotide polymorphism analysis, phosphate-affinity polyacrylamide gel electrophoresis, high-throughput SNP genotyping platforms, molecular beacons, 5' nuclease reaction, Taqman assay, MassArray (single base primer extension coupled with matrix-assisted laser desorption/ionization time-of-flight mass spectrometry), trityl mass tags, genotyping platforms (such as the Invader Assay®), single base primer extension (SBE) assays, PCR amplification (e.g. PCR amplification on magnetic nanoparticles (MNPs), restriction enzyme analysis of PCR products (RFLP methods), allele-specific PCR, multiple primer extension (MPEX), isothermal smart amplification. (Methods in Molecular Biology, Single Nucleotide Polymorphisms, $2^{nd}$ edition, editor Anton Komar, Humana Press 2009; Chapters 7-28), PCR amplification of simple sequence length polymorphisms (SSLPs), ligase chain reaction (LCR), RNase A cleavage, chemical cleavage of heteroduplex DNA, single-strand conformation polymorphism (SSCP) analysis (Warren et al., Current Protocol in Human Genetics, Supp 15: 7.4.1-7.4.23 (2001), bead-chip microarray (Lambert et al., Current Protocol in Human Genetics, Supp 78: 2.9.1-2.9.3 (2013)), single-strand conformation polymorphism (SSCP) analysis, primer single-base extension (SBE) (Deshpande et al., Current Protocol in Human Genetics, Supp 34: 13.4.1-13.4.11 (2005)), primer extension assay (Kwok et al., Current Protocol in Human Genetics, Supp 39: 2.11.1-2.11.10 (2003). The presence of a SNP may also be inferred from analysis of protein based techniques (to examine, for example, levels of protein expression or function), including immunoassay (e.g. ELISA, ELIFA, immunohistochemical and/or Western blot analysis, immunoprecipitation, molecular binding assays, fluorescence activated cell sorting (FACS) and the like, quantitative blood based assays (as for example Serum ELISA) in situ hybridization, or functional assays including biochemical enzymatic activity assays or cell based systems, as well as any one of the wide variety of assays that can be performed by gene and/or tissue array analysis. Typical protocols for evaluating the status of genes and gene products are found, for example in Ausubel et al. eds., 1995, Current Protocols In Molecular Biology, Units 2 (Northern Blotting), 4 (Southern Blotting), 15 (Immunoblotting) and 18 (PCR Analysis). Multiplexed immunoassays such as those available from Rules Based Medicine, bead based immunoassays e.g. Luminex, ELISA or Meso Scale Discovery (MSD) may also be used.

One technique that is sensitive and amenable for SNP analysis of the invention is allele-specific PCR (AS-PCR) described in e.g. U.S. Pat. No. 6,627,402. This technique detects mutations or polymorphisms in nucleic acid sequences in the presence of wild-type variants of the sequences. In a successful allele-specific PCR, the desired variant of the target nucleic acid is amplified, while the other variants are not, at least not to a detectable level.

One measure of discrimination of an allele-specific PCR is the difference between Ct values ($\Delta$Ct) in the amplification reactions involving the two alleles. Each amplification reaction is characterized by a "growth curve" or "amplification curve" in the context of a nucleic acid amplification assay is a graph of a function, where an independent variable is the number of amplification cycles and a dependent variable is an amplification-dependent measurable parameter measured at each cycle of amplification, such as fluorescence emitted by a fluorophore. Typically, the amplification-dependent measurable parameter is the amount of fluorescence emitted by the probe upon hybridization, or upon the hydrolysis of the probe by the nuclease activity of the nucleic acid polymerase, see Holland et al., (1991) Proc. Natl. Acad. Sci. 88:7276-7280 and U.S. Pat. No. 5,210,015. A growth curve is characterized by a "threshold value" (or Ct value) which is a number of cycles where a predetermined magnitude of the measurable parameter is achieved. A lower Ct value represents more rapid amplification, while the higher Ct value represents slower amplification. In the context of an allele-specific reaction the difference between Ct values of the two templates represents allelic discrimination in the reaction.

In an allele-specific PCR, at least one primer is allele-specific such that primer extension occurs only (or preferentially) when the specific variant of the sequence is present and does not occur (or occurs less efficiently, i.e. with a substantial $\Delta$Ct) when another variant is present. Design of successful allele-specific primers is an unpredictable art. While it is routine to design a primer for a known sequence, no formula exists for designing a primer that can discriminate between very similar sequences. The discrimination is especially challenging when one or more allele-specific primers targeting one or more polymorphic sites are present in the same reaction mixture.

Typically, the discriminating nucleotide in the primer, i.e. the nucleotide matching only one variant of the target sequence, is the 3'-terminal nucleotide. However, the 3' terminus of the primer is only one of many determinants of specificity. For example, additional mismatches may also affect discrimination. See U.S. patent application Ser. No. 12/582,068 filed on Oct. 20, 2009 (published as US20100099110.) Another approach is to include non-natural or modified nucleotides that alter base pairing between the primer and the target sequence (U.S. Pat. No. 6,001,611, incorporated herein in its entirety by reference.) The reduced extension kinetics and thus specificity of a primer is influenced by many factors including overall sequence context of the mismatch and other nucleic acids present in the reaction. The effect of these external factors on each additional mismatch as well as of each additional non-natural nucleotide either alone or in combination cannot be predicted. The applicants tested multiple variants of the primers and found that surprisingly, certain variants are dramatically different with respect to their ability to discriminate between closely related target sequences.

In one embodiment the present invention comprises oligonucleotides specific for determining polymorphism in CFI, C2, CFB, C3 or CFH, respectively. In one embodiment, the invention comprises oligonucleotides selected from SEQ ID NOs: 17-41 (Table 9) as well as variations at least 90% identical to and having the 3'-terminal nucleotide of said oligonucleotides, for specifically detecting risk alleles in CFI SNP rs4698775, CFH SNP rs1329428 and C2/CFB SNP rs429608, respectively. As illustrated in Table 9, the mismatches and non-natural nucleotides typically occur within the 3'-terminal portion of the oligonucleotides used as primers, specifically within 5 penultimate nucleotides. However, some oligonucleotides sharing 90% identity with a given oligonucleotide also include those having 1, 2 or 3 mismatches elsewhere in the oligonucleotide, e.g. in the 5'-portion of the oligonucleotide.

In a particular embodiment the presence of polymorphism is detected with a probe. The probe may be labeled with a radioactive, or a chromophore (fluorophore) label, e.g. a label incorporating FAM, JA270, CY5 family dyes, or HEX dyes. As one example of detection using a fluorescently labeled probe, the mutation may be detected by real-time polymerase chain reaction (rt-PCR), where hybridization of the probe results in enzymatic digestion of the probe and detection of the resulting fluorescence (TaqMan™ probe method, Holland et al. (1991) P.N.A.S. USA 88:7276-7280). Table 9 lists exemplary probes for detecting risk alleles in CFI SNP rs4698775, CFH SNP rs1329428 and C2/CFB SNP rs429608, respectively. Alternatively, the presence of polymorphism and the amplification product may be detected by gel electrophoresis followed by staining or by blotting and hybridization as described e.g., in Sambrook, J. and Russell, D. W. (2001) Molecular Cloning, 3rd ed. CSHL Press, Chapters 5 and 9.

A "fluorescent dye" or a "fluorophore" is a compound or a moiety attached for example, to a nucleic acid, which is capable of emitting light radiation when excited by a light of a suitable wavelength. Typical fluorescent dyes include rhodamine dyes, cyanine dyes, fluorescein dyes and BODIPY® dyes. A fluorophore is a fluorescent chromophore. "FRET" or "fluorescent resonance energy transfer" or "Foerster resonance energy transfer" is a transfer of energy between at least two chromophores, a donor chromophore and an acceptor chromophore (referred to as a quencher). The donor typically transfers the energy to the acceptor when the donor is excited by light radiation with a suitable wavelength. When the acceptor is a "dark" quencher, it dissipates the transferred energy in a form other than light. Commonly used dark quenchers are BlackHole Quenchers™ (BHQ), Biosearch Technologies, Inc. (Novato, Calif.), Iowa Black™, Integrated DNA Tech., Inc. (Coralville, Iowa), BlackBerry™ Quencher 650 (BBQ-650), Berry & Assoc., (Dexter, Mich.). Commonly used donor-quencher pairs include the FAM-BHQ pair, the CY5-BHQ pair and the HEX-BHQ pair."

A sample comprising a biomarker or SNP can be obtained by methods well known in the art. See under Definitions. In addition, the progress of therapy can be monitored more easily by testing such body samples for SNPs.

Genotyping arrays may be used to analyze DNA or RNA to detect the presence of SNPs or other genetic based mechanisms. One such example is the Illumina based array technology which is a commercially available microarray system which comprises >700K loci. (Oliphant et al., Biotechniques, Supp: 56-8, 60-1 (2002)) and is a common method used for DNA and RNA analysis (e.g. identification of SNPs in nucleic acid samples). The Illumina microarray technology utilizes 3-micron silica beads that self assemble in microwells on either of two substrates: fiber optic bundles or planar silica slides. Each bead is covered with hundreds of thousands of copies of specific oligonucleotides that act as the capture sequences.

Expression of a selected gene or biomarker in a tissue or cell sample may also be examined by way of functional or activity-based assays. For instance, if the biomarker is an enzyme, one may conduct assays known in the art to determine or detect the presence of the given enzymatic activity in the tissue or cell sample.

The SNP status of a patient based on the test results may be provided in a report. The report may be in any form of written materials (e.g., in paper or digital form, or on internet) or oral presentation(s) (e.g., either in person (live) or as recorded). The report may further indicates to a health professional (e.g., a physician) that the patient may benefit from or is likely to respond to an factor D inhibitor treatment.

The kits of the invention have a number of embodiments. In certain embodiments, a kit comprises a container, a label on said container, and a composition contained within said container; wherein the composition includes one or more primary antibodies that bind to one or more target polypeptide sequences corresponding to an autoantibody to a SNP, the label on the container indicating that the composition can be used to evaluate the presence of one or more target proteins in at least one type of mammalian cell, and instructions for using the antibodies for evaluating the presence of one or more target proteins in at least one type of mammalian cell. The kit can further comprise a set of instructions and materials for preparing a tissue sample and applying antibody and probe to the same section of a tissue sample. The kit may include both a primary and secondary antibody, wherein the secondary antibody is conjugated to a label, e.g., an enzymatic label.

In one embodiment, the subject has never been previously treated with drug(s), such as immunosuppressive agent(s), to treat AMD and/or has never been previously treated with an antibody or antigen-binding fragment thereof to factor D. In another embodiment, the subject has been previously treated with drug(s) to treat the degenerative disease and/or has been previously treated with such antibody. In another embodiment, the anti-factor D antibody or antigen-binding fragment thereof is the only medicament administered to the subject to treat the degenerative disease. In another embodiment, the anti-factor D antibody or antigen-binding fragment thereof is one of the medicaments used to treat AMD.

The antibody is administered by any suitable means, including parenteral, topical, subcutaneous, intraperitoneal, intrapulmonary, intranasal, intralesional and/or intravitreal administration. Parenteral infusions include intramuscular, intravenous, intraarterial, intraperitoneal, or subcutaneous administration. Intrathecal administration is also contemplated. In addition, the antibody may suitably be administered by pulse infusion, e.g., with declining doses of the antibody. Preferably, the dosing is given intravenously or subcutaneously, and more preferably by intravenous infusion(s). Each exposure may be provided using the same or a different administration means. In one embodiment, each exposure is by IVT administration.

One may administer a second medicament with the anti-factor D antibody or antigen-binding fragment thereof, such as an VEGF antagonist or antibody.

For instance, the antibody may be combined with an anti-VEGF drug such as (AVASTIN (bevacizumab) or LUCENTIS (ranibizumab)) or another factor D antagonist/antibody or antigen-binding fragment thereof.

More specific examples of such second medicaments, if the anti-factor D antibody or antigen-binding fragment thereof is called the first medicament, include a VEGF antagonist or antibody.

These second medicaments are generally used in the same dosages and with administration routes as used hereinbefore or about from 1 to 99% of the heretofore-employed dosages. If such second medicaments are used at all, preferably, they are used in lower amounts than if the anti-factor D antibody or antigen-binding fragment thereof were not present, especially in subsequent dosings beyond the initial dosing with antibody, so as to eliminate or reduce side effects caused thereby.

Where a second medicament is administered in an effective amount with an antibody exposure, it may be administered with any exposure, for example, only with one exposure, or with more than one exposure. In one embodiment, the second medicament is administered with the initial exposure. In another embodiment, the second medicament is administered with the initial and second exposures. In a still further embodiment, the second medicament is administered with all exposures.

The combined administration includes co-administration (concurrent administration), using separate formulations or a single pharmaceutical formulation, and consecutive administration in either order, wherein preferably there is a time period while both (or all) active agents simultaneously exert their biological activities. In a preferred embodiment, after the initial exposure, the amount of such agent is reduced or eliminated so as to reduce the exposure of the subject to an agent with side effects such as prednisone and cyclophosphamide, especially when the agent is a corticosteroid. In another embodiment, the amount of the second medicament is not reduced or eliminated.

IV. Antibodies Directed to a Factor D Antibody or Antigen-Binding Fragment Thereof Any factor D antibodies or fragments thereof known in the art may be used in the methods described herein. For example, in one embodiment, the anti-factor D antibodies that may be used in the invention are any of those disclosed in U.S. Pat. No. 8,067,002 or U.S. Pat. No. 8,273,352, and may further include chimeric, humanized, or human versions of these antibodies (if not already a chimeric, humanized, or human version), and may further include fragments or derivatives thereof.

In some embodiments, the anti-human factor D monoclonal antibody or antigen-binding fragment thereof binds to and neutralizes a biological activity of at least human factor D. In certain embodiments, the human factor D monoclonal antibody or antigen-binding fragment thereof can significantly reduce or eliminate a biological activity of the human factor D in question. In one embodiment, the human factor D monoclonal antibody or antigen-binding fragment thereof is capable of neutralizing at least 60%, or at least 70%, preferably at least 75%, more preferably at least 80%, even more preferably at least 85%, still more preferably at least 90%, still more preferably at least 95%, most preferably at least 99% of a biological activity of the subject human factor D. Binding and neutralization assays are well known in the art. See, e.g., U.S. Pat. No. 7,087,726 for assays useful in screening for antibodies having the desired binding and neutralization properties.

In certain embodiments, the anti-factor D antibody, or antigen-binding fragment thereof is capable of reducing alternative pathway hemolysis, due to factor D, by at least about 60%, or at least 70%, preferably at least 75%, more preferably at least 80%, even more preferably at least 85%, still more preferably at least 90%, still more preferably at least 95%, most preferably at least 99% as determined by an alternative pathway hemolysis assay.

In some embodiments, the anti-factor D monoclonal antibody comprises the following HVRs (a) L1 of the formula
ITSTDIDDDMN; (SEQ ID NO: 1)

(b) L2 of the formula
GGNTLRP; (SEQ ID NO: 2)
and (c) L3 of the formula
LQSDSLPYT; (SEQ ID NO: 3)
and/or (d) H1 of the formula
GYTFTNYGMN; (SEQ ID NO: 4)

(e) H2 of the formula
WINTYTGETTYADDFKG; (SEQ ID NO: 5)
and (f) H3 of the formula
EGGVNN. (SEQ ID NO: 6)

In certain embodiments, the anti-human factor D monoclonal antibody comprises in its heavy and light chain variable domain amino acid sequences of EVQLVQSGPELKKPGASVKVSCKASGYTFTNYG-MNWVRQAPGQGLEWMG WINTYTGETTYADD-FKGRFVFSLDTSVSTAYLQISSLKAEDTAVYYC-EREGG VNNWGQGTLVTVSS (SEQ ID NO:7) and DIQVTQSPSSLSASVGDRVTITCITSTDIDDDMN-WYQQKPGKVPKLLISGGNTL RPGVPSRFSGSGS-GTDFTLTISSLQPEDVATYYCLQSDSLPYTF-GQGTKVEIK (SEQ ID NO:8), respectively.

In certain embodiments, the anti-factor D antibody comprises the sequences of SEQ ID NO:15 and SEQ ID NO:16 as shown below, wherein 238-1 refers to the specific humanized anti-factor D Fab described in U.S. Pat. No. 8,273,352:

Heavy chain sequence of humanized anti-factor D Fab (238-1):

(SEQ ID NO: 15)
EVQLVQSGPELKKPGASVKVSCKASGYTFTNYGMNWVRQAPGQGLEWMG

WINTYTGETTYADDFKGRFVFSLDTSVSTAYLQISSLKAEDTAVYYCER

EGGVNNWGQGTLVTVSSASTKGPSVFPLAPSSKSTSGGTAALGCLVKDY

FPEPVTVSWNSGALTSGVHTFPAVLQSSGLYSLSSVVTVPSSSLGTQTY

ICNVNHKPSNTKVDKKVEPKSCDKTHT

Light chain sequence of humanized anti-Factor D Fab (238-1):

(SEQ ID NO: 16)
DIQVTQSPSSLSASVGDRVTITCITSTDIDDDMNWYQQKPGKVPKLLIS

GGNTLRPGVPSRFSGSGSGTDFTLTISSLQPEDVATYYCLQSDSLPYTF

GQGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

In another embodiment, the antibody comprises the variable region sequences of SEQ ID NO:15 and SEQ ID NO:16. In another embodiment, the antibody comprises the HVR sequences of SEQ ID NO:15 and SEQ ID NO:16. In another embodiment, the antibody comprises the HVR sequences that are 95% or more identical to the HVR sequences of SEQ ID NO: 15 and SEQ ID NO: 16 and/or an antibody comprising HVR sequences that are 95% identical to the HVR sequences of SEQ ID NO:15 and SEQ ID NO:16.

In any of the above embodiments, an anti-factor D antibody can be humanized. In one embodiment, an anti-factor D antibody comprises HVRs as in any of the above embodiments, and further comprises an acceptor human framework, e.g. a human immunoglobulin framework or a human consensus framework.

In another aspect, an anti-factor D antibody comprises a heavy chain variable domain (VH) sequence having at least 90%, 91%, 92%, 93%, 94%, 95%, 96%, 97%, 98%, 99% or 100% sequence identity to the amino acid sequence of SEQ ID NO: 15. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but a factor D antibody comprising that sequence retains the ability to bind to factor D. In certain embodiments, a total of 1 to 10 amino acids have been substituted, inserted and/or deleted in SEQ ID NO:15. In certain embodiments, substitutions, insertions, or deletions occur in regions outside the HVRs (i.e., in the FRs). Optionally, the anti-factor D antibody comprises the VH sequence in SEQ ID NO:15, including post-translational modifications of that sequence.

In another aspect, an anti-factor D antibody comprises a light chain variable domain (VL) sequence having at least 90%, 91%, 92%, 93%, 94%, 95%, 96%, 97%, 98%, 99% or 100% sequence identity to the amino acid sequence of SEQ ID NO: 16. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but a factor D antibody comprising that sequence retains the ability to bind to factor D. In certain embodiments, a total of 1 to 10 amino acids have been substituted, inserted and/or deleted in SEQ ID NO:16. In certain embodiments, substitutions, insertions, or deletions occur in regions outside the HVRs (i.e., in the FRs). Optionally, the anti-factor D antibody comprises the VL sequence in SEQ ID NO:16, including post-translational modifications of that sequence.

In another aspect, a factor D antibody is provided, wherein the antibody comprises a VH as in any of the embodiments provided above, and a VL as in any of the embodiments provided above.

In a further aspect, the invention provides an antibody that binds to the same epitope as another factor D antibody. In one embodiment, the invention provides an antibody that binds to the same epitope as a factor D antibody provided herein. In one embodiment, the anti-factor D antibody binds to the same epitope on factor D bound by the anti-factor D antibody comprising a light chain comprising HVR-L1 comprising the amino acid sequence ITSTDIDDDMN (SEQ ID NO:1), HVR-L2 comprising the amino acid sequence GGNTLRP (SEQ ID NO:2), and HVR-L3 comprising the amino acid sequence LQSDSLPYT (SEQ ID NO: 3); and/or a heavy chain comprising HVR-H1 comprising the amino acid sequence GYTFTNYGMN (SEQ ID NO: 4), HVR-H2 comprising the amino acid sequence WINTYTGETTY-ADDFKG (SEQ ID NO:5), and HVR-H3 comprising the amino acid sequence EGGVNN (SEQ ID NO:6). In one embodiment, the anti-factor D antibody binds to the same epitope on factor D bound by the antibody comprising a heavy chain variable region sequence of at least 95% sequence identity to the amino acid sequence of SEQ ID NO:7; and/or a light chain variable region sequence of at least 95% sequence identity to the amino acid sequence of SEQ ID NO:8. In one embodiment, the anti-factor D antibody binds to the same epitope on factor D bound by the antibody comprising a heavy chain variable region comprising the amino acid sequence of SEQ ID NO:7; and/or a light chain variable region comprising the amino acid sequence of SEQ ID NO:8. In one embodiment, the anti-factor D antibody binds to the same epitope on factor D bound by the antibody comprising a heavy chain sequence of at least 95% sequence identity to the amino acid sequence of SEQ ID NO:15; and/or a light chain sequence of at least 95% sequence identity to the amino acid sequence of SEQ ID NO:16. In one embodiment, the anti-factor D antibody binds to the same epitope on factor D bound by the antibody comprising a heavy chain comprising the amino acid sequence of SEQ ID NO:15; and/or a light chain comprising the amino acid sequence of SEQ ID NO:16. In one embodiment, the anti-factor D antibody binds to the same epitope on factor D bound by lampalizumab having CAS registration number 1278466-20-8.

In a further aspect, the invention provides an antibody that competitively inhibits the binding of an anti-factor D antibody to its respective antigenic epitope. For example, in certain embodiments, anti-factor D antibody competitively inhibits the binding of the anti-factor D antibody comprising a light chain comprising HVR-L1 comprising the amino acid sequence ITSTDIDDDMN (SEQ ID NO:1), HVR-L2 comprising the amino acid sequence GGNTLRP (SEQ ID NO:2), and HVR-L3 comprising the amino acid sequence LQSDSLPYT (SEQ ID NO: 3); and/or a heavy chain comprising HVR-H1 comprising the amino acid sequence GYTFTNYGMN (SEQ ID NO: 4), HVR-H2 comprising the amino acid sequence WINTYTGETTYADDFKG (SEQ ID NO:5), and HVR-H3 comprising the amino acid sequence EGGVNN (SEQ ID NO:6) to its respective antigenic epitope. In one embodiment, the anti-factor D antibody competitively inhibits the binding of the antibody comprising a heavy chain variable region sequence of at least 95% sequence identity to the amino acid sequence of SEQ ID NO:7; and/or a light chain variable region sequence of at least 95% sequence identity to the amino acid sequence of SEQ ID NO:8 to its respective antigenic epitope. In one embodiment, the anti-factor D antibody competitively inhibits the binding of the antibody comprising a heavy chain variable region comprising the amino acid sequence of SEQ ID NO:7; and/or a light chain variable region comprising the amino acid sequence of SEQ ID NO:8 to its respective antigenic epitope. In one embodiment, the anti-factor D antibody binds to the same epitope on factor D bound by the antibody comprising a heavy chain sequence of at least 95% sequence identity to the amino acid sequence of SEQ ID NO:15; and/or a light chain sequence of at least 95% sequence identity to the amino acid sequence of SEQ ID NO:16. In one embodiment, the anti-factor D antibody binds to the same epitope on factor D bound by the antibody comprising a heavy chain comprising the amino acid sequence of SEQ ID NO:15; and/or a light chain comprising the amino acid sequence of SEQ ID NO:16. In one embodiment, the anti-factor D antibody competitively inhibits the binding of lampalizumab having CAS registration number 1278466-20-8 to its respective antigenic epitope.

In a further aspect of the invention, a factor D antibody according to any of the above embodiments is a monoclonal antibody, including a chimeric, humanized or human antibody. In one embodiment, a factor D antibody is an antibody fragment, e.g., a Fv, Fab, Fab', scFv, diabody, or F(ab')2 fragment. In another embodiment, the antibody is a full length antibody, e.g., an intact IgG1 or IgG4 antibody or other antibody class or isotype as defined herein. In another embodiment, the antibody is a bispecific antibody In a further aspect, a Factor D antibody according to any of the above embodiments may incorporate any of the features, singly or in combination, as described in this Section IV and Section V below.

In some embodiments, the anti-factor D monoclonal antibody or antigen-binding fragment thereof has an amino acid sequence that is identical to the anti-human factor D monoclonal antibody having the non-proprietary name adopted by the USAN Council designated as Lampalizumab. In other embodiments, the anti-human factor D monoclonal antibody or antigen-binding fragment thereof has an amino acid sequence identity that is at least 80%, at least 85%, at least 90%, at least 95%, at least 96%, at least 97%, at least 98%, or at least 99% to Lampalizumab. See U.S. Pat. No. 8,067,002 or U.S. Pat. No. 8,273,352. In certain embodiments, the anti-human factor D monoclonal antibody is Lampalizumab. In some embodiments, the anti-human factor D monoclonal antibody has an amino acid sequence as disclosed in CAS Registry Number 1278466-20-8.

In some embodiments, the anti-human factor D monoclonal antibody comprises the HVRs encoded by the following sequences:

(a) L1 of the formula

ATTACCAGCACTGATATTGATGATGATATGAAC; (SEQ ID NO: 9)

(b) L2 of the formula

GGAGGCAATACTCTTCGTCCT; (SEQ ID NO: 10)

(c) L3 of the formula

TTGCAAAGTGATTCTTTGCCGTACACG; (SEQ ID NO: 11)

(d) H1 of the formula

GGATACACCTTCACTAACTATGGAATGAAC; (SEQ ID NO: 12)

(e) H2 of the formula

TGGATTAACACCTACACTGGAGAGACAACATATGCTGACGACTTCAAGG
GA; (SEQ ID NO: 13)
and (f) H3 of the formula

GAGGGGGGGGTTAATAAC. (SEQ ID NO: 14)

V. Production of Antibodies

The methods and articles of manufacture of the present invention may use, or incorporate, an antibody that binds to factor D. Accordingly, methods for generating such antibodies will be described here.

Factor D antigen to be used for production of, or screening for, antibody(ies) may be, e.g., a soluble form of factor D, or a portion thereof, containing the desired epitope. Alternatively, or additionally, cells expressing factor D at their cell surface can be used to generate, or screen for, antibody(ies). Other forms of factor D useful for generating antibodies will be apparent to those skilled in the art.

A description follows as to exemplary techniques for the production of the antibodies used in accordance with the present invention.

(i) Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N$=$C$=$NR$, where R and $R^1$ are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later the animals are boosted with ⅕ to ⅒ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(ii) Monoclonal Antibodies

Monoclonal antibodies are obtained from a population of substantially homogeneous antibodies, i.e., the individual antibodies comprising the population are identical and/or bind the same epitope except for possible variants that arise during production of the monoclonal antibody, such variants generally being present in minor amounts. Thus, the modifier "monoclonal" indicates the character of the antibody as not being a mixture of discrete or polyclonal antibodies.

For example, the monoclonal antibodies may be made using the hybridoma method first described by Kohler et al., Nature, 256:495 (1975), or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., Anal. Biochem., 107:220 (1980).

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-SEPHAROSE™ crosslinked agarose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as E. coli cells, simian COS cells, Chinese Hamster Ovary (CHO) cells, or myeloma cells that do not otherwise produce immunoglobulin protein, to obtain the synthesis of monoclonal antibodies in the recombinant host cells. Review articles on recombinant expression in bacteria of DNA encoding the antibody include Skerra et al., Curr. Opinion in Immunol., 5:256-262 (1993) and Pliickthun, Immunol. Revs., 130:151-188 (1992).

In a further embodiment, antibodies or antibody fragments can be isolated from antibody phage libraries generated using the techniques described in McCafferty et al., Nature, 348:552-554 (1990). Clackson et al., Nature, 352: 624-628 (1991) and Marks et al., J. Mol. Biol., 222:581-597 (1991) describe the isolation of murine and human antibodies, respectively, using phage libraries. Subsequent publications describe the production of high-affinity (nM range) human antibodies by chain shuffling (Marks et al., Bio/Technology, 10:779-783 (1992)), as well as combinatorial infection and in vivo recombination as a strategy for constructing very large phage libraries (Waterhouse et al., Nuc. Acids. Res., 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., Proc. Natl. Acad. Sci. USA, 81:6851 (1984)), or by covalently joining to the immunoglobulin-coding sequence all or part of the coding sequence for a non-immunoglobulin polypeptide.

Typically, such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

(iii) Humanized Antibodies

Methods for humanizing non-human antibodies have been described in the art. Preferably, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting hypervariable-region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable-region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence that is closest to that of the rodent is then accepted as the human framework region (FR) for the humanized antibody (Sims et al., J. Immunol., 151:2296 (1993); Chothia et al., J. Mol. Biol., 196:901 (1987)). Another method uses a particular framework region derived from the consensus sequence of all human antibodies of a particular subgroup of light- or heavy-chain variable regions. The same framework may be used for several different humanized antibodies (Carter et al., Proc. Natl. Acad. Sci. USA, 89:4285 (1992); Presta et al., J. Immunol., 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available that illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

(iv) Human Antibodies

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain-joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggermann et al., Year in Immuno., 7:33 (1993); and U.S. Pat. Nos. 5,591,669, 5,589,369 and 5,545,807.

Alternatively, phage-display technology (McCafferty et al., Nature 348:552-553 (1990)) can be used to produce human antibodies and antibody fragments in vitro, from immunoglobulin variable (V)-domain gene repertoires from unimmunized donors. According to this technique, antibody V-domain genes are cloned in-frame into either a major or minor coat-protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for their review see, e.g., Johnson, Kevin S, and Chiswell, David J., Current Opinion in Structural Biology 3:564-571 (1993). Several sources of V-gene segments can be used for phage display. Clackson et al., Nature, 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222:581-597 (1991), or Griffith et al., EMBO J. 12:725-734 (1993). See, also, U.S. Pat. Nos. 5,565,332 and 5,573,905.

Human antibodies may also be generated by in vitro-activated B cells (see U.S. Pat. Nos. 5,567,610 and 5,229,275).

(v) Antibody Fragments

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992) and Brennan et al., Science, 229:81 (1985)). However, these fragments can now be produced directly by recombinant host cells. For example, the antibody fragments can be isolated from the antibody phage libraries discussed above. Alternatively, Fab'-SH fragments can be directly recovered from E. coli and chemically coupled to form $F(ab')_2$ fragments (Carter et al., Bio/Technology 10:163-167 (1992)). According to another approach, $F(ab')_2$ fragments can be isolated directly from recombinant host-cell culture. Other techniques for the production of antibody fragments will be apparent to the skilled practitioner. In other embodiments, the antibody of choice is a single-chain Fv fragment (scFv). See WO 1993/16185 and U.S. Pat. Nos. 5,571,894 and 5,587,458. The antibody fragment may also be a "linear antibody", e.g., as described in U.S. Pat. No. 5,641,870. Such linear antibody fragments may be monospecific or bispecific.

(vi) Bispecific Antibodies

Bispecific antibodies are antibodies that have binding specificities for at least two different epitopes. Exemplary bispecific antibodies may bind to two different epitopes of the factor D antigen. Alternatively, an anti-factor D-binding arm may be combined with an arm that binds to a triggering molecule on a leukocyte such as a T-cell receptor molecule (e.g. CD2 or CD3), or Fc receptors for IgG (FcγR), such as FcγRI (CD64), FcγRII (CD32) and FcγRIII (CD16). Bispecific antibodies may also be used to localize cytotoxic agents. These antibodies possess a factor D binding arm and an arm that binds the cytotoxic agent (e.g. saporin, vinca alkaloid, ricin A chain, methotrexate or radioactive isotope hapten). Bispecific antibodies can be prepared as full-length antibodies or antibody fragments (e.g. $F(ab')_2$ bispecific antibodies).

Methods for making bispecific antibodies are known in the art. Traditional production of full-length bispecific antibodies is based on the coexpression of two immunoglobulin heavy-chain-light-chain pairs, where the two chains have different specificities (Millstein et al., Nature, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 1993/08829, and in Traunecker et al., EMBO J., 10:3655-3659 (1991).

According to a different approach, antibody variable domains with the desired binding specificities (antibody-antigen combining sites) are fused to immunoglobulin constant-domain sequences. The fusion preferably is with an immunoglobulin heavy-chain constant domain, comprising at least part of the hinge, CH2, and CH3 regions. It is preferred to have the first heavy-chain constant region (CH1), containing the site necessary for light-chain binding, present in at least one of the fusions. DNAs encoding the immunoglobulin heavy-chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy-chain-light-chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 1994/04690. For further details of generating bispecific antibodies, see, for example, Suresh et al., Methods in Enzymology, 121:210 (1986).

According to another approach described in U.S. Pat. No. 5,731,168, the interface between a pair of antibody molecules can be engineered to maximize the percentage of heterodimers that are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 1991/00360, WO 1992/200373, and EP 03089). Heteroconjugate antibodies may be made using any convenient cross-linking methods. Suitable cross-linking agents are well known in the art, and are disclosed, for example, in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Various techniques for making and isolating bispecific antibody fragments directly from recombinant cell culture have also been described. For example, bispecific antibodies have been produced using leucine zippers. Kostelny et al., J. Immunol., 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90:6444-6448 (1993) has provided an alternative mechanism for making bispecific antibody fragments. The fragments comprise a heavy-chain variable domain ($V_H$) connected to a light-chain variable domain ($V_L$) by a linker that is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., J. Immunol., 152:5368 (1994).

Antibodies with more than two valencies are contemplated. For example, trispecific antibodies can be prepared. Tutt et al. J. Immunol. 147: 60 (1991).

VI. Conitmates and Other Modifications of the Antibody

The antibody used in the methods or included in the articles of manufacture herein is optionally conjugated to a cytotoxic agent. For instance, the (factor D) antibody may be conjugated to a drug as described in WO 2004/032828.

Chemotherapeutic agents useful in the generation of such antibody-cytotoxic agent conjugates have been described above.

Conjugates of an antibody and one or more small-molecule toxins, such as a calicheamicin, a maytansine (U.S. Pat. No. 5,208,020), a trichothene, and CC 1065 are also contemplated herein. In one embodiment of the invention, the antibody is conjugated to one or more maytansine molecules (e.g. about 1 to about 10 maytansine molecules per antibody molecule). Maytansine may, for example, be converted to May-SS-Me, which may be reduced to May-SH3 and reacted with modified antibody (Chari et al. Cancer Research 52: 127-131 (1992)) to generate a maytansinoid-antibody conjugate.

Alternatively, the antibody is conjugated to one or more calicheamicin molecules. The calicheamicin family of antibiotics is capable of producing double-stranded DNA breaks at sub-picomolar concentrations. Structural analogues of calicheamicin that may be used include, but are not limited to, $\gamma_1^I$, $\alpha_2^I$, $\alpha_3^I$, N-acetyl-$\gamma_1^I$, PSAG and $\theta_1^I$ (Hinman et al. Cancer Research 53: 3336-3342 (1993) and Lode et al. Cancer Research 58: 2925-2928 (1998)).

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, Aleurites fordii proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. See, for example, WO 1993/21232 published Oct. 28, 1993.

The present invention further contemplates antibody conjugated with a compound with nucleolytic activity (e.g. a ribonuclease or a DNA endonuclease such as a deoxyribonuclease; DNase).

A variety of radioactive isotopes is available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu.

Conjugates of the antibody and cytotoxic agent may be made using a variety of bifunctional protein-coupling agents such as N-succinimidyl-3-(2-pyridyldithiol) propionate (SPDP), succinimidyl-4-(N-maleimidomethyl)cyclohexane-1-carboxylate, iminothiolane (IT), bifunctional derivatives of imidoesters (such as dimethyl adipimidate HCl), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al. Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO 1994/11026. The linker may be a "cleavable linker" facilitating release of the cytotoxic drug in the cell. For example, an acid-labile linker, peptidase-sensitive linker, dimethyl linker, or disulfide-containing linker (Chari et al. Cancer Research 52: 127-131 (1992)) may be used.

Alternatively, a fusion protein comprising the antibody and cytotoxic agent may be made, e.g. by recombinant techniques or peptide synthesis.

In yet another embodiment, the antibody may be conjugated to a "receptor" (such as streptavidin) for utilization in tumor pretargeting wherein the antibody-receptor conjugate is administered to the subject, followed by removal of unbound conjugate from the circulation using a clearing agent and then administration of a "ligand" (e.g. avidin) that is conjugated to a cytotoxic agent (e.g. a radionucleotide).

The antibodies of the present invention may also be conjugated with a prodrug-activating enzyme that converts a prodrug (e.g. a peptidyl chemotherapeutic agent, see WO 1981/01145) to an active anti-cancer drug. See, for example, WO 1988/07378 and U.S. Pat. No. 4,975,278.

The enzyme component of such conjugates includes any enzyme capable of acting on a prodrug in such a way so as to convert it into its more active, cytotoxic form.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as *serratia* protease, thermolysin, subtilisin, carboxypeptidases, and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, Nature 328: 457-458 (1987)). Antibody-abzyme conjugates can be prepared as described herein for delivery of the abzyme to a tumor cell population.

The enzymes of this invention can be covalently bound to the antibody by techniques well known in the art such as the use of the heterobifunctional crosslinking reagents discussed above. Alternatively, fusion proteins comprising at least the antigen-binding region of an antibody of the invention linked to at least a functionally active portion of an enzyme of the invention can be constructed using recombinant DNA techniques well known in the art (see, e.g., Neuberger et al., Nature, 312: 604-608 (1984)).

Other modifications of the antibody are contemplated herein. For example, the antibody may be linked to one of a variety of nonproteinaceous polymers, e.g., polyethylene glycol (PEG), polypropylene glycol, polyoxyalkylenes, or copolymers of polyethylene glycol and polypropylene glycol. Antibody fragments, such as Fab', linked to one or more PEG molecules are an especially preferred embodiment of the invention.

The antibodies disclosed herein may also be formulated as liposomes. Liposomes containing the antibody are prepared by methods known in the art, such as described in Epstein et al., Proc. Natl. Acad. Sci. USA, 82:3688 (1985); Hwang et al., Proc. Natl. Acad. Sci. USA, 77:4030 (1980); U.S. Pat. Nos. 4,485,045 and 4,544,545; and WO 1997/38731 published Oct. 23, 1997. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of an antibody of the present invention can be conjugated to the liposomes as described in Martin et al. J. Biol. Chem. 257: 286-288 (1982) via a disulfide-interchange reaction. A chemotherapeutic agent is optionally contained within the liposome. See Gabizon et al. J. National Cancer Inst. 81(19) 1484 (1989).

Amino acid sequence modification(s) of protein or peptide antibodies described herein are contemplated. For example, it may be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid changes also may alter post-translational processes of the antibody, such as changing the number or position of glycosylation sites.

A useful method for identification of certain residues or regions of the antibody that are preferred locations for mutagenesis is called "alanine-scanning mutagenesis" as described by Cunningham and Wells Science, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody of an enzyme, or a polypeptide that increases the serum half-life of the antibody.

Another type of variant is an amino acid substitution variant. These variants have at least one amino acid residue in the antibody molecule replaced by a different residue. The sites of greatest interest for substitutional mutagenesis of antibodies include the hypervariable regions, but FR alterations are also contemplated. Conservative substitutions are shown in Table 1 under the heading of "preferred substitutions". If such substitutions result in a change in biological activity, then more substantial changes, denominated "exemplary substitutions" in Table 1, or as further described below in reference to amino acid classes, may be introduced and the products screened.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains (in A. L. Lehninger, in Biochemistry, second ed., pp. 73-75, Worth Publishers, New York (1975)):
 (1) non-polar: Ala (A), Val (V), Leu (L), Ile (I), Pro (P), Phe (F), Trp (W), Met (M)
 (2) uncharged polar: Gly (G), Ser (S), Thr (T), Cys (C), Tyr (Y), Asn (N), Gln (O)
 (3) acidic: Asp (D), Glu (E)
 (4) basic: Lys (K), Arg (R), H is(H)

Alternatively, naturally occurring residues may be divided into groups based on common side-chain properties:
 (1) hydrophobic: Norleucine, Met, Ala, Val, Leu, Ile;
 (2) neutral hydrophilic: Cys, Ser, Thr, Asn, Gln;
 (3) acidic: Asp, Glu;
 (4) basic: His, Lys, Arg;
 (5) residues that influence chain orientation: Gly, Pro;
 (6) aromatic: Trp, Tyr, Phe.

Non-conservative substitutions will entail exchanging a member of one of these classes for another class.

Any cysteine residue not involved in maintaining the proper conformation of the antibody also may be substituted, generally with serine, to improve the oxidative stability of the molecule and prevent aberrant crosslinking Conversely, cysteine bond(s) may be added to the antibody to improve its stability (particularly where the antibody is an antibody fragment such as an Fv fragment).

A particularly preferred type of substitutional variant involves substituting one or more hypervariable region residues of a parent antibody. Generally, the resulting variant(s) selected for further development will have improved biological properties relative to the parent antibody from which they are generated. A convenient way for generating such substitutional variants is affinity maturation using phage display. Briefly, several hypervariable region sites (e.g. 6-7 sites) are mutated to generate all possible amino acid substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine-scanning mutagenesis can be performed to identify hypervariable region residues contributing significantly to antigen binding. Alternatively, or in additionally, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. Such altering includes deleting one or more carbohydrate moieties found in the antibody, and/or adding one or more glycosylation sites that are not present in the antibody.

Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Where the antibody comprises an Fc region, the carbohydrate attached thereto may be altered. For example, antibodies with a mature carbohydrate structure that lacks fucose attached to an Fc region of the antibody are described in US 2003/0157108 (Presta, L.). See also US 2004/

0093621 (Kyowa Hakko Kogyo Co., Ltd.). Antibodies with a bisecting N-acetylglucosamine (GlcNAc) in the carbohydrate attached to an Fc region of the antibody are referenced in WO 2003/011878, Jean-Mairet et al. and U.S. Pat. No. 6,602,684, Umana et al. Antibodies with at least one galactose residue in the oligosaccharide attached to an Fc region of the antibody are reported in WO 1997/30087, Patel et al. See, also, WO 1998/58964 (Raju, S.) and WO 1999/22764 (Raju, S.) concerning antibodies with altered carbohydrate attached to the Fc region thereof.

The preferred glycosylation variant herein comprises an Fc region, wherein a carbohydrate structure attached to the Fc region lacks fucose. Such variants have improved ADCC function. Optionally, the Fc region further comprises one or more amino acid substitutions therein that further improve ADCC, for example, substitutions at positions 298, 333, and/or 334 of the Fc region (Eu numbering of residues). Examples of publications related to "defucosylated" or "fucose-deficient" antibodies include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; Okazaki et al. J. Mol. Biol. 336:1239-1249 (2004); and Yamane-Ohnuki et al. Biotech. Bioeng.87: 614 (2004). Examples of cell lines producing defucosylated antibodies include Lec13 CHO cells deficient in protein fucosylation (Ripka et al. Arch. Biochem. Biophys. 249: 533-545 (1986); US 2003/0157108, Presta, L; and WO 2004/056312, Adams et al., especially at Example 11), and knockout cell lines, such as alpha-1,6-fucosyltransferase gene, FUT8,-knockout CHO cells (Yamane-Ohnuki et al. Biotech. Bioeng. 87: 614 (2004)).

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to modify the antibody of the invention with respect to effector function, e.g. so as to enhance ADCC and/or CDC of the antibody. This may be achieved by introducing one or more amino acid substitutions in an Fc region of an antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and ADCC. See Caron et al., J. Exp Med. 176:1191-1195 (1992) and Shopes, B. J. Immunol. 148:2918-2922 (1992). Homodimeric antibodies with enhanced anti-tumor activity may also be prepared using heterobifunctional cross-linkers as described in Wolff et al. Cancer Research 53:2560-2565 (1993). Alternatively, an antibody can be engineered that has dual Fc regions and may thereby have enhanced complement lysis and ADCC capabilities. See Stevenson et al. Anti-Cancer Drug Design 3:219-230 (1989).

WO 2000/42072 (Presta, L.) describes antibodies with improved ADCC function in the presence of human effector cells, where the antibodies comprise amino acid substitutions in the Fc region thereof. Preferably, the antibody with improved ADCC comprises substitutions at positions 298, 333, and/or 334 of the Fc region. Preferably, the altered Fc region is a human IgG1 Fc region comprising or consisting of substitutions at one, two, or three of these positions.

Antibodies with altered C1q binding and/or CDC are described in WO 1999/51642 and U.S. Pat. Nos. 6,194,551, 6,242,195, 6,528,624, and 6,538,124 (Idusogie et al.). The antibodies comprise an amino acid substitution at one or more of amino acid positions 270, 322, 326, 327, 329, 313, 333, and/or 334 of the Fc region thereof.

To increase the serum half-life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule. Antibodies with substitutions in an Fc region thereof and increased serum half-lives are also described in WO 2000/42072 (Presta, L.).

Engineered antibodies with three or more (preferably four) functional antigen-binding sites are also contemplated (US 2002/0004587 A1, Miller et al.).

VII. Pharmaceutical Formulations

Therapeutic formulations of the antibodies used in accordance with the present invention are prepared for storage by mixing an antibody having the desired degree of purity with optional pharmaceutically acceptable carriers, excipients, or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, histidine, citrate, and other organic acids; salts such as sodium chloride, calcium chloride and ammonium sulfate; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low-molecular-weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™, or PEG.

Exemplary anti-factor D antibody, or antigen-binding fragment thereof formulations are described in U.S. Pat. Nos. 8,067,002, 8,193,329, 8,187,604, 8,372,403, 8,273, 352, 6,954,107, 7,943,135, 7,439,331, 7,112,327, 8,124,090, and 8,236,317.

Lyophilized formulations adapted for subcutaneous administration are described, for example, in U.S. Pat. No. 6,267,958 (Andya et al.). Lyophilized formulations adapted for intravitreal administration are described, for example, in U.S. Pat. Nos. 7,807,164, 8,481,046. Such lyophilized formulations may be reconstituted with a suitable diluent to a high protein concentration (described for example, in U.S. Pat. No. 8,142,776) and the reconstituted formulation may be administered subcutaneously or intravitreally to the mammal to be treated herein.

Crystallized forms of the antibody are also contemplated. See, for example, US 2002/0136719A1 (Shenoy et al.).

The formulation herein may also contain more than one active compound (a second medicament) as necessary for the particular indication being treated, preferably those with complementary activities that do not adversely affect each other. For example, it may be desirable to further provide a VEGF inhibitor in the formulation. The type and effective amounts of such other agents (called herein second medicaments, wherein the first medicament is the anti-factor D antibody) depend, for example, on the amount of antibody present in the formulation, the type of degenerative disease being treated, and clinical parameters of the subjects.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug-delivery systems (for example, liposomes, albumin microspheres, microemulsions, nano-particles and nanocapsules) or in macroemulsions. Such techniques are disclosed, e.g., in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes.

VIII. Articles of Manufacture

Various articles of manufacture are contemplated within the scope of the invention. In another embodiment of the invention, an article of manufacture containing materials useful for the treatment of degenerative disease described above is provided. Preferably, the article of manufacture comprises (a) a container comprising a composition comprising an anti-factor D antibody or antigen-binding fragment thereof and a pharmaceutically acceptable carrier or diluent within the container; and (b) a package insert with instructions for treating degenerative disease in a subject, wherein the instructions indicate that an amount of the antibody is administered to the subject that is effective to provide an initial antibody exposure of about 0.5 to 4 grams followed by a second antibody exposure of about 0.5 to 4 grams, wherein the second exposure is not provided until from about 16 to 54 weeks from the initial exposure and each of the antibody exposures is provided to the subject as a single dose or as two or three separate doses of antibody.

The package insert is on or associated with the container. Suitable containers include, for example, bottles, vials, syringes, etc. The containers may be formed from a variety of materials such as glass or plastic. The container holds or contains a composition that is effective for treating AMD and may have a sterile access port (for example, the container may be an intravenous solution bag or a vial having a stopper pierceable by a hypodermic injection needle). At least one active agent in the composition is the antibody. The label or package insert indicates that the composition is used for treating degenerative disease in a subject eligible for treatment with specific guidance regarding dosing amounts and intervals of antibody and any other drug being provided. The article of manufacture may further comprise a second container comprising a pharmaceutically acceptable diluent buffer, such as bacteriostatic water for injection (BWFI), phosphate-buffered saline, Ringer's solution, and dextrose solution. The article of manufacture may still further comprise a second or third container comprising a second medicament, wherein the anti-factor D antibody or antigen-binding fragment thereof is a first medicament, where the article further comprises instructions on the package insert for treating the subject with the second medicament. Exemplary second medicaments include a chemotherapeutic agent, an immunosuppressive agent, an anti-malarial agent, a cytotoxic agent, an integrin antagonist, a cytokine antagonist, or a hormone. In some embodiments, the second medicament is a chemotherapeutic agent, an anti-malarial agent, or an immunosuppressive agent, including, e.g., hydroxychloroquine, chloroquine, quinacrine, cyclophosphamide, prednisone, mycophenolate mofetil, methotrexate, azathiprine, or 6-mercaptopurine; a corticosteroid such as prednisone (along with optionally methotrexate, hydroxychloroquine, chloroquine, quinacrine, MMF, or azathioprine with or without 6-mercaptopurine); or a corticosteroid such as prednisone as well as MMF or cyclophosphamide. The article of manufacture may further include other materials desirable from a commercial and user standpoint, including other buffers, diluents, filters, needles, and syringes.

In another aspect, the invention provides an article of manufacture comprising an IVT or long-acting delivery device, which delivers to a patient a fixed dose of an anti-factor D antibody or antigen-binding fragment thereof, wherein the fixed dose is in the microgram to milligram range of the anti-factor D antibody or antigen-binding fragment thereof. In some embodiments, the fixed dose is about 10 mg monthly or about 10 mg every other month. In some embodiments, the concentration of the antibody in the device is about 10 mg. In another aspect, the invention provides an article of manufacture comprising an anti-factor D antibody or antigen-binding fragment thereof in a concentration of about 10 mg. In some embodiments, the anti-factor D antibody comprises a light chain comprising HVR-L1 comprising the amino acid sequence ITSTDID-DDMN (SEQ ID NO:1), HVR-L2 comprising the amino acid sequence GGNTLRP (SEQ ID NO:2), and HVR-L3 comprising the amino acid sequence LQSDSLPYT (SEQ ID NO: 3); and/or a heavy chain comprising HVR-H1 comprising the amino acid sequence GYTFTNYGMN (SEQ ID NO: 4), HVR-H2 comprising the amino acid sequence WINTYTGETTYADDFKG (SEQ ID NO:5), and HVR-H3 comprising the amino acid sequence EGGVNN (SEQ ID NO:6) In some embodiments, the antibody comprises a heavy chain variable region sequence of at least 95% sequence identity to the amino acid sequence of SEQ ID NO:7; and/or a light chain variable region sequence of at least 95% sequence identity to the amino acid sequence of SEQ ID NO:8. In some embodiments, the antibody comprises a heavy chain variable region comprising the amino acid sequence of SEQ ID NO:7; and/or a light chain variable region comprising the amino acid sequence of SEQ ID NO:8. In some embodiments, the antibody is lampalizumab having CAS registration number 1278466-20-8. In some embodiments, the anti-factor D antibody may be a monoclonal antibody, antibody fragment, chimeric antibody, humanized antibody, single-chain antibody or antibody that competitively inhibits the binding of an anti-factor D antibody to its respective antigenic epitope. In one embodiment, the anti-factor D antibody competitively inhibits the binding of the anti-factor D antibody comprising a light chain comprising HVR-L1 comprising the amino acid sequence ITSTDIDDDMN (SEQ ID NO:1), HVR-L2 comprising the amino acid sequence GGNTLRP (SEQ ID NO:2), and HVR-L3 comprising the amino acid sequence LQSDSLPYT (SEQ ID NO: 3); and/or a heavy chain comprising HVR-H1 comprising the amino acid sequence GYTFTNYGMN (SEQ ID NO: 4), HVR-H2 comprising the amino acid sequence WINTYTGETTYADDFKG (SEQ ID NO:5), and HVR-H3 comprising the amino acid sequence EGGVNN (SEQ ID NO:6) to its respective antigenic epitope. In one embodiment, the anti-factor D antibody competitively inhibits the binding of the antibody comprising a heavy chain variable region sequence of at least 95% sequence identity to the amino acid sequence of SEQ ID NO:7; and/or a light chain variable region sequence of at least 95% sequence identity to the amino acid sequence of SEQ ID NO:8 to its respective antigenic epitope. In one embodiment, the anti-factor D antibody competitively inhibits the binding of the antibody comprising a heavy chain sequence of at least 95% sequence identity to the amino acid sequence of SEQ ID NO:15; and/or a light chain sequence of at least 95% sequence identity to the amino acid sequence of SEQ ID NO:16 to its respective antigenic epitope. In one embodiment, the anti-factor D antibody competitively inhibits the binding of the antibody comprising a heavy chain variable region comprising the amino acid sequence of SEQ ID NO:7; and/or a light chain variable region comprising the amino acid sequence of SEQ ID NO:8 to its respective antigenic epitope. In one embodiment, the anti-factor D antibody competitively inhibits the binding of the antibody comprising a heavy chain comprising the amino acid sequence of SEQ ID NO:15; and/or a light chain comprising the amino acid sequence of SEQ ID NO:16 to its respective antigenic epitope. In one embodiment, the anti-factor D antibody competitively inhibits the binding of lampalizumab having CAS registration number 1278466-20-8 to its respective antigenic epitope. In some embodiments, the anti-factor D antibody binds to the same epitope on factor D bound by another factor D antibody. In one embodiment, the anti-factor D antibody binds to the same epitope on factor D bound by the anti-factor D antibody comprising a light chain comprising HVR-L1 comprising the amino acid sequence ITSTDIDDDMN (SEQ ID NO:1), HVR-L2 comprising the amino acid sequence GGNTLRP (SEQ ID NO:2), and HVR-L3 comprising the amino acid sequence LQSDSLPYT (SEQ ID NO: 3); and/or a heavy chain comprising HVR-H1 comprising the amino acid sequence GYTFTNYGMN (SEQ ID NO: 4), HVR-H2 comprising the amino acid sequence WINTYTGETTYADDFKG (SEQ ID NO:5), and HVR-H3 comprising the amino acid sequence EGGVNN (SEQ ID NO:6). In one embodiment, the anti-factor D antibody binds to the same epitope on factor D bound by the antibody comprising a heavy chain variable region sequence of at least 95% sequence identity to the amino acid sequence of SEQ ID NO:7; and/or a light chain variable region sequence of at least 95% sequence identity to the amino acid sequence of SEQ ID NO:8. In one embodiment, the anti-factor D antibody binds to the same epitope on factor D bound by the antibody comprising a heavy chain sequence of at least 95% sequence identity to the amino acid sequence of SEQ ID NO:15; and/or a light chain sequence of at least 95% sequence identity to the amino acid sequence of SEQ ID NO:16. In one embodiment, the anti-factor D antibody binds to the same epitope on factor D bound by the antibody comprising a heavy chain variable region comprising the amino acid sequence of SEQ ID NO:7; and/or a light chain variable region comprising the amino acid sequence of SEQ ID NO:8. In one embodiment, the anti-factor D antibody binds to the same epitope on factor D bound by the antibody comprising a heavy chain comprising the amino acid sequence of SEQ ID NO:15; and/or a light chain comprising the amino acid sequence of SEQ ID NO:16. In one embodiment, the anti-factor D antibody binds to the same epitope on factor D bound by lampalizumab having CAS registration number 1278466-20-8.

IX. Exemplar Embodiments

The invention includes a method of treating a patient having a degenerative disease, the method comprising:
  (a) determining the presence of at least one degenerative disease-associated polymorphism in a sample from the patient;
    (i) by providing a nucleic acid sample the patient;
    (ii) genotyping the presence of at least one degenerative disease-associated polymorphism wherein the polymorphism is a risk allele selected from the group consisting of a CFI allele, a CFH allele, a C2 allele, a CFB allele, or a C3 allele;
  (b) identifying the patient as more likely to respond to a therapy comprising anti-factor D antibody, or an antigen-binding fragment thereof, when at least one risk allele, selected from the group consisting of a CFI allele, a CFH allele, a C2 allele, a CFB allele, or a C3 allele is present; and
  (c) administering the anti-factor D antibody, or antigen-binding fragment thereof, to the patient when at least one risk allele selected from the group consisting of a CFI allele, a CFH allele, a C2 allele, a C3B allele, or a C3 allele is present. In one embodiment, the CFI allele is an equivalent allele thereof, the CFH allele is an equivalent allele thereof, the C2 allele is an equivalent allele thereof, the CFB allele is an equivalent allele thereof, or the C3 allele is an equivalent allele thereof. In a further embodiment, the CFI allele comprises a G at the single nucleotide polymorphism (SNP) rs4698775 or rs17440077, the CFH allele comprises an A at the single nucleotide polymorphism (SNP) rs10737680 or a G at the single nucleotide polymorphism (SNP) rs1329428, the C2 allele comprises a G at the single nucleotide polymorphism (SNP) rs429608, the CFB allele comprises a G at the single nucleotide polymorphism (SNP) rs429608, and the C3 allele comprises a G at the single nucleotide polymorphism (SNP) rs2230199. In an even further embodiment, the sample is a blood sample, saliva, cheek swab, tissue sample or a sample of a bodily fluid. In an even further embodiment, the nucleic acid sample comprises DNA. In another embodiment, the nucleic acid sample comprises RNA. In another embodiment, the nucleic acid sample is amplified. In another embodiment, the nucleic acid sample is amplified by a polymerase chain reaction. In another embodiment, at least one polymorphism is detected by polymerase chain reaction. In another embodiment, at least one polymorphism is detected by sequencing. In another embodiment, at least one polymorphism is detected by a technique selected from the group consisting of scanning probe and nanopore DNA sequencing, pyrosequencing, Denaturing Gradient Gel Electrophoresis (DGGE), Temporal Temperature Gradient Electrophoresis (TTGE), Zn(II)-cyclen polyacrylamide gel electrophoresis, homogeneous fluorescent PCR-based single nucleotide polymorphism analysis, phosphate-affinity polyacrylamide gel electrophoresis, high-throughput SNP genotyping platforms, molecular beacons, 5'nuclease reaction, Taqman assay, MassArray (single base primer extension coupled with matrix-assisted laser desorption/ionization time-of-flight mass spectrometry), trityl mass tags, genotyping platforms (such as the Invader Assay®), single base primer extension (SBE) assays, PCR amplification (e.g. PCR amplification on magnetic nanoparticles (MNPs), restriction enzyme analysis of PCR products (RFLP methods), allele-specific PCR, multiple primer extension (MPEX), and isothermal smart amplification. In another embodiment, at least one polymorphism is detected by amplification of a target region containing at least one polymorphism, and hybridization with at least one sequence-specific oligonucleotide that hybridizes under stringent conditions to at least one polymorphism and detecting the hybridization. In another embodiment, the presence of one or two alleles of the G genotype at the SNP rs4698775, SNP rs17440077, SNP rs1329428, SNP rs429608 or SNP rs2230199 or one or two alleles of the A genotype at the SNP rs10737680 in the patient indicates an increased likelihood of response to anti-factor D antibody treatment. In another embodiment, a polymorphism that is in linkage disequilibrium with at least one single nucleotide polymorphism selected from the group consisting of single nucleotide polymorphism (SNP) rs4698775, rs17440077, rs10737680, rs1329428, rs429608, and rs2230199 is detected. In another embodiment, the degenerative disease is age related macular degeneration. In another embodiment, the age related macular degeneration is early, intermediate or advanced AMD. In another embodiment, the advanced AMD is geographic atrophy. In another embodiment, the anti-factor D antibody, or antigen-binding fragment thereof is lampalizumab.

The invention further includes a method of identifying a patient having a degenerative disease as more likely to respond to a therapy comprising an anti-factor D antibody, or antigen-binding fragment thereof, the method comprising:
  (a) determining the presence of at least one degenerative disease-associated polymorphism in a sample from the patient;
    (i) by providing a nucleic acid sample from the patient;
    (ii) genotyping the presence of at least one degenerative disease-associated polymorphism wherein the polymorphism is a risk allele selected from the group consisting of a CFI allele, a CFH allele, a C2 allele, a CFB allele, or a C3 allele;
  (b) identifying the patient as more likely to respond to a therapy comprising anti-factor D antibody, or an antigen-binding fragment thereof, when at least one risk allele, selected from the group consisting of a CFI allele, a CFH allele, a C2 allele, a CFB allele, or a C3 allele is present; and
  (c) selecting the therapy comprising anti-factor D antibody, or antigen binding fragment thereof. In one embodiment, the CFI allele is an equivalent allele thereof, the CFH allele is an equivalent allele thereof, the C2 allele is an equivalent allele thereof, the CFB allele is an equivalent allele thereof, or the C3 allele is an equivalent allele thereof In another embodiment, the CFI allele comprises a G at the single nucleotide polymorphism (SNP) rs4698775 or rs17440077, the CFH allele comprises an A at the single nucleotide polymorphism (SNP) rs10737680 or a G at the single nucleotide polymorphism (SNP) rs1329428, the C2 allele comprises a G at the single nucleotide polymorphism (SNP) rs429608, the CFB allele comprises a G at the single nucleotide polymorphism (SNP) rs429608, and the C3 allele comprises a G at the single nucleotide polymorphism (SNP) rs2230199. In another embodiment, the sample is a blood sample, saliva, cheek swab, tissue sample or a sample of a bodily fluid. In another embodiment, the nucleic acid sample comprises DNA. In another embodiment, the nucleic acid sample comprises RNA. In another embodiment, the nucleic acid sample is amplified. In another embodiment, the nucleic acid sample is amplified by a polymerase chain reaction. In another embodiment, at least one polymorphism is detected by polymerase chain reaction. In another embodiment, at least one polymorphism is detected by sequencing. In another embodiment, at least one polymorphism is detected by a technique selected from the group consisting of scanning probe and nanopore DNA sequencing, pyrosequencing, Denaturing Gradient Gel Electrophoresis (DGGE), Temporal Temperature Gradient Electrophoresis (TTGE), Zn(II)-cyclen polyacrylamide gel electrophoresis, homogeneous fluorescent PCR-based single nucleotide polymorphism analysis, phosphate-affinity polyacrylamide gel electrophoresis, high-throughput SNP genotyping platforms, molecular beacons, 5'nuclease reaction, Taqman assay, MassArray (single base primer extension coupled with matrix-assisted laser desorption/ionization time-of-flight mass spectrometry), trityl mass tags, genotyping platforms (such as the Invader Assay®), single base primer extension (SBE) assays, PCR amplification (e.g. PCR amplification on magnetic nanoparticles (MNPs), restriction enzyme analysis of PCR products (RFLP methods), allele-specific PCR, multiple primer extension (MPEX), and isothermal smart amplification. In another embodiment, at least one polymorphism is detected by amplification of a target region containing at least one polymorphism, and hybridization with at least one sequence-specific oligonucleotide that hybridizes under stringent conditions to at least one polymorphism and detecting the hybridization. In another embodiment, the presence of one or two alleles of the G genotype at the SNP rs4698775, SNP rs17440077, SNP rs1329428, SNP rs429608 or SNP rs2230199 or one or two alleles of the A genotype at the SNP rs10737680 in the patient indicates an increased likelihood of response to anti-factor D antibody treatment. In another embodiment, a polymorphism that is in linkage disequilibrium with at least one single nucleotide polymorphism selected from the group consisting of single nucleotide polymorphism (SNP) rs4698775, rs17440077, rs10737680, rs1329428, rs429608, and rs2230199 is detected. In another embodiment, the degenerative disease is age related macular degeneration. In another embodiment, the age related macular degeneration is early, intermediate or advanced AMD. In another embodiment, the advanced AMD is geographic atrophy. In another embodiment, the anti-factor D antibody, or fragment thereof is lampalizumab. In another embodiment, The invention further includes a method of optimizing therapeutic efficacy of treatment of a patient having a degenerative disease with an anti-factor D antibody, or antigen binding fragment thereof, the method comprising:
- (a) determining the presence of at least one degenerative disease-associated polymorphism n a sample from the patient;
  - (i) by providing a nucleic acid sample from the patient;
  - (ii) genotyping the presence of at least one degenerative disease-associated polymorphism wherein the polymorphism is a risk allele, selected from the group consisting of a CFI allele, a CFH allele, a C2 allele, a CFB allele, or a C3 allele;
- (b) identifying the patient as more likely to respond to a therapy comprising anti-factor D antibody, or an antigen-binding fragment thereof, when at least one risk allele, selected from the group consisting of a CFI allele, a CFH allele, a C2 allele, a CFB allele, or a C3 allele is present; and
- (c) selecting the therapy comprising anti-factor D antibody, or antigen-binding fragment thereof. In another embodiment, the CFI allele is an equivalent allele thereof, the CFH allele is an equivalent allele thereof, the C2 allele is an equivalent allele thereof, the CFB allele is an equivalent allele thereof, or the C3 allele is an equivalent allele thereof In another embodiment, the CFI allele comprises a G at the single nucleotide polymorphism (SNP) rs4698775 or rs17440077, the CFH allele comprises an A at the single nucleotide polymorphism (SNP) rs10737680 or a G at the single nucleotide polymorphism (SNP) rs1329428, the C2 allele comprises a G at the single nucleotide polymorphism (SNP) rs429608, the CFB allele comprises a G at the single nucleotide polymorphism (SNP) rs429608, and the C3 allele comprises a G at the single nucleotide polymorphism (SNP) rs2230199. In another embodiment, the sample is a blood sample, saliva, cheek swab, tissue sample or a sample of a bodily fluid. In another embodiment, the nucleic acid sample comprises DNA. In another embodiment, the nucleic acid sample comprises RNA. In another embodiment, the nucleic acid sample is amplified. In another embodiment, the nucleic acid sample is amplified by a polymerase chain reaction. In another embodiment, at least one polymorphism is detected by polymerase chain reaction. In another embodiment, at least one polymorphism is detected by sequencing. In another embodiment, at least one polymorphism is detected by a technique selected from the group consisting of scanning probe and nanopore DNA sequencing, pyrosequencing, Denaturing Gradient Gel Electrophoresis (DGGE), Temporal Temperature Gradient Electrophoresis (TTGE), Zn(II)-cyclen polyacrylamide gel electrophoresis, homogeneous fluorescent PCR-based single nucleotide polymorphism analysis, phosphate-affinity polyacrylamide gel electrophoresis, high-throughput SNP genotyping platforms, molecular beacons, 5'nuclease reaction, Taqman assay, MassArray (single base primer extension coupled with matrix-assisted laser desorption/ionization time-of-flight mass spectrometry), trityl mass tags, genotyping platforms (such as the Invader Assay®), single base primer extension (SBE) assays, PCR amplification (e.g. PCR amplification on magnetic nanoparticles (MNPs), restriction enzyme analysis of PCR products (RFLP methods), allele-specific PCR, multiple primer extension (MPEX), and isothermal smart amplification. In another embodiment, at least one polymorphism is detected by amplification of a target region containing at least one polymorphism, and hybridization with at least one sequence-specific oligonucleotide that hybridizes under stringent conditions to at least one polymorphism and detecting the hybridization. In another embodiment, the presence of one or two alleles of the G genotype at the SNP rs4698775, SNP rs17440077, SNP rs1329428, SNP rs429608 or SNP rs2230199 or one or two alleles of the A genotype at the SNP rs10737680 in the patient indicates an increased likelihood of response to anti-factor D antibody treatment. In another embodiment, a polymorphism that is in linkage disequilibrium with at least one single nucleotide polymorphism selected from the group consisting of single nucleotide polymorphism (SNP) rs4698775, rs17440077, rs10737680, rs1329428, rs429608, and rs2230199 is detected. In another embodiment, the degenerative disease is age related macular degeneration. In another embodiment, the age related macular degeneration is early, intermediate or advanced AMD. In another embodiment, the advanced AMD is geographic atrophy. In another embodiment, the anti-factor D antibody, or antigen-binding fragment thereof is lampalizumab.

The invention further includes a method of predicting responsiveness of a degenerative disease patient to treatment with an anti-factor D antibody, or antigen-binding fragment thereof, the method comprising
- (a) determining the presence of at least one degenerative disease-associated polymorphism in a sample from the patient;
  - (i) by providing a nucleic acid sample from the patient;
  - (ii) genotyping the presence of at least one degenerative disease-associated polymorphism wherein the polymorphism is a risk allele, selected from the group consisting of a CFI allele, a CFH allele, a C2 allele, a CFB allele, or a C3 allele;
- (b) identifying the patient as more likely to respond to a therapy comprising anti-factor D antibody, or an antigen-binding fragment thereof, when at least one risk allele, selected from the group consisting of a CFI allele, a CFH allele, a C2 allele, a CFB allele, or a C3 allele is present. In one embodiment, the CFI allele is an equivalent allele thereof, the CFH allele is an equivalent allele thereof, the C2 allele is an equivalent allele thereof, the CFB allele is an equivalent allele thereof, or the C3 allele is an equivalent allele thereof In one embodiment, the CFI allele comprises a G at the single nucleotide polymorphism (SNP) rs4698775 or rs17440077, the CFH allele comprises an A at the single nucleotide polymorphism (SNP) rs10737680 or a G at the single nucleotide polymorphism (SNP) rs1329428, the C2 allele comprises a G at the single nucleotide polymorphism (SNP) rs429608, the CFB allele comprises a G at the single nucleotide polymorphism (SNP) rs429608, and the C3 allele comprises a G at the single nucleotide polymorphism (SNP) rs2230199. In one embodiment, the sample is a blood sample, saliva, cheek swab, tissue sample or a sample of a bodily fluid. In one embodiment, the nucleic acid sample comprises DNA. In one embodiment, the nucleic acid sample comprises RNA. In one embodiment, the nucleic acid sample is amplified. In another embodiment, the nucleic acid sample is amplified by a polymerase chain reaction. In another embodiment, at least one polymorphism is detected by polymerase chain reaction. In another embodiment, at least one polymorphism is detected by sequencing. In another embodiment, at least one polymorphism is detected by a technique selected from the group consisting of scanning probe and nanopore DNA sequencing, pyrosequencing, Denaturing Gradient Gel Electrophoresis (DGGE), Temporal Temperature Gradient Electrophoresis (TTGE), Zn(II)-cyclen polyacrylamide gel electrophoresis, homogeneous fluorescent PCR-based single nucleotide polymorphism analysis, phosphate-affinity polyacrylamide gel electrophoresis, high-throughput SNP genotyping platforms, molecular beacons, 5'nuclease reaction, Taqman assay, MassArray (single base primer extension coupled with matrix-assisted laser desorption/ionization time-of-flight mass spectrometry), trityl mass tags, genotyping platforms (such as the Invader Assay®), single base primer extension (SBE) assays, PCR amplification (e.g. PCR amplification on magnetic nanoparticles (MNPs), restriction enzyme analysis of PCR products (RFLP methods), allele-specific PCR, multiple primer extension (MPEX), and isothermal smart amplification. In another embodiment, at least one polymorphism is detected by amplification of a target region containing at least one polymorphism, and hybridization with at least one sequence-specific oligonucleotide that hybridizes under stringent conditions to at least one polymorphism and detecting the hybridization. In another embodiment, the presence of one or two alleles of the G genotype at the SNP rs4698775, SNP rs17440077, SNP rs1329428, SNP rs429608 or SNP rs2230199 or one or two alleles of the A genotype at the SNP rs10737680 in the patient indicates an increased likelihood of response to anti-factor D antibody treatment. In another embodiment, a polymorphism that is in linkage disequilibrium with at least one single nucleotide polymorphism selected from the group consisting of single nucleotide polymorphism (SNP) rs4698775, rs17440077, rs10737680, rs1329428, rs429608, and rs2230199 is detected. In another embodiment, the degenerative disease is age related macular degeneration. In another embodiment, the age related macular degeneration is early, intermediate or advanced AMD. In another embodiment, the advanced AMD is geographic atrophy. In another embodiment, the anti-factor D antibody, or antigen-binding fragment thereof is lampalizumab.

The invention further includes a method of determining the likelihood that a degenerative disease patient benefits from treatment with an anti-factor D antibody, or antigen-binding fragment thereof, the method comprising
 (a) determining the presence of at least one degenerative disease-associated polymorphism a sample from the patient;
  (i) by providing a nucleic acid sample from the patient;
  (ii) genotyping the presence of at least one degenerative disease-associated polymorphism wherein the polymorphism is a risk allele, selected from the group consisting of a CFI allele, a CFH allele, a C2 allele, a CFB allele, or a C3 allele;
 (b) identifying the patient as more likely to respond to a therapy comprising anti-factor D antibody, or an antigen-binding fragment thereof, when at least one risk allele, selected from the group consisting of a CFI allele, a CFH allele, a C2 allele, a CFB allele, or a C3 allele is present. In one embodiment, the CFI allele is an equivalent allele thereof, the CFH allele is an equivalent allele thereof, the C2 allele is an equivalent allele thereof, the CFB allele is an equivalent allele thereof, or the C3 allele is an equivalent allele thereof. In another embodiment, the CFI allele comprises a G at the single nucleotide polymorphism (SNP) rs4698775 or rs17440077, the CFH allele comprises an A at the single nucleotide polymorphism (SNP) rs10737680 or a G at the single nucleotide polymorphism (SNP) rs1329428, the C2 allele comprises a G at the single nucleotide polymorphism (SNP) rs429608, the CFB allele comprises a G at the single nucleotide polymorphism (SNP) rs429608, and the C3 allele comprises a G at the single nucleotide polymorphism (SNP) rs2230199. In another embodiment, the sample is a blood sample, saliva, cheek swab, tissue sample or a sample of a bodily fluid. In another embodiment, the nucleic acid sample comprises DNA. In another embodiment, the nucleic acid sample comprises RNA. In another embodiment, the nucleic acid sample is amplified. In another embodiment, the nucleic acid sample is amplified by a polymerase chain reaction. In another embodiment, at least one polymorphism is detected by polymerase chain reaction. In another embodiment, at least one polymorphism is detected by sequencing. In another embodiment, at least one polymorphism is detected by a technique selected from the group consisting of scanning probe and nanopore DNA sequencing, pyrosequencing, Denaturing Gradient Gel Electrophoresis (DGGE), Temporal Temperature Gradient Electrophoresis (TTGE), Zn(II)-cyclen polyacrylamide gel electrophoresis, homogeneous fluorescent PCR-based single nucleotide polymorphism analysis, phosphate-affinity polyacrylamide gel electrophoresis, high-throughput SNP genotyping platforms, molecular beacons, 5'nuclease reaction, Taqman assay, MassArray (single base primer extension coupled with matrix-assisted laser desorption/ionization time-of-flight mass spectrometry), trityl mass tags, genotyping platforms (such as the Invader Assay®), single base primer extension (SBE) assays, PCR amplification (e.g. PCR amplification on magnetic nanoparticles (MNPs), restriction enzyme analysis of PCR products (RFLP methods), allele-specific PCR, multiple primer extension (MPEX), and isothermal smart amplification. In another embodiment, at least one polymorphism is detected by amplification of a target region containing at least one polymorphism, and hybridization with at least one sequence-specific oligonucleotide that hybridizes under stringent conditions to at least one polymorphism and detecting the hybridization. In another embodiment, the presence of one or two alleles of the G genotype at the SNP rs4698775, SNP rs17440077, SNP rs1329428, SNP rs429608 or SNP rs2230199 or one or two alleles of the A genotype at the SNP rs10737680 in a patient indicates an increased likelihood of response to anti-factor D antibody treatment. In another embodiment, a polymorphism that is in linkage disequilibrium with at least one single nucleotide polymorphism selected from the group consisting of single nucleotide polymorphism (SNP) rs4698775, rs17440077, rs10737680, rs1329428, rs429608, and rs2230199 is detected. In another embodiment, the degenerative disease is age related macular degeneration. In another embodiment, the age related macular degeneration is early, intermediate or advanced AMD. In another embodiment, the advanced AMD is geographic atrophy. In another embodiment, the anti-factor D antibody, or antigen-binding fragment thereof is lampalizumab.

The invention further includes a method of assessing degenerative disease in an individual, the method comprising:
(a) determining the presence of at least one degenerative disease-associated polymorphism in a sample from the patient;
  (i) by providing a nucleic acid sample from the patient;
  (ii) genotyping the presence of at least one degenerative disease-associated polymorphism wherein the polymorphism is a risk allele, selected from the group consisting of a CFI allele, a CFH allele, a C2 allele, a CFB allele, or a C3 allele;
(b) providing an assessment of degenerative disease when at least one risk allele, selected from the group consisting of a CFI allele, a CFH allele, a C2 allele, a CFB allele, or a C3 allele is present in the sample from the individual. In one embodiment, the CFI allele is an equivalent allele thereof, the CFH allele is an equivalent allele thereof, the C2 allele is an equivalent allele thereof, the CFB allele is an equivalent allele thereof, or the C3 allele is an equivalent allele thereof. In another embodiment, the CFI allele comprises a G at the single nucleotide polymorphism (SNP) rs4698775 or rs17440077, the CFH allele comprises an A at the single nucleotide polymorphism (SNP) rs10737680 or a G at the single nucleotide polymorphism (SNP) rs1329428, the C2 allele comprises a G at the single nucleotide polymorphism (SNP) rs429608, the CFB allele comprises a G at the single nucleotide polymorphism (SNP) rs429608, and the C3 allele comprises a G at the single nucleotide polymorphism (SNP) rs2230199. In another embodiment, the sample is a blood sample, saliva, cheek swab, tissue sample or a sample of a bodily fluid. In another embodiment, the nucleic acid sample comprises DNA. In another embodiment, the nucleic acid sample comprises RNA. In another embodiment, the nucleic acid sample is amplified. In another embodiment, the nucleic acid sample is amplified by a polymerase chain reaction. In another embodiment, at least one polymorphism is detected by polymerase chain reaction. In another embodiment, at least one polymorphism is detected by sequencing. In another embodiment, at least one polymorphism is detected by a technique selected from the group consisting of scanning probe and nanopore DNA sequencing, pyrosequencing, Denaturing Gradient Gel Electrophoresis (DGGE), Temporal Temperature Gradient Electrophoresis (TTGE), Zn(II)-cyclen polyacrylamide gel electrophoresis, homogeneous fluorescent PCR-based single nucleotide polymorphism analysis, phosphate-affinity polyacrylamide gel electrophoresis, high-throughput SNP genotyping platforms, molecular beacons, 5'nuclease reaction, Taqman assay, MassArray (single base primer extension coupled with matrix-assisted laser desorption/ionization time-of-flight mass spectrometry), trityl mass tags, genotyping platforms (such as the Invader Assay®), single base primer extension (SBE) assays, PCR amplification (e.g. PCR amplification on magnetic nanoparticles (MNPs), restriction enzyme analysis of PCR products (RFLP methods), allele-specific PCR, multiple primer extension (MPEX), and isothermal smart amplification. In another embodiment, at least one polymorphism is detected by amplification of a target region containing at least one polymorphism, and hybridization with at least one sequence-specific oligonucleotide that hybridizes under stringent conditions to at least one polymorphism and detecting the hybridization. In another embodiment, a patient having one or two alleles of the G genotype at the SNP rs4698775, SNP rs17440077, SNP rs1329428, SNP rs429608 or SNP rs2230199 or one or two alleles of the A genotype at the SNP rs10737680 is more likely to respond to anti-factor D antibody treatment. In another embodiment, a polymorphism that is in linkage disequilibrium with at least one single nucleotide polymorphism selected from the group consisting of single nucleotide polymorphism (SNP) rs4698775, rs17440077, rs10737680, rs1329428, rs429608, and rs2230199 is detected. In another embodiment, the degenerative disease is age related macular degeneration. In another embodiment, the age related macular degeneration is early, intermediate or advanced AMD. In another embodiment, the advanced AMD is geographic atrophy.

The invention further includes a method of identifying an individual who has an increased risk for developing more advanced forms of age related macular degeneration, the method comprising:
(a) determining the presence of at least one degenerative disease-associated polymorphism in a sample from the individual;
  (i) by providing a nucleic acid sample from the individual;
  (ii) genotyping the presence of at least one degenerative disease-associated polymorphism wherein the polymorphism is a risk allele, selected from the group consisting of a CFI allele, a CFH allele, a C2 allele, a CFB allele, or a C3 allele;
(b) identifying the individual as more likely to develop more advanced forms of AMD when at least one risk allele, selected from the group consisting of a CFI allele, a CFH allele, a C2 allele, a CFB allele, or a C3 allele is present. In one embodiment, the individual is more likely to respond to a therapy comprising anti-factor D antibody, or an antigen-binding fragment thereof, when at least one risk allele, selected from the group consisting of a CFI allele, a CFH allele, a C2 allele, a CFB allele, or a C3 allele is present; and further comprises selecting the therapy comprising anti-factor D antibody, or antigen-binding fragment thereof In another embodiment, the CFI allele is an equivalent allele thereof, the CFH allele is an equivalent allele thereof, the C2 allele is an equivalent allele thereof, the CFB allele is an equivalent allele thereof, or the C3 allele is an equivalent allele thereof. In another embodiment, the CFI allele comprises a G at the single nucleotide polymorphism (SNP) rs4698775 or rs17440077, the CFH allele comprises an A at the single nucleotide polymorphism (SNP) rs10737680 or a G at the single nucleotide polymorphism (SNP) rs1329428, the C2 allele comprises a G at the single nucleotide polymorphism (SNP) rs429608, the CFB allele comprises a G at the single nucleotide polymorphism (SNP) rs429608, and the C3 allele comprises a G at the single nucleotide polymorphism (SNP) rs2230199. In another embodiment, the sample is a blood sample, saliva, cheek swab, tissue sample or a sample of a bodily fluid. In another embodiment, the nucleic acid sample comprises DNA. In another embodiment, the nucleic acid sample comprises RNA. In another embodiment, the nucleic acid sample is amplified. In another embodiment, the nucleic acid sample is amplified by a polymerase chain reaction. In another embodiment, at least one polymorphism is detected by polymerase chain reaction. In another embodiment, at least one polymorphism is detected by sequencing. In another embodiment, at least one polymorphism is detected by a technique selected from the group consisting of scanning probe and nanopore DNA sequencing, pyrosequencing, Denaturing Gradient Gel Electrophoresis (DGGE), Temporal Temperature Gradient Electrophoresis (TTGE), Zn(II)-cyclen polyacrylamide gel electrophoresis, homogeneous fluorescent PCR-based single nucleotide polymorphism analysis, phosphate-affinity polyacrylamide gel electrophoresis, high-throughput SNP genotyping platforms, molecular beacons, 5'nuclease reaction, Taqman assay, MassArray (single base primer extension coupled with matrix-assisted laser desorption/ionization time-of-flight mass spectrometry), trityl mass tags, genotyping platforms (such as the Invader Assay®), single base primer extension (SBE) assays, PCR amplification (e.g. PCR amplification on magnetic nanoparticles (MNPs), restriction enzyme analysis of PCR products (RFLP methods), allele-specific PCR, multiple primer extension (MPEX), and isothermal smart amplification. In another embodiment, at least one polymorphism is detected by amplification of a target region containing at least one polymorphism, and hybridization with at least one sequence-specific oligonucleotide that hybridizes under stringent conditions to at least one polymorphism and detecting the hybridization. In another embodiment, a patient having one or two alleles of the G genotype at the SNP rs4698775, SNP rs17440077, SNP rs1329428, SNP rs429608 or SNP rs2230199 or one or two alleles of the A genotype at the SNP rs10737680 is more likely to respond to anti-factor D antibody treatment. In another embodiment, a polymorphism that is in linkage disequilibrium with at least one single nucleotide polymorphism selected from the group consisting of single nucleotide polymorphism (SNP) rs4698775, rs17440077, rs10737680, rs1329428, rs429608, and rs2230199 is detected. In another embodiment, the degenerative disease is age related macular degeneration. In another embodiment, the age related macular degeneration is early, intermediate or advanced AMD. In another embodiment, the advanced AMD is geographic atrophy. In another embodiment, the anti-factor D antibody, or antigen-binding fragment thereof is lampalizumab.

The invention further includes a method of predicting progression of AMD in an individual, the method comprising:
  (a) determining the presence of at least one degenerative disease-associated polymorphism in a sample from the individual;
    (i) by providing a nucleic acid sample from the individual;
    (ii) genotyping the presence of at least one degenerative disease-associated polymorphism wherein the polymorphism is a risk allele, selected from the group consisting of a CFI allele, a CFH allele, a C2 allele, a CFB allele, or a C3 allele;
  (b) identifying the individual as more likely to develop more advanced forms of AMD when at least one risk allele, selected from the group consisting of a CFI allele, a CFH allele, a C2 allele, a CFB allele, or a C3 allele is present. In one embodiment, the individual is more likely to respond to a therapy comprising anti-factor D antibody, or an antigen-binding fragment thereof, when at least one risk allele, selected from the group consisting of a CFI allele, a CFH allele, a C2 allele, a CFB allele, or a C3 allele is present; and further comprises selecting the therapy comprising anti-factor D antibody, or antigen-binding fragment thereof In another embodiment, the CFI allele is an equivalent allele thereof, the CFH allele is an equivalent allele thereof, the C2 allele is an equivalent allele thereof, the CFB allele is an equivalent allele thereof, or the C3 allele is an equivalent allele thereof. In another embodiment, the CFI allele comprises a G at the single nucleotide polymorphism (SNP) rs4698775 or rs17440077, the CFH allele comprises an A at the single nucleotide polymorphism (SNP) rs10737680 or a G at the single nucleotide polymorphism (SNP) rs1329428, the C2 allele comprises a G at the single nucleotide polymorphism (SNP) rs429608, the CFB allele comprises a G at the single nucleotide polymorphism (SNP) rs429608, and the C3 allele comprises a G at the single nucleotide polymorphism (SNP) rs2230199. In another embodiment, the sample is a blood sample, saliva, cheek swab, tissue sample or a sample of a bodily fluid. In another embodiment, the nucleic acid sample comprises DNA. In another embodiment, the nucleic acid sample comprises RNA. In another embodiment, the nucleic acid sample is amplified. In another embodiment, the nucleic acid sample is amplified by a polymerase chain reaction. In another embodiment, at least one polymorphism is detected by polymerase chain reaction. In another embodiment, at least one polymorphism is detected by sequencing. In another embodiment, at least one polymorphism is detected by a technique selected from the group consisting of scanning probe and nanopore DNA sequencing, pyrosequencing, Denaturing Gradient Gel Electrophoresis (DGGE), Temporal Temperature Gradient Electrophoresis (TTGE), Zn(II)-cyclen polyacrylamide gel electrophoresis, homogeneous fluorescent PCR-based single nucleotide polymorphism analysis, phosphate-affinity polyacrylamide gel electrophoresis, high-throughput SNP genotyping platforms, molecular beacons, 5'nuclease reaction, Taqman assay, MassArray (single base primer extension coupled with matrix-assisted laser desorption/ionization time-of-flight mass spectrometry), trityl mass tags, genotyping platforms (such as the Invader Assay®), single base primer extension (SBE) assays, PCR amplification (e.g. PCR amplification on magnetic nanoparticles (MNPs), restriction enzyme analysis of PCR products (RFLP methods), allele-specific PCR, multiple primer extension (MPEX), and isothermal smart amplification. In another embodiment, at least one polymorphism is detected by amplification of a target region containing at least one polymorphism, and hybridization with at least one sequence-specific oligonucleotide that hybridizes under stringent conditions to at least one polymorphism and detecting the hybridization. In another embodiment, a patient having one or two alleles of the G genotype at the SNP rs4698775, SNP rs17440077, SNP rs1329428, SNP rs429608 or SNP rs2230199 or one or two alleles of the A genotype at the SNP rs10737680 is more likely to respond to anti-factor D antibody treatment. In another embodiment, a polymorphism that is in linkage disequilibrium with at least one single nucleotide polymorphism selected from the group consisting of single nucleotide polymorphism (SNP) rs4698775, rs17440077, rs10737680, rs1329428, rs429608, and rs2230199 is detected. In another embodiment, the degenerative disease is age related macular degeneration. In another embodiment, the age related macular degeneration is early, intermediate or advanced AMD. In another embodiment, the advanced AMD is geographic atrophy. In another embodiment, the anti-factor D antibody, or antigen-binding fragment thereof is lampalizumab.

The invention includes a method for determining a degenerative disease individual's risk for progression of degenerative disease comprising:
 (a) detecting the presence of at least one degenerative disease-associated polymorphism in a sample of the individual,
  (i) by providing a nucleic acid sample from the individual;
  (ii) genotyping the presence of at least one degenerative disease-associated polymorphism wherein the polymorphism is a risk allele selected from the group consisting of a CFI risk allele, a CFH risk allele, a C2 risk allele, a CFB risk allele or a C3 risk allele;
 (b) identifying the individual as having increased risk for degenerative disease progression when the risk allele polymorphism is present wherein the increased risk is relative to the risk when the major allele of the polymorphism is present. In one embodiment, the CFI allele is an equivalent allele thereof, the CFH allele is an equivalent allele thereof, the C2 allele is an equivalent allele thereof, the CFB allele is an equivalent allele thereof, or the C3 allele is an equivalent allele thereof. In another embodiment, the CFI allele comprises a G at the single nucleotide polymorphism (SNP) rs4698775 or rs17440077, the CFH allele comprises an A at the single nucleotide polymorphism (SNP) rs10737680 or a G at the single nucleotide polymorphism (SNP) rs1329428, the C2 allele comprises a G at the single nucleotide polymorphism (SNP) rs429608, the CFB allele comprises a G at the single nucleotide polymorphism (SNP) rs429608, and the C3 allele comprises a G at the single nucleotide polymorphism (SNP) rs2230199. In another embodiment, the sample is a blood sample, saliva, cheek swab, tissue sample or a sample of a bodily fluid. In another embodiment, the nucleic acid sample comprises DNA. In another embodiment, the nucleic acid sample comprises RNA. In another embodiment, the nucleic acid sample is amplified. In another embodiment, the nucleic acid sample is amplified by a polymerase chain reaction. In another embodiment, at least one polymorphism is detected by polymerase chain reaction. In another embodiment, at least one polymorphism is detected by sequencing. In another embodiment, at least one polymorphism is detected by a technique selected from the group consisting of scanning probe and nanopore DNA sequencing, pyrosequencing, Denaturing Gradient Gel Electrophoresis (DGGE), Temporal Temperature Gradient Electrophoresis (TTGE), Zn(II)-cyclen polyacrylamide gel electrophoresis, homogeneous fluorescent PCR-based single nucleotide polymorphism analysis, phosphate-affinity polyacrylamide gel electrophoresis, high-throughput SNP genotyping platforms, molecular beacons, 5'nuclease reaction, Taqman assay, MassArray (single base primer extension coupled with matrix-assisted laser desorption/ionization time-of-flight mass spectrometry), trityl mass tags, genotyping platforms (such as the Invader Assay®), single base primer extension (SBE) assays, PCR amplification (e.g. PCR amplification on magnetic nanoparticles (MNPs), restriction enzyme analysis of PCR products (RFLP methods), allele-specific PCR, multiple primer extension (MPEX), and isothermal smart amplification. In another embodiment, at least one polymorphism is detected by amplification of a target region containing at least one polymorphism, and hybridization with at least one sequence-specific oligonucleotide that hybridizes under stringent conditions to at least one polymorphism and detecting the hybridization. In another embodiment, the presence of two alleles of the G genotype at the SNP rs4698775, SNP rs17440077, SNP rs1329428, SNP rs429608 or SNP rs2230199 or one or two alleles of the A genotype at the SNP rs10737680 in the individual indicates an increased risk for degenerative disease progression. In another embodiment, a polymorphism that is in linkage disequilibrium with at least one single nucleotide polymorphism selected from the group consisting of single nucleotide polymorphism (SNP) rs4698775, rs17440077, rs10737680, rs1329428, rs429608, and rs2230199 is detected. In another embodiment, the degenerative disease is age related macular degeneration. In another embodiment, the age related macular degeneration is early, intermediate or advanced AMD. In another embodiment, the advanced AMD is geographic atrophy.

The invention includes a method of treating a degenerative disease comprising administering an anti-factor D antibody, or antigen-binding fragment thereof, comprising HVRH1, HVRH2, HVRH3, HVRL1, HVRL2, HVRL3, and HVRL3, wherein the respective HVRs have the amino acid sequence of SEQ ID NO: 1, SEQ ID NO: 2, SEQ ID NO: 3, SEQ ID NO: 4, SEQ ID NO: 5 and SEQ ID NO: 6 to a patient suffering from a degenerative disease in a 10 mg dose every month. In one embodiment, the age related macular degeneration is early, intermediate or advanced AMD. In another embodiment, the advanced AMD is geographic atrophy. In another embodiment, a second medicament is administered. In another embodiment, the second medicament is a VEGF inhibitor. In another embodiment, the VEGF inhibitor is ranibizumab. In another embodiment, the anti-factor D antibody, or antigen binding fragment thereof, is an antibody or antigen binding fragment thereof comprising a VH comprising SEQ II) NO: 7 and a VL comprising SEQ ID NO: 8. In another embodiment, the treatment results in a greater than or equal to 20% reduction of change in GA area from baseline GA area. In another embodiment, the treatment results in a greater than or equal to 15% reduction of change in GA area from baseline GA area. In another embodiment, the treatment results in a greater than or equal to 10% reduction of change in GA area from baseline GA area. In another embodiment, the treatment results in a greater than or equal to 5% reduction of change in GA area from baseline GA area. In another embodiment, the patient has geographic atrophy secondary to AMD In another embodiment, the study eye in the patient has a BCVA between 20/25 and 20/400. In another embodiment, the study eye in the patient has a BCVA between 20/25 and 20/100. In another embodiment, the study eye in the patient has a BCVA between 20/50 and 20/400. In another embodiment, the study eye in the patient has a BCVA better than 20/25 or worse than 20/400. In another embodiment, the patient has not received any previous intravitreal treatment, retinal surgery or other retinal therapeutic procedures in the study eye.

The invention includes a kit for genotyping in a biological sample from a degenerative disease patient, wherein the kit comprises oligonucleotides for polymerase chain reaction or sequencing for detection of a risk allele. In one embodiment, the biological sample is a blood sample, saliva, cheek swab, tissue sample or a sample of bodily fluids. In another embodiment, the biological sample is a nucleic acid sample. In another embodiment, the nucleic acid sample comprises DNA. In another embodiment, the nucleic acid sample comprises RNA. In another embodiment, the nucleic acid sample is amplified. In another embodiment, the kit further comprises a package insert for determining whether a degenerative disease patient is likely to respond to an anti-factor D antibody, or antigen binding fragment thereof. In another embodiment, the kit is used to detect the presence of a CFI risk allele, a CFH risk allele, a C2 risk allele, a CFB risk allele or a C3 risk allele. In another embodiment, the kit is used to detect the presence of one or two alleles of the G genotype at the SNP rs4698775, SNP rs17440077, SNP rs1329428, SNP rs429608 or SNP rs2230199 or two alleles of the A genotype at the SNP rs10737680.

The invention includes a kit for predicting whether a patient has an increased likelihood of benefiting from treatment with an anti-factor D antibody or antigen binding fragment thereof comprising a first oligonucleotide and a second oligonucleotide specific for a polymorphism in CFI, C2, CFB, C3 or CFH. In one embodiment, said first oligonucleotide and said second oligonucleotide may be used to amplify a region of the CFI, C2, CFB, C3 or CFH gene comprising a polymorphism in CFI, C2, CFB, C3 or CFH respectively, selected from the group consisting of the G genotype at the SNP rs4698775, SNP rs17440077, SNP rs1329428, SNP rs429608 or SNP rs2230199 or the A genotype at the SNP rs10737680. In another embodiment, the anti-factor D antibody, or antigen-binding fragment thereof, comprises HVRH1, HVRH2, HVRH3, HVRL1, HVRL2, HVRL3, and HVRL3, wherein the respective HVRs have the amino acid sequence of SEQ ID NO: 1, SEQ ID NO: 2, SEQ ID NO: 3, SEQ ID NO: 4, SEQ ID NO: 5 and SEQ ID NO: 6. In another embodiment, the anti-factor D antibody, or antigen-binding fragment thereof, comprises the variable heavy chain of SEQ ID NO: 7 and/or the variable light chain of SEQ ID NO: 8. In another embodiment, the polymorphism is a CFI polymorphism. In another embodiment, the CFI polymorphism is present in combination with one or more additional polymorphisms selected from the group consisting of a CFH polymorphism, a C2 polymorphism, a C3 polymorphism or a CFB polymorphism.

The invention includes use of an agent that specifically binds to at least one degenerative disease-associated polymorphism wherein the polymorphism is a risk allele selected from the group consisting of a CFI risk allele, a CFH risk allele, a C2 risk allele, a CFB risk allele or a C3 risk allele for the manufacture of a diagnostic for diagnosing a degenerative disease. In one embodiment, the CFI allele is an equivalent allele thereof, the CFH allele is an equivalent allele thereof, the C2 allele is an equivalent allele thereof, the CFB allele is an equivalent allele thereof, or the C3 allele is an equivalent allele thereof. In another embodiment, the CFI allele comprises a G at the single nucleotide polymorphism (SNP) rs4698775 or rs17440077, the CFH allele comprises an A at the single nucleotide polymorphism (SNP) rs10737680 or a G at the single nucleotide polymorphism (SNP) rs1329428, the C2 allele comprises a G at the single nucleotide polymorphism (SNP) rs429608, the CFB allele comprises a G at the single nucleotide polymorphism (SNP) rs429608, and the C3 allele comprises a G at the single nucleotide polymorphism (SNP) rs2230199. In another embodiment, at least one polymorphism is detected by a technique selected from the group consisting of scanning probe and nanopore DNA sequencing, pyrosequencing, Denaturing Gradient Gel Electrophoresis (DGGE), Temporal Temperature Gradient Electrophoresis (TTGE), Zn(II)-cyclen polyacrylamide gel electrophoresis, homogeneous fluorescent PCR-based single nucleotide polymorphism analysis, phosphate-affinity polyacrylamide gel electrophoresis, high-throughput SNP genotyping platforms, molecular beacons, 5'nuclease reaction, Taqman assay, MassArray (single base primer extension coupled with matrix-assisted laser desorption/ionization time-of-flight mass spectrometry), trityl mass tags, genotyping platforms (such as the Invader Assay®), single base primer extension (SBE) assays, PCR amplification (e.g. PCR amplification on magnetic nanoparticles (MNPs), restriction enzyme analysis of PCR products (RFLP methods), allele-specific PCR, multiple primer extension (MPEX), and isothermal smart amplification. In another embodiment, at least one polymorphism is detected by amplification of a target region containing at least one polymorphism, and hybridization with at least one sequence-specific oligonucleotide that hybridizes under stringent conditions to at least one polymorphism and detecting the hybridization. In another embodiment, the presence of one or two alleles of the G genotype at the SNP rs4698775, SNP rs17440077, SNP rs1329428, SNP rs429608 or SNP rs2230199 or one or two alleles of the A genotype at the SNP rs10737680 in the individual indicates an increased risk for degenerative disease progression. In another embodiment, a polymorphism that is in linkage disequilibrium with at least one single nucleotide polymorphism selected from the group consisting of single nucleotide polymorphism (SNP) rs4698775, rs17440077, rs10737680, rs1329428, rs429608, and rs2230199 is detected. In another embodiment, the degenerative disease is age related macular degeneration. In another embodiment, the age related macular degeneration is early, intermediate or advanced AMD. In another embodiment, the advanced AMD is geographic atrophy.

The invention includes in vitro use of an agent that binds to at least one degenerative disease-associated polymorphism wherein the polymorphism is a risk allele selected from the group consisting of a CFI risk allele, a CFH risk allele, a C2 risk allele, a CFB risk allele or a C3 risk allele for identifying a patient having a degenerative disease likely to respond to a therapy comprising an anti-factor D antibody, or antigen binding fragment thereof, wherein the presence of said polymorphisms identifies that the patient is more likely to respond to the therapy. In one embodiment, the CFI allele is an equivalent allele thereof, the CFH allele is an equivalent allele thereof, the C2 allele is an equivalent allele thereof, the CFB allele is an equivalent allele thereof, or the C3 allele is an equivalent allele thereof. In another embodiment, the CFI allele comprises a G at the single nucleotide polymorphism (SNP) rs4698775 or rs17440077, the CFH allele comprises an A at the single nucleotide polymorphism (SNP) rs10737680 or a G at the single nucleotide polymorphism (SNP) rs1329428, the C2 allele comprises a G at the single nucleotide polymorphism (SNP) rs429608, the CFB allele comprises a G at the single nucleotide polymorphism (SNP) rs429608, and the C3 allele comprises a G at the single nucleotide polymorphism (SNP) rs2230199. In another embodiment, at least one polymorphism is detected by a technique selected from the group consisting of scanning probe and nanopore DNA sequencing, pyrosequencing, Denaturing Gradient Gel Electrophoresis (DGGE), Temporal Temperature Gradient Electrophoresis (TTGE), Zn(II)-cyclen polyacrylamide gel electrophoresis, homogeneous fluorescent PCR-based single nucleotide polymorphism analysis, phosphate-affinity polyacrylamide gel electrophoresis, high-throughput SNP genotyping platforms, molecular beacons, 5'nuclease reaction, Taqman assay, MassArray (single base primer extension coupled with matrix-assisted laser desorption/ionization time-of-flight mass spectrometry), trityl mass tags, genotyping platforms (such as the Invader Assay®), single base primer extension (SBE) assays, PCR amplification (e.g. PCR amplification on magnetic nanoparticles (MNPs), restriction enzyme analysis of PCR products (RFLP methods), allele-specific PCR, multiple primer extension (MPEX), and isothermal smart amplification. In another embodiment, at least one polymorphism is detected by amplification of a target region containing at least one polymorphism, and hybridization with at least one sequence-specific oligonucleotide that hybridizes under stringent conditions to at least one polymorphism and detecting the hybridization. In another embodiment, the presence of one or two alleles of the G genotype at the SNP rs4698775, SNP rs17440077, SNP rs1329428, SNP rs429608 or SNP rs2230199 or one or two alleles of the A genotype at the SNP rs10737680 in the individual indicates an increased risk for degenerative disease progression. In another embodiment, a polymorphism that is in linkage disequilibrium with at least one single nucleotide polymorphism selected from the group consisting of single nucleotide polymorphism (SNP) rs4698775, rs17440077, rs10737680, rs1329428, rs429608, and rs2230199 is detected. In another embodiment, the degenerative disease is age related macular degeneration. In another embodiment, the age related macular degeneration is early, intermediate or advanced AMD. In another embodiment, the advanced AMD is geographic atrophy.

The invention includes in vitro use of a degenerative disease-associated polymorphism for selecting a patient having a degenerative disease as likely to respond to a therapy comprising anti-factor D or an antigen-binding fragment thereof, wherein the patient is identified as being more likely to respond to the therapy when the degenerative disease-associated polymorphism is detected in the sample from the patient. In one embodiment, the degenerative disease-associated polymorphism is an AMD-associated polymorphism. In another embodiment, the polymorphisms is a risk allele selected from the group consisting of a CFI risk allele, a CFH risk allele, a C2 risk allele, a CFB risk allele or a C3 risk allele for the manufacture of a diagnostic for diagnosing a degenerative disease. In another embodiment, the CFI allele is an equivalent allele thereof, the CFH allele is an equivalent allele thereof, the C2 allele is an equivalent allele thereof, the CFB allele is an equivalent allele thereof, or the C3 allele is an equivalent allele thereof In another embodiment, the CFI allele comprises a G at the single nucleotide polymorphism (SNP) rs4698775 or rs17440077, the CFH allele comprises an A at the single nucleotide polymorphism (SNP) rs10737680 or a G at the single nucleotide polymorphism (SNP) rs1329428, the C2 allele comprises a G at the single nucleotide polymorphism (SNP) rs429608, the CFB allele comprises a G at the single nucleotide polymorphism (SNP) rs429608, and the C3 allele comprises a G at the single nucleotide polymorphism (SNP) rs2230199.

The invention includes the use of a degenerative disease-associated polymorphism for the manufacture of a diagnostic for assessing the likelihood of a response of a patient having a degenerative disease to a therapy comprising an anti-factor D antibody, or antigen-binding fragment thereof. In one embodiment, the degenerative disease-associated polymorphism is an AMD-associated polymorphism. In another embodiment, the polymorphisms is a risk allele selected from the group consisting of a CFI risk allele, a CFH risk allele, a C2 risk allele, a CFB risk allele or a C3 risk allele for the manufacture of a diagnostic for diagnosing a degenerative disease. In another embodiment, the CFI allele is an equivalent allele thereof, the CFH allele is an equivalent allele thereof, the C2 allele is an equivalent allele thereof, the CFB allele is an equivalent allele thereof, or the C3 allele is an equivalent allele thereof. In another embodiment, the CFI allele comprises a G at the single nucleotide polymorphism (SNP) rs4698775 or rs17440077, the CFH allele comprises an A at the single nucleotide polymorphism (SNP) rs10737680 or a G at the single nucleotide polymorphism (SNP) rs1329428, the C2 allele comprises a G at the single nucleotide polymorphism (SNP) rs429608, the CFB allele comprises a G at the single nucleotide polymorphism (SNP) rs429608, and the C3 allele comprises a G at the single nucleotide polymorphism (SNP) rs2230199:

In certain embodiments, a detection, preventative and/or treatment regimen is specifically prescribed and/or administered to individuals who will most benefit from it based upon their risk of AMD progression to more advanced AMD (e.g. intermediate AMD or CNV or geographic atrophy), as assessed by the methods described herein. Methods are thus provided for identifying a patient at risk of AMD progression and then prescribing detection, therapeutic or preventative regime to individuals identified as being at increased risk of AMD progression. The certain embodiments are directed to for treating AMD in a subject, reducing progression of AMD in a subject, or early detection of AMD progression in a subject, which comprise: detecting the presence or absence of a polymorphic variant associated with AMD or AMD progression at a SNP in a nucleotide sequence (includes SNP rs4698775, rs17440077, rs10737680, rs1329428, rs429608, rs2230199) (Genome Reference Consortium GRCh37; UCSC Genome HG19 Assembly; February 2009), and prescribing or administering an AMD treatment regimen, preventative regimen and/or detection regimen to a subject from whom the sample originated wherein the presence of the polymorphic variant associated with AMD or progression of AMD are detected at one or more SNPs in the nucleotide sequence. In these methods, genetic results may be utilized in combination with other test results to diagnose AMD or AMD progression, as described herein.

In other embodiments, pharmacogenomics methods may be used to analyze and predict a response to an AMD treatment or drug. If the pharmacogenomics analysis indicates a likelihood that an individual will respond positively to an AMD treatment with a particular drug (e.g. anti-factor D antibody, or antigen-binding fragment thereof), the drug may be administered to the individual. If the analysis indicates that an individual is likely to respond negatively to treatment with a particular drug, an alternative course of treatment may be prescribed. A negative response may be defined as either absence of an efficacious response or the presence of toxic side effects. The response to a therapeutic treatment can be predicted in a background study in which subjects in any of the following populations, but not limited to the following populations, are genotyped: a population that responds favorably to a treatment regimen, a population that does not respond significantly to a treatment regimen, and a population that responds adversely to a treatment regimen (e.g. exhibits one or more side effects). An individual may be genotyped to predict which population they fall into.

The methods described herein are also applicable to clinical drug trials. Polymorphic variants indicative of response to an agent for treating AMD or to side effects to an agent for treating AMD may be identified at one or more SNPs. Thereafter, potential participants in clinical trials of such an agent may be screened to identify those individuals most likely to respond favorably to the drug and to exclude those less likely to respond or to experience side effects. Accordingly, the efficacy of the treatment may be measured in individuals who respond positively to the drug, without lowering the measurement as a result of the inclusion of individuals who are unlikely to respond positively to the treatment. Thus, another embodiment is a method of selecting an individual for inclusion in a clinical trial of a treatment comprising the steps of: (a) obtaining a nucleic acid sample for an individual, (b) determining the identity of a polymorphic variant which is associated with a positive response to the treatment, or a polymorphic variant which is associated with a negative response to the treatment and (c) including the individual in the clinical trial if the nucleic acid sample contains the polymorphic variant associated with a positive response to the treatment. Step (c) can also include administering the treatment to the individual if the nucleic acid sample contains the polymorphic variant that is associated with a positive response to the treatment and/or if the nucleic acid sample lacks the polymorphic variant associated with a negative response to the treatment.

Further details of the invention are illustrated by the following non-limiting Examples. The disclosures of all citations in the specification are expressly incorporated herein by reference.

EXAMPLES

Example 1

Geographic Atrophy Clinical Study

1. Summary

A Phase 1b/II, randomized, single-masked, sham injection—controlled multicenter study was carried out to evaluate the safety, tolerability and evidence of activity of lampalizumab intravitreal (ITV) injections administered monthly or every other month for an 18-month treatment period in patients with geographic atrophy (GA). The randomized study was preceded by a safety run-in assessment. Primary, secondary and exploratory outcomes were assessed at the conclusion of the 18-month treatment period. A 3-month safety follow-up period commenced after administration of the final ITV or sham injection for study patients who did not qualify or chose not to continue into the open-label extension study (OLE). For the safety run-in assessment, multiple monthly administrations with 10 mg of lampalizumab ITV was conducted prior to initiating enrollment in the randomized phase of the study. All patients in the safety run-in assessment received a minimum of 3 monthly doses of lampalizumab to obtain safety data from 10 evaluable patients. An evaluable patient was a patient that had received at least three study drug injections.

For the four-arm randomized phase, patients were randomized using an interactive web response system (IWRS) in a ratio of drug to sham allocation of 2:1:2:1 so that 43 patients received a lampalizumab injection monthly, 21 patients received a sham injection monthly for a total of 18 injections, 44 patients received a lampalizumab injection every other month, and 21 patients received a sham injection every other month for a total of 9 injections.

A summary of the trial design is in Table 2.

TABLE 2

| | |
|---|---|
| Design | Randomized, single-masked, sham injection controlled, single dose study to evaluate safety, tolerability and evidence of activity of Lampalizumab vs sham injection on geographic atrophy (GA) |
| Population | Patients had a diagnosis of GA secondary to AMD according to reading center evaluation and criteria |
| Sample Size | 129 patients were enrolled; 123were in the efficacy-evaluable population |
| Study Duration | 18 months (and 3 month safety follow-up) |
| Schedule, Dose | Intravitreal (IVT) formulation, monthly (Q4w) or every other month (Q8w), 1 active dose (10 mg) |
| 1° endpoint | Growth rate of GA lesion area from baseline to month 18 as measured by fundus autofluorescence (FAF) |
| 2° endpoint | Growth rate of GA lesion area from baseline to month 18 as assessed by digitized stereoscopic color fundus photographs (CFP) Mean change in BCVA from baseline to month 18 using the ETDRS VA chart |

Patient population in this study included 57% female and had a mean age of 79. The majority of patients in this study were white (>98%) and were not Hispanic or Latino (>98%). Demographics and baseline characteristics were generally balanced across treatment groups. 58% of all efficacy-evaluable patients had baseline geographic atrophy lesion area <4DA (1DA=2.54 mm2), and the distribution across the treatment groups was generally similar.

A run-in assessment of the safety and tolerability of multiple monthly administrations with 10 mg of lampalizumab ITV was conducted prior to initiating enrollment in the randomized phase of the study. All patients in the safety run-in assessment received a minimum of 3 monthly doses of lampalizumab (FIG. 1 to obtain safety data from 10 evaluable patients. An evaluable patient is a patient that received at least three study drug injections. Patient eligibility and enrollment in the safety run-in assessment followed the process described for the randomized phase (see below) of the study with the exception of BCVA inclusion criteria (see below; 3.1.1.b.1)).

For the safety run-in assessment, each patient received study drug injection on Day 0 and was assessed on Day 1, Day 7 (±2), and Day 30 (±7) after each injection until the start of the dosing hiatus. After the tenth evaluable patient completed the Day 90 (±7) visit following the third study drug administration, a hiatus in dosing of approximately 1 week ensued. During the hiatus, the safety and tolerability of multiple drug administration. The safety run-in assessment demonstrated acceptable safety and tolerability for the 10-mg dose of lampalizumab in accordance with the dose-limiting criteria (DLC; see below), and the randomized phase was initiated. Following the hiatus and determination of acceptable safety and tolerability for the 10 mg dose of lampalizumab, patients who participated in the safety run-in assessment continued monthly study drug administration at the 10 mg. These patients received a maximum of 18 lampalizumab treatments during the study.

Patients who were discontinued from the study treatment early were encouraged to undergo the scheduled monthly assessments until completion of their study period. If monthly assessments were not possible, patients were evaluated at least every 3 months and completed the 12-month and 18-month visits. Patients who were discontinued from the study treatment prematurely were not permitted to enter the OLE study.

Patients withdrawn from the study prior to completion were asked to return for an early termination evaluation 30 (±7) days following their last study treatment for monitoring of adverse events and the final study visit assessments. Patients withdrawn from the study prior to completion were not permitted to enter the OLE study.

If ≥2 patients experienced the same dose-limiting toxicity (DLT) during the safety run-in assessment (e.g., ≥2 patients with vitritis that meet the DLT criteria), then the 10-mg dosing cohort would have been suspended, and all patients in this cohort would have been discontinued from the study and the early termination evaluation process would have been followed. A new cohort would have been enrolled to obtain 10 evaluable patients at the 5-mg dose; the same process and rules for the safety run-in assessment would have applied to the patients in the 5-mg cohort as outlined for the 10-mg cohort. If the dose-reduction plan with 5 mg was activated, successful completion of this cohort in accordance with DLC would have been required to initiate the randomized phase (FIG. 1).

Individual DLTs were defined as any of the following adverse events that occurred during the safety run-in assessment period and were believed to be study drug-related:
1. Vitritis or uveitis, which was defined as a change of 2 units on standard grading scales after the study drug injection (grading scale for assessment of anterior chamber flare or cells and vitreous cells). In accordance with this definition, study exclusion criteria established a baseline grade of 0, and an increase to 2+ or greater would have constituted a DLT. Anterior chamber or vitreous cell count of Grade 4+ would have been considered a major toxicity requiring interruption of enrollment and further evaluation by the internal Safety Review Committee to determine if further enrollment/treatment was appropriate
2. Endophthalmitis
3. Sustained elevation (measured on 3 consecutive scheduled visits) of intraocular pressure (IOP)≥30 mmHg
4. Sustained loss (measured on 3 consecutive scheduled visits) of visual acuity (VA) ≥15 letters after the study drug injection that is not attributable to the injection procedure or progression of GA The safety run-in patients were assessed for DLTs after each study drug injection on Day 1, Day 7 (±2), and Day 30 (±7) visits. This regimen was continued until the tenth evaluable patient received the third study drug injection and completed the Day 90 (±7) visit.

The study drug dose of 10 mg that demonstrated acceptable safety and tolerability in accordance with DLC defined in the safety run-in assessment was used for the randomized phase of the study. 129 patients with GA secondary to AMD were enrolled in the randomized phase. The study consisted of a screening period of up to 14 days (Days-14 to -1), and a treatment period of 18 months for all randomized patients, and a 3-month safety follow-up period after the final study drug or sham administration for patients who did not qualify or chose not to continue into the open-label extension study.

A patient was required to satisfy all eligibility criteria at both the screening and the Day 0 visits, including receipt of all screening visit images by the central reading center. As part of the screening process, the central reading center evaluated fundus autofluorescence (FAF) images, digital fundus photographs (FP), and fluorescein angiograms (FA) to provide an objective, masked assessment of patient eligibility regarding GA. Eligible patients were enrolled on Day 0 and randomized using an interactive web response system (IWRS) in a ratio of drug to sham allocation of 2:1:2:1 so that 43 patients received an lampalizumab injection monthly, 21 patients received a sham injection monthly for a total of 18 injections, 44 patients received an lampalizumab injection every other month, and 21 patients received a sham injection every other month for a total of 9 injections (FIG. 1). Eligible patients were stratified based on GA lesion size. Patients were enrolled on the same day the treatment was to be initiated (Day 0).

Only one eye was chosen as the study eye. If both eyes were eligible, the eye with the worse vision (worse VA and/or least function) was selected for study treatment (study eye). The investigators and other site staff members were not masked to patients' treatment assignment. Only patients were masked to their treatment assignment. All patients had scheduled monthly visits for the duration of the study. Enrolled patients had the first ITV injection of lampalizumab or sham administered by the investigator on Day 0. The randomized phase patients had safety and ocular assessments performed 7 (±2) days after the first injection. At the subsequent visits (every month), patients in the monthly treatment arms had safety evaluations performed by the investigator prior to receiving study drug or sham injection. Patients in the every-other-month treatment arms also had safety evaluations performed monthly but received study drug or sham only at the every-other-month visit. Randomized phase patients were contacted by site personnel 7 (±2) days after each injection to elicit reports of decrease in vision, eye pain, unusual redness, or any other new ocular symptoms in the study eye. Patients were also asked to verify that they took the prescribed, self-administered, post-injection antimicrobials. Patients who qualified and chose to continue into the OLE study had a final safety visit at the Month 18 visit. Patients who did not qualify or chose not to continue into the OLE study had a final safety visit at the Month 19 visit (the every-other-month treatment arms), or at the Month 20 visit (monthly treatment arms). Missed doses were not be made up.

Patients who were prematurely discontinued from study treatment were encouraged to undergo the scheduled monthly assessments until completion of their study period. If monthly assessments were not possible, patients were evaluated at least every 3 months and completed the 12-month and 18-month visits. Patients who were prematurely discontinued from study treatment were not permitted to continue to the OLE study. Patients withdrawn from the study prior to completion were asked to return for an early termination evaluation 30 (±7) days following their last study treatment for monitoring of adverse events and the final study visit assessments. Patients withdrawn from the study prior to completion were not permitted to continue to the OLE study.

2. Outcome Measures 2.1 Primary Outcome Measure

The primary efficacy outcome for evidence of activity in the Phase 1b/II study was an anatomic endpoint, growth rate of GA lesion area from baseline to month 18 as measured by FAF. The anatomic primary endpoint provided a more sensitive metric of GA progression and served as a surrogate for vision loss.

2.2 Secondary Outcome Measures

The secondary efficacy outcome measure was growth rate of GA lesion area from baseline to month 18 as assessed by digitized stereoscopic color fundus photographs and mean change in BCVA from baseline to month 18 using the ETDRS VA chart.

2.3 Additional Outcome Measures

Additional exploratory outcome measures included the following: a) growth rate of GA area from baseline assessed by spectral domain-optical coherence tomography (SD-OCT); b) change in drusen volume assessed by SD-OCT; c) conversion rate to wet AMD in study eyes treated with lampalizumab versus sham control; d) change from baseline in the number of words read per minute on the Submacular Surgery Trial (SST) Reading Speed assessment; (e) change from baseline in the number of words read per minute binocularly on the Minnesota Reading Speed Assessment (MNRead); (f) change from baseline in contrast sensitivity as measured by the number of letters read correctly on the Pelli-Robson chart; (g) change from baseline in the National Eye Institute Visual Functioning Questionnaire-25 (NEI VFQ-25_composite score and the 12 subscale scores; (h) change from baseline in the Functional Reading Independence Index (FRII); (i) clinical genotyping to assess relationships between genetic polymorphisms associated with AMD, disease characteristics, and response to administration to lampalizumab.

2.4 Pharmacokinetic and Pharmacodynamic Outcome Measures

The PK profile from the serum concentration-time data following administration of lampalizumab was determined. Derived PK parameters included the following: (a) exposure after first dose (AUC); (b) maximum observed serum concentration ($C_{max}$); (c) observed steady-state trough concentration; (d) time to reach steady-state; and (e) accumulation ratio based on trough concentration. Anterior chamber (aqueous humor) paracentesis samples were collected to assess PK and PD relationships. Additional PK and PD analysis were conducted.

2.5 Exploratory Outcome Measures a. Growth rate of GA area from baseline assessed by spectral domain-optical coherence tomography (SD-OCT)
b. Change in drusen volume assessed by SD-OCT
c. Conversion rate to wet AMD in study eyes treated with lampalizumab versus sham control
d. Change from baseline in the number of words read per minute on the Submacular Surgery Trial (SST) Reading Speed assessment
e. Change from baseline in the number of words read per minute binocularly on the Minnesota Reading Speed Assessment (MNRead)
f. Change from baseline in contrast sensitivity as measured by the number of letters read correctly on the Pelli-Robson chart
g. Change from baseline in the National Eye Institute Visual Functioning Questionnaire-25 (NEI VFQ-25) composite score and the 12 subscale scores
h. Change from baseline in the Functional Reading Independence Index (FRII)
i. Clinical genotyping to assess relationships between genetic polymorphisms associated with AMD, disease characteristics, and response to administration of lampalizumab

2.5 Safety Plan

Potential safety issues associated with the route of administration or pharmacology of lampalizumab included decreased BCVA; conjunctival hemorrhage; uveitis or vitritis (see the definitions of uveitis and vitritis in (defined above; grading scale for assessment of anterior chamber flare or cells and vitreous cells for anterior chamber and vitreous inflammation grading scales); intraocular infection; transient and/or sustained elevation of IOP; cataract development or progression; retinal or intravitreal hemorrhage, macular edema; and retinal break or detachment. The incidence of all adverse events (serious and non-serious) were recorded on electronic Case Report Forms (eCRFs) for the duration of this study.

Systemic levels of lampalizumab following multiple ITV administrations were anticipated to be low. Nevertheless, patients were monitored for evidence of systemic inhibition of ACP activity such as lowered infection threshold, particularly to encapsulated bacteria (i.e., *Neisseria meningitidis*, *Streptococcus pneumonia*, and *Haemophilus influenza*).

The incidence and characteristics of adverse events, serious adverse events, and laboratory abnormalities were assessed. Ongoing review of safety was performed.

Safety Run-In Phase: Prompt safety monitoring and review of post-study drug treatment safety data was performed to determine whether the DLC are met. All DLTs occurring within prespecified window of study drug administration was reported and the reports were reviewed.

After study drug injection on Day 0, all patients returned for safety assessment visits on Day 1, Day 7 (±2), and Day 30 (±7) after each monthly injection until the start of the dosing hiatus. The identical safety assessments were performed for the safety run-in patients as listed for the randomized phase patients below.

Randomized Phase: All patients returned for a safety assessment visit on Day 7 (±2 days) after the first injection. For subsequent injections, randomized patients were contacted by study site personnel 7 (±2) days after each injection to elicit reports of any decrease in vision, eye pain, unusual redness, or any other new ocular symptoms in the study eye. Patients were asked whether they have taken the prescribed, self-administered, post-injection antimicrobials. Patients were instructed to contact the investigator at any time if they had any health-related concerns. If warranted, patients were asked to return to the clinic as soon as possible for a safety assessment visit.

A finger-counting test was conducted for each patient within 15 minutes following study treatment by the physician; hand motion or light perception was tested when necessary. Following the study treatment, patients remained at the clinic for at least 60 (±10) minutes. Intraocular pressure was measured bilaterally prior to treatment and 60 (±10) minutes after study treatment for the study eye only. If there was no safety concerns at 60 (±10) minutes, the patient was discharged from the clinic. If the IOP is increased by ≥10 mm Hg from the pre-injection measurement at 60 (±10) minutes, the study eye was measured again at 120 (±10) minutes post-injection. If there was no safety concerns at the repeat measurement, the patient was permitted to leave the clinic. If the IOP remains elevated by ≥10 mm Hg from the pre-injection measurement, and was of concern to the investigator following the repeat measurement, the patient remained in the clinic and was treated in accordance with the investigator's clinical judgment prior to the patient's discharge. An adverse event eCRF page was completed.

Detailed ocular examinations, including indirect ophthalmoscopy and slit-lamp examination, was performed throughout the study. Routine hematology, serum chemistry, coagulation, and urinalysis profiles, as well as blood samples for serum study drug concentrations, CH50 and AH50 assays, and antibodies to lampalizumab, were obtained from all patients. Aqueous humor paracentesis samples were also obtained from the patients who consent to this procedure and sample collection.

With the exception of patients that continue into the OLE study at the Month 18 visit, patients withdrawn from the study prior to completion (Month 19 visit for every-other-month treatment arms and Month 20 visit for monthly treatment arms) were asked to return for early termination visit assessments after 30 (±7) days following the last study treatment visit. The visit included assessment of all adverse events (serious and nonserious; ocular and non-ocular).

3. Materials and Methods 3.1 Patient Selection and Sex Distribution

Written informed consent was obtained prior to initiation of any study procedures. Screening evaluation was performed any time within 14 days preceding Day 0 (the day of the first study treatment). Patient selection criteria were identical for the safety run-in phase and randomization phase, with the exception of ocular inclusion criteria; patients with less severe visual impairment were enrolled in the randomized phase.

Enrollment of both men and women were allowed, provided the entry criteria were met. However, pregnancy or breastfeeding were listed as exclusion criteria, thus women who were pregnant or breastfeeding were excluded from the trial.

The remaining inclusion/exclusion criteria applied to both male and female patients and pertain to issues of patient health performance and safety issues.

Randomization was not made on the basis of sex, so the enrollment of patients was expected to reflect the demographics of the disease under study.

3.1.1.b.1

3.1.1 Inclusion Criteria

Patients must meet the following criteria to be eligible for study entry:

a. General Inclusion Criteria

1. Willingness and ability to provide signed Informed Consent and comply with study procedures as defined in the protocol.
2. Age 60-89 years
3. For sexually active women of childbearing potential, agreement to the use of an appropriate form of contraception (or abstinence) for the duration of the study. A woman was considered not to be of childbearing potential if she was postmenopausal or had undergone hysterectomy and/or bilateral oophorectomy. Sexually active men were required to use a contraceptive method (condom) to ensure that pregnancy was avoided in their female partners unless a successful vasectomy (surgical male sterilization) had been performed
4. Ability and willingness to undertake all scheduled visits and assessments b. Ocular Inclusion Criteria for the Study Eye One eye was designated as the study eye. If both eyes were eligible, the eye with the worse VA and/or least function was selected for study treatment (study eye).

1. Visual acuity
   (a) For the safety run-in phase: BCVA of 20/125 to 20/400 inclusive (Snellen equivalent) using ETDRS charts
   (b) For the randomized phase: BCVA of 20/50 to 20/400 inclusive (Snellen equivalent) using ETDRS charts
2. Well-demarcated area of GA secondary to AMD in the absence of choroidal neovascularization (CNV)
3. GA was ≥1 disc area (DA) (2.5 mm$^2$)
4. If GA was multifocal, at least one focal lesion was ≥0.5 DA (1.25 mm$^2$)
5. The total lesion size was ≤7 DA (17.5 mm$^2$) and resided completely within the FAF imaging field
6. Presence of hyperautofluorescence adjacent to the area of GA (e.g., banded or diffuse junctional FAF patterns; Holz et al., *Am J Ophthalmol,* 143:463-472 (2007))
7. Sufficiently clear ocular media, adequate pupillary dilation, and fixation to permit quality fundus imaging c. Ocular Inclusion Criteria for the Non-Study Eye 1. GA secondary to AMD in the absence of CNV 3.1.2 Exclusion Criteria Patients who met any of the following criteria were excluded from study entry:

1. History of vitrectomy surgery, submacular surgery, or other surgical intervention for AMD in the study eye
2. Previous subfoveal focal laser photocoagulation in the study eye
3. Laser photocoagulation (juxtafoveal or extrafoveal) in the study eye
4. Prior treatment with Visudyne®, external-beam radiation therapy, or transpupillary thermotherapy in the study eye
5. Previous treatment with fenretinide or participation in fenretinide studies
6. Previous treatment with eculizumab or participation in eculizumab studies
7. Previous ITV drug delivery (e.g., ITV corticosteroid injection, anti-angiogenic drugs, anti-complement agents, or device implantation) in the study eye with the exception of the patients previously treated ITV with lampalizumab. A single intraoperative administration of an anti-VEGF agent during cataract surgery for cystoid macular edema prophylaxis at least 3 months prior to screening is permitted.

a. GA Characteristics

1. GA in the study eye that extends beyond FAF imaging field or fails to meet single or multifocal lesion criteria
2. Absence or minimal hyperautofluorescence adjacent to GA in the study eye (e.g., focal FAF pattern; Holz et al. 2007)
3. GA in either eye due to causes other than AMD (e.g., Stargardt disease, pattern dystophies, cone-rod dystrophy, or chloroquine/hydroxychloroquine toxicity)

b. Concurrent Ocular Conditions

1. RPE tear involving the macula in the study eye
2. History of retinal tear in the study eye
3. Any concurrent ocular or intraocular condition in the study eye (e.g., cataract or epiretinal membrane) that, in the opinion of the investigator, could either:
   (a) Require medical or surgical intervention during the study period to prevent or treat vision loss that might result from that condition; or
   (b) If allowed to progress untreated, could likely contribute to loss of at least 2 Snellen equivalent lines of BCVA during the study period.
4. History of other ocular or intraocular conditions that contraindicate the use of an investigational drug or may affect interpretation of the study results or may render the patient at high risk for treatment complications
5. Active uveitis and/or vitritis (grade trace or above) in either eye (see the definitions of uveitis and vitritis and for uveitis and vitritis grading scales)
6. Current vitreous hemorrhage in the study eye
7. History of retinal detachment or macular hole (Stage 3 or 4) in the study eye
8. Aphakia or absence of the posterior capsule in the study eye (a) Previous violation of the posterior capsule in the study eye is also excluded unless it occurred as a result of yttrium aluminum garnet (YAG) laser posterior capsulotomy in association with prior posterior chamber intraocular lens implantation
9. Spherical equivalent of the refractive error in the study eye demonstrating more than 8 diopters of myopia
10. For patients who have undergone prior refractive or cataract surgery in the study eye, the preoperative refractive error in the study eye should not have exceeded 8 diopters of myopia
11. Intraocular surgery (including cataract surgery) in the study eye within 3 months preceding Day 0
12. Uncontrolled glaucoma in the study eye (defined as IOP ≥30 mmHg despite treatment with anti-glaucoma medication)
13. History of glaucoma-filtering surgery in the study eye
14. History of corneal transplant in the study eye
15. Diabetic retinopathy in either eye
16. Active or history of wet AMD in either eye
17. History of idiopathic or autoimmune-associated uveitis in either eye
18. Active infectious conjunctivitis, keratitis, scleritis, or endophthalmitis in either eye
19. History of infectious or inflammatory ocular disease in either eye
c. Concurrent Systemic Conditions
1. Uncontrolled blood pressure (defined as systolic >180 mmHg and/or diastolic>110 mmHg while patient is sitting)
   (a) If a patient's initial measurement exceeded these values, a second reading may be taken 30 or more minutes later. If the patient's blood pressure must be controlled by antihypertensive medication, the patient was eligible if medication is taken continuously for at least 30 days prior to Day 0.
2. Medical conditions that may be associated with a clinically significant risk for bleeding
3. History of other disease, metabolic dysfunction, physical examination finding, or clinical laboratory finding giving reasonable suspicion of a disease or condition that contraindicates the use an investigational drug or that might affect interpretation of the results of the study or that renders the patient at high risk for treatment complications
4. Treatment for active systemic infection
5. Predisposition or history of increased risk for infection
6. Known deficiency of complement factor D or alternative complement pathway activity
7. Active malignancy or history of malignancy within the past 5 years (except completely resolved cutaneous basal cell carcinoma)
8. History of allergy to fluorescein, not amenable to treatment
9. Inability to obtain FP, FAF, FA, SD-OCT, or NI images of sufficient quality to be analyzed and graded by the central reading center
10. Inability to comply with study or follow-up procedures
11. Previous participation in any studies of investigational drugs within 3 months preceding Day 0 (excluding vitamins and minerals)
12. Requirement for continuous use of any medications/treatments indicated in the "Excluded Therapy" section (see Section 3.4.2)

3.3 Study Treatment
3.3.1 Trial Drug
Formulation

Lampalizumab drug product was provided as a sterile, white to off-white, lyophilized powder in a 6-cc USP/Ph. Eur. Type 1 glass vial intended for ITV administration. Each glass vial contained nominal 40 mg of lampalizumab. Reconstitution of the drug product with sterile water for injection (SWFI), USP/Ph. Eur., was required. After reconstitution, the drug product was formulated as 100 mg/mL lampalizumab in 40 mM L-histidine hydrochloride, 20 mM sodium chloride, 180 mM sucrose, 0.04% (w/v) polysorbate 20, pH 5.5. The drug product contained no preservatives and was suitable for single use only.

Dosage, Administration and Storage

Dosing for Safety Run-In Phase: An open-label, 10-mg dose of lampalizumab was administered monthly to all safety run-in patients. The study-drug treatment visits was scheduled every 30 (±7) days relative to the date of the first injection (Day 0) until the tenth evaluable patient completed the Day 90 (±7) visit following the third study drug treatment, when a dosing hiatus ensued lasting approximately 7 days. During the hiatus, the safety of multiple dosing was reviewed. As the safety run-in assessment demonstrated acceptable multidose safety and tolerability with lampalizumab as delineated in the DLC (see Section 3.1.2), the randomized phase was initiated.

Following the hiatus, safety run-in patients continued monthly study drug administration at the same dose as the patients in the randomized phase for the remainder of their 18-month treatment period, following the same visit frequency and assessments as the randomized phase monthly dosing arm. These patients received a maximum of 18 lampalizumab treatments during the study. Dosing was not repeated earlier than 22 days after the previous dosing. Missed doses were not made up.

Dosing for Randomized Phase: As determined in the safety run-in assessment, the dose of lampalizumab was administered monthly or every other month to patients in the study drug arms starting at the Day 0 visit for a total of 18 injections in the monthly treatment arm and 9 injections in the every-other-month treatment arm.

The sham injections were administered monthly or every other month to patients in the sham arms starting at the Day 0 visit for a total of 18 injections in the monthly treatment arm and 9 injections in the every-other-month treatment arm. Dosing was not repeated earlier than 22 days after the previous dosing. Missed treatments were not made up.

Administration: Lampalizumab was reconstituted with Sterile Water For Injection SWFI preparation of the dose. Vials of lampalizumab were for single-use only. Vials used for one patient were not used for any other patient.

Prior to the injection, patients were required to verify that they had self-administered their antimicrobials 4 times daily for 3 days and were instructed to self-administer their antimicrobials again 4 times daily for 3 days post-injection. Prior to the Month 18 visit, patients electing to continue into the OLE study were asked to sign the OLE study Informed Consent Form and take protocol-specified antimicrobials as instructed. For these patients, eligibility for enrollment into the OLE study were determined at their Month 18 visit. Patients who did not qualify or chose not to continue into the OLE study continued in the study for safety follow-up and have a final safety visit at the Month 19 visit (the every-other-month treatment arms) or the Month 20 visit (monthly treatment arms).

Storage: Upon receipt of lampalizumab, vials were refrigerated at 2° C.-8° C. (36° F.-46° F.) until use. Lampalizumab vials were not used beyond the expiration date provided by manufacturer. No preservative was used in lampalizumab drug product; therefore, the vial was intended for single use only. Vial contents were not frozen or shaken and were protected from direct sunlight. Within 2 hours following dose preparation (reconstituted), lampalizumab was administered; the prepared dose may be maintained at room temperature prior to administration.

3.4 Other Treatments 3.4.1 Concomitant Therapy

Concomitant medications were any prescription drugs or over-the-counter preparations other than protocol-specified procedural medications (e.g., dilating drops or fluorescein dyes) and pre- and post-injection medications (e.g., proparacaine or antimicrobials) used by a patient within 7 days preceding Day 0 and through the conclusion of the patient's study participation or early termination visit.

Patients who used other maintenance therapies continued their use. Patients required to use medications that were excluded were not be eligible for enrollment in the study. All concomitant medications were reported to the investigator and recorded on the appropriate eCRF.

The onset of glaucoma in the study eye during a patient's study participation was treated as clinically indicated.

A patient with onset of mild non-proliferative diabetic retinopathy in either eye during the study participation (e.g., an occasional hemorrhage or microaneurysm) was permitted to continue on study treatment after consultation with the Medical Monitor.

The onset of cataract or posterior capsular opacification in either eye during the patient's study participation was treated as clinically indicated. Dose-holding criteria was applied with cataract surgery or YAG laser treatment.

Laser photocoagulation treatment of new onset CNV in either eye during the patient's study participation was permitted provided the CNV was sufficiently distant to the GA lesion as determined by the reading center, could be resolved with a single laser treatment, and had been approved by the Medical Monitor. Dose-holding criteria was applied with laser photocoagulation treatment.

3.4.2 Excluded Therapy

At the discretion of the investigator, patients were allowed to continue to receive medications and standard treatments administered for other conditions. However, the following medications/treatments were prohibited from use during the patient's participation in the study:

1. Systemic anti-VEGF agents
2. ITV anti-VEGF agents in either eye
3. ITV, subtenon, or topical (ocular) corticosteroids in either eye (short-term use of topical corticosteroids is permitted after cataract surgery)
4. Oral corticosteroids (prednisone or equivalent) at doses>10 mg/day
5. Intra-articular or intra-muscular corticosteroids may be used in a limited fashion after consultation with the Medical Monitor
6. Intravenous corticosteroids
7. Systemic or IV immunomodulatory therapy (e.g., azathioprine, methotrexate, mycophenolate mofetil, cyclosporine, cyclophosphamide, anti-TNFs, eculizumab)
8. Treatment with Visudyne® in either eye Other experimental therapies (except those with vitamins and minerals)

3.5 Study Assessments 3.5.1 Definitions of Study Assessments

Study assessments are detailed below and were undertaken at various study visits.

The patients enrolled in the safety run-in phase had approximately 29 visits and patients enrolled to randomized phase had up to 22 study visits (excluding screening visit) during the study. With the exception of patients that continued into the OLE study at Month 18, any patient that discontinued the factor D study prematurely (prior to the Month 19 visit for every other month treatment arms and Month 20 visit for monthly treatment arms) had an early termination (ET) visit completed 30 days (±7) after their last study treatment.

Study treatment visits were scheduled every 30 (±7) days relative to Day 0 visit.

Routine hematology, serum chemistry, coagulation, urinalysis, and complement assessment (CH50 and AH50) was evaluated by the central laboratory. Other specimen evaluations were performed at Genentech (PK, anti-lampalizumab antibody, aqueous humor, and genotyping).

a. Patient Reported Outcomes

The NEI VFQ-25 questionnaire was administered by site personnel (other than the VA examiner), before the patient completed any other study procedures for that visit.

The FRII questionnaire was administered (for patients who are enrolled to the randomized phase and who read English) by site personnel (other than the VA examiner), before the patient completed any other study procedures for that visit.

b. Ocular Assessments

BCVA on ETDRS chart at a starting distance of 4 meters (performed prior to dilating eyes)

Contrast sensitivity measured by the number of letters read correctly on the Pelli-Robson chart; performed prior to dilating eyes SST Reading Speed assessment; performed prior to dilating eyes for patients who read English)

MNRead binocular reading speed assessment (for patients who were enrolled to the randomized phase and who read English; performed pre-injection prior to dilating eyes)

IOP measurement (performed prior to dilating eyes; the method used for a patient remained consistent throughout the study)

Slit-lamp examination (for grading scales for cells)

Dilated binocular indirect high-magnification ophthalmoscopy

Finger-counting test, or hand motion, or light perception tests performed within 15 minutes post-injection for the study eye only by physician IOP measurement pre-injection both eyes and 60 (±10) minutes post-injection for the study eye only; if IOP increased 10 mmHg from pre-injection, then measured again at 120 (±10) minutes post-injection; the method used for a patient remained consistent throughout the study.

c. Ocular Imaging

The central reading center provided sites with a study manual and training materials for specified study ocular images. Before any study images were obtained, site personnel, test images, systems and software (where applicable) were certified/validated by the reading center as specified in the study manual. All ocular images were obtained by trained site personnel at the study sites and forwarded to the central reading center for independent analysis and/or storage.

Ocular images obtained included the following:
  Stereoscopic, digital color fundus photographs of both eyes
  Fluorescein angiograms of both eyes (perform after laboratory samples are obtained
  FAF, NI, and SD-OCT images of both eyes
Additional details on obtaining these images were included in the central reading centermanual.

d. Laboratory Assessments

At the scheduled visit, specimens were collected prior to study eye treatment and FA assessments (if applicable). Fasting was not required prior to specimen collection. All specimens were forwarded to the central laboratory for processing. The central laboratory either performed the analysis or forwarded to Genentech for analysis. Instructions for obtaining, processing, storing, and shipping of all specimens was provided in the Laboratory Manual. Lab supply kits was provided to the sites by the central laboratory.

The following assessments were performed:
1. Hematology: hemoglobin, hematocrit, quantitative platelet count, red blood cells (RBC), white blood cells (WBC), and differentials including neutrophils, bands, lymphocytes, basophils, eosinophils, and monocytes (absolute and percent)
2. Serum chemistry: sodium, potassium, chloride, bicarbonate, glucose, blood urea nitrogen (BUN), creatinine, calcium, phosphorus, total and direct bilirubin, total protein, albumin, AST, ALT, lactic dehydrogenase (LDH), alkaline phosphatase, and uric acid
3. Urinalysis: specific gravity, pH, blood, protein, ketones, glucose, bilirubin, urobilinogen, microscopic examination (if any of the preceding urinalysis tests, other that glucose and ketones, are abnormal)
4. Coagulation: aPTT and PTS.
5. Serum pregnancy test (β-human chorionic gonadotropin): for women of child-bearing potential, including those who have had tubal ligation. If positive, study drug will not be administered.
6. Complement assessment: AH50 and CH50
7. PK assays:
  (a) Serum samples were obtained to measure lampalizumab concentration
  (b) Serum samples were obtained for measurement of anti-lampalizumab antibodies
  (c) Anterior chamber (aqueous humor) paracentesis samples was collected to assess PK and PD relationships e. Clinical Genotyping Samples A single whole-blood sample was collected from patients for genetic marker analysis during the study. Collection of this sample was required for all patients enrolled in the randomized phase of the study and residing in the United States, with the exception of study centers located in Alaska and Oregon, where prohibited by law, and at study centers with policies in place that prohibit collection of samples for genetic marker analysis. The genetic marker sample was used to evaluate relationships between genetic polymorphisms associated with AMD, baseline disease characteristics, and response to administration of lampalizumab.

f. Assay Methods

Drug concentration was determined in serum using an ELISA method. Anti-therapeutic antibodies (ATA) was detected in serum using a bridging ELISA.

3.5.2 Safety Run-In Phase: Assessments During Treatment

When a patient satisfied all eligibility criteria at both the screening and the Day 0 visit (the day of initial study drug administration), including the receipt and evaluation of select images (FAF, NI, FP, FA, and SD-OCT obtained at screening visit) at the central reading center, the patient was assigned an identification number (a number different from the patient's screening number) and drug kit on Day 0 by IWRS. Patient drug kit assignment occurred following pretreatment assessments and prior to study treatment administration on Day 0.

a. Day 0

Day 0 was the day of the first injection of lampalizumab. The following assessments was performed on Day 0:
1. NEI VFQ-25 questionnaire; was administered by site personnel (other than VA examiner), prior to the patient completing any other study procedures)
2. Vital signs (blood pressure, respiration, pulse, and temperature; perform pre-injection)
3. Ocular assessments
  (i) BCVA testing at a starting distance of 4 meters (perform pre-injection prior to dilating eyes)
  (ii) Contrast sensitivity measured by the number of letters read correctly on the Pelli-Robson chart (perform pre-injection prior to dilating eyes)
  (iii) SST Reading Speed assessment (perform pre-injection prior to dilating eyes)
  (iv) IOP measurement (obtain pre-injection for both eyes prior to dilation; the method used for a patient must remain consistent throughout the study)
  (v) Slit-lamp examination (perform pre-injection)
  (vi) Dilated binocular indirect high-magnification ophthalmoscopy (perform pre-injection)
4. Review of the inclusion and exclusion criteria
5. Contact IWRS for patient's identification number and study drug kit assignment prior to the initiation of treatment
6. Reconstitution of study drug (see the Pharmacy Binder)
7. Administration of lampalizumab injection in the study eye
  (a) Prior to the injection, ensure that patients have self-administered their antimicrobials 4 times daily for 3 days and instruct them to self-administer their antimicrobials again 4 times daily for 3 days post-injection
8. Post-injection ocular assessments
  (a) Finger-counting test, followed by hand-motion or light-perception tests (when necessary) performed by the physician within 15 minutes post-injection for the study eye only
  (b) IOP measurement 60 (±10) minutes post-injection for the study eye only; the method used for a patient must remain consistent throughout the study
9. Clinical evaluations
  (a) Monitoring and recording of all adverse events
  (b) Recording of concomitant medications used by the patient within 7 days preceding Day 0
  (c) Recording of concurrent ocular procedures b. Day 1 and Day 7 Safety Assessment Visits Safety run-in patients were seen in clinic for a safety evaluation on Day 1 (±0) and Day 7 (±2) following each study drug treatment until the start of the hiatus. The following assessments were performed:
1. Clinical evaluations
  (a) Vital signs (blood pressure, respiration, pulse, and temperature)
  (b) Recording of concomitant medications
  (c) Recording of concurrent ocular procedures
  (d) Monitoring and recording of all adverse events 2. Ocular assessments
   (a) BCVA testing at a starting test distance of 4 meters (perform prior to dilating eyes). Note: perform finger counting test, followed by hand motion and light perception tests, if necessary.
   (b) IOP measurement (obtain for both eyes; the method used for a patient must remain consistent throughout the study)
   (c) Slit-lamp examination (perform pre-injection)
   (d) Dilated binocular indirect high-magnification ophthalmoscopy (perform pre-injection)
3. Serum sample for measurement of lampalizumab concentration collection at Day 1 and Day 7 visits after the first study drug treatment only
4. Whole blood sample for genetic marker analysis at Day 1 visit after the first study drug treatment only c. Safety Month X Safety run-in patients had study drug treatment visits scheduled every 30 (±7) days relative to Day 0 until the start of the hiatus. The following assessments were performed:
1. Vital signs (blood pressure, respiration, pulse, and temperature)
2. Ocular assessments
   (a) BCVA testing at a starting distance of 4 meters (perform prior to dilating eyes)
   (b) IOP measurement (obtain for both eyes prior to dilation; the method used for a patient must remain consistent throughout the study)
   (c) Slit-lamp examination Dilated binocular indirect high-magnification ophthalmoscopy
3. Ocular Imaging
   (a) SD-OCT for both eyes
4. Contact IWRS for study drug kit assignment prior to the initiation of treatment
5. Reconstitution of study drug (see Pharmacy Binder)
6. Administration of lampalizumab injection in the study eye
   (a) Prior to the injection, ensure that patients have self-administered their antimicrobials 4 times daily for 3 days and instruct them to self-administer their antimicrobials again 4 times daily for 3 days post-injection
7. Post-injection ocular assessments
   (a) Finger-counting test, followed by hand-motion or light-perception tests (if applicable) performed by the physician within 15 minutes post-injection for the study eye only
   (b) IOP measurement 60 (±10) minutes post-injection for the study eye only; (the method used for a patient must remain consistent throughout the study)
8. Clinical evaluations
   (a) Monitoring and recording of all adverse events
   (b) Recording of concomitant medications
   (c) Recording of concurrent ocular procedures
9. Laboratory sample collection to be collected at each study treatment visit until the start of the hiatus:
   (a) Serum samples will be obtained to measure lampalizumab concentration
   (b) Serum samples will be obtained for measurement of anti-lampalizumab antibodies
   (c) Complement AH50 and CH50
   (d) Hematology
   (e) Serum chemistry
   (f) Coagulation: aPTT and PT
   (g) Urinalysis 3.5.3 Randomized Phase: Assessments During Treatment When a patient satisfied all eligibility criteria at both the screening and the Day 0 visit (the first day when study drug is administered), including the receipt and evaluation of select images (FAF, NI, FP, FA, and SD-OCT obtained at screening visit) at the central reading center, the patient was assigned an identification number (a number different from the patient's screening number) and drug kit on Day 0 by IWRS. Patient drug kit assignment occurred following pre-treatment assessments and prior to study treatment administration on Day 0.

a. Day 0

Day 0 was the day of the first study treatment injection. The following assessments was performed on Day 0:
1. NEI VFQ-25 questionnaire; was administered by site personnel (other than VA examiner), prior to the patient completing any other study procedures) The FRII questionnaire was administered (for patients who were enrolled to the randomized phase and who read English) by site personnel (other than the VA examiner), before the patient completed any other study procedures for that visit.
2. Vital signs (blood pressure, respiration, pulse, and temperature; perform pre-injection)
3. Ocular assessments
   (a) BCVA testing at a starting distance of 4 meters (perform pre-injection prior to dilating eyes)
   (b) Contrast sensitivity measured by the number of letters read correctly on the Pelli-Robson chart (perform pre-injection prior to dilating eyes
   (c) SST Reading Speed assessment (perform pre-injection prior to dilating eyes)
   (d) MNRead binocular reading speed assessment (for patients who are enrolled to the randomized phase and who read English); perform pre-injection prior to dilating eyes)
   (e) IOP measurement (obtain pre-injection for both eyes prior to dilation; the method used for a patient must remain consistent throughout the study)
   (f) Slit-lamp examination (perform pre-injection)
   (g) Dilated binocular indirect high-magnification ophthalmoscopy (perform pre-injection)
4. Review of the inclusion and exclusion criteria
5. Contact IWRS for patient's randomization identification number and study treatment kit assignment prior to the initiation of treatment
6. Reconstitution of study drug if applicable
7. Administration of study treatment injection (drug or sham as per randomization) in the study eye
   (a) Prior to the injection, ensure that patients have self-administered their antimicrobials as prescribed and instruct them to self-administer their antimicrobials again 4 times daily for 3 days post-injection
8. Post-injection ocular assessments
   (a) Finger-counting test, followed by hand-motion or light-perception tests (when necessary) performed by the physician within 15 minutes post-injection for the study eye only
   (b) IOP measurement 60 (±10) minutes post-injection for the study eye only; the method used for a patient must remain consistent throughout the study
9. Clinical evaluations
   (a) Monitoring and recording of all adverse events
   (b) Recording of concomitant medications used by the patient within 7 days preceding Day 0
   (c) Recording of concurrent ocular procedures b. Day 7 Visit
1. Clinical Evaluations
   (a) Vital signs (blood pressure, temperature, respiration, and pulse)
   (b) Recording of concomitant medications
   (c) Recording of concurrent ocular procedures
   (d) Monitoring of concurrent ocular procedures
2. Ocular Assessments
   (a) BCVA on ETDRS chart at a starting distance of 4 meters (perform prior to dilating eyes)
   (b) IOP measurement (perform prior to dilating eyes; the method used for a patient must remain consistent throughout the study)
   (c) Slit-lamp examination
   (d) Dilated binocular indirect high-magnification ophthalmoscopy
3. Sample Collection
   (a) Serum PK sample for lampalizumab concentration c. Month 1 through Month 18 Visits Month 18 was the final study visit for patients who qualified and chose to continue into the OLE study. Prior to the Month 18 visit, these patients were asked to sign the OLE Informed Consent Form and were instructed to take the protocol-specified antimicrobials. Eligibility for enrollment into the OLE study was determined at the Month 18 visit.

1. NEI VFQ-25 questionnaire at the Month 6, 12, and 18 visits was administered by site personnel (other than VA examiner), prior to the patient completing any other study procedures)
2. The FRII questionnaire at the Month 6, 12, and 18 visits was administered (for patients who are enrolled to the randomized phase and who read English) by site personnel (other than the VA examiner), before the patient completed any other study procedures for that visit.
3. Vital signs (blood pressure, respiration, pulse, and temperature; perform pre-injection)
4. Physical exam at the Month 12 and 18 visits
5. Ocular assessments
   (a) BCVA testing at a starting distance of 4 meters (perform pre-injection prior to dilating eyes)
   (b) Contrast sensitivity at Month 6, 12, and 18 visits measured by the number of letters read correctly on the Pelli-Robson chart (perform pre-injection prior to dilating eyes)
   (c) SST Reading Speed assessment at Months 6, 12, and 18 visits (perform pre-injection prior to dilating eyes)
   (d) MNRead binocular reading speed assessment (for patients are enrolled to the randomized phase and who read English) at the visits at Months 6, 12, and 18 (perform pre-injection prior to dilating eyes)
   (e) IOP measurement (obtain pre-injection for both eyes prior to dilation; the method used for a patient must remain consistent throughout the study)
   (f) Slit-lamp examination (perform pre-injection
   (g) Dilated binocular indirect high-magnification ophthalmoscopy (perform pre-injection)
6. Ocular imaging (forward images to the central reading center
   (a) FAF and NI for both eyes at Month 6, 12, and 18 visits
   (b) Fundus photographs of both eyes at Month 6, 12, and 18 visits
   (c) SD-OCT images of both eyes starting at Month 1 and continuing monthly through the Month 12 visit; subsequently, the images will be taken at the Month 15 and 18 visits only
   (d) Fluorescein angiography at Month 6, 12, and 18 visits
7. Study treatment administration:
   (a) Monthly treatment arms: visits Month 1 through Month 17
   (b) Every-other-month treatment arms: visits Month 2, 4, 6, 8, 10, 12, 14, and 16
   (c) Contact IWRS for patient's study treatment kit assignment (if applicable) prior to the initiation of treatment
   (d) Reconstitution of study drug (see Pharmacy Binder for details)
8. Administration of study treatment injection (drug or sham as per randomization) in the study eye
   (a) Prior to the injection, ensure that patients have self-administered their antimicrobials as prescribed and instruct them to self-administer their antimicrobials again 4 times daily for 3 days post-injection. Prior to the Month 18 visit, patients electing to continue into the OLE study were asked to sign the OLE study Informed Consent Form and take protocol-specified antimicrobials as instructed.
9. Post-injection ocular assessments
   (a) Finger-counting test, followed by hand-motion or light-perception tests (when necessary) performed by the physician within 15 minutes post-injection for the study eye only
   (b) IOP measurement 60 (±10) minutes post-injection for the study eye only; the method used for a patient must remain consistent throughout the study
10. Clinical evaluations
    (a) Monitoring and recording of all adverse events
    (b) Recording of concomitant medications
    (c) Recording of concurrent ocular procedures
11. Central laboratory assessments
    (a) The central laboratory assessments are to be performed prior to the FA assessment; patients do not need to fast prior to collecting the specimen.
    (b) Hematology, serum chemistry, coagulation: aPTT and PT, serum chemistry, urinalysis at Month 6, Month 12, and Month 18 visits
    (c) Serum pregnancy test at Month 12 and Month 18 visits
    (d) Serum lampalizumab concentration at visits Month 1, 2, 3, 6, 9, 12, 15, and 18
    (e) Serum anti-lampalizumab antibody visits at Month 1, 2, 3, 6, 9, 12, 15, and 18
    (f) Complement assessment: AH50 and CH50 at Month 3, 6, 9, 12, 15, and 18
    (g) Collect a whole blood sample for genetic markers at Month 1 visit
    (h) Anterior chamber (aqueous humor) paracentesis samples will be collected sites at Day 0, Month 6, and Month 12 visits to assess PK and PD relationships
12. For a complete list of laboratory tests, refer to the Laboratory Manual.
13. Subsequent to the initial treatment visit, patients treated with study drug or sham received a telephone call 7 (±2) days after each treatment visit to solicit adverse events.

d. Month 19 and Month 20 or Early Termination Visit

Month 19 (every-other-month treatment arms) and Month 20 (monthly treatment arms) safety visits were conducted only for factor D study patients who were not eligible or who chose not to continue into the OLE study.

The following assessments were performed at the Month 19, Month 20, and early termination visits unless noted otherwise:
1. NEI VFQ-25 questionnaire only at the early termination visit; was administered by site personnel (other than VA examiner), prior to the patient completing any other study procedures)
2. The FRII questionnaire only at the early termination visit; was administered (for patients who are enrolled to the randomized phase and who read English) by site personnel (other than the VA examiner), before the patient completed any other study procedures for that visit.
3. Clinical evaluations
   (a) Vital signs (blood pressure, respiration, pulse, and temperature)
   (b) Physical examination: perform only at the early termination visit
   (c) Monitoring and recording of all adverse events
   (d) Recording of concomitant medications
   (e) Recording of concurrent ocular procedures
4. Ocular assessments
   (a) BCVA testing at a starting distance of 4 meters
   (b) Contrast sensitivity only at the early termination visit; it is measured by the number of letters read correctly on the Pelli-Robson chart (perform prior to dilating eyes)
   (c) SST Reading Speed assessment at the early termination visit only (perform prior to dilating eyes)
   (d) MNRead binocular reading speed assessment (for patients who were enrolled to the randomized phase and who read English) at the early termination visit only (perform prior to dilating eyes)
   (e) IOP measurement; the method used for a patient remained consistent throughout the study)
   (f) Slit-lamp examination (for grading scales of flare/cells)
   (g) Dilated binocular indirect high-magnification ophthalmoscopy
5. Central laboratory assessments were performed only at the early termination visit
   (a) The central laboratory assessments were performed prior to the FA assessment; patients did need to fast prior to collecting the specimen.
   (b) Hematology
   (c) Serum chemistry
   (d) Coagulation: aPTT and PT
   (e) Urinalysis
   (f) Serum pregnancy test
   (g) Serum lampalizumab concentration
   (h) Serum anti-lampalizumab antibody
   (i) Complement assessment: AH50 and CH50

3.5.4 Study Completion/Early Termination Visit

If a patient experienced eye pain, a decrease in vision, unusual redness, or any other new ocular symptoms in the study eye, the investigator determined whether the patient was to return to the clinic for a safety assessment. If a visit was required, the assessments were performed.

3.6 Assay Methods

Drug concentration was determined in serum using an ELISA method. ATAs will be detected in serum using a bridging ELISA.

3.7 Statistical Methods

The database was cleaned and locked when all patients completed or discontinued the treatment and safety follow-up period. Only patients and study personnel who were scoring visual acuity of patients were masked to treatment assignment. Two analyses were planned during the study: 1) a primary analysis after all patients in the randomized phase completed the 18-month treatment period; and 2) a final analysis at Month 20 performed for patients who did not participated in the OLE study and completed the factor D safety follow-up period.

The efficacy analysis was based on the modified intent-to-treat population, which was defined as all randomized patients who receive at least one dose of treatment and had at least one post-baseline primary efficacy measurement. For the efficacy analysis, patients were grouped according to the treatment assigned at randomization.

The safety analysis was based on all patients who receive at least one dose of treatment. Patients were grouped according to treatment received.

All statistical tests were two-sided with a type I error rate of 0.2. To understand the clinical significance of the estimated treatment effects and to aid in the interpretation of the formal hypothesis testing, two-sided 80% confidence intervals were provided.

Descriptive summaries included mean, standard deviation, median, and range for continuous variables and counts and percentages for categorical variables. All analyses, summaries, and listings were performed using SAS software (Version 9.1 or higher). Detailed statistical methods were outlined in the Data Analysis Plan (DAP).

3.7.1 Analysis of Treatment Group Comparability

Demographic and baseline characteristics—such as age, sex, race, total lesion size, and baseline VA score—were summarized for all randomized patients by treatment group by use of descriptive statistics.

3.7.2 Efficacy Analysis a. Primary Efficacy Endpoint

The primary efficacy endpoint was mean GA area growth rate from baseline at Month 18 as measured by FAF; the primary efficacy endpoint was analyzed at Month 18. Stratified ANOVA was used for the primary analysis with baseline lesion size as the stratification variable. Confidence intervals on treatment effect sizes was provided, along with descriptive summary statistics for each treatment group.

b. Secondary Efficacy Endpoint

Similar analysis methods as for the primary endpoint was used for the following secondary endpoints:
1. D Mean growth rate of GA area from baseline at 18 months by digitized stereoscopic color fundus photographs
2. Mean change from baseline in BCVA at 18 months using the ETDRS system 3.8 Pharmacokinetic and Pharmacodynamic Analyses R Individual and mean serum lampalizumab concentration-time data was tabulated and plotted by dose level. The serum pharmacokinetics of lampalizumab was summarized by parameters estimates of exposure between dose intervals (AUC), maximum observed serum concentration ($C_{max}$), and time to steady-state and accumulation ratio. Estimates for these parameters was tabulated and summarized by descriptive statistics. Anterior chamber (aqueous humor) paracentesis samples were collected to assess PK and PD relationships. Additional PK, PD, and biomarker investigations were conducted.

3.9 Handling of Missing Data

All efforts were made to minimize missing data. For the primary efficacy analysis, all patients in the modified ITT population were included in the analysis. If the primary efficacy measure at Month 18 was missing, data was imputed using the last observation prior to Month 18. If deemed appropriate, additional imputation methods were applied to further characterize the results. The details of missing data handling methods were specified in the DAP.

Example 2

Efficacy Analysis

Treatment effects at 18 months from patients who received lampalizumab administered IVT versus or sham injection as described in Example 1 are set forth in FIGS. 3-7 below. FIGS. 3-7 set forth the treatment effect by measuring mean change from in GA area (mm2) from baseline at month 18.

Figure 3B:
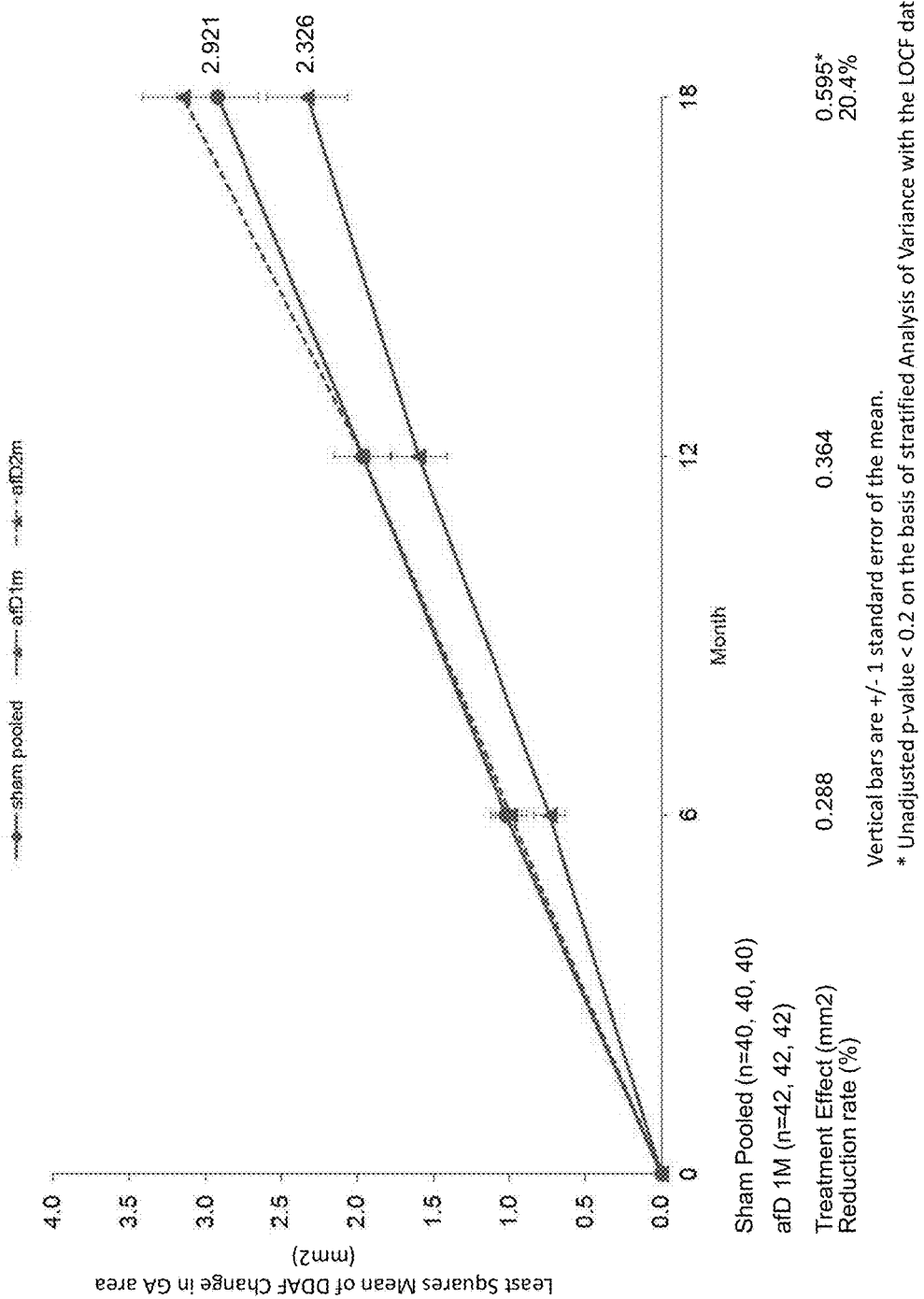

FIGS. 3A and 3B shows the preliminary efficacy results right after the primary database lock for the MAHALO phase II study with an all-corners population. The study met its primary endpoint of mean change from baseline in GA area at 18 months as measured by fundus autofluorescence (FAF) and met its secondary endpoint of mean change from baseline in GA area at 18 months as assessed by color fundus photography (CFP) in the lampalizumab monthly group. A positive treatment effect in slowing the progression of GA area growth was observed in the monthly group beginning at 6 months and extending through 18 months. On the basis of the unadjusted means with the LOCF data, the lampalizumab monthly arm had a 23.1% reduction in progression of GA area growth relative to the pooled sham arm (FIG. 3A). On the basis of the least squares means from the stratified analysis of variance (Henry Scheffe. Chapter 1.2 "Mathematical Models" in The Analysis of Variance, New York: John Wiley & Sons, Inc., 1999, p. 4-7), stratified by lesion size categories at baseline, <4 DA vs.>4 DA) with the LOCF data, the lampalizumab monthly arm had a 20.4% reduction in the progression of GA area growth relative to the pooled sham arm (FIG. 3B). The results demonstrated a clinically meaningful and statistically significant effect of lampalizumab administered monthly on reducing GA area growth over the 18-month study-treatment period. "Sham pooled" refers to the control treatment groups receiving sham monthly and sham every other month combined. "afD1m" refers to the treatment group receiving lampalizumab every month. "afD2m" refers to the treatment group receiving lampalizumab every other month. LOCF method refers to the last-observation-carried-forward method used for the imputation of missing data.

Figure 7:
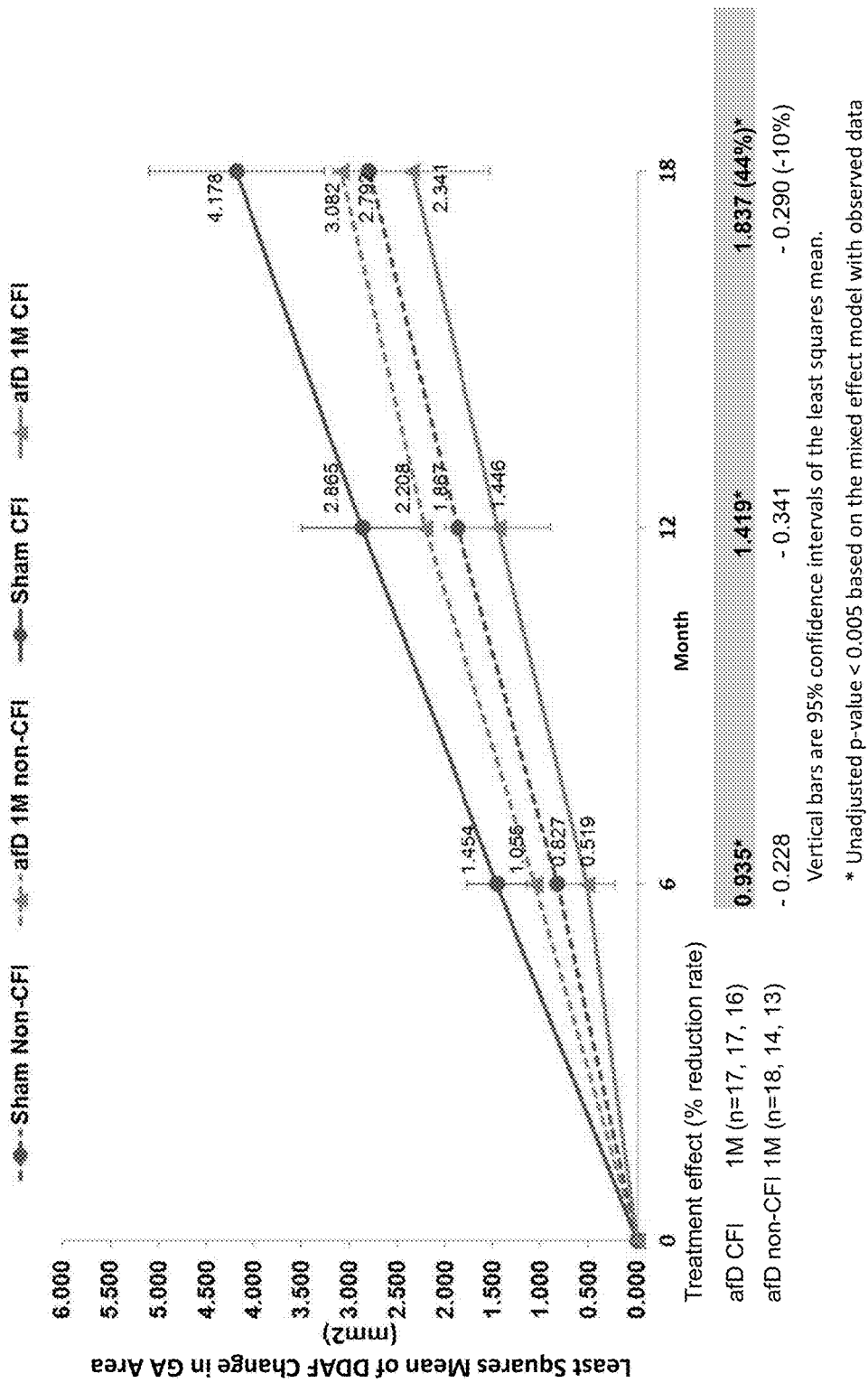
FIG. 7 shows the least squares mean of DDAF change from baseline in GA area by FAF in patients carrying the CFH, C2/CFB and CFI risk alleles compared to patients carrying the CFH and C2/CFB risk alleles without the CFI risk allele in the sham and lampalizumab monthly treatment groups. The data in this figure are adjusted for lesion size at baseline as continuous variable and lesion size category at baseline (<4 DA and ≥4 DA). The treatment effect and reduction rate are calculated at month 18, the primary efficacy time point. The absolute treatment effect at month 18 was 1.837 mm2 which corresponds to a reduction rate of 44% as shown in FIG. 6; however, no treatment effect was observed in lampalizumab treated patients without the CFI risk allele. In addition, patients with the CFI risk allele showed more rapid progression in the sham control group versus the sham group without the CFI risk allele. These findings suggest the CFI biomarker is both prognostic for progression of AMD (e.g. GA) and predictive for treatment response to lampalizumab. Vertical bars are 95% confidence intervals of the least squares mean. Asterisks (*) refer to unadjusted p-value <0.005 based on the mixed effect model with observed data.

FIG. 7 summarizes the least squares mean of DDAF change from baseline in GA area by FAF in patients carrying the CFH, C2/CFB and CFI risk alleles compared to patients carrying the CFH and C2/CFB risk alleles without the CFI risk allele in the sham and lampalizumab monthly treatment groups. The data in this figure are adjusted for lesion size at baseline as continuous variable and lesion size category at baseline (<4DA and >=4DA). The treatment effect and reduction rate are calculated at month 18, the primary efficacy time point. The absolute treatment effect at month 18 was 1.837 mm2 which corresponds to a reduction rate of 44%. In contrast, no treatment effect was observed in lampalizumab treated patients without the CFI risk allele. Moreover, patients with the CFI risk allele showed a more rapid progression in the sham control group versus the sham group without the CFI risk allele.

The above findings suggest the CFI biomarker is both prognostic for AMD progression and predictive for treatment response to lampalizumab.

Example 3

Genotyping Analysis Results

Participants in the anti-factor D study (n=93) were genotyped using the Illumina Omni 2.5M SNP chip. For the genotyping, single whole blood samples were collected from each patient. Genomic DNA was extracted from each sample and analyzed using the Illumina Omni 2.5M SNP chip (Oliphant et al., *Biotechniques*, Suppl: 56-8, 60-1 (2002)). We applied the following quality control measures to the genome-wide data, removing as follows: samples with >5% missing SNPs (n=44,180), samples with >5% missing SNPs (n=0), SNPs with minor allele frequency <0.1 (n=831,590), Hardy-Weinberg Equilibrium <1e-8 (n=1,678), duplicated/related samples (n=0), SNPs that did not map to the proper chromosome (n=3,624), SNPs with no rs identifier (n=56, 333). This left a total of 1,442,450 SNPs after quality control measures.

From this set of 1,442,450 SNPs, we selected 4 index SNPs (rs10737680 (CFH); rs429608 (C2/CFB); rs2230199 (C3); rs4698775 (CFI)) from the manuscript Fritsche et al. (Nature Genetics, 45(4): 435-441 (2013)) (or surrogate SNPs ($r^2$>0.8 if the index SNP identified in the manuscript was not in our dataset) associated with five genes (CFH, C2, CFB, C3 and CFI) associated with risk of age-related macular degeneration. Surrogate SNPs were rs1329428 (CFH) and rs17440077 (CFI)). C2 and CFB are located close to each other on the chromosome and thus are both tagged by the rs429608 SNP and the risk locus is referred to herein as the "C2/CFB risk locus" that includes both the C2 and CFB genes. The C2/CFB locus, which is tagged by rs429608, is associated with risk of age-related macular degeneration. As sample size in this study was limited, we grouped individuals for each SNP as "risk allele carriers" (heterozygous or homozygous for the risk allele) or "non-risk allele carriers" (homozygous for the non-risk allele). For all SNPs (rs1329428, rs17440077, rs429608 and rs2230199), the risk allele was a guanine (G) in our dataset. "Index SNP" when used herein refers to the SNP with the strongest p value within a particular region in a given study. For example, the index SNP for CFH, CFI, C2/CFB or C3 is the SNP with the strongest p value within the Fritche Nature Genetics (Fritsche et al., Nature Genetics, 45(4): 435-441 (2013)) study for the CFH, CFI, C2/CFB or C3 risk loci, respectively.

We compared the difference in the FAF measure of lesion size in $mm^2$ from baseline to 18 months using the observed dataset.

The difference between anti-factor D monthly and sham (pooled) was calculated as: mean DDAF pooled sham—DDAF in anti-factor D monthly/mean DDAF in the pooled sham.

Figure 4:
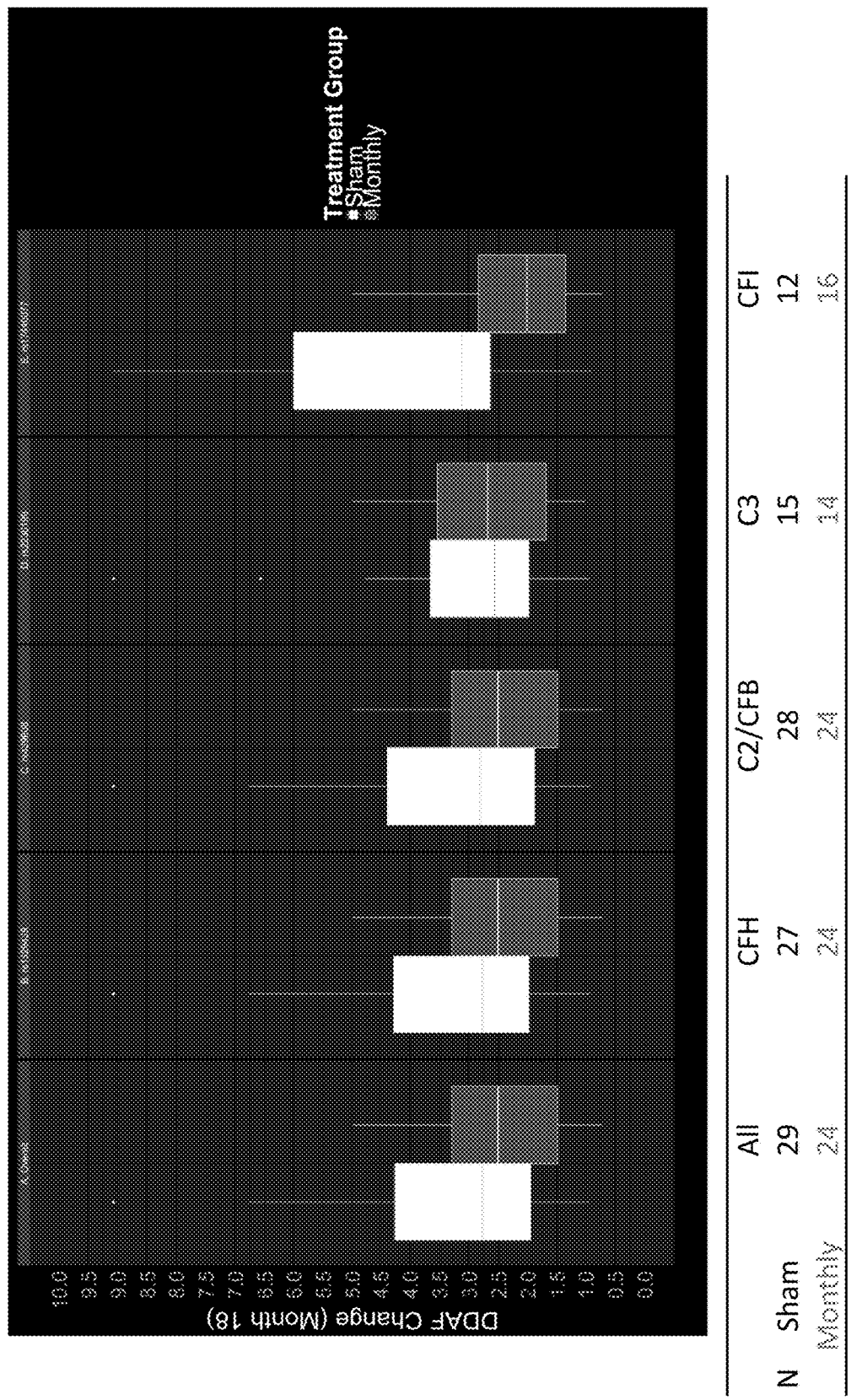
FIG. 4 compares the definitive decreased autofluorescence (DDAF) change (DDAF change in GA area as used herein refers to the change in lesion size (in mm2) from baseline to 18 months) in the sham and lampalizumab monthly treatment groups. The total number of patients in the sham and lampalizumab monthly treatment group are indicated as "All". The number of patients carrying the CFH risk allele (rs1329428), C2/CFB risk allele (rs429608), C3 risk allele (rs2230199) or CFI risk allele (rs17440077) in the sham and lampalizumab monthly treatment groups is indicated. All patients carried the C2/CFB risk allele (except 1 patient in the sham group). All patients also carried the CFH risk allele (excluding 2 patients in the sham group).
Figure 6:
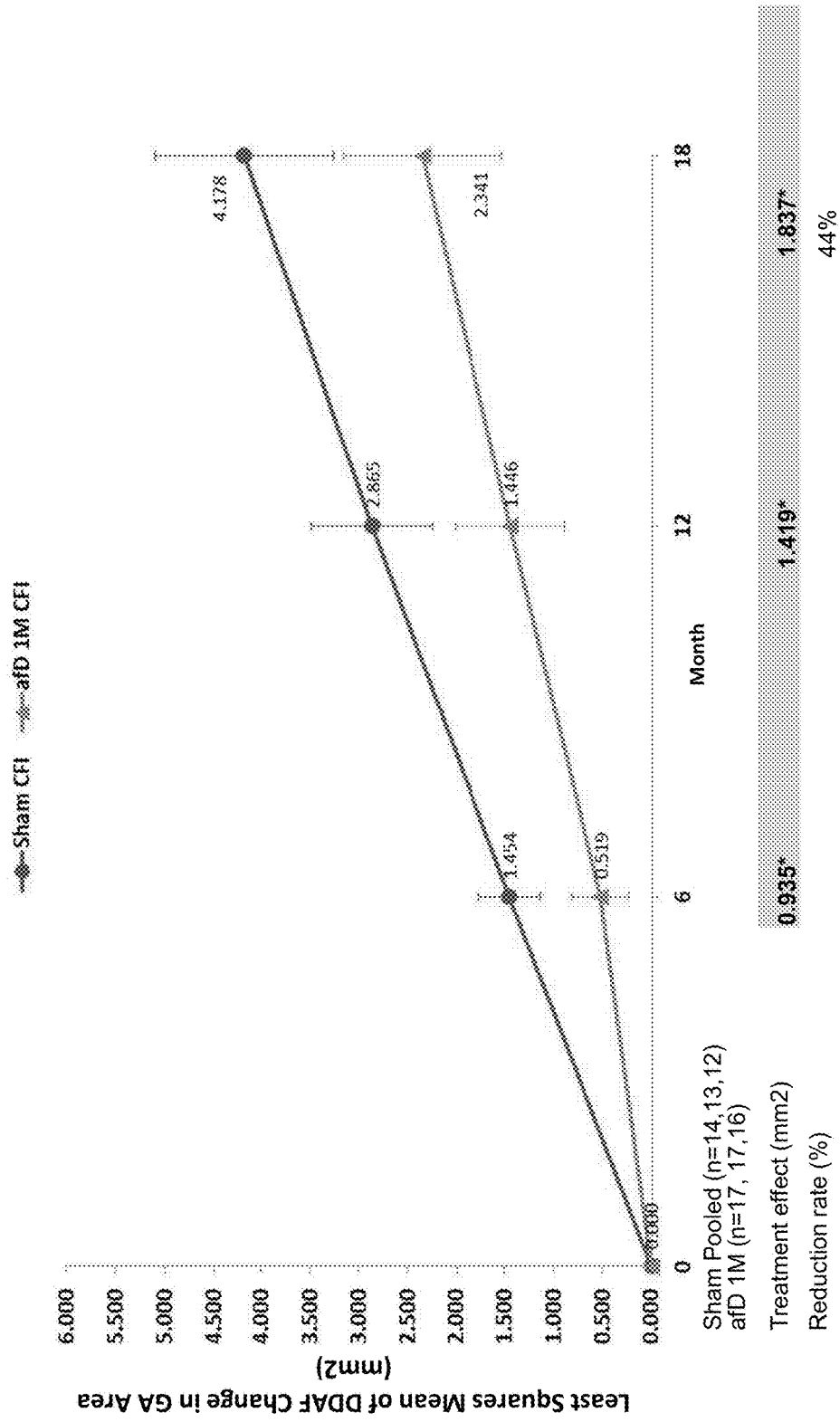
FIG. 6 shows the least squares mean of DDAF change from baseline in GA area by FAF in patients carrying the CFH, C2/CFB and CFI risk alleles in the sham and lampalizumab monthly treatment groups. The data in this figure are adjusted for lesion size at baseline as continuous variable and lesion size category at baseline (<4 DA and ≥4 DA). The treatment effect and reduction rate are calculated at month 18, the primary efficacy time point; the absolute treatment effect at month 18 was 1.837 mm2 which corresponds to a reduction rate of 44%. Vertical bars are 95% confidence intervals of the least squares mean. Asterisks (*) refer to unadjusted p-value <0.005 based on the mixed effect model with observed data.
Figure 8:
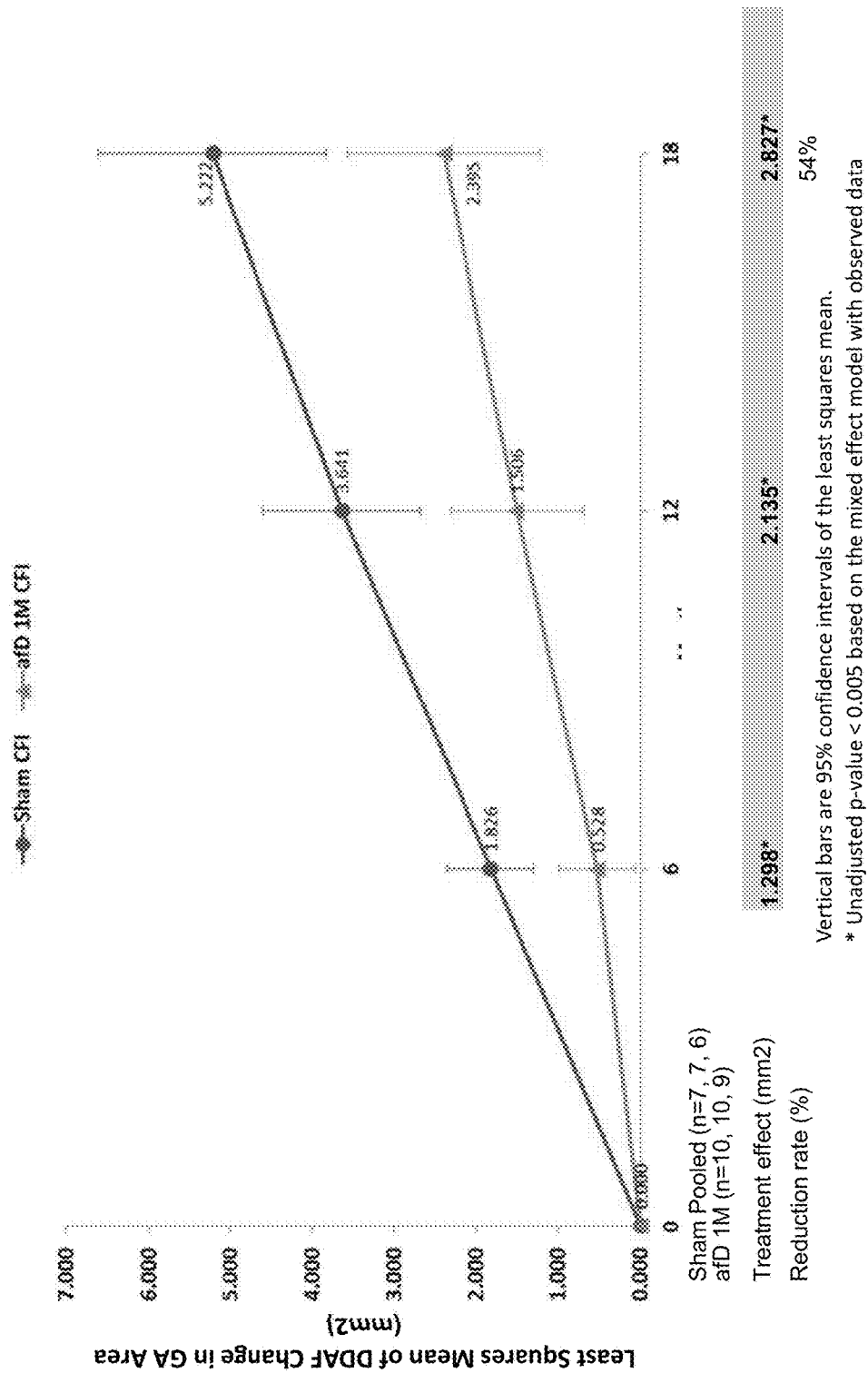
FIG. 8 shows the least squares mean of DDAF change from baseline in GA area by FAF in patients carrying the CFH, C2/CFB and CFI risk alleles and a baseline BCVA of 20/50-20/100 in the sham and lampalizumab monthly treatment groups. The data in this figure are adjusted for lesion size at baseline as continuous variable and lesion size category at baseline (<4 DA and ≥4 DA). The treatment effect and reduction rate are calculated at month 18, the primary efficacy time point; the absolute treatment effect at month 18 was 2.827 mm2 which corresponds to a reduction rate of 54%. Vertical bars are 95% confidence intervals of the least squares mean. Asterisks (*) refer to unadjusted p-value <0.005 based on the mixed effect model with observed data.

We found that all individuals (except 2 in the sham group) in our study carried the CFH risk allele (FIG. 4). All individuals (except 1 in the sham group) carried the C2/CFB risk allele (FIG. 4). As such, we were not able to determine if carrying the risk allele for these two genes had any effect on efficacy of anti-factor D. We saw no difference between risk allele and non-risk allele carriers for C3. For CFI, we saw patients in the treatment group (n=16) with the CFI risk allele had a 44% reduction at month 18 in lesion growth compared to patients in the sham group with the CFI risk allele (n=12) (FIG. 6; data was least squares mean). Patients in the treatment group without the CFI risk allele (n=8) had a negligible 9% progression (FIG. 5, bottom row) in lesion growth compared to patients in the sham group without the risk allele (n=17) (FIG. 5). Further, we saw patients in the treatment group (n=9) with the CFI risk allele and a baseline BCVA of 20/50-20/100 had 54% reduction at month 18 in lesion growth compared to patients in the sham group with the CFI risk allele and a baseline BCVA of 20/50-20/100 (n=6) (FIG. 8; data was least squares mean).

Since the rs4698775 SNP(CFI SNP) was not on the Illumina Omni 2.5M SNP chip, we also subsequently genotyped the same patients samples from the anti-Factor D study for the rs4698775 SNP (identified in the Fritsche et al. manuscript (Fritsche et al., *Nature Genetics*, 45(4): 435-441 (2013)) directly using a Taqman assay. Results using SNP rs4698775 did not significantly differ from results using SNP rs17440077. Specifically, because of the linkage disequilibrium pattern between SNP rs17440077 and SNP rs4698775, both SNPs provided nearly identical genotype information in the patient samples. Further, an effect on lesion growth comparable to that seen with the rs17440077 SNP (FIG. 6) was also observed with the rs4698775 SNP.

This data suggests that the CFI risk allele may be useful in predicting responsiveness to lampalizumab as patients with the CFI risk allele had a greater reduction in lesion growth compared to patients without the CFI risk allele. This data also suggests that the CFI risk allele may be useful in the prognosis of AMD progression as patients with the CFI risk allele had worse prognosis (e.g. AMD progression) than patients who did not carry the CFI risk allele. Alternate SNPs (for example those listed in Tables 4-7 for rs17440077) with LD with the selected CFI SNPs (rs4698775 and/or rs17440077) may also be useful in predicting responsiveness to lampalizumab as patients and may be useful in the prognosis of AMD progression. Alternate SNPs with LD with the selected CFH SNPs (rs10737680 and/or rs1329428), C2 or CFB SNPs (rs429608) and/or C3 SNP (rs2230199) may also be useful in predicting responsiveness to lampalizumab as patients and may be useful in the prognosis of AMD progression.

Example 4

Adverse Events

The most common adverse event (AE) was conjunctival haemorrhage: 2.4% in the sham group, 48.8% in the lampalizumab monthly group and 34.1% in the lampalizumab every other month group (see Table 8). The most common anti-factor D-related adverse event (AE) was the increased intraocular pressure (IOP), occurring in 1 patient in the lampalizumab monthly group (1 out of 43 patients; 2.3% in the monthly group) and 3 patients in lampalizumab every other month group (3 out of 44 patients, 6.8%) (Table 8 shows all AE regardless of whether it is drug-related or not drug-related; see note in Table 8).

The proportion of patients who discontinued treatment due to ocular adverse events in the study eye was 7% and 2.3% for patients receiving the anti-factor D antibody (monthly and every other month, respectively) and 2.4% for sham-injected treated patients. A summary of adverse events is shown in Table 3. There were no deaths, no ocular SAEs suspected to be caused by study drug, and no ocular SAEs in study eye leading to treatment discontinuation. At this stage of development, the safety profile for lampalizumab remains acceptable.

TABLE 3

Overall Adverse Event Profile

| | Sham Pooled (n = 42) | lampalizumab Monthly (n = 43) | lampalizumab Every Other Month (n = 44) |
|---|---|---|---|
| | # (%) of patients with at least one event | | |
| Ocular SAEs in study eye | 1 (2.4%) | (0.0%) | 3 (6.8%) |
| Ocular SAEs in fellow eye | 1 (2.4%) | (0.0%) | 2 (4.5%) |
| Systemic (non-ocular) SAEs | 15 (35.7%) | 11 (25.6%) | 10 (22.7%) |
| Ocular AE in the study eye suspected to be caused by study drug | (0.0%) | 4 (9.3%) | 3 (6.8%) |
| Ocular AE in study eye leading to treatment discontinuation | 1 (2.4%) | 3 (7.0%) | 1 (2.3%) |
| Non-ocular AE suspected to be caused by study drug | (0.0%) | 1 (2.3%) | 1 (2.3%) |
| Non-ocular AE leading to treatment discontinuation | 3 (7.1%) | (0.0%) | 4 (9.1%) |

TABLE 8

Ocular AEs in Study Eye (Occurring in ≥ 3 Patients in Any Group)

| MedDRA Preferred Term | Sham Pooled (n = 42) | lampalizumab Monthly (n = 43) | lampalizumab Every Other Month (n = 44) |
|---|---|---|---|
| >-Any adverse events- | 24 (57.1%) | 36 (83.7%) | 30 (68.2%) |
| AGE-RELATED MACULAR DEGENERATION | (0.0%) | 2 (4.7%) | 3 (6.8%) |
| BLEPHARITIS | 2 (4.8%) | 1 (2.3%) | 5 (11.4%) |
| CATARACT | 3 (7.1%) | 2 (4.7%) | 3 (6.8%) |
| CONJUNCTIVAL HAEMORRHAGE | 9 (21.4%) | 21 (48.8%) | 15 (34.1%) |
| CONJUNCTIVAL OEDEMA | (0.0%) | 1 (2.3%) | 3 (6.8%) |
| DRY EYE | (0.0%) | 2 (4.7%) | 3 (6.8%) |
| EYE IRRITATION | 1 (2.4%) | 4 (9.3%) | 4 (9.1%) |
| EYE PAIN | 4 (9.5%) | 10 (23.3%) | 6 (13.6%) |
| EYE PRURITUS | 3 (7.1%) | 1 (2.3%) | 3 (6.8%) |
| FOREIGN BODY SENSATION IN EYES | 1 (2.4%) | 4 (9.3%) | 2 (4.5%) |
| INTRAOCULAR PRESSURE INCREASED * | (0.0%) | 6 (14.0%) | 7 (15.9%) |
| LACRIMATION INCREASED | 1 (2.4%) | 3 (7.0%) | 4 (9.1%) |
| OCULAR HYPERAEMIA | 2 (4.8%) | 3 (7.0%) | 5 (11.4%) |
| PUNCTATE KERATITIS | 1 (2.4%) | 4 (9.3%) | 2 (4.5%) |
| RETINAL HAEMORRHAGE | 3 (7.1%) | 1 (2.3%) | 3 (6.8%) |
| VISION BLURRED | 1 (2.4%) | 2 (4.7%) | 3 (6.8%) |
| VITREOUS DETACHMENT | 3 (7.1%) | 2 (4.7%) | 4 (9.1%) |
| VITREOUS FLOATERS | 1 (2.4%) | 3 (7.0%) | 2 (4.5%) |

* Note:
1 patient in the lampalizumab monthly group and 3 patients in the lampalizumab every other month group were reported to have increased intraocular pressure suspected to be related to the study drug.

Example 5 eQTL Analysis

While SNP rs4698775 is located in an intron of gene CCDC109B, CFI is by far the most compelling candidate gene at the locus based on genetic and biologic evidence. We examined whether this rs4698775 SNP may be an expression quantitative trait locus (eQTL) affecting levels of CFI mRNA in the liver, To perform eQTL analysis, TCGA RNA-seq data was obtained from the Cancer Genomics Hub at UC Santa Cruz (Cancer Genome Atlas (TCGA) database) (Cancer Genome Atlas Research Network, Nature, Comprehensive Genomic Characterization Defines Human Gioblasoma Genes and Core Pathways, 455(7216):1061-8 (Oct. 23, 2008); Collins et al., *Sci. Am*, Mapping the Cancer Genome. Pinpointing the Genes Involved in Cancer Will Help Chart a New Course Across the Complex Landscape of Human Malignancies, 296(3): 50-7 (March 2007)). TCGA contains RNA-seq and genotype data for tumor and normal samples from multiple tissues in the body. For this study, we used 34 samples of normal liver tissue. RNAseq data for these was analyzed using HTSegGenie (Pau, G. B. et al., HTSeqGenie: a software package to analyse high-throughput sequencing experiments (2012)), as follows: first, reads with low nucleotide qualities were removed (70% of bases with quality <23). The reads that passed were then aligned to the reference genome GRCh37 (Genome Research Consortium 37) using GSNAP (Genomic Short-read Nucleotide Alignment Program) (Wu, T D. et al., *Bioinformatics*, Fast and SNP-tolerant detection of complex variants and splicing in short reads, 26(7):873-81 (Apr. 1, 2010). Alignments of the reads that were reported by GSNAP as "uniquely mapping" were used for subsequent analysis. CH gene expression level for each sample was then quantified in terms of RPKM=number of reads aligning to CFI gene/(total number of uniquely mapped reads for the samples×CFI gene length). Genotype data for these samples was obtained through the database of Genotypes and Phenotypes (dbGaP; dbGaP is a site hosted by NCBI to archive and distribute results of studies that investigate the interaction between genotype and phenotype) and included genotypes for the Affymetrix 6.0 (1 million) SNP array. As the SNP of interest, rs4698775 was not directly assayed by this array, genotype imputation was performed using a workflow that included pre-phasing using SHAPEIT (Delaneau, O., *Nature Methods*, Improved whole-chromosome phasing for disease and population genetic studies, 10: 5-6 (2013)), followed by imputation using IMPUTE2 (Howie, B. N. et al., *PLoS Genet*, A Flexible and Accurate Genotype Imputation Method for the Next Generation of Genome-Wide Association Studies, 5(6): e1000529 (2009)) and reference haplotypes from the 1000 Genomes project (1000 Genomes Project Consortium, Abecasis G R. et al., *Nature*, A map of human genome variation from populationscale sequencing, 467(7319):1061-73 (2010)). Association analysis was then carried out which included performing linear regression of log (CFI RPKM) on the rs4698775 genotype coded additively (i.e. 0, 1, 2 copies of "T" allele).

Figure 9:
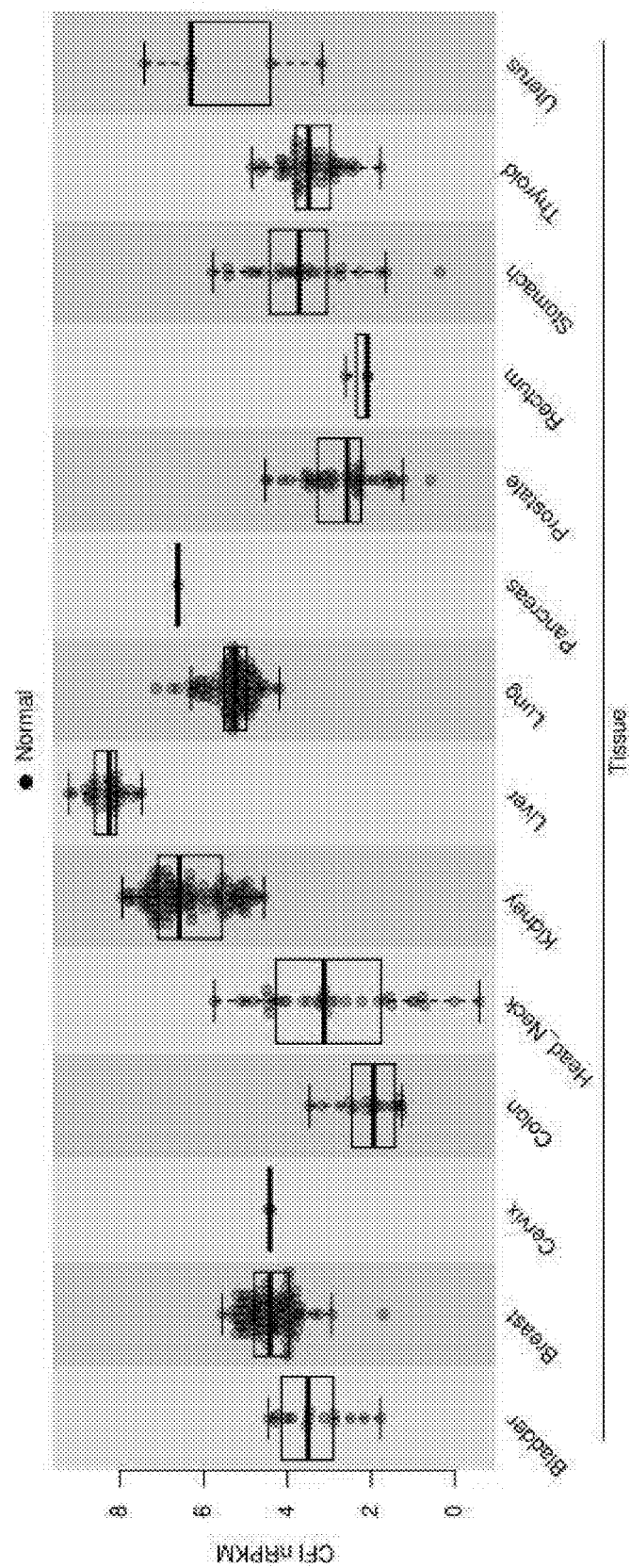
FIG. 9 shows that mRNA levels of CFI (CFI nRPKM) from the publicly available Cancer Genome Atlas (TCGA) database are highest in liver tissue. (RPKM=reads per Kb of transcript length per million mapped read; nRPKM is a normalized value for RPKM accounting for the fact that some areas of the genome sequence more efficiently than others).
Figure 10:
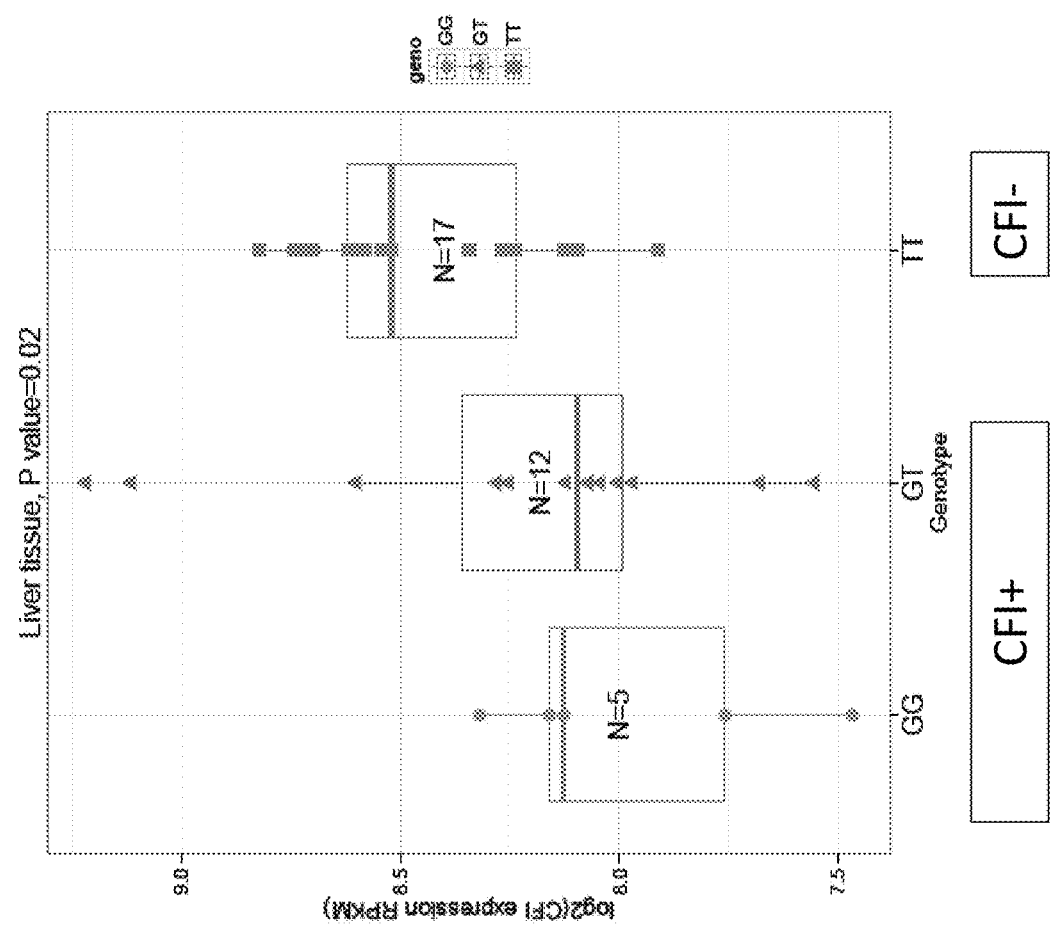
FIG. 10 shows the levels of CFI mRNA in normal liver tissue by rs4698775 SNP genotype. The rs698775 SNP genotype is significantly associated with CFI mRNA levels in normal TCGA liver samples (p=0.02). Risk allele homozygotes (GG) have less CFI mRNA than heteorzygotes (GT) who in turn have less CFI mRNA than non-risk allele homozygotes (TT).

The results showed that CFI expression is highest in liver tissue of the body, the site of synthesis for CFI (FIG. 9). When grouping by genotype for rs4698775, we saw a significant reduction in CH mRNA (p=0.02) in normal TCGA liver samples. In short, rs4698775 genotype was significantly associated with CFI mRNA levels normal TCGA liver samples (p=0.02). Risk allele homozygotes (GG) had less CFI mRNA than heterozygotes (GT), who in turn had less CFI mRNA than non-risk allele homozygotes (TT) (FIG. 10). These results were consistent with our hypothesis in which CFI is a negative regulator of the alternative complement pathway and that Risk allele carriers have lower levels of CFI available to regulate the alternative complement pathway. With these results, we showed a possible functional effect of the common GWAS associated SNP (rs4689775) used in our phase II MAHALO analysis.

Example 6

CFI Rare Variant Analysis

A recent report has shown a significant excess (p=1.7× 10-8) of rare missense variation in the CH gene of AMD patients (7.8%) compared to controls (2.3%) (Seddon, et al. *Nat. Genet.* 2013 45:1366-70). A second report, mainly focusing on one particular rare variant within the CFI gene, G119R, showed that these types of variants have a large impact on AMD risk (p=3.79×10-6; OR 22.20) (van de Ven, et al. *Nat. Genet.* 2013 45:813-7).

Sanger dideoxy sequencing was used to re-sequence exons in the CH gene for all patients in the MAHALO study with available DNA. Polymerase Chain Reaction (PCR) amplification was performed using standard PCR techniques using AmpliTaq Gold PCR Master Mix (Applied Biosystems) which includes all of the chemical components, except primers and template, necessary for amplification of samples via PCR and the Applied Biosystems 3730/3730x1 DNA Analyzer which is an automated, high-throughput, capillary electrophoresis system used for analysing fluorescently labelled DNA fragments. A two step "boost/nest" PCR strategy was used which involves the amplification of a large portion of a genomic DNA template first to generate a boost product, and then using the boost product as a template, to amplify a smaller region that was used for sequencing. Using the "boost/nest" strategy, we amplified large regions of the CFI gene from genomic DNA from patients in the MAHALO study with "boost" primers to generate a product for use as a template in a secondary nested reaction. "Nest" primers were used in the secondary nested PCR reaction to amplify a smaller region. The product of the nested reaction was used as a template for sequencing using standard sequencing techniques.

Figure 11:
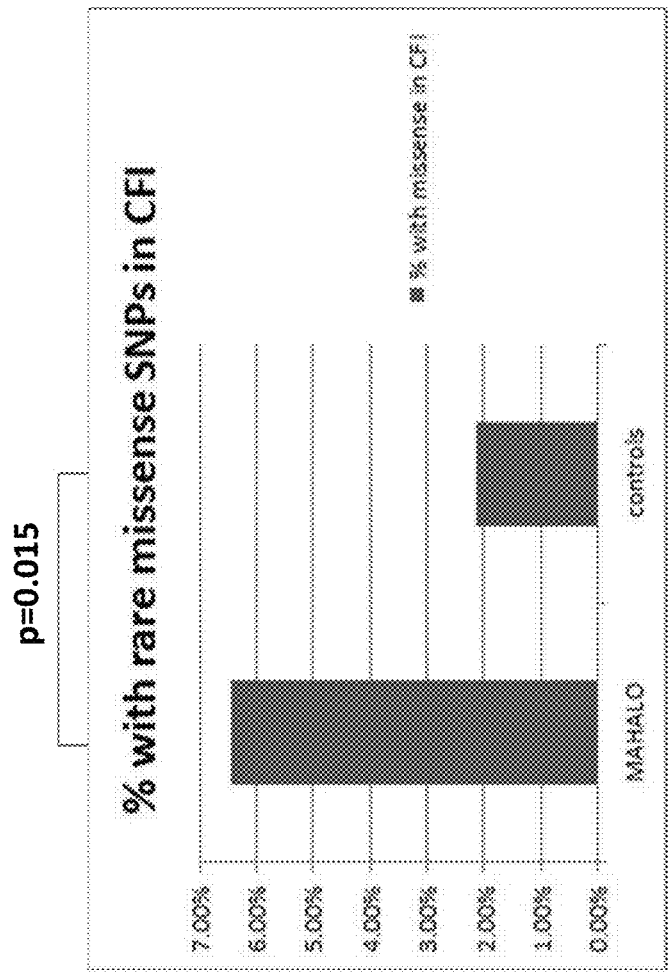
FIG. 11 shows an enrichment of CFI rare missense variation in samples from the MAHALO clinical trial samples compared to controls (p=0.015).
Figure 12:
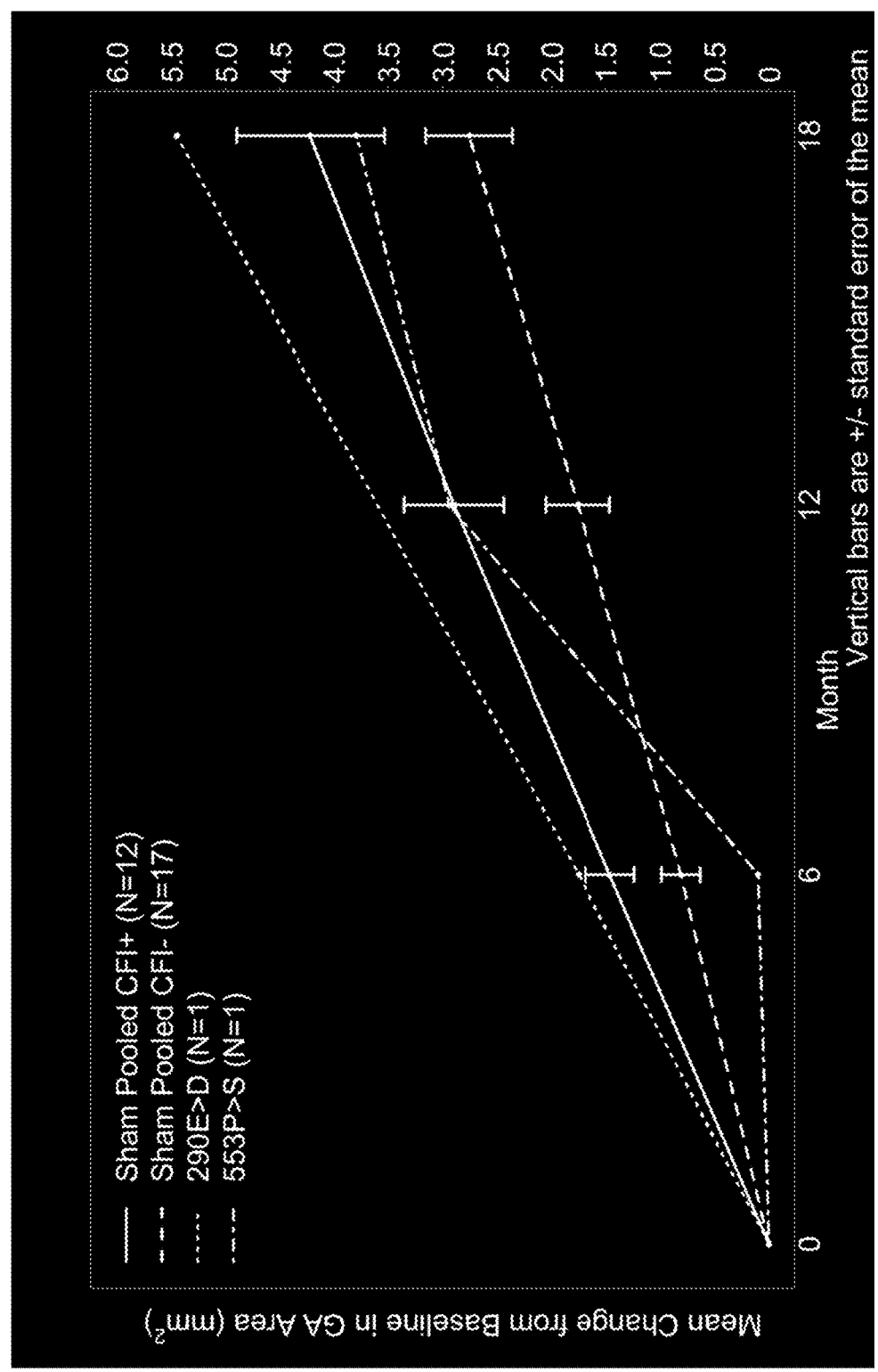
FIG. 12 shows CFI− (CFI− based on rs17440077) rare missense variant carriers have progression rates (mean change from baseline in GA area) similar to CFI+ (CFI+ based on rs17440077).

We re-sequenced all exons of CFI in our MAHALO patients with available DNA and found that 6 (6.9%) of them carried a rare missense variant (FIG. 11) We saw a significant enrichment of CFI rare missense variation in our MAHALO trial samples from patients with GA, compared to controls (p=0.015). These patients that carried the rare missense variant were equally divided between our sham, every other month and monthly arms. In the sham group, both individuals (290E>D and 553P>S in the CFI gene) with rare variants were non-risk allele carriers for rs17440077 (CFI-based on rs17440077). We observed that these rare variant positive individuals who are non-risk allele carriers for the rs17440077 SNP(CFI-based on rs17440077) used in the MAHALO study have a lesion area growth differential from baseline to 18 months (e.g. GA progression rates) similar to risk allele carriers (CFI+ based on rs17440077) (FIG. 12).

Because the growth rate for these non-risk allele carriers with rare variants is similar to those of risk allele carriers, GA patients who carry these rare missense variants may progress at a rate similar to risk allele carriers, regardless of whether they are classified as risk allele carriers or non-risk allele carriers based on the common rs17440077 SNP at CFI.

Example 7

Selection of Patients for Anti-Factor D Therapy

Patients diagnosed with GA were genotyped for the presence of polymorphisms associated with genes encoding selected complement factors. Presence of identified risk alleles and combinations thereof is indicative of the patient's likelihood to respond to treatment with anti-Factor D, such as lampalizumab.

Specifically, genotypes of the patients were detected by TaqMan real-time PCR. Each reaction included 0.4 µM each of forward and reverse primer and 0.15-0.3 µM detection probe (Table 9), uracil-N-glycosylase, 0.04-0.32 mM dNTPs (including dUTP), DNA polymerase and a suitable DNA polymerase buffer (including aptamer). The reactions were subjected to the following thermal cycling profile on the COBAS® 4800 instrument (Roche Molecular Diagnostics, Indianapolis, Ind.): 50° C. for 5 minutes, followed by 2 cycles of 95° C. (10 seconds) to 62° C. (30 seconds), and 55 cycles of 93° C. (10 seconds) to 62° C. (30 seconds), followed by 37° C. (10 minutes) and 25° C. (10 minutes). Fluorescence data was collected at the start of each 62° C. step.

described in Table 10. CFI Profile+patients were further assessed as likely to respond to treatment with anti-Factor D. One selection process is exemplified in Table 10. "+" indicates that the patient is "biomarker-positive" and thus more likely to respond to anti-factor D therapy; while "−" indicates that the patient is "biomarker-negative" and thus less likely to respond to anti-factor D therapy. As shown in Table 10, patients having at least one CFI allele (G) combined with at least one C2/CFB allele (G) or CFH allele (C on the complimentary strand) are likely responders to anti-

TABLE 9

Oligonucleotides used in TaqMan RT-PCR

| SEQ ID NO: | Name | Purpose | Sequence |
|---|---|---|---|
| SEQ ID NO: 17 | CCDC-LP03 | CFI FWD Primer | GCCTGCTAGCAACAAATTCACTCAL |
| SEQ ID NO: 18 | CCDC-LP02 | CFI FWD Primer | CCTGCTAGCAACAAATTCACTCAL |
| SEQ ID NO: 19 | CCDC-RP05 | CFI REV Primer | CACATACGTATATCATTTTCAAACTGCAGAL |
| SEQ ID NO: 20 | CCDC-RP02 | CFI REV Primer | GTATATCATTTTCAAACTGCAGAAAATCAL |
| SEQ ID NO: 21 | CCDC-G03 | CFI Probe for G SNP | FTCGGQAATGCTAAATATTTTATCCCACTTCTTP |
| SEQ ID NO: 22 | CCDC-G01 | CFI Probe for G SNP | FTTCTCGGQAATGCTAAATATTTTATCCCACTP |
| SEQ ID NO: 23 | CCDC-T05 | CFI Probe for T SNP | HCTCTGAQATGCTAAATATTTTATCCCACTTCTP |
| SEQ ID NO: 24 | CCDC-T01 | CFI Probe for T SNP | HTTCTCTGQAATGCTAAATATTTTATCCCACTP |
| SEQ ID NO: 25 | SKIV2L_LP02 | C2 FWD Primer | TCGGTGAGAGATGGACACTCAATL |
| SEQ ID NO: 26 | SKIV2L-LP03 | C2 FWD Primer | CGGTGAGAGATGGACACTCAATACL |
| SEQ ID NO: 27 | SKIV2L_RP02 | C2 REV Primer | ACATCGTTGATATAGTGAACCTCATCL |
| SEQ ID NO: 28 | SKIV2L-RP01 | C2 REV Primer | TCGTTGATATAGTGAACCTCATCL |
| SEQ ID NO: 29 | SKIV2L_G11 | C2 probe for G SNP | FCTGSGGQAGTCAATCCTTGGCCTCTTP |
| SEQ ID NO: 30 | SKIV2L_G12 | C2 probe for G SNP | FCTGGSGQAGTCAATCCTTGGCCTCTTP |
| SEQ ID NO: 31 | SKIV2L_G13 | C2 probe for G SNP | FCTGGSGQAGTCAATCCTTGGCCTCTTP |
| SEQ ID NO: 32 | SKIV2L_A01 | C2 probe for A SNP | HACTGGAGQAGTCAATCCTTGGCCTCTP |
| SEQ ID NO: 33 | SKIV2L_A03 | C2 probe for A SNP | HACTGGAQGAGTCAATCCTTGGCCTCTP |
| SEQ ID NO: 34 | CFH-LP01 | CFH FWD Primer | GGAAGTGCTTACACACCCATATAL |
| SEQ ID NO: 35 | CFH-LP02 | CFH_FWD Primer | CCTGGAAGTGCTTACACACCCATATAL |
| SEQ ID NO: 36 | CFH-RP01 | CFH REV Primer | CCAGTGATACATCCAGGTACATTAL |
| SEQ ID NO: 37 | CFH-RP02 | CFH REV Primer | ATACATCCAGGTACATTAATCACTCTTAGAACAAL |
| SEQ ID NO: 38 | CFH-C01 | CFH probe for C SNP | FAGAGCTQTTAGAATACAGTCCCTGAATGAAAP |
| SEQ ID NO: 39 | CFH-C04 | CFH probe for C SNP | FCTTQTAGAATACAGTCCCTGAATGAAAGTTGTAAAGGP |
| SEQ ID NO: 40 | CFH-T03 | CFH probe for T SNP | HAGTTQTTAGAATACAGTCCCTGAATGAAAGTTGTAAP |
| SEQ ID NO: 41 | CFH-T04 | CFH probe for T SNP | HTTTQTAGAATACAGTCCCTGAATGAAAGTTGTAAAGTTAP |

L = N6-tert-butyl-benzyl dA
F = threoninol-FAM
Q = BHQ2
P = 3'-Phosphate
H = threoninol-HEX
S = 7-deaza dG
E = CY5.5

Once the genotype of a GA patient was determined using the above-described TaqMan RT-PCR, it was analyzed for the presence of particular risk alleles at the complement loci CFI, C2/CFB and CFH to derive a CFI Profile Status as factor D therapy. In another instance, patients having at least one CFI allele (G) are likely responders to anti-factor D therapy. Other similar selection criteria may be developed involving these SNPs and SNPs at other complement loci.

TABLE 10

Genotypes at Selected Complement Loci and Definition of CFI Profile Status

| Genotypes at the complement loci | | | |
|---|---|---|---|
| CFI | C2/CFB | CFH (complementary strand) | CFI Profile Status |
| rs4698775 GG | rs429608 GG | rs1329428 CC | + |
| rs4698775 GG | rs429608 GG | rs1329428 CT | + |
| rs4698775 GG | rs429608 GG | rs1329428 TT | + |
| rs4698775 GG | rs429608 GA | rs1329428 CC | + |
| rs4698775 GG | rs429608 GA | rs1329428 CT | + |
| rs4698775 GG | rs429608 GA | rs1329428 TT | + |
| rs4698775 GG | rs429608 AA | rs1329428 CC | + |
| rs4698775 GG | rs429608 AA | rs1329428 CT | + |
| rs4698775 GG | rs429608 AA | rs1329428 TT | +/− |
| rs4698775 TG | rs429608 GG | rs1329428 CC | + |
| rs4698775 TG | rs429608 GG | rs1329428 CT | + |
| rs4698775 TG | rs429608 GG | rs1329428 TT | + |
| rs4698775 TG | rs429608 GA | rs1329428 CC | + |
| rs4698775 TG | rs429608 GA | rs1329428 CT | + |
| rs4698775 TG | rs429608 GA | rs1329428 TT | + |
| rs4698775 TG | rs429608 AA | rs1329428 CC | + |
| rs4698775 TG | rs429608 AA | rs1329428 CT | + |
| rs4698775 TG | rs429608 AA | rs1329428 TT | − |
| rs4698775 TT | rs429608 GG | rs1329428 CC | − |
| rs4698775 TT | rs429608 GG | rs1329428 CT | − |
| rs4698775 TT | rs429608 GG | rs1329428 TT | − |
| rs4698775 TT | rs429608 GA | rs1329428 CC | − |
| rs4698775 TT | rs429608 GA | rs1329428 CT | − |
| rs4698775 TT | rs429608 GA | rs1329428 TT | − |
| rs4698775 TT | rs429608 AA | rs1329428 CC | − |
| rs4698775 TT | rs429608 AA | rs1329428 CT | − |
| rs4698775 TT | rs429608 AA | rs1329428 TT | − |

Lengthy table referenced here
US10093978-20181009-T00001
Please refer to the end of the specification for access instructions.

Lengthy table referenced here
US10093978-20181009-T00002
Please refer to the end of the specification for access instructions.

Lengthy table referenced here
US10093978-20181009-T00003
Please refer to the end of the specification for access instructions.

Lengthy table referenced here
US10093978-20181009-T00004
Please refer to the end of the specification for access instructions.

LENGTHY TABLES

The patent contains a lengthy table section. A copy of the table is available in electronic form from the USPTO web site (http://seqdata.uspto.gov/?pageRequest=docDetail&DocID=US10093978B2). An electronic copy of the table will also be available from the USPTO upon request and payment of the fee set forth in 37 CFR 1.19(b)(3).

What is claimed is:

1. A kit for determining the presence of the degenerative disease-associated polymorphism rs4698775 in the CFI gene and rs1329428 in the CFH gene in a biological sample, comprising reagents and instructions for detecting the genotype of the biological sample for the presence of the degenerative disease-associated polymorphisms rs4698775 in the CFI gene and rs1329428 in the CFH gene, wherein the reagents comprise a set of oligonucleotides having at least 90% identity to and the 3' terminal nucleotide of SEQ ID NOs: 17, 19, 34, and 36, a set of oligonucleotides having at least 90% identity to SEQ ID NOs: 21 and 38 and a 5' threoninol-FAM, and a set of oligonucleotides having at least 90% identity to SEO ID NOs: 23 and 40 and a 5'-threoninol-HEX.

2. The kit according to claim 1, wherein the reagents comprise (i) the forward primer of SEQ ID NO: 17 combined with the reverse primer of SEQ ID NO: 19, the probe of SEQ ID NO: 21 and the probe of SEQ ID NO: 23; and (ii) the forward primer of SEQ ID NO: 34 combined with the reverse primer of SEQ ID NO: 36, the probe of SEQ ID NO: 38 and the probe of SEQ ID NO: 40.

3. The kit of claim 1 wherein the biological sample is a blood sample, saliva, cheek swab, tissue sample or a sample of bodily fluids.

4. The kit of claim 1 wherein the biological sample is obtained from a patient diagnosed with a degenerative disease.

5. The kit of claim 1, wherein the degenerative disease is age related macular degeneration (AMD).

6. The kit of claim 5, wherein the AMD is early, intermediate or advanced AMD.

7. The kit of claim 6, wherein the advanced AMD is geographic atrophy (GA).

* * * * *

```
                          SEQUENCE LISTING

<160> NUMBER OF SEQ ID NOS: 41

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ile Thr Ser Thr Asp Ile Asp Asp Asp Met Asn
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

-continued

<400> SEQUENCE: 2

Gly Gly Asn Thr Leu Arg Pro
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Leu Gln Ser Asp Ser Leu Pro Tyr Thr
1               5

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Tyr Thr Phe Thr Asn Tyr Gly Met Asn
1               5                   10

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Trp Ile Asn Thr Tyr Thr Gly Glu Thr Thr Tyr Ala Asp Asp Phe Lys
1               5                   10                  15

Gly

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Glu Gly Gly Val Asn Asn
1               5

<210> SEQ ID NO 7
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr

```
            20                   25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Tyr Ala Asp Asp Phe
 50                  55                  60

Lys Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                 85                  90                  95

Glu Arg Glu Gly Gly Val Asn Asn Trp Gly Gln Gly Thr Leu Val Thr
                100                 105                 110

Val Ser Ser
        115

<210> SEQ ID NO 8
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Gln Val Thr Gln Ser Pro Ser Ser Leu Ser Ala Ser Val Gly
1               5                  10                  15

Asp Arg Val Thr Ile Thr Cys Ile Thr Ser Thr Asp Ile Asp Asp Asp
            20                  25                  30

Met Asn Trp Tyr Gln Gln Lys Pro Gly Lys Val Pro Lys Leu Leu Ile
        35                  40                  45

Ser Gly Gly Asn Thr Leu Arg Pro Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Leu Gln Ser Asp Ser Leu Pro Tyr
                 85                  90                  95

Thr Phe Gly Gln Gly Thr Lys Val Glu Ile Lys
                100                 105

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
attaccagca ctgatattga tgatgatatg aac                          33

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ggaggcaata ctcttcgtcc t                                       21
```

```
<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ttgcaaagtg attctttgcc gtacacg                                            27

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ggatacacct tcactaacta tggaatgaac                                         30

<210> SEQ ID NO 13
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tggattaaca cctacactgg agagacaaca tatgctgacg acttcaaggg a                 51

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14 gaggggggggg ttaataac                                                     18

<210> SEQ ID NO 15
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95
```

```
Glu Arg Glu Gly Gly Val Asn Asn Trp Gly Gln Gly Thr Leu Val Thr
                100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr
    210                 215                 220
```

<210> SEQ ID NO 16
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

```
Asp Ile Gln Val Thr Gln Ser Pro Ser Ser Leu Ser Ala Ser Val Gly
1               5                   10                  15

Asp Arg Val Thr Ile Thr Cys Ile Thr Ser Thr Asp Ile Asp Asp Asp
                20                  25                  30

Met Asn Trp Tyr Gln Gln Lys Pro Gly Lys Val Pro Lys Leu Leu Ile
            35                  40                  45

Ser Gly Gly Asn Thr Leu Arg Pro Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Leu Gln Ser Asp Ser Leu Pro Tyr
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (25)..(25)
<223> OTHER INFORMATION: N6-tert-butyl-benzyl dA

<400> SEQUENCE: 17
gcctgctagc aacaaattca ctcaa                                              25

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (24)..(24)
<223> OTHER INFORMATION: N6-tert-butyl-benzyl dA

<400> SEQUENCE: 18
cctgctagca acaaattcac tcaa                                               24

<210> SEQ ID NO 19
<211> LENGTH: 31
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (31)..(31)
<223> OTHER INFORMATION: N6-tert-butyl-benzyl dA

<400> SEQUENCE: 19
cacatacgta tatcattttc aaactgcaga a                                       31

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (30)..(30)
<223> OTHER INFORMATION: N6-tert-butyl-benzyl dA

<400> SEQUENCE: 20
gtatatcatt tcaaactgc agaaaatcaa                                          30

<210> SEQ ID NO 21
<211> LENGTH: 31
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: misc_feature
<222> LOCATION: (1)..(1)
<223> OTHER INFORMATION: 5'-threoninol-FAM
```

```
<220> FEATURE:
<221> NAME/KEY: misc_feature
<222> LOCATION: (4)..(5)
<223> OTHER INFORMATION: BHQ2 dye between nucleotides
<220> FEATURE:
<221> NAME/KEY: misc_feature
<222> LOCATION: (31)..(31)
<223> OTHER INFORMATION: 3'-Phosphate

<400> SEQUENCE: 21
tcggaatgct aaatatttta tcccacttct t                              31

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: misc_feature
<222> LOCATION: (1)..(1)
<223> OTHER INFORMATION: 5'-threoninol-FAM
<220> FEATURE:
<221> NAME/KEY: misc_feature
<222> LOCATION: (7)..(8)
<223> OTHER INFORMATION: BHQ2 dye between nucleotides
<220> FEATURE:
<221> NAME/KEY: misc_feature
<222> LOCATION: (30)..(30)
<223> OTHER INFORMATION: 3'-Phosphate

<400> SEQUENCE: 22
ttctcggaat gctaaatatt ttatcccact                                30

<210> SEQ ID NO 23
<211> LENGTH: 31
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: misc_feature
<222> LOCATION: (1)..(1)
<223> OTHER INFORMATION: 5'-threoninol-HEX
<220> FEATURE:
<221> NAME/KEY: misc_feature
<222> LOCATION: (6)..(7)
<223> OTHER INFORMATION: BHQ2 dye between nucleotides
<220> FEATURE:
<221> NAME/KEY: misc_feature
<222> LOCATION: (31)..(31)
<223> OTHER INFORMATION: 3'-Phosphate

<400> SEQUENCE: 23
ctctgaatgc taaatatttt atcccacttc t                              31

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: misc_feature
<222> LOCATION: (1)..(1)
<223> OTHER INFORMATION: 5'-threoninol-HEX
<220> FEATURE:
<221> NAME/KEY: misc_feature
<222> LOCATION: (7)..(8)
<223> OTHER INFORMATION: BHQ2 dye between nucleotides
```

```
<220> FEATURE:
<221> NAME/KEY: misc_feature
<222> LOCATION: (30)..(30)
<223> OTHER INFORMATION: 3'-Phosphate

<400> SEQUENCE: 24
ttctctgaat gctaaatatt ttatcccact                                      30

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (24)..(24)
<223> OTHER INFORMATION: N6-tert-butyl-benzyl dA

<400> SEQUENCE: 25
tcggtgagag atggacactc aata                                            24

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (25)..(25)
<223> OTHER INFORMATION: N6-tert-butyl-benzyl dA

<400> SEQUENCE: 26
cggtgagaga tggacactca ataca                                           25

<210> SEQ ID NO 27
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (27)..(27)
<223> OTHER INFORMATION: N6-tert-butyl-benzyl dA

<400> SEQUENCE: 27
acatcgttga tatagtgaac ctcatca                                         27

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (24)..(24)
<223> OTHER INFORMATION: N6-tert-butyl-benzyl dA

<400> SEQUENCE: 28
tcgttgatat agtgaacctc atca                                            24

<210> SEQ ID NO 29
```

```
<211> LENGTH: 25
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: misc_feature
<222> LOCATION: (1)..(1)
<223> OTHER INFORMATION: 5'-threoninol-FAM
<220> FEATURE:
<221> NAME/KEY: modified_base
<222> LOCATION: (4)..(4)
<223> OTHER INFORMATION: 7-deaza dG
<220> FEATURE:
<221> NAME/KEY: misc_feature
<222> LOCATION: (6)..(7)
<223> OTHER INFORMATION: BHQ2 dye between nucleotides
<220> FEATURE:
<221> NAME/KEY: misc_feature
<222> LOCATION: (25)..(25)
<223> OTHER INFORMATION: 3'-Phosphate

<400> SEQUENCE: 29
ctggggagtc aatccttggc ctctt                                          25

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: misc_feature
<222> LOCATION: (1)..(1)
<223> OTHER INFORMATION: 5'-threoninol-FAM
<220> FEATURE:
<221> NAME/KEY: modified_base
<222> LOCATION: (5)..(5)
<223> OTHER INFORMATION: 7-deaza dG
<220> FEATURE:
<221> NAME/KEY: misc_feature
<222> LOCATION: (6)..(7)
<223> OTHER INFORMATION: BHQ2 dye between nucleotides
<220> FEATURE:
<221> NAME/KEY: misc_feature
<222> LOCATION: (25)..(25)
<223> OTHER INFORMATION: 3'-Phosphate

<400> SEQUENCE: 30
ctggggagtc aatccttggc ctctt                                          25

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: misc_feature
<222> LOCATION: (1)..(1)
<223> OTHER INFORMATION: 5'-threoninol-FAM
<220> FEATURE:
<221> NAME/KEY: modified_base
<222> LOCATION: (5)..(5)
<223> OTHER INFORMATION: 7-deaza dG
<220> FEATURE:
<221> NAME/KEY: misc_feature
<222> LOCATION: (6)..(7)
<223> OTHER INFORMATION: BHQ2 dye between nucleotides
<220> FEATURE:
<221> NAME/KEY: misc_feature
<222> LOCATION: (25)..(25)
```

```
<223> OTHER INFORMATION: 3'-Phosphate

<400> SEQUENCE: 31
ctggggagtc aatccttggc ctctt                                        25

<210> SEQ ID NO 32
<211> LENGTH: 25
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: misc_feature
<222> LOCATION: (1)..(1)
<223> OTHER INFORMATION: 5'-threoninol-HEX
<220> FEATURE:
<221> NAME/KEY: misc_feature
<222> LOCATION: (7)..(8)
<223> OTHER INFORMATION: BHQ2 dye between nucleotides
<220> FEATURE:
<221> NAME/KEY: misc_feature
<222> LOCATION: (25)..(25)
<223> OTHER INFORMATION: 3'-Phosphate

<400> SEQUENCE: 32
actggagagt caatccttgg cctct                                        25

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: misc_feature
<222> LOCATION: (1)..(1)
<223> OTHER INFORMATION: 5'-threoninol-HEX
<220> FEATURE:
<221> NAME/KEY: misc_feature
<222> LOCATION: (6)..(7)
<223> OTHER INFORMATION: BHQ2 dye between nucleotides
<220> FEATURE:
<221> NAME/KEY: misc_feature
<222> LOCATION: (25)..(25)
<223> OTHER INFORMATION: 3'-Phosphate

<400> SEQUENCE: 33
actggagagt caatccttgg cctct                                        25

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (24)..(24)
<223> OTHER INFORMATION: N6-tert-butyl-benzyl dA

<400> SEQUENCE: 34
ggaagtgctt acacacccat ataa                                         24

<210> SEQ ID NO 35
<211> LENGTH: 27
<212> TYPE: DNA
<213> ORGANISM: Artificial Sequence
<220> FEATURE:
```

-continued

```
<223> OTHER INFORMATION: Description of Artificial Sequence: Synthetic
      primer
<220> FEATURE:
<221> NAME/KEY: modified_base
<222> LOCATION: (27)..(27)
<223> OTHER INFORMATION: N6-tert-butyl-benzyl dA

<400> SEQUENCE: 35
cctggaagtg cttacacacc catataa                                              27

<210> SEQ ID NO 36
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (25)..(25)
<223> OTHER INFORMATION: N6-tert-butyl-benzyl dA

<400> SEQUENCE: 36
ccagtgatac atccaggtac attaa                                                25

<210> SEQ ID NO 37
<211> LENGTH: 35
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (35)..(35)
<223> OTHER INFORMATION: N6-tert-butyl-benzyl dA

<400> SEQUENCE: 37
atacatccag gtacattaat cactcttaga acaaa                                     35

<210> SEQ ID NO 38
<211> LENGTH: 30
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: misc_feature
<222> LOCATION: (1)..(1)
<223> OTHER INFORMATION: 5'-threoninol-FAM
<220> FEATURE:
<221> NAME/KEY: misc_feature
<222> LOCATION: (6)..(7)
<223> OTHER INFORMATION: BHQ2 dye between nucleotides
<220> FEATURE:
<221> NAME/KEY: misc_feature
<222> LOCATION: (30)..(30)
<223> OTHER INFORMATION: 3'-Phosphate

<400> SEQUENCE: 38
agagctttag aatacagtcc ctgaatgaaa                                           30

<210> SEQ ID NO 39
<211> LENGTH: 36
<212> TYPE: DNA
<213> ORGANISM: Artificial Sequence
<220> FEATURE:
<223> OTHER INFORMATION: Description of Artificial Sequence: Synthetic
      probe
<220> FEATURE:
```

```
<221> NAME/KEY: misc_feature
<222> LOCATION: (1)..(1)
<223> OTHER INFORMATION: 5'-threoninol-FAM
<220> FEATURE:
<221> NAME/KEY: misc_feature
<222> LOCATION: (3)..(4)
<223> OTHER INFORMATION: BHQ2 dye between nucleotides
<220> FEATURE:
<221> NAME/KEY: misc_feature
<222> LOCATION: (36)..(36)
<223> OTHER INFORMATION: 3'-Phosphate

<400> SEQUENCE: 39
ctttagaata cagtccctga atgaaagttg taaagg                                    36

<210> SEQ ID NO 40
<211> LENGTH: 35
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: misc_feature
<222> LOCATION: (1)..(1)
<223> OTHER INFORMATION: 5'-threoninol-HEX
<220> FEATURE:
<221> NAME/KEY: misc_feature
<222> LOCATION: (4)..(5)
<223> OTHER INFORMATION: BHQ2 dye between nucleotides
<220> FEATURE:
<221> NAME/KEY: misc_feature
<222> LOCATION: (35)..(35)
<223> OTHER INFORMATION: 3'-Phosphate

<400> SEQUENCE: 40
agttttagaa tacagtccct gaatgaaagt tgtaa                                     35

<210> SEQ ID NO 41
<211> LENGTH: 39
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: misc_feature
<222> LOCATION: (1)..(1)
<223> OTHER INFORMATION: 5'-threoninol-HEX
<220> FEATURE:
<221> NAME/KEY: misc_feature
<222> LOCATION: (3)..(4)
<223> OTHER INFORMATION: BHQ2 dye between nucleotides
<220> FEATURE:
<221> NAME/KEY: misc_feature
<222> LOCATION: (39)..(39)
<223> OTHER INFORMATION: 3'-Phosphate

<400> SEQUENCE: 41
ttttagaata cagtccctga atgaaagttg taaaagtta                                 39
```